US007662394B2

(12) United States Patent
Chang

(10) Patent No.: US 7,662,394 B2
(45) **Date of Patent: *Feb. 16, 2010**

(54) **NUCLEIC ACIDS ENCODING CHIMERIC *FLAVIVIRUS* IMMUNOGENS COMPRISING THE JAPANESE ENCEPHALITIS VIRUS (JEV) PRM SIGNAL SEQUENCE**

(75) Inventor: Gwong-Jen J. Chang, Fort Collins, CO (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 352 days.

This patent is subject to a terminal disclaimer.

(21) Appl. No.: 10/500,796

(22) PCT Filed: Apr. 4, 2002

(86) PCT No.: PCT/US02/10764

§ 371 (c)(1),
(2), (4) Date: Jul. 6, 2004

(87) PCT Pub. No.: WO02/081754

PCT Pub. Date: Oct. 17, 2002

(65) Prior Publication Data

US 2005/0163804 A1 Jul. 28, 2005

Related U.S. Application Data

(63) Continuation-in-part of application No. 09/826,115, filed on Apr. 4, 2001, now Pat. No. 7,227,011, which is a continuation-in-part of application No. 09/701,536, filed as application No. PCT/US99/12298 on Jun. 3, 1999.

(60) Provisional application No. 60/087,908, filed on Jun. 4, 1998.

(51) Int. Cl.
*A61K 39/12* (2006.01)
*A61K 39/295* (2006.01)

(52) U.S. Cl. ............... 424/199.1; 424/202.1; 424/218.1

(58) Field of Classification Search ............... 424/218.1
See application file for complete search history.

(56) References Cited

U.S. PATENT DOCUMENTS

| | | | | |
|---|---|---|---|---|
| 4,810,492 | A | 3/1989 | Fujita et al. | |
| 5,021,347 | A | 6/1991 | Yasui et al. | |
| 5,229,293 | A | 7/1993 | Matsuura et al. | |
| 5,494,671 | A | 2/1996 | Lai et al. | |
| 5,514,375 | A | 5/1996 | Paoletti et al. | |
| 6,074,865 | A | 6/2000 | Kelly et al. | |
| 6,136,561 | A * | 10/2000 | Ivy et al. | 435/69.3 |
| 6,165,477 | A | 12/2000 | Ivy et al. | |
| 6,258,788 | B1 | 7/2001 | Schmaljohn | |
| 6,455,509 | B1 * | 9/2002 | Kochel et al. | 514/44 |
| 6,696,281 | B1 * | 2/2004 | Chambers et al. | 435/235.1 |

FOREIGN PATENT DOCUMENTS

| | | |
|---|---|---|
| JP | 53133627 | 11/1978 |
| JP | 63105682 | 5/1988 |
| JP | 89025725 | 5/1989 |
| JP | 5276941 | 10/1993 |
| JP | 7265093 | 10/1995 |
| WO | WO 90/01946 | 3/1990 |
| WO | WO 92/02548 | 2/1992 |
| WO | WO 92/03545 | 3/1992 |
| WO | WO 93/06214 | 4/1993 |
| WO | WO 98/37911 | 9/1998 |
| WO | WO 99/06068 | 2/1999 |
| WO | WO 99/63095 | 12/1999 |
| WO | WO 02/072036 | 9/2002 |
| WO | WO 02/083903 | 10/2002 |

OTHER PUBLICATIONS

Pletnev, A. G., et al., 1992, "Construction and characterization of chimeric tick-borne encephalitis/dengue type 4 viruses", Proc. Natl. Acad. Sci. USA 89:10532-10536.*

Yasui, K, et al., 1990, "Analysis of Japanese encephalitis (JE) virus genome and implications for recombinant JE vaccine", Southeast Asian J. Trop. Med. Public Health 21(4):663-669.*

Phillpotts, R. J., et al., 1996, "Immunization with DNA polynucleotides protects mice against lethal challenge with St. Louis encephalitis virus", Arch. Virol. 141:743-749.*

Kozak, M., 1987, "At least six nucleotides preceding the AUG initiator codon enhance translation in mammalian cells", J. Mol. Biol. 196:947-950.*

Rothman, A. L., 2004, Dengue: defining protective versus pathologic immunity, J. Clin. Invest. 113(7):946-951.*

Stephenson, J. R., 2005, Understanding dengue pathogenesis: implications for vaccine design, Bull. World Health Org. 83:308-314 (abstract only provided).*

Kitchener, S., et al., 2006, Immunogenicity and safety of two live-attenuated tetravalent dengue vaccine formulations in healty Australian adults, Vaccine 24:1238-1241.*

Monath, T. P., 2007, Dengue and yellow fever-challenges for the development and use of vaccines, N. Engl. J. Med. 357(22): 2222-2225.*

(Continued)

*Primary Examiner*—Jeffrey S. Parkin
(74) *Attorney, Agent, or Firm*—Klarquist Sparkman, LLP

(57) ABSTRACT

The present invention encompasses isolated nucleic acids containing transcriptional units which encode a signal sequence of one *flavivirus* and an immunogenic *flavivirus* antigen of a second *flavivirus* or of a chimeric immunogenic *flavivirus* antigen comprising sequence from more than one *flavivirus*. The invention further encompasses a nucleic acid and protein vaccine and the use of the vaccine to immunize a subject against *flavivirus* infection. The invention also provides antigens encoded by nucleic acids of the invention, antibodies elicited in response to the antigens and use of the antigens and/or antibodies in detecting *flavivirus* or diagnosing *flavivirus* infection.

47 Claims, 8 Drawing Sheets

OTHER PUBLICATIONS

Stocks, C. E., and M. Lobigs, 1995, Posttranslational signal peptidase cleavage at the flavivirus C-prM junction in vitro, J. Virol. 69(12):8123-8126.*

Aberle et al., "A DNA Immunization Model Study with Constructs Expressing the Tick-Borne Encephalitis Virus Envelope Protein E in Different Physical Forms," *J Immunology* 163:6756-6761 (1999).

Allison et al., "Synthesis and Secretion of Recombinant Tick-Borne Encephalitis Virus Protein E in Soluble and Particulate Form," *J Virology* 69(9):5816-5820 (Sep. 1995).

Alvarez et al., "A Phase I Study of Recombinant Adenovirus Vector-Mediated Delivery of an Anti-erbB-2 Single-Chain (sFv) Antibody Gene for Previously Treated Ovarian and Extraovarian Cancer Patients," *Hum. Gene Ther.* 8:229-242 (Jan. 20, 1997).

Anderson et al., "Isolation of West Nile Virus from Mosquitoes, Crows, and a Cooper's Hawk in Connecticut," *Science* 286(5448):2331-2333 (Dec. 17, 1999).

Asnis et al., "The West Nile Virus Outbreak of 1999 in New York: The Flushing Hospital Experience," *Clin. Infect. Dis.* 30: 413-418 (2000).

Azevedo et al., "Main features of DNA-based immunization vectors," *Braz. J. Med. Biol. Res.* 32(2):147-153 (1999).

Bray et al., "Mice Immunized with Recombinant Vaccinia Virus Expressing Dengue 4 Virus Structural Proteins with or without Nonstructural Protein NSI Are Protected Against Fatal Dengue Virus Encephalitis," *J. Virol.* 63(6):2853-2856 (Jun. 1989).

Cavener and Ray, "Eukaryotic start and stop translation sites," *Nucleic Acids Research*, 19(12):3185-3192 (1991).

Chang et al., "A Single Intramuscular Injection of Recombinant Plasmid DNA Induces Protective Immunity and Prevents Japanese Encephalitis in Mice," *J. Virol.* 74(9):4244-4252 (May 2000).

Chang et al., "Enhancing biosynthesis and secretion of premembrane and envelope proteins by the chimeric plasmid of dengue virus type 2 and Japanese encephalitis virus," *Virology*, 306:170-180 (2003).

Chang et al., "Flavivirus DNA Vaccines," *Annals New York Academy of Sciences*, 951:272-285 (2001).

Chang et al., "Recent advancement in flavivirus vaccine development," *Expert Rev. Vaccines*, 3(2):199-220 (2004).

Chen et al., "Construction of Intertypic Chimeric Dengue Viruses Exhibiting Type 3 Antigenicity and Neurovirulence for Mice," *J Virology*, 69(8):5186-5190 (Aug. 1995).

Clarke et al., "Techniques for Hemagglutination And Hemagglutination-Inhibition With Arthropod-Borne Viruses," *Amer. J. Trop. Med. And Hyg.*, 7:561-573 (1958).

Colombage et al., "DNA-Based and Alphavirus-Vectored Immunisation with PrM and E Proteins Elicits Long-Lived and Protective Immunity against te Flavivirus, Murray Valley Encephalitis Virus," *Virology* 250:151-163 (1998).

Davis et al., "West Nile Virus Recombinant DNA Vaccine Protects Mouse and Horse from Virus Challenge and Expresses in Vitro a Noninfectious Recombinant Antigen That Can Be Used in Enzyme-Linked Immunosorbent Assays," *J. Virol.* 75(9):4040-4047, 2001 (published on-line Apr. 4, 2001).

Deubel et al., "Nucleotide Sequence and Deduced Amino Acid Sequence of the Structural Proteins of Dengue Type 2 Virus, Jamaica Genotype," Virology 155:365-377 (1986).

Deubel et al., "Nucleotide Sequence and Deduced Amino Acid Sequence of the Nonstructural Proteins of Dengue Type 2 Virus, Jamaica Genotype: Comparative Analysis of the Full-Length Genome," *Virology* 165:234-244 (1988).

Dmitriev et al., "Immunization with recombinant vaccinia viruses expressing structural and part of the nonstructural region of tick-borne encephalitis virus cDNA protect mice against lethal encephalitis," *J. Biotechnol.* 44:97-103 (1996).

Duarte dos Santos et al., "Complete nucleotide sequence of yellow fever virus vaccine strains 17DD and 17D-213," *Virus Res.* 35:35-41 (1995).

Falgout et al., "Proper Processing of Dengue Virus Nonstructural Glycoprotein NSI Requires the N-Terminal Hydrophobic Signal Sequence and the Downstream Nonstructural Protein NS2a," *J. Virol.* 63(5):1852-1860 (May 1989).

Falgout et al., "Immunization of Mice with Recombinant Vaccinia Virus Expressing Authentic Dengue Virus Nonstructural Protein NSI Protects Against Lethal Dengue Virus Encephalitis," *J. Virol.* 64(9):4356-4363 (1990).

Fonseca et al., "Recombinant vaccinia viruses co-expressing dengue-1 glycoprotein prM and E induce neutralizing antibodies in mice," Vaccine 12(3):279-285 (1994).

Garmendia et al., "Recovery and Identification of West Nile Virus from a Hawk in Winter," *J. Clin. Microbiol.* 38(8):3110-3111 (Aug. 2000).

Gruenberg et al., "Partial Nucleotide Sequence and Deduced Amino Acid Sequence of the Structural Proteins of Dengue Virus Type 2, New Guinea C and PUO-218 Strains," *J. Gen. Virol.*, 69:1391-1398 (1988).

Guirakhoo et al., "Recombinant Chimeric Yellow Fever-Dengue Type 2 Virus is Immunogenic and Protective in Nonhuman Primates," *J. Virol.*, 74(12):5477-5485 (2000).

Hahn et al., "Nucleotide Sequence of Dengue 2 RNA and Comparison of the Encoded Proteins with Those of Other Flaviviruses," *Virology* 162:167-180 (1988).

Hashimoto et al., "Molecular Cloning and Complete Nucleotide Sequence of the Genome of Japanese Encephalitis Virus Beijing-1 Strain," *Virus Genes* 1(3):305-317 (1988).

Heinz et al., "Flaviviruses." In *Immunochemistry of Viruses II: The Basis for Serodiagnosis and Vaccines*. (edited by von Regenmortel and Neurath) Elsevier Science Publishers, Chapter 14, pp. 89-305 (1990).

Henchal et al., "Dengue Virus-Specific and Flavivirus Group Determinants Identified With Monoclonal Antibodies by Indirect Immunofluorescence," *Amer. J. Trop. Med. Hyg.* 31:830-836 (1982).

Hennessy et al., "Effectiveness of live-attenuated Japanese encephalitis vaccine (SA14-14-2): a case-control study," Lancet 347:1583-1586 (Jun. 8, 1996).

Ho et al., "DNA vaccination induces a long-term antibody response and protective immunity against pseudorabies virus in mice," *Arch Virol*, 143:115-125 (1998).

Hubàlek et al., "West Nile Fever-a Reemerging Mosquito-Borne Viral Disease in Europe," *Emerg. Infect. Dis.*, 5(5):643-650 (1999).

Hunt et al., "A recombinant particulate antigen of Japanese encephalitis virus produced in stably-transformed cells is an effective noninfectious antigen and subunit immunogen," *J. Virological Methods*, 97:133-149 (2001).

Hunt and Calisher, "Relationships of Bunyamwera Group Viruses by Neutralization," *Amer. J. Trop. Med. Hyg.*, 28(4):740-749 (1979).

Jacobs et al., "High-level expression of the tick-borne encephalitis virus NS1 protein by using an adenovirus-based vector: protection elicited in a murine model," *J. Virol.*, 66(4):2086-2095 (Apr. 1992).

Jacobs, "A novel recombinant adenovirus vector expressing a flavivirus non-structural protein protects against lethal flavivirus challenge," *Clinical Science*, 85:117-122 (1993).

Jia et al., "Genetic analysis of West Nile New York 1999 encephalitis virus," *Lancet*, 354:1971-1972 (Dec. 4, 1999).

Johnson et al., "Detection of Anti-Arboviral Immunoglobulin G by Using a Monoclonal Antibody-Based Capture Enzyme-Linked Immunosorbent Assay," *J. Clin. Microbiol.*, 38(5):1827-1831 (May 2000).

Kimura-Kuroda and Yasui, "Antigenic Comparison of Envelope Protein E between Japanese Encephalitis Virus and Some Other Flaviviruses Using Monoclonal Antibodies," *J. Gen. Virol.*, 67:2663-2672 (1986).

Kimura-Kuroda and Yasui, "Topographical Analysis of Antigenic Determinants on Envelope Glycoprotein V3 (E) of Japanese Encephalitis Virus, Using Monoclonal Antibodies," *J. Virol.*, 45(1):124-132 (Jan. 1983).

Klinman et al., "CpG motifs as immune adjuvants," *Vaccine*, 17:19-25 (1999).

Kochel et al., "Inoculation of plasmids expressing the dengue-2 envelope gene elicit neutralizing antibodies in mice," *Vaccine*, 15(5):547-552 (1997).

Köhler et al., "Continuous cultures of fused cells secreting antibody of predefined specificity," *Nature*, 256:495-497 (Aug. 7, 1975).

Konishi et al., "A DNA vaccine expressing dengue type 2 virus premembrane envelope genes induces neutralizing antibody and memory B cells in mice," *Vaccine* 18:1133-1139 (2000).
Konishi et al., "Comparison of Protective Immunity Elicited by Recombinant Vaccinia Viruses That Synthesize E or NS1 of Japanese Encephalitis Virus," *Virology*, 185:401-410 (1991).
Konishi et al., "Avipox virus-vectored Japanese encephalitis virus vaccines: use a vaccine candidates in combination with purified subunit immunogens," *Vaccine*, 12(7):633-638 (1994).
Konishi et al., "Generation and Characterization of a Mammalian Cell Line Continuously Expressing Japanese Encephalitis Virus Subviral Particles," *J. Virol.* 75(5):2204-2212 (Mar. 2001).
Konishi et al., "The Anamnestic Neutralizing Antibody Response Is Critical for Protection of Mice from Challenge following Vaccination with a Plasmid Encoding the Japanese Encephalitis Virus Premembrane and Envelope Genes," *J. Virology* 73(7):5527-5534 (Jul. 1999).
Konishi et al., "Induction of Protective Immunity against Japanese Encephalitis in Mice by Immunization with a Plasmid Encoding Japanese Encephalitis Virus Premembrane and Envelope Genes," *J Virology*, 72(6):4925-4930 (Jun. 1998).
Konishi et al., "Mice Immunized with a Subviral Particle Containing the Japanese Encephalitis Virus prM/M and E Proteins Are Protected from Lethal JEV Infection," *Virology*, 188:714-720 (1992).
Kozak, "Circumstances and Mechanisms of Inhibition of Translation by Secondary Structure in Eucaryotic mRNAs," *Mol. Cell. Biol.*, 9(11):5134-5142 (Nov. 1989).
Kozak, "At Least Six Nucleotides Preceding the AUG Initiator Codon Enhance Translation in Mammalian Cells," *J. Mol. Biol.*, 196:947-950 (1987).
Kozak, "Point Mutations Define a Sequence Flanking the AUG Initiator Codon That Modulates Translation by Eukaryotic Ribosomes," *Cell*, 44:283-292 (Jan. 31, 1986).
Kuno et al., "Phylogeny of the Genus Flavivirus," *J. Virol.*, 72(1):73-83 (Jan. 1998).
Laemmli, "Cleavage of Structural Proteins during the Assembly of the Head of Bateriophage T4," *Nature*, 277:680-685 (Aug. 15, 1970).
Lai et al., "Immunization of Monkeys with Baculovirus Recombinant-expressed Dengue Envelope and NSI Glycoproteins Induces Partial Resistance to Challenge with Homotypic Dengue Virus," In *Vaccines 90: Modern Approaches to New Vaccines including Prevention of AIDS*, Cold Spring Harbor Laboratory, Cold Springs Harbor, NY, pp. 119-124 (1990).
Lanciotti et al., Origin of the West Nile Virus Responsible for an Outbreak of Encephalitis in the Northeastern United States, *Science*, 286:2333-2337 (Dec. 17, 1999).
Lin et al., "DNA Immunization with Japanese Encephalitis Virus Nonstructural Protein NS1 Elicits Protective Immunity in Mice," *J. Virol.*, 72(1):191-200 (Jan. 1998).
Mackow et al., "The Nucleotide Sequence of Dengue Type 4 Virus: Analysis of Genes Coding for Nonstructural Proteins," *Virology*, 159:217-228 (1987).
Mandl et al., "Complete Genomic Sequence of Powassan Virus: Evaluation of Genetic Elements in Tick-Borne Versus Mosquito-Borne Flaviviruses," *Virology*, 194:173-184 (1993).
Martin et al., "Standardization of Immunoglobulin M Capture Enzyme-Linked Immunosorbent Assays for Routine Diagnosis of Arboviral Infections," *J. Clin. Microbiol.*, 38(5):1823-1826 (May 2000).
Mason et al., "Sequence of the Dengue-1 Virus genome in the Region Encoding the Three Structural Proteins and the Major Nonstructural Protein NS1," *Virology*, 161:262-267 (1987).
Mason et al., "Japanese Encephalitis Virus-Vaccinia Recombinants Produce Particulate Forms of the Structural Membrane Proteins and Induce High Levels of Protection against Lethal JEV Infection," *Virology*, 180:294-305 (1991).
Mir et al., "High-efficiency gene transfer into skeletal muscle mediated by electric pulses," *Proc. Nat. Acad. Sci. USA*, 96:4262-4267 (Apr. 1999).
Monath, "Flaviviruse," *Virology* (*R.N. Fields, ed.*), 763-814 (1990).
Nitayaphan et al., "Nucleotide Sequence of the Virulent SA-14 Strain of Japanese Encephalitis Virus and Its Attenuated Vaccine Derivative, SA-14-14-2," *Virology*, 177:541-552 (1990).
Osatomi and Sumiyoshi, "Complete Nucleotide Sequence of Dengue Type 3 Virus Genome RNA," *Virology*, 176:643-647 (1990).
Osatomi et al., "Nucleotide Sequence of Dengue Type 3 Virus Genomic RNA Encoding Viral Structural Proteins," *Virus Genes*, 2(1):99-108 (1988).
Phillpotts et al., "Immunization with DNA polynucleotides protects mice against lethal challenge with St. Louis encephalitis virus," *Arch. Virol.*, 141:743-749.
Pincus et al., "Recombinant vaccinia virus producing the prM and E proteins of yellow fever virus protects mice from lethal yellow fever encephalitis," *Virology*, 187:290-297 (1992).
Porter et al., "Protective efficacy of a dengue 2 DNA vaccine in mice and the effect of CpG immuno-stimulatory motifs on antibody responses," *Arch. Virol.* 143:997-1003 (1998).
Ramelow et al., "Detection of tick-borne encephalitis virus RNA in ticks (*Ixodes ricinus*) by the polymerase chain reaction," *J. Virol. Meth.*, 45:115-9 (1993).
Raviprakash et al., "Immunogenicity of dengue virus type 1 DNA vaccines expressing truncated and full length envelope protein," *Vaccine* 18:2426-2434 (2000).
Rice et al., "Nucleotide Sequence of Yellow Fever Virus: Implications for Flavivirus Gene Expression and Evolution," *Science*, 229:726-733 (Aug. 23, 1985).
Roehrig et al., "Identification of Epitopes on the E Glycoprotein of Saint Louis Encephalitis Virus Using Monoclonal Antibodies," *Virology*, 128:118-126 (1983).
Roehrig et al., "Synthetic Peptides Derived from the Deduced Amino Acid Sequence of the E-Glycoprotein of Murray Valley Encephalitis Virus Elicit Antiviral Antibody," *Virology*, 171:49-60 (1989).
Sato et al., "Immunostimulatory DNA Sequences Necessary for Effective Intradermal Gene Immunization," *Science*, 273(5273):352-354 (Jul. 19, 1996).
Schalich et al., "Recombinant subviral particles from tick-borne encephalitis virus are fusogenic and provide a model system for studying flavivirus envelope glycoprotein functions," *J. Virol.*, 70:4549-4557 (Jul. 1996).
Schimaljohn et al., "Naked DNA Vaccines Expressing the prM and E Genes of Russian Spring Summer Encephalitis Virus and Central European Encephalitis Virus Protect Mice from Homologous and Heterologous Challenge," *J. Virology* 71(12):9563-9569 (Dec. 1997).
Seeger et al., "The cloned genome of ground squirrel hepatitis virus is infectious in the animal," *Proc Natl Aca Sci U.S.A.*, 81(18):5849-4852 (Sep. 1984).
Sela, *The Choice of Carrier. Synthetic Vaccines vol. 1* (edited by Arnon) CRC Press Inc, Boca Raton, FL., pp. 83-92 (1987).
Simmons et al., "Short Report: Antibody Responses of Mice Immunized with a Tetravalent Dengue Recombinant Protein Subunit Vaccine," *Am. J. Trop. Med. Hyg.* 65(2):159-161 (2001).
Smithburn et al., "A Neurotropic Virus Isolated From the Blood Of A Native of Uganda," *Am. J. Trop. Med. Hyg.*, 20:471-492 (1940).
Sumiyoshi et al., "Complete Nucleotide Sequence of the Japanese Encephalitis Virus Genome RNA," *Virology*, 161:497-510 (1987).
Tardei et al., "Evaluation of Immunoglobulin M (IgM) and IgG Enzyme Immunoassays in Serologic Diagnosis of West Nile Virus Infection," *J. Clin. Microbiol.* 38(6):2232-2239 (Jun. 2000).
Trent et al., "Partial Nucleotide Sequence of St. Louis Encephalitis Virus RNA: Structural Proteins. NS1 ns2a and ns2b," *Virology*, 156:293-304 (1987).
Tsai et al., Japanese Encephalitis Vaccines. In Vaccines ($2^{nd}$ edition) (edited by Plotkin and Mortimer), W.B. Saunders Co., Philadelphia, PA, Chapter 24, pp. 671-713 (1994).
Tsai et al., Japanese Encephalitis Vaccines. In Vaccines ($3^{rd}$ edition) (edited by Plotkin and Orenstein), W.B. Saunders Co., Philadelphia, PA, Chapter 27, pp. 672-710 (1999).
Venugopal et al., "Immunity to St. Louis encephalitis virus by sequential immunization with recombinant vaccinia and baculovirus derived PrM/E proteins," *Vaccines*, 13(11):1000-1005 (1995).
Wang et al., "Immunization of Mice Against West Nile Virus with Recombinant Envelope Protein," *J. Immunol.* 167:5273-5277 (2001).
Wang et al., "Immune Response to Neonatal Genetic Immunization," *Virology*, 228:278-284 (1997).

Wolff et al., "Long-term persistence of plasmid DNA and foreign gene expression in mouse muscle," *Hum Mol Genet*, 1(6):363-369 (Sep. 1992).

Yang et al., "A p300/CBP-associated factor that competes with the adenoviral oncoprotein E1A," *Nature*, 382:319-324 (Jul. 25, 1996).

Yasui et al., "Analysis of Japanese encephalitis (JE) virus genome and implications for recombinant JE vaccine," *Southeast Asian J. Trop. Med. Public Health*, 21(4):663-669 (1990).

Zhang et al., "Immunization of Mice with Dengue Structural Proteins and Nonstructural Protein NSI Expressed by Baculovirus Recombinant Induces Resistance to Dengue Virus Encephalitis," *J. Virol.*, 62(8):3027-3031 (Aug. 1988).

Zhang et al., "Passive Protection of Mice, Goats, and Monkeys Against Japanese Encephalitis With Monoclonal Antibodies," *J. Med. Virol.*, 29:133-138 (1989).

Zhao et al., "Cloning Full-Length Dengue Type 4 Viral DNA Sequences: Analysis of Genes Coding for Structural Proteins," *Virology*, 155:77-88 (1986).

Zhao et al., "Expression of Dengue Virus Structural Proteins and Nonstructural Protein $NS_1$ by a Recombinant Vaccinia Virus," *J. Virol.*, 61(12):4019-4022 (Dec. 1987).

"Update: Surveillance for West Nile Virus in Overwintering Mosquitoes—New York, 2000," *Morb. Mortal. Wkly. Rep.*, 49(09):178-179 (Mar. 10, 2000).

"Update: West Nile Virus Activity—Northeastern United States, 2000," *Morb. Mortal. Wkly. Rep.*, 49(36):820-822 (Sep. 15, 2000).

Arroyo, J., et al., "Molecular basis for attenuation of neurovirulence of a yellow fever virus/Japanese encephalitis virus chimera vaccine (chimerivax-je)," *Journal of Virology*, The American Society for Microbiology, US, vol. 75, No. 2, Jan. 2001, pp. 934-942, XP002967301.

Pletnev A.G. et al., "Construction and Characterization of Chimeric Tick-Borne Encephalitis/Dengue Type 4 Viruses," *Proceedings of the National Academy of Sciences of USA, National Academy of Science*, Washington, U.S. vol. 89, No. 21, Nov. 1, 1992, pp. 10532-10536.

Kozak, "An Analysis of 5'-noncoding sequences from 699 vertebrate messenger RNAs," *Nucleic Acids Research*, 15(20):8125-8148, 1987.

* cited by examiner

SEQUENCE LISTING

```
<160> NUMBER OF SEQ ID NOS: 64

<210> SEQ ID NO 1
<211> LENGTH: 48
<212> TYPE: DNA
<213> ORGANISM: Artificial Sequence
<220> FEATURE:
<223> OTHER INFORMATION: Description of artificial sequence; note =
      synthetic construct
<220> FEATURE:
<221> NAME/KEY: misc_feature
<222> LOCATION: (1)..(48)
<223> OTHER INFORMATION: Amplimer 14DV389
<220> FEATURE:
<221> NAME/KEY: CDS
<222> LOCATION: (25)..(48)

<400> SEQUENCE: 1

cttggtacct ctagagccgc cgcc atg ggc aga aag caa aac aaa aga            48
                           Met Gly Arg Lys Gln Asn Lys Arg
                           1               5


<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Met Gly Arg Lys Gln Asn Lys Arg
1               5


<210> SEQ ID NO 3
<211> LENGTH: 50
<212> TYPE: DNA
<213> ORGANISM: Artificial Sequence
<220> FEATURE:
<223> OTHER INFORMATION: Description of artificial sequence; note =
      synthetic construct
<220> FEATURE:
<221> NAME/KEY: misc_feature
<222> LOCATION: (1)..(50)
<223> OTHER INFORMATION: Amplimer c14DV2453

<400> SEQUENCE: 3

ttttcttttg cggccgctca aacttaagca tgcacattgg tcgctaagaa                50


<210> SEQ ID NO 4
<211> LENGTH: 48
<212> TYPE: DNA
<213> ORGANISM: Artificial Sequence
<220> FEATURE:
<223> OTHER INFORMATION: Description of artificial sequence; note =
      synthetic construct
<220> FEATURE:
<221> NAME/KEY: misc_feature
<222> LOCATION: (1)..(48)
<223> OTHER INFORMATION: Amplimer YFDV389
<220> FEATURE:
<221> NAME/KEY: CDS
<222> LOCATION: (25)..(48)

<400> SEQUENCE: 4

cttggtacct ctagagccgc cgcc atg cgt tcc cat gat gtt ctg act            48
                           Met Arg Ser His Asp Val Leu Thr
                           1               5
```

-continued

<210> SEQ ID NO 5
<211> LENGTH: 8
<212> TYPE: PRT
<213> ORGANISM: Artificial Sequence
<220> FEATURE:
<223> OTHER INFORMATION: Synthetic Construct

<400> SEQUENCE: 5

Met Arg Ser His Asp Val Leu Thr
1               5

<210> SEQ ID NO 6
<211> LENGTH: 41
<212> TYPE: DNA
<213> ORGANISM: Artificial Sequence
<220> FEATURE:
<223> OTHER INFORMATION: Description of artificial sequence; note = synthetic construct
<220> FEATURE:
<221> NAME/KEY: misc_feature
<222> LOCATION: (1)..(41)
<223> OTHER INFORMATION: Amplimer cYFDV2452

<400> SEQUENCE: 6
ttttcttttg cggccgctca cgccccaact cctagagaaa c                          41

<210> SEQ ID NO 7
<211> LENGTH: 51
<212> TYPE: DNA
<213> ORGANISM: Artificial Sequence
<220> FEATURE:
<223> OTHER INFORMATION: Description of artificial sequence; note = synthetic construct
<220> FEATURE:
<221> NAME/KEY: misc_feature
<222> LOCATION: (1)..(51)
<223> OTHER INFORMATION: Amplimer SLEDV410
<220> FEATURE:
<221> NAME/KEY: CDS
<222> LOCATION: (25)..(51)

<400> SEQUENCE: 7
cttggtacct ctagagccgc cgcc atg tct aaa aaa aga gga ggg acc aga        51
                           Met Ser Lys Lys Arg Gly Gly Thr Arg
                           1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Met Ser Lys Lys Arg Gly Gly Thr Arg
1               5

<210> SEQ ID NO 9
<211> LENGTH: 38
<212> TYPE: DNA
<213> ORGANISM: Artificial Sequence
<220> FEATURE:
<223> OTHER INFORMATION: Description of artificial sequence; note = synthetic construct
<220> FEATURE:
<221> NAME/KEY: misc_feature
<222> LOCATION: (1)..(38)
<223> OTHER INFORMATION: Amplimer cSLEDV2449

<400> SEQUENCE: 9

-continued

```
ttttcttttg cggccgctta ggcttgcacg ctggttgc                          38


<210> SEQ ID NO 10
<211> LENGTH: 7500
<212> TYPE: DNA
<213> ORGANISM: Artificial Sequence
<220> FEATURE:
<223> OTHER INFORMATION: Description of artificial sequence; note =
      synthetic construct
<220> FEATURE:
<221> NAME/KEY: misc_feature
<222> LOCATION: (1)..(7500)
<223> OTHER INFORMATION: pCDJE 2-7
<220> FEATURE:
<221> NAME/KEY: CDS
<222> LOCATION: (916)..(3009)

<400> SEQUENCE: 10

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttggtacc    900

gagctcgccg ccgcc atg ggc aga aag caa aac aaa aga gga gga aat gaa     951
                 Met Gly Arg Lys Gln Asn Lys Arg Gly Gly Asn Glu
                 1               5                   10

ggc tca atc atg tgg ctc gcg agc ttg gca gtt gtc ata gct tgt gcg      999
Gly Ser Ile Met Trp Leu Ala Ser Leu Ala Val Val Ile Ala Cys Ala
        15                  20                  25

gga gcc atg aag ttg tcg aat ttc cag ggg aag ctt ttg atg acc atc     1047
Gly Ala Met Lys Leu Ser Asn Phe Gln Gly Lys Leu Leu Met Thr Ile
    30                  35                  40

aac aac acg gac att gca gac gtt atc gtg att ccc acc tca aaa gga     1095
Asn Asn Thr Asp Ile Ala Asp Val Ile Val Ile Pro Thr Ser Lys Gly
45                  50                  55                  60

gag aac aga tgc tgg gtc cgg gca atc gac gtc ggc tac atg tgt gag     1143
Glu Asn Arg Cys Trp Val Arg Ala Ile Asp Val Gly Tyr Met Cys Glu
                65                  70                  75

gac act atc acg tac gaa tgt cct aag ctt acc atg ggc aat gat cca     1191
Asp Thr Ile Thr Tyr Glu Cys Pro Lys Leu Thr Met Gly Asn Asp Pro
            80                  85                  90

gag gat gtg gat tgc tgg tgt gac aac caa gaa gtc tac gtc caa tat     1239
Glu Asp Val Asp Cys Trp Cys Asp Asn Gln Glu Val Tyr Val Gln Tyr
        95                  100                 105

gga cgg tgc acg cgg acc agg cat tcc aag cga agc agg aga tcc gtg     1287
```

-continued

```
Gly Arg Cys Thr Arg Thr Arg His Ser Lys Arg Ser Arg Arg Ser Val
    110                 115                 120

tcg gtc caa aca cat ggg gag agt tca cta gtg aat aaa aaa gag gct      1335
Ser Val Gln Thr His Gly Glu Ser Ser Leu Val Asn Lys Lys Glu Ala
125                 130                 135                 140

tgg ctg gat tca acg aaa gcc aca cga tat ctc atg aaa act gag aac      1383
Trp Leu Asp Ser Thr Lys Ala Thr Arg Tyr Leu Met Lys Thr Glu Asn
                145                 150                 155

tgg atc ata agg aat cct ggc tat gct ttc ctg gcg gcg gta ctt ggc      1431
Trp Ile Ile Arg Asn Pro Gly Tyr Ala Phe Leu Ala Ala Val Leu Gly
            160                 165                 170

tgg atg ctt ggc agt aac aac ggt caa cgc gtg gta ttt acc atc ctc      1479
Trp Met Leu Gly Ser Asn Asn Gly Gln Arg Val Val Phe Thr Ile Leu
        175                 180                 185

ctg ctg ttg gtc gct ccg gct tac agt ttt aat tgt ctg gga atg ggc      1527
Leu Leu Leu Val Ala Pro Ala Tyr Ser Phe Asn Cys Leu Gly Met Gly
    190                 195                 200

aat cgt gac ttc ata gaa gga gcc agt gga gcc act tgg gtg gac ttg      1575
Asn Arg Asp Phe Ile Glu Gly Ala Ser Gly Ala Thr Trp Val Asp Leu
205                 210                 215                 220

gtg ctg gaa gga gat agc tgc ttg aca atc atg gca aac gac aaa cca      1623
Val Leu Glu Gly Asp Ser Cys Leu Thr Ile Met Ala Asn Asp Lys Pro
                225                 230                 235

aca ttg gac gtc cgc atg att aac atc gaa gct agc caa ctt gct gag      1671
Thr Leu Asp Val Arg Met Ile Asn Ile Glu Ala Ser Gln Leu Ala Glu
            240                 245                 250

gtc aga agt tac tgc tat cat gct tca gtc act gac atc tcg acg gtg      1719
Val Arg Ser Tyr Cys Tyr His Ala Ser Val Thr Asp Ile Ser Thr Val
        255                 260                 265

gct cgg tgc ccc acg act gga gaa gcc cac aac gag aag cga gct gat      1767
Ala Arg Cys Pro Thr Thr Gly Glu Ala His Asn Glu Lys Arg Ala Asp
    270                 275                 280

agt agc tat gtg tgc aaa caa ggc ttc act gac cgt ggg tgg ggc aac      1815
Ser Ser Tyr Val Cys Lys Gln Gly Phe Thr Asp Arg Gly Trp Gly Asn
285                 290                 295                 300

gga tgt gga ctt ttc ggg aag gga agc att gac aca tgt gca aaa ttc      1863
Gly Cys Gly Leu Phe Gly Lys Gly Ser Ile Asp Thr Cys Ala Lys Phe
                305                 310                 315

tcc tgc acc agt aaa gcg att ggg aga aca atc cag cca gaa aac atc      1911
Ser Cys Thr Ser Lys Ala Ile Gly Arg Thr Ile Gln Pro Glu Asn Ile
            320                 325                 330

aaa tac gaa gtt ggc att ttt gtg cat gga acc acc act tcg gaa aac      1959
Lys Tyr Glu Val Gly Ile Phe Val His Gly Thr Thr Thr Ser Glu Asn
        335                 340                 345

cat ggg aat tat tca gcg caa gtt ggg gcg tcc cag gcg gca aag ttt      2007
His Gly Asn Tyr Ser Ala Gln Val Gly Ala Ser Gln Ala Ala Lys Phe
    350                 355                 360

aca gta aca ccc aat gct cct tcg ata acc ctc aaa ctt ggt gac tac      2055
Thr Val Thr Pro Asn Ala Pro Ser Ile Thr Leu Lys Leu Gly Asp Tyr
365                 370                 375                 380

gga gaa gtc aca ctg gac tgt gag cca agg agt gga ctg aac act gaa      2103
Gly Glu Val Thr Leu Asp Cys Glu Pro Arg Ser Gly Leu Asn Thr Glu
                385                 390                 395

gcg ttt tac gtc atg acc gtg ggg tca aag tca ttt ctg gtc cat agg      2151
Ala Phe Tyr Val Met Thr Val Gly Ser Lys Ser Phe Leu Val His Arg
            400                 405                 410

gag tgg ttt cat gac ctc gct ctc ccc tgg acg tcc cct tcg agc aca      2199
Glu Trp Phe His Asp Leu Ala Leu Pro Trp Thr Ser Pro Ser Ser Thr
        415                 420                 425
```

-continued

```
gcg tgg aga aac aga gaa ctc ctc atg gaa ttt gaa gag gcg cac gcc      2247
Ala Trp Arg Asn Arg Glu Leu Leu Met Glu Phe Glu Glu Ala His Ala
    430                 435                 440

aca aaa cag tcc gtt gtt gct ctt ggg tca cag gaa gga ggc ctc cat      2295
Thr Lys Gln Ser Val Val Ala Leu Gly Ser Gln Glu Gly Gly Leu His
445                 450                 455                 460

cag gcg ttg gca gga gcc atc gtg gtg gag tac tca agc tca gtg aag      2343
Gln Ala Leu Ala Gly Ala Ile Val Val Glu Tyr Ser Ser Ser Val Lys
                465                 470                 475

tta aca tca ggc cac ctg aaa tgt agg ctg aaa atg gac aaa ctg gct      2391
Leu Thr Ser Gly His Leu Lys Cys Arg Leu Lys Met Asp Lys Leu Ala
            480                 485                 490

ctg aaa ggc aca acc tat ggc atg tgt aca gaa aaa ttc tcg ttc gcg      2439
Leu Lys Gly Thr Thr Tyr Gly Met Cys Thr Glu Lys Phe Ser Phe Ala
        495                 500                 505

aaa aat ccg gcg gac act ggt cac gga aca gtt gtc att gaa ctc tcc      2487
Lys Asn Pro Ala Asp Thr Gly His Gly Thr Val Val Ile Glu Leu Ser
    510                 515                 520

tac tct ggg agt gat ggc ccc tgc aaa att ccg att gct tcc gtt gcg      2535
Tyr Ser Gly Ser Asp Gly Pro Cys Lys Ile Pro Ile Ala Ser Val Ala
525                 530                 535                 540

agc ctc aat gac atg acc ccc gtt ggg cgg ctg gtg aca gtg aac ccc      2583
Ser Leu Asn Asp Met Thr Pro Val Gly Arg Leu Val Thr Val Asn Pro
                545                 550                 555

ttc gtc gcg act tcc agt gcc agc tca aag gtg ctg gtc gag atg gaa      2631
Phe Val Ala Thr Ser Ser Ala Ser Ser Lys Val Leu Val Glu Met Glu
            560                 565                 570

ccc ccc ttc gga gac tcc tac atc gta gtt gga agg gga gac aag cag      2679
Pro Pro Phe Gly Asp Ser Tyr Ile Val Val Gly Arg Gly Asp Lys Gln
        575                 580                 585

atc aac cac cat tgg cac aaa gct gga agc acg ctg ggc aag gcc ttt      2727
Ile Asn His His Trp His Lys Ala Gly Ser Thr Leu Gly Lys Ala Phe
    590                 595                 600

tca aca act ttg aag gga gct caa aga ctg gca gcg ttg ggc gac aca      2775
Ser Thr Thr Leu Lys Gly Ala Gln Arg Leu Ala Ala Leu Gly Asp Thr
605                 610                 615                 620

gcc tgg gac ttt ggc tct att gga ggg gtc ttc aac tcc ata gga aaa      2823
Ala Trp Asp Phe Gly Ser Ile Gly Gly Val Phe Asn Ser Ile Gly Lys
                625                 630                 635

gcc gtt cac caa gtg ttt ggt ggt gcc ttc aga aca ctc ttt ggg gga      2871
Ala Val His Gln Val Phe Gly Gly Ala Phe Arg Thr Leu Phe Gly Gly
            640                 645                 650

atg tct tgg atc aca caa ggg cta atg ggt gcc cta ctg ctc tgg atg      2919
Met Ser Trp Ile Thr Gln Gly Leu Met Gly Ala Leu Leu Leu Trp Met
        655                 660                 665

ggc gtc aac gca cga gac cga tca att gct ttg gcc ttc tta gcc aca      2967
Gly Val Asn Ala Arg Asp Arg Ser Ile Ala Leu Ala Phe Leu Ala Thr
    670                 675                 680

ggg ggt gtg ctc gtg ttc tta gcg acc aat gtg cat gct taa              3009
Gly Gly Val Leu Val Phe Leu Ala Thr Asn Val His Ala
685                 690                 695

ttagtttgag cggccgctcg agcatgcatc tagagggccc tattctatag tgtcacctaa    3069

atgctagagc tcgctgatca gcctcgactg tgccttctag ttgccagcca tctgttgttt    3129

gcccctcccc cgtgccttcc ttgaccctgg aaggtgccac tcccactgtc ctttcctaat    3189

aaaatgagga aattgcatcg cattgtctga gtaggtgtca ttctattctg gggggtgggg    3249

tggggcagga cagcaagggg gaggattggg aagacaatag caggcatgct ggggatgcgg    3309

tgggctctat ggcttctgag gcggaaagaa ccagctgggg ctctaggggg tatccccacg    3369
```

-continued

```
cgccctgtag cggcgcatta agcgcggcgg gtgtggtggt tacgcgcagc gtgaccgcta   3429
cacttgccag cgccctagcg cccgctcctt tcgctttctt cccttccttt ctcgccacgt   3489
tcgccggctt tccccgtcaa gctctaaatc ggggcatccc tttagggttc cgatttagtg   3549
ctttacggca cctcgacccc aaaaaacttg attagggtga tggttcacgt agtgggccat   3609
cgccctgata gacggttttt cgccctttga cgttggagtc cacgttcttt aatagtggac   3669
tcttgttcca aactggaaca acactcaacc ctatctcggt ctattctttt gatttataag   3729
ggattttggg gatttcggcc tattggttaa aaaatgagct gatttaacaa aaatttaacg   3789
cgaattaatt ctgtggaatg tgtgtcagtt agggtgtgga aagtccccag gctccccagg   3849
caggcagaag tatgcaaagc atgcatctca attagtcagc aaccaggtgt ggaaagtccc   3909
caggctcccc agcaggcaga agtatgcaaa gcatgcatct caattagtca gcaaccatag   3969
tcccgcccct aactccgccc atcccgcccc taactccgcc cagttccgcc cattctccgc   4029
cccatggctg actaattttt tttatttatg cagaggccga ggccgcctct gcctctgagc   4089
tattccagaa gtagtgagga ggcttttttg gaggcctagg cttttgcaaa aagctcccgg   4149
gagcttgtat atccattttc ggatctgatc aagagacagg atgaggatcg tttcgcatga   4209
ttgaacaaga tggattgcac gcaggttctc cggccgcttg ggtggagagg ctattcggct   4269
atgactgggc acaacagaca atcggctgct ctgatgccgc cgtgttccgg ctgtcagcgc   4329
aggggcgccc ggttcttttt gtcaagaccg acctgtccgg tgccctgaat gaactgcagg   4389
acgaggcagc gcggctatcg tggctggcca cgacgggcgt tccttgcgca gctgtgctcg   4449
acgttgtcac tgaagcggga agggactggc tgctattggg cgaagtgccg gggcaggatc   4509
tcctgtcatc tcaccttgct cctgccgaga aagtatccat catggctgat gcaatgcggc   4569
ggctgcatac gcttgatccg gctacctgcc cattcgacca ccaagcgaaa catcgcatcg   4629
agcgagcacg tactcggatg gaagccggtc ttgtcgatca ggatgatctg gacgaagagc   4689
atcaggggct cgcgccagcc gaactgttcg ccaggctcaa ggcgcgcatg cccgacggcg   4749
aggatctcgt cgtgacccat ggcgatgcct gcttgccgaa tatcatggtg gaaaatggcc   4809
gcttttctgg attcatcgac tgtggccggc tgggtgtggc ggaccgctat caggacatag   4869
cgttggctac ccgtgatatt gctgaagagc ttggcggcga atgggctgac cgcttcctcg   4929
tgctttacgg tatcgccgct cccgattcgc agcgcatcgc cttctatcgc cttcttgacg   4989
agttcttctg agcgggactc tggggttcga aatgaccgac caagcgacgc ccaacctgcc   5049
atcacgagat ttcgattcca ccgccgcctt ctatgaaagg ttgggcttcg gaatcgtttt   5109
ccgggacgcc ggctggatga tcctccagcg cggggatctc atgctggagt tcttcgccca   5169
ccccaacttg tttattgcag cttataatgg ttacaaataa agcaatagca tcacaaattt   5229
cacaaataaa gcattttttt cactgcattc tagttgtggt ttgtccaaac tcatcaatgt   5289
atcttatcat gtctgtatac cgtcgacctc tagctagagc ttggcgtaat catggtcata   5349
gctgtttcct gtgtgaaatt gttatccgct cacaattcca cacaacatac gagccggaag   5409
cataaagtgt aaagcctggg gtgcctaatg agtgagctaa ctcacattaa ttgcgttgcg   5469
ctcactgccc gctttccagt cgggaaacct gtcgtgccag ctgcattaat gaatcggcca   5529
acgcgcgggg agaggcggtt tgcgtattgg gcgctcttcc gcttcctcgc tcactgactc   5589
gctgcgctcg gtcgttcggc tgcggcgagc ggtatcagct cactcaaagg cggtaatacg   5649
gttatccaca gaatcagggg ataacgcagg aaagaacatg tgagcaaaag gccagcaaaa   5709
```

-continued

```
ggccaggaac cgtaaaaagg ccgcgttgct ggcgtttttc cataggctcc gcccccctga   5769

cgagcatcac aaaaatcgac gctcaagtca gaggtggcga aacccgacag gactataaag   5829

ataccaggcg tttccccctg gaagctccct cgtgcgctct cctgttccga ccctgccgct   5889

taccggatac ctgtccgcct ttctcccttc gggaagcgtg gcgctttctc aatgctcacg   5949

ctgtaggtat ctcagttcgg tgtaggtcgt tcgctccaag ctgggctgtg tgcacgaacc   6009

ccccgttcag cccgaccgct gcgccttatc cggtaactat cgtcttgagt ccaacccggt   6069

aagacacgac ttatcgccac tggcagcagc cactggtaac aggattagca gagcgaggta   6129

tgtaggcggt gctacagagt tcttgaagtg gtggcctaac tacggctaca ctagaaggac   6189

agtatttggt atctgcgctc tgctgaagcc agttaccttc ggaaaaagag ttggtagctc   6249

ttgatccggc aaacaaacca ccgctggtag cggtggtttt tttgtttgca agcagcagat   6309

tacgcgcaga aaaaaaggat ctcaagaaga tcctttgatc ttttctacgg ggtctgacgc   6369

tcagtggaac gaaaactcac gttaagggat tttggtcatg agattatcaa aaaggatctt   6429

cacctagatc cttttaaatt aaaaatgaag ttttaaatca atctaaagta tatatgagta   6489

aacttggtct gacagttacc aatgcttaat cagtgaggca cctatctcag cgatctgtct   6549

atttcgttca tccatagttg cctgactccc cgtcgtgtag ataactacga tacgggaggg   6609

cttaccatct ggccccagtg ctgcaatgat accgcgagac ccacgctcac cggctccaga   6669

tttatcagca ataaaccagc cagccggaag ggccgagcgc agaagtggtc ctgcaacttt   6729

atccgcctcc atccagtcta ttaattgttg ccgggaagct agagtaagta gttcgccagt   6789

taatagtttg cgcaacgttg ttgccattgc tacaggcatc gtggtgtcac gctcgtcgtt   6849

tggtatggct tcattcagct ccggttccca acgatcaagg cgagttacat gatcccccat   6909

gttgtgcaaa aaagcggtta gctccttcgg tcctccgatc gttgtcagaa gtaagttggc   6969

cgcagtgtta tcactcatgg ttatggcagc actgcataat tctcttactg tcatgccatc   7029

cgtaagatgc ttttctgtga ctggtgagta ctcaaccaag tcattctgag aatagtgtat   7089

gcggcgaccg agttgctctt gcccggcgtc aatacgggat aataccgcgc cacatagcag   7149

aactttaaaa gtgctcatca ttggaaaacg ttcttcgggg cgaaaactct caaggatctt   7209

accgctgttg agatccagtt cgatgtaacc cactcgtgca cccaactgat cttcagcatc   7269

ttttactttc accagcgttt ctgggtgagc aaaaacagga aggcaaaatg ccgcaaaaaa   7329

gggaataagg gcgacacgga aatgttgaat actcatactc ttcctttttc aatattattg   7389

aagcatttat cagggttatt gtctcatgag cggatacata tttgaatgta tttagaaaaa   7449

taaacaaata ggggttccgc gcacatttcc ccgaaaagtg ccacctgacg t            7500
```

```
<210> SEQ ID NO 11
<211> LENGTH: 697
<212> TYPE: PRT
<213> ORGANISM: Artificial Sequence
<220> FEATURE:
<223> OTHER INFORMATION: Synthetic Construct

<400> SEQUENCE: 11

Met Gly Arg Lys Gln Asn Lys Arg Gly Gly Asn Glu Gly Ser Ile Met
1               5                   10                  15

Trp Leu Ala Ser Leu Ala Val Val Ile Ala Cys Ala Gly Ala Met Lys
            20                  25                  30

Leu Ser Asn Phe Gln Gly Lys Leu Leu Met Thr Ile Asn Asn Thr Asp
        35                  40                  45
```

-continued

```
Ile Ala Asp Val Ile Val Ile Pro Thr Ser Lys Gly Glu Asn Arg Cys
    50                  55                  60

Trp Val Arg Ala Ile Asp Val Gly Tyr Met Cys Glu Asp Thr Ile Thr
65                  70                  75                  80

Tyr Glu Cys Pro Lys Leu Thr Met Gly Asn Asp Pro Glu Asp Val Asp
                85                  90                  95

Cys Trp Cys Asp Asn Gln Glu Val Tyr Val Gln Tyr Gly Arg Cys Thr
            100                 105                 110

Arg Thr Arg His Ser Lys Arg Ser Arg Arg Ser Val Ser Val Gln Thr
        115                 120                 125

His Gly Glu Ser Ser Leu Val Asn Lys Lys Glu Ala Trp Leu Asp Ser
    130                 135                 140

Thr Lys Ala Thr Arg Tyr Leu Met Lys Thr Glu Asn Trp Ile Ile Arg
145                 150                 155                 160

Asn Pro Gly Tyr Ala Phe Leu Ala Ala Val Leu Gly Trp Met Leu Gly
                165                 170                 175

Ser Asn Asn Gly Gln Arg Val Val Phe Thr Ile Leu Leu Leu Leu Val
            180                 185                 190

Ala Pro Ala Tyr Ser Phe Asn Cys Leu Gly Met Gly Asn Arg Asp Phe
        195                 200                 205

Ile Glu Gly Ala Ser Gly Ala Thr Trp Val Asp Leu Val Leu Glu Gly
    210                 215                 220

Asp Ser Cys Leu Thr Ile Met Ala Asn Asp Lys Pro Thr Leu Asp Val
225                 230                 235                 240

Arg Met Ile Asn Ile Glu Ala Ser Gln Leu Ala Glu Val Arg Ser Tyr
                245                 250                 255

Cys Tyr His Ala Ser Val Thr Asp Ile Ser Thr Val Ala Arg Cys Pro
            260                 265                 270

Thr Thr Gly Glu Ala His Asn Glu Lys Arg Ala Asp Ser Ser Tyr Val
        275                 280                 285

Cys Lys Gln Gly Phe Thr Asp Arg Gly Trp Gly Asn Gly Cys Gly Leu
    290                 295                 300

Phe Gly Lys Gly Ser Ile Asp Thr Cys Ala Lys Phe Ser Cys Thr Ser
305                 310                 315                 320

Lys Ala Ile Gly Arg Thr Ile Gln Pro Glu Asn Ile Lys Tyr Glu Val
                325                 330                 335

Gly Ile Phe Val His Gly Thr Thr Thr Ser Glu Asn His Gly Asn Tyr
            340                 345                 350

Ser Ala Gln Val Gly Ala Ser Gln Ala Ala Lys Phe Thr Val Thr Pro
        355                 360                 365

Asn Ala Pro Ser Ile Thr Leu Lys Leu Gly Asp Tyr Gly Glu Val Thr
    370                 375                 380

Leu Asp Cys Glu Pro Arg Ser Gly Leu Asn Thr Glu Ala Phe Tyr Val
385                 390                 395                 400

Met Thr Val Gly Ser Lys Ser Phe Leu Val His Arg Glu Trp Phe His
                405                 410                 415

Asp Leu Ala Leu Pro Trp Thr Ser Pro Ser Ser Thr Ala Trp Arg Asn
            420                 425                 430

Arg Glu Leu Leu Met Glu Phe Glu Glu Ala His Ala Thr Lys Gln Ser
        435                 440                 445

Val Val Ala Leu Gly Ser Gln Glu Gly Gly Leu His Gln Ala Leu Ala
    450                 455                 460

Gly Ala Ile Val Val Glu Tyr Ser Ser Ser Val Lys Leu Thr Ser Gly
```

-continued

```
465                 470                 475                 480

His Leu Lys Cys Arg Leu Lys Met Asp Lys Leu Ala Leu Lys Gly Thr
                485                 490                 495

Thr Tyr Gly Met Cys Thr Glu Lys Phe Ser Phe Ala Lys Asn Pro Ala
            500                 505                 510

Asp Thr Gly His Gly Thr Val Val Ile Glu Leu Ser Tyr Ser Gly Ser
        515                 520                 525

Asp Gly Pro Cys Lys Ile Pro Ile Ala Ser Val Ala Ser Leu Asn Asp
    530                 535                 540

Met Thr Pro Val Gly Arg Leu Val Thr Val Asn Pro Phe Val Ala Thr
545                 550                 555                 560

Ser Ser Ala Ser Ser Lys Val Leu Val Glu Met Glu Pro Pro Phe Gly
                565                 570                 575

Asp Ser Tyr Ile Val Val Gly Arg Gly Asp Lys Gln Ile Asn His His
            580                 585                 590

Trp His Lys Ala Gly Ser Thr Leu Gly Lys Ala Phe Ser Thr Thr Leu
        595                 600                 605

Lys Gly Ala Gln Arg Leu Ala Ala Leu Gly Asp Thr Ala Trp Asp Phe
    610                 615                 620

Gly Ser Ile Gly Gly Val Phe Asn Ser Ile Gly Lys Ala Val His Gln
625                 630                 635                 640

Val Phe Gly Gly Ala Phe Arg Thr Leu Phe Gly Gly Met Ser Trp Ile
                645                 650                 655

Thr Gln Gly Leu Met Gly Ala Leu Leu Leu Trp Met Gly Val Asn Ala
            660                 665                 670

Arg Asp Arg Ser Ile Ala Leu Ala Phe Leu Ala Thr Gly Gly Val Leu
        675                 680                 685

Val Phe Leu Ala Thr Asn Val His Ala
    690                 695


<210> SEQ ID NO 12
<211> LENGTH: 46
<212> TYPE: DNA
<213> ORGANISM: Artificial Sequence
<220> FEATURE:
<223> OTHER INFORMATION: Description of artificial sequence; note =
      synthetic construct
<220> FEATURE:
<221> NAME/KEY: misc_feature
<222> LOCATION: (1)..(46)
<223> OTHER INFORMATION: WN 466

<400> SEQUENCE: 12

cttggtaccc gtctcggcgc cgtgaccctc tcgaacttcc agggca                    46


<210> SEQ ID NO 13
<211> LENGTH: 43
<212> TYPE: DNA
<213> ORGANISM: Artificial Sequence
<220> FEATURE:
<223> OTHER INFORMATION: Description of artificial sequence; note =
      synthetic construct
<220> FEATURE:
<221> NAME/KEY: misc_feature
<222> LOCATION: (1)..(43)
<223> OTHER INFORMATION: CWN2444

<400> SEQUENCE: 13

agaggcactt gcacgtgcgg acttccgccg gcgaaaaaga aaa                       43
```

<210> SEQ ID NO 14
<211> LENGTH: 24
<212> TYPE: PRT
<213> ORGANISM: Artificial Sequence
<220> FEATURE:
<223> OTHER INFORMATION: Description of artificial sequence; note = synthetic construct
<220> FEATURE:
<221> NAME/KEY: MISC_FEATURE
<223> OTHER INFORMATION: JE Signal

<400> SEQUENCE: 14

```
Met Gly Lys Arg Ser Ala Gly Ser Ile Met Trp Leu Ala Ser Leu Ala
 1               5                  10                  15
Val Val Ile Ala Cys Ala Gly Ala
            20
```

<210> SEQ ID NO 15
<211> LENGTH: 5308
<212> TYPE: DNA
<213> ORGANISM: Artificial Sequence
<220> FEATURE:
<223> OTHER INFORMATION: Description of artificial sequence; note = synthetic construct
<220> FEATURE:
<221> NAME/KEY: misc_feature
<222> LOCATION: (1)..(5308)
<223> OTHER INFORMATION: pCBWN
<220> FEATURE:
<221> NAME/KEY: CDS
<222> LOCATION: (911)..(2986)

<400> SEQUENCE: 15

```
gacggatcgg gagatctccc gatccctat ggtgcactct cagtacaatc tgctctgatg      60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttgg cagtacatca atgggcgtgg atagcggttt    660

gactcacggg gatttccaag tctccacccc attgacgtca atgggagttt gttttggcac    720

caaaatcaac gggactttcc aaaatgtcgt aacaactccg ccccattgac gcaaatgggc    780

ggtaggcgtg tacggtggga ggtctatata agcagagctc tctggctaac tagagaaccc    840

actgcttact ggcttatcga aattaatacg actcactata gggagaccca agcttggtac    900

cgccgccgcc atg ggc aag agg tcc gcc ggc tca atc atg tgg ctc gcg       949
            Met Gly Lys Arg Ser Ala Gly Ser Ile Met Trp Leu Ala
             1               5                  10

agc ttg gca gtt gtc ata gct tgt gca ggc gcc gtg acc ctc tcg aac       997
Ser Leu Ala Val Val Ile Ala Cys Ala Gly Ala Val Thr Leu Ser Asn
     15                  20                  25

ttc cag ggc aag gtg atg atg acg gta aat gct act gac gtc aca gat     1045
Phe Gln Gly Lys Val Met Met Thr Val Asn Ala Thr Asp Val Thr Asp
 30                  35                  40                  45
```

-continued

```
gtc atc acg att cca aca gct gct gga aag aac cta tgc att gtc aga      1093
Val Ile Thr Ile Pro Thr Ala Ala Gly Lys Asn Leu Cys Ile Val Arg
                50                  55                  60

gca atg gat gtg gga tac atg tgc gat gat act atc act tat gaa tgc      1141
Ala Met Asp Val Gly Tyr Met Cys Asp Asp Thr Ile Thr Tyr Glu Cys
            65                  70                  75

cca gtg ctg tcg gct ggt aat gat cca gaa gac atc gac tgt tgg tgc      1189
Pro Val Leu Ser Ala Gly Asn Asp Pro Glu Asp Ile Asp Cys Trp Cys
        80                  85                  90

aca aag tca gca gtc tac gtc agg tat gga aga tgc acc aag aca cgc      1237
Thr Lys Ser Ala Val Tyr Val Arg Tyr Gly Arg Cys Thr Lys Thr Arg
    95                  100                 105

cac tca aga cgc agt cgg agg tca ctg aca gtg cag aca cac gga gaa      1285
His Ser Arg Arg Ser Arg Arg Ser Leu Thr Val Gln Thr His Gly Glu
110                 115                 120                 125

agc act cta gcg aac aag aag ggg gct tgg atg gac agc acc aag gcc      1333
Ser Thr Leu Ala Asn Lys Lys Gly Ala Trp Met Asp Ser Thr Lys Ala
                130                 135                 140

aca agg tat ttg gta aaa aca gaa tca tgg atc ttg agg aac cct gga      1381
Thr Arg Tyr Leu Val Lys Thr Glu Ser Trp Ile Leu Arg Asn Pro Gly
            145                 150                 155

tat gcc ctg gtg gca gcc gtc att ggt tgg atg ctt ggg agc aac acc      1429
Tyr Ala Leu Val Ala Ala Val Ile Gly Trp Met Leu Gly Ser Asn Thr
        160                 165                 170

atg cag aga gtt gtg ttt gtc gtg cta ttg ctt ttg gtg gcc cca gct      1477
Met Gln Arg Val Val Phe Val Val Leu Leu Leu Leu Val Ala Pro Ala
    175                 180                 185

tac agc ttc aac tgc ctt gga atg agc aac aga gac ttc ttg gaa gga      1525
Tyr Ser Phe Asn Cys Leu Gly Met Ser Asn Arg Asp Phe Leu Glu Gly
190                 195                 200                 205

gtg tct gga gca aca tgg gtg gat ttg gtt ctc gaa ggc gac agc tgc      1573
Val Ser Gly Ala Thr Trp Val Asp Leu Val Leu Glu Gly Asp Ser Cys
                210                 215                 220

gtg act atc atg tct aag gac aag cct acc atc gat gtg aag atg atg      1621
Val Thr Ile Met Ser Lys Asp Lys Pro Thr Ile Asp Val Lys Met Met
            225                 230                 235

aat atg gag gcg gcc aac ctg gca gag gtc cgc agt tat tgc tat ttg      1669
Asn Met Glu Ala Ala Asn Leu Ala Glu Val Arg Ser Tyr Cys Tyr Leu
        240                 245                 250

gct acc gtc agc gat ctc tcc acc aaa gct gcg tgc ccg acc atg gga      1717
Ala Thr Val Ser Asp Leu Ser Thr Lys Ala Ala Cys Pro Thr Met Gly
    255                 260                 265

gaa gct cac aat gac aaa cgt gct gac cca gct ttt gtg tgc aga caa      1765
Glu Ala His Asn Asp Lys Arg Ala Asp Pro Ala Phe Val Cys Arg Gln
270                 275                 280                 285

gga gtg gtg gac agg ggc tgg ggc aac ggc tgc gga cta ttt ggc aaa      1813
Gly Val Val Asp Arg Gly Trp Gly Asn Gly Cys Gly Leu Phe Gly Lys
                290                 295                 300

gga agc att gac aca tgc gcc aaa ttt gcc tgc tct acc aag gca ata      1861
Gly Ser Ile Asp Thr Cys Ala Lys Phe Ala Cys Ser Thr Lys Ala Ile
            305                 310                 315

gga aga acc atc ttg aaa gag aat atc aag tac gaa gtg gcc att ttt      1909
Gly Arg Thr Ile Leu Lys Glu Asn Ile Lys Tyr Glu Val Ala Ile Phe
        320                 325                 330

gtc cat gga cca act act gtg gag tcg cac gga aac tac tcc aca cag      1957
Val His Gly Pro Thr Thr Val Glu Ser His Gly Asn Tyr Ser Thr Gln
    335                 340                 345

gtt gga gcc act cag gca ggg aga ttc agc atc act cct gcg gcg cct      2005
Val Gly Ala Thr Gln Ala Gly Arg Phe Ser Ile Thr Pro Ala Ala Pro
350                 355                 360                 365
```

-continued

```
tca tac aca cta aag ctt gga gaa tat gga gag gtg aca gtg gac tgt      2053
Ser Tyr Thr Leu Lys Leu Gly Glu Tyr Gly Glu Val Thr Val Asp Cys
                370                 375                 380

gaa cca cgg tca ggg att gac acc aat gca tac tac gtg atg act gtt      2101
Glu Pro Arg Ser Gly Ile Asp Thr Asn Ala Tyr Tyr Val Met Thr Val
            385                 390                 395

gga aca aag acg ttc ttg gtc cat cgt gag tgg ttc atg gac ctc aac      2149
Gly Thr Lys Thr Phe Leu Val His Arg Glu Trp Phe Met Asp Leu Asn
        400                 405                 410

ctc cct tgg agc agt gct gga agt act gtg tgg agg aac aga gag acg      2197
Leu Pro Trp Ser Ser Ala Gly Ser Thr Val Trp Arg Asn Arg Glu Thr
    415                 420                 425

tta atg gag ttt gag gaa cca cac gcc acg aag cag tct gtg ata gca      2245
Leu Met Glu Phe Glu Glu Pro His Ala Thr Lys Gln Ser Val Ile Ala
430                 435                 440                 445

ttg ggc tca caa gag gga gct ctg cat caa gct ttg gct gga gcc att      2293
Leu Gly Ser Gln Glu Gly Ala Leu His Gln Ala Leu Ala Gly Ala Ile
                450                 455                 460

cct gtg gaa ttt tca agc aac act gtc aag ttg acg tcg ggt cat ttg      2341
Pro Val Glu Phe Ser Ser Asn Thr Val Lys Leu Thr Ser Gly His Leu
            465                 470                 475

aag tgt aga gtg aag atg gaa aaa ttg cag ttg aag gga aca acc tat      2389
Lys Cys Arg Val Lys Met Glu Lys Leu Gln Leu Lys Gly Thr Thr Tyr
        480                 485                 490

ggc gtc tgt tca aag gct ttc aag ttt ctt ggg act ccc gcg gac aca      2437
Gly Val Cys Ser Lys Ala Phe Lys Phe Leu Gly Thr Pro Ala Asp Thr
    495                 500                 505

ggt cac ggc act gtg gtg ttg gaa ttg cag tac act ggc acg gat gga      2485
Gly His Gly Thr Val Val Leu Glu Leu Gln Tyr Thr Gly Thr Asp Gly
510                 515                 520                 525

cct tgc aaa gtt cct atc tcg tca gtg gct tca ttg aac gac cta acg      2533
Pro Cys Lys Val Pro Ile Ser Ser Val Ala Ser Leu Asn Asp Leu Thr
                530                 535                 540

cca gtg ggc aga ttg gtc act gtc aac cct ttt gtt tca gtg gcc acg      2581
Pro Val Gly Arg Leu Val Thr Val Asn Pro Phe Val Ser Val Ala Thr
            545                 550                 555

gcc aac gct aag gtc ctg att gaa ttg gaa cca ccc ttt gga gac tca      2629
Ala Asn Ala Lys Val Leu Ile Glu Leu Glu Pro Pro Phe Gly Asp Ser
        560                 565                 570

tac ata gtg gtg ggc aga gga gaa caa cag atc aat cac cat tgg cac      2677
Tyr Ile Val Val Gly Arg Gly Glu Gln Gln Ile Asn His His Trp His
    575                 580                 585

aag tct gga agc agc att ggc aaa gcc ttt aca acc acc ctc aaa gga      2725
Lys Ser Gly Ser Ser Ile Gly Lys Ala Phe Thr Thr Thr Leu Lys Gly
590                 595                 600                 605

gcg cag aga cta gcc gct cta gga gac aca gct tgg gac ttt gga tca      2773
Ala Gln Arg Leu Ala Ala Leu Gly Asp Thr Ala Trp Asp Phe Gly Ser
                610                 615                 620

gtt gga ggg gtg ttc acc tca gtt ggg aag gct gtc cat caa gtg ttc      2821
Val Gly Gly Val Phe Thr Ser Val Gly Lys Ala Val His Gln Val Phe
            625                 630                 635

gga gga gca ttc cgc tca ctg ttc gga ggc atg tcc tgg ata acg caa      2869
Gly Gly Ala Phe Arg Ser Leu Phe Gly Gly Met Ser Trp Ile Thr Gln
        640                 645                 650

gga ttg ctg ggg gct ctc ctg ttg tgg atg ggc atc aat gct cgt gat      2917
Gly Leu Leu Gly Ala Leu Leu Leu Trp Met Gly Ile Asn Ala Arg Asp
    655                 660                 665

agg tcc ata gct ctc acg ttt ctc gca gtt gga gga gtt ctg ctc ttc      2965
Arg Ser Ile Ala Leu Thr Phe Leu Ala Val Gly Gly Val Leu Leu Phe
```

-continued

```
670                 675                 680                 685

ctc tcc gtg aac gtg cac gcc tgaaggcggc cgctcgagca tgcatctaga        3016
Leu Ser Val Asn Val His Ala
                690

gggccctatt ctatagtgtc acctaaatgc tagagctcgc tgatcagcct cgactgtgcc   3076

ttctagttgc cagccatctg ttgtttgccc ctcccccgtg ccttccttga ccctggaagg   3136

tgccactccc actgtccttt cctaataaaa tgaggaaatt gcatcgcatt gtctgagtag   3196

gtgtcattct attctggggg gtggggtggg gcaggacagc aagggggagg attgggaaga   3256

caatagcagg catgctgggg atgcggtggg ctctatggct tctgaggcgg aaagaaccag   3316

ctgcattaat gaatcggcca acgcgcgggg agaggcggtt tgcgtattgg gcgctcttcc   3376

gcttcctcgc tcactgactc gctgcgctcg gtcgttcggc tgcggcgagc ggtatcagct   3436

cactcaaagg cggtaatacg gttatccaca gaatcagggg ataacgcagg aaagaacatg   3496

tgagcaaaag gccagcaaaa ggccaggaac cgtaaaaagg ccgcgttgct ggcgtttttc   3556

cataggctcc gcccccctga cgagcatcac aaaaatcgac gctcaagtca gaggtggcga   3616

aacccgacag gactataaag ataccaggcg tttccccctg gaagctccct cgtgcgctct   3676

cctgttccga ccctgccgct taccggatac ctgtccgcct ttctcccttc gggaagcgtg   3736

gcgctttctc atagctcacg ctgtaggtat ctcagttcgg tgtaggtcgt tcgctccaag   3796

ctgggctgtg tgcacgaacc ccccgttcag cccgaccgct gcgccttatc cggtaactat   3856

cgtcttgagt ccaacccggt aagacacgac ttatcgccac tggcagcagc cactggtaac   3916

aggattagca gagcgaggta tgtaggcggt gctacagagt tcttgaagtg gtggcctaac   3976

tacggctaca ctagaagaac agtatttggt atctgcgctc tgctgaagcc agttaccttc   4036

ggaaaaagag ttggtagctc ttgatccggc aaacaaacca ccgctggtag cggtggtttt   4096

tttgtttgca agcagcagat tacgcgcaga aaaaaaggat ctcaagaaga tcctttgatc   4156

ttttctacgg ggtctgacgc tcagtggaac gaaaactcac gttaagggat tttggtcatg   4216

agattatcaa aaaggatctt cacctagatc cttttaaatt aaaaatgaag ttttaaatca   4276

atctaaagta tatatgagta aacttggtct gacagttacc aatgcttaat cagtgaggca   4336

cctatctcag cgatctgtct atttcgttca tccatagttg cctgactccc cgtcgtgtag   4396

ataactacga tacgggaggg cttaccatct ggccccagtg ctgcaatgat accgcgagac   4456

ccacgctcac cggctccaga tttatcagca ataaaccagc cagccggaag ggccgagcgc   4516

agaagtggtc ctgcaacttt atccgcctcc atccagtcta ttaattgttg ccgggaagct   4576

agagtaagta gttcgccagt taatagtttg cgcaacgttg ttgccattgc tacaggcatc   4636

gtggtgtcac gctcgtcgtt tggtatggct tcattcagct ccggttccca acgatcaagg   4696

cgagttacat gatcccccat gttgtgcaaa aaagcggtta gctccttcgg tcctccgatc   4756

gttgtcagaa gtaagttggc cgcagtgtta tcactcatgg ttatggcagc actgcataat   4816

tctcttactg tcatgccatc cgtaagatgc ttttctgtga ctggtgagta ctcaaccaag   4876

tcattctgag aatagtgtat gcggcgaccg agttgctctt gcccggcgtc aatacgggat   4936

aataccgcgc cacatagcag aactttaaaa gtgctcatca ttggaaaacg ttcttcgggg   4996

cgaaaactct caaggatctt accgctgttg agatccagtt cgatgtaacc cactcgtgca   5056

cccaactgat cttcagcatc ttttactttc accagcgttt ctgggtgagc aaaaacagga   5116

aggcaaaatg ccgcaaaaaa gggaataagg gcgacacgga aatgttgaat actcatactc   5176

ttcctttttc aatattattg aagcatttat cagggttatt gtctcatgag cggatacata   5236
```

-continued

```
tttgaatgta tttagaaaaa taaacaaata ggggttccgc gcacatttcc ccgaaaagtg   5296

ccacctgacg tc                                                        5308


<210> SEQ ID NO 16
<211> LENGTH: 692
<212> TYPE: PRT
<213> ORGANISM: Artificial Sequence
<220> FEATURE:
<223> OTHER INFORMATION: Synthetic Construct

<400> SEQUENCE: 16

Met Gly Lys Arg Ser Ala Gly Ser Ile Met Trp Leu Ala Ser Leu Ala
1               5                   10                  15

Val Val Ile Ala Cys Ala Gly Ala Val Thr Leu Ser Asn Phe Gln Gly
            20                  25                  30

Lys Val Met Met Thr Val Asn Ala Thr Asp Val Thr Asp Val Ile Thr
        35                  40                  45

Ile Pro Thr Ala Ala Gly Lys Asn Leu Cys Ile Val Arg Ala Met Asp
    50                  55                  60

Val Gly Tyr Met Cys Asp Asp Thr Ile Thr Tyr Glu Cys Pro Val Leu
65                  70                  75                  80

Ser Ala Gly Asn Asp Pro Glu Asp Ile Asp Cys Trp Cys Thr Lys Ser
                85                  90                  95

Ala Val Tyr Val Arg Tyr Gly Arg Cys Thr Lys Thr Arg His Ser Arg
            100                 105                 110

Arg Ser Arg Arg Ser Leu Thr Val Gln Thr His Gly Glu Ser Thr Leu
        115                 120                 125

Ala Asn Lys Lys Gly Ala Trp Met Asp Ser Thr Lys Ala Thr Arg Tyr
    130                 135                 140

Leu Val Lys Thr Glu Ser Trp Ile Leu Arg Asn Pro Gly Tyr Ala Leu
145                 150                 155                 160

Val Ala Ala Val Ile Gly Trp Met Leu Gly Ser Asn Thr Met Gln Arg
                165                 170                 175

Val Val Phe Val Val Leu Leu Leu Leu Val Ala Pro Ala Tyr Ser Phe
            180                 185                 190

Asn Cys Leu Gly Met Ser Asn Arg Asp Phe Leu Glu Gly Val Ser Gly
        195                 200                 205

Ala Thr Trp Val Asp Leu Val Leu Glu Gly Asp Ser Cys Val Thr Ile
    210                 215                 220

Met Ser Lys Asp Lys Pro Thr Ile Asp Val Lys Met Met Asn Met Glu
225                 230                 235                 240

Ala Ala Asn Leu Ala Glu Val Arg Ser Tyr Cys Tyr Leu Ala Thr Val
                245                 250                 255

Ser Asp Leu Ser Thr Lys Ala Ala Cys Pro Thr Met Gly Glu Ala His
            260                 265                 270

Asn Asp Lys Arg Ala Asp Pro Ala Phe Val Cys Arg Gln Gly Val Val
        275                 280                 285

Asp Arg Gly Trp Gly Asn Gly Cys Gly Leu Phe Gly Lys Gly Ser Ile
    290                 295                 300

Asp Thr Cys Ala Lys Phe Ala Cys Ser Thr Lys Ala Ile Gly Arg Thr
305                 310                 315                 320

Ile Leu Lys Glu Asn Ile Lys Tyr Glu Val Ala Ile Phe Val His Gly
                325                 330                 335

Pro Thr Thr Val Glu Ser His Gly Asn Tyr Ser Thr Gln Val Gly Ala
```

-continued

```
            340                 345                 350

Thr Gln Ala Gly Arg Phe Ser Ile Thr Pro Ala Ala Pro Ser Tyr Thr
        355                 360                 365

Leu Lys Leu Gly Glu Tyr Gly Glu Val Thr Val Asp Cys Glu Pro Arg
    370                 375                 380

Ser Gly Ile Asp Thr Asn Ala Tyr Tyr Val Met Thr Val Gly Thr Lys
385                 390                 395                 400

Thr Phe Leu Val His Arg Glu Trp Phe Met Asp Leu Asn Leu Pro Trp
                405                 410                 415

Ser Ser Ala Gly Ser Thr Val Trp Arg Asn Arg Glu Thr Leu Met Glu
            420                 425                 430

Phe Glu Glu Pro His Ala Thr Lys Gln Ser Val Ile Ala Leu Gly Ser
        435                 440                 445

Gln Glu Gly Ala Leu His Gln Ala Leu Ala Gly Ala Ile Pro Val Glu
    450                 455                 460

Phe Ser Ser Asn Thr Val Lys Leu Thr Ser Gly His Leu Lys Cys Arg
465                 470                 475                 480

Val Lys Met Glu Lys Leu Gln Leu Lys Gly Thr Thr Tyr Gly Val Cys
                485                 490                 495

Ser Lys Ala Phe Lys Phe Leu Gly Thr Pro Ala Asp Thr Gly His Gly
            500                 505                 510

Thr Val Val Leu Glu Leu Gln Tyr Thr Gly Thr Asp Gly Pro Cys Lys
        515                 520                 525

Val Pro Ile Ser Ser Val Ala Ser Leu Asn Asp Leu Thr Pro Val Gly
    530                 535                 540

Arg Leu Val Thr Val Asn Pro Phe Val Ser Val Ala Thr Ala Asn Ala
545                 550                 555                 560

Lys Val Leu Ile Glu Leu Glu Pro Pro Phe Gly Asp Ser Tyr Ile Val
                565                 570                 575

Val Gly Arg Gly Glu Gln Gln Ile Asn His His Trp His Lys Ser Gly
            580                 585                 590

Ser Ser Ile Gly Lys Ala Phe Thr Thr Thr Leu Lys Gly Ala Gln Arg
        595                 600                 605

Leu Ala Ala Leu Gly Asp Thr Ala Trp Asp Phe Gly Ser Val Gly Gly
    610                 615                 620

Val Phe Thr Ser Val Gly Lys Ala Val His Gln Val Phe Gly Gly Ala
625                 630                 635                 640

Phe Arg Ser Leu Phe Gly Gly Met Ser Trp Ile Thr Gln Gly Leu Leu
                645                 650                 655

Gly Ala Leu Leu Leu Trp Met Gly Ile Asn Ala Arg Asp Arg Ser Ile
            660                 665                 670

Ala Leu Thr Phe Leu Ala Val Gly Gly Val Leu Leu Phe Leu Ser Val
        675                 680                 685

Asn Val His Ala
    690
```

<210> SEQ ID NO 17
<211> LENGTH: 5334
<212> TYPE: DNA
<213> ORGANISM: Artificial Sequence
<220> FEATURE:
<223> OTHER INFORMATION: Description of artificial sequence; note = synthetic construct
<220> FEATURE:
<221> NAME/KEY: misc_feature
<222> LOCATION: (1)..(5334)

-continued

<223> OTHER INFORMATION: pCBJE 1-14
<220> FEATURE:
<221> NAME/KEY: CDS
<222> LOCATION: (916)..(3006)

<400> SEQUENCE: 17
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttggtacc 900
tctagagccg ccgcc atg ggc aga aag caa aac aaa aga gga gga aat gaa 951
Met Gly Arg Lys Gln Asn Lys Arg Gly Gly Asn Glu
1 5 10 ggc tca atc atg tgg ctc gcg agc ttg gca gtt gtc ata gct tgt gcg 999
Gly Ser Ile Met Trp Leu Ala Ser Leu Ala Val Val Ile Ala Cys Ala
15 20 25 gga gcc atg aag ttg tcg aat ttc cag ggg aag ctt ttg atg acc atc 1047
Gly Ala Met Lys Leu Ser Asn Phe Gln Gly Lys Leu Leu Met Thr Ile
30 35 40 aac aac acg gac att gca gac gtt atc gtg att ccc acc tca aaa gga 1095
Asn Asn Thr Asp Ile Ala Asp Val Ile Val Ile Pro Thr Ser Lys Gly
45 50 55 60 gag aac aga tgc tgg gtc cgg gca atc gac gtc ggc tac atg tgt gag 1143
Glu Asn Arg Cys Trp Val Arg Ala Ile Asp Val Gly Tyr Met Cys Glu
65 70 75 gac act atc acg tac gaa tgt cct aag ctt acc atg ggc aat gat cca 1191
Asp Thr Ile Thr Tyr Glu Cys Pro Lys Leu Thr Met Gly Asn Asp Pro
80 85 90 gag gat gtg gat tgc tgg tgt gac aac caa gaa gtc tac gtc caa tat 1239
Glu Asp Val Asp Cys Trp Cys Asp Asn Gln Glu Val Tyr Val Gln Tyr
95 100 105 gga cgg tgc acg cgg acc agg cat tcc aag cga agc agg aga tcc gtg 1287
Gly Arg Cys Thr Arg Thr Arg His Ser Lys Arg Ser Arg Arg Ser Val
110 115 120 tcg gtc caa aca cat ggg gag agt tca cta gtg aat aaa aaa gag gct 1335
Ser Val Gln Thr His Gly Glu Ser Ser Leu Val Asn Lys Lys Glu Ala
125 130 135 140 tgg ctg gat tca acg aaa gcc aca cga tat ctc atg aaa act gag aac 1383
Trp Leu Asp Ser Thr Lys Ala Thr Arg Tyr Leu Met Lys Thr Glu Asn
145 150 155 tgg atc ata agg aat cct ggc tat gct ttc ctg gcg gcg gta ctt ggc 1431
Trp Ile Ile Arg Asn Pro Gly Tyr Ala Phe Leu Ala Ala Val Leu Gly -continued

```
            160                 165                 170

tgg atg ctt ggc agt aac aac ggt caa cgc gtg gta ttt acc atc ctc     1479
Trp Met Leu Gly Ser Asn Asn Gly Gln Arg Val Val Phe Thr Ile Leu
        175                 180                 185

ctg ctg ttg gtc gct ccg gct tac agt ttt aat tgt ctg gga atg ggc     1527
Leu Leu Leu Val Ala Pro Ala Tyr Ser Phe Asn Cys Leu Gly Met Gly
    190                 195                 200

aat cgt gac ttc ata gaa gga gcc agt gga gcc act tgg gtg gac ttg     1575
Asn Arg Asp Phe Ile Glu Gly Ala Ser Gly Ala Thr Trp Val Asp Leu
205                 210                 215                 220

gtg ctg gaa gga gat agc tgc ttg aca atc atg gca aac gac aaa cca     1623
Val Leu Glu Gly Asp Ser Cys Leu Thr Ile Met Ala Asn Asp Lys Pro
                225                 230                 235

aca ttg gac gtc cgc atg att aac atc gaa gct agc caa ctt gct gag     1671
Thr Leu Asp Val Arg Met Ile Asn Ile Glu Ala Ser Gln Leu Ala Glu
            240                 245                 250

gtc aga agt tac tgc tat cat gct tca gtc act gac atc tcg acg gtg     1719
Val Arg Ser Tyr Cys Tyr His Ala Ser Val Thr Asp Ile Ser Thr Val
        255                 260                 265

gct cgg tgc ccc acg act gga gaa gcc cac aac gag aag cga gct gat     1767
Ala Arg Cys Pro Thr Thr Gly Glu Ala His Asn Glu Lys Arg Ala Asp
    270                 275                 280

agt agc tat gtg tgc aaa caa ggc ttc act gac cgt ggg tgg ggc aac     1815
Ser Ser Tyr Val Cys Lys Gln Gly Phe Thr Asp Arg Gly Trp Gly Asn
285                 290                 295                 300

gga tgt gga ctt ttc ggg aag gga agc att gac aca tgt gca aaa ttc     1863
Gly Cys Gly Leu Phe Gly Lys Gly Ser Ile Asp Thr Cys Ala Lys Phe
                305                 310                 315

tcc tgc acc agt aaa gcg att ggg aga aca atc cag cca gaa aac atc     1911
Ser Cys Thr Ser Lys Ala Ile Gly Arg Thr Ile Gln Pro Glu Asn Ile
            320                 325                 330

aaa tac gaa gtt ggc att ttt gtg cat gga acc acc act tcg gaa aac     1959
Lys Tyr Glu Val Gly Ile Phe Val His Gly Thr Thr Thr Ser Glu Asn
        335                 340                 345

cat ggg aat tat tca gcg caa gtt ggg gcg tcc cag gcg gca aag ttt     2007
His Gly Asn Tyr Ser Ala Gln Val Gly Ala Ser Gln Ala Ala Lys Phe
    350                 355                 360

aca gta aca ccc aat gct cct tcg ata acc ctc aaa ctt ggt gac tac     2055
Thr Val Thr Pro Asn Ala Pro Ser Ile Thr Leu Lys Leu Gly Asp Tyr
365                 370                 375                 380

gga gaa gtc aca ctg gac tgt gag cca agg agt gga ctg aac act gaa     2103
Gly Glu Val Thr Leu Asp Cys Glu Pro Arg Ser Gly Leu Asn Thr Glu
                385                 390                 395

gcg ttt tac gtc atg acc gtg ggg tca aag tca ttt ctg gtc cat agg     2151
Ala Phe Tyr Val Met Thr Val Gly Ser Lys Ser Phe Leu Val His Arg
            400                 405                 410

gag tgg ttt cat gac ctc gct ctc ccc tgg acg tcc cct tcg agc aca     2199
Glu Trp Phe His Asp Leu Ala Leu Pro Trp Thr Ser Pro Ser Ser Thr
        415                 420                 425

gcg tgg aga aac aga gaa ctc ctc atg gaa ttt gaa gag gcg cac gcc     2247
Ala Trp Arg Asn Arg Glu Leu Leu Met Glu Phe Glu Glu Ala His Ala
    430                 435                 440

aca aaa cag tcc gtt gtt gct ctt ggg tca cag gaa gga ggc ctc cat     2295
Thr Lys Gln Ser Val Val Ala Leu Gly Ser Gln Glu Gly Gly Leu His
445                 450                 455                 460

cag gcg ttg gca gga gcc atc gtg gtg gag tac tca agc tca gtg aag     2343
Gln Ala Leu Ala Gly Ala Ile Val Val Glu Tyr Ser Ser Ser Val Lys
                465                 470                 475

tta aca tca ggc cac ctg aaa tgt agg ctg aaa atg gac aaa ctg gct     2391
```

-continued

```
Leu Thr Ser Gly His Leu Lys Cys Arg Leu Lys Met Asp Lys Leu Ala
            480                 485                 490

ctg aaa ggc aca acc tat ggc atg tgt aca gaa aaa ttc tcg ttc gcg     2439
Leu Lys Gly Thr Thr Tyr Gly Met Cys Thr Glu Lys Phe Ser Phe Ala
        495                 500                 505

aaa aat ccg gcg gac act ggt cac gga aca gtt gtc att gaa ctc tcc     2487
Lys Asn Pro Ala Asp Thr Gly His Gly Thr Val Val Ile Glu Leu Ser
    510                 515                 520

tac tct ggg agt gat ggc ccc tgc aaa att ccg att gct tcc gtt gcg     2535
Tyr Ser Gly Ser Asp Gly Pro Cys Lys Ile Pro Ile Ala Ser Val Ala
525                 530                 535                 540

agc ctc aat gac atg acc ccc gtt ggg cgg ctg gtg aca gtg aac ccc     2583
Ser Leu Asn Asp Met Thr Pro Val Gly Arg Leu Val Thr Val Asn Pro
            545                 550                 555

ttc gtc gcg act tcc agt gcc agc tca aag gtg ctg gtc gag atg gaa     2631
Phe Val Ala Thr Ser Ser Ala Ser Ser Lys Val Leu Val Glu Met Glu
            560                 565                 570

ccc ccc ttc gga gac tcc tac atc gta gtt gga agg gga gac aag cag     2679
Pro Pro Phe Gly Asp Ser Tyr Ile Val Val Gly Arg Gly Asp Lys Gln
        575                 580                 585

atc aac cac cat tgg cac aaa gct gga agc acg ctg ggc aag gcc ttt     2727
Ile Asn His His Trp His Lys Ala Gly Ser Thr Leu Gly Lys Ala Phe
    590                 595                 600

tca aca act ttg aag gga gct caa aga ctg gca gcg ttg ggc gac aca     2775
Ser Thr Thr Leu Lys Gly Ala Gln Arg Leu Ala Ala Leu Gly Asp Thr
605                 610                 615                 620

gcc tgg gac ttt ggc tct att gga ggg gtc ttc aac tcc ata gga aaa     2823
Ala Trp Asp Phe Gly Ser Ile Gly Gly Val Phe Asn Ser Ile Gly Lys
            625                 630                 635

gcc gtt cac caa gtg ttt ggt ggt gcc ttc aga aca ctc ttt ggg gga     2871
Ala Val His Gln Val Phe Gly Gly Ala Phe Arg Thr Leu Phe Gly Gly
            640                 645                 650

atg tct tgg atc aca caa ggg cta atg ggt gcc cta ctg ctc tgg atg     2919
Met Ser Trp Ile Thr Gln Gly Leu Met Gly Ala Leu Leu Leu Trp Met
        655                 660                 665

ggc gtc aac gca cga gac cga tca att gct ttg gcc ttc tta gcc aca     2967
Gly Val Asn Ala Arg Asp Arg Ser Ile Ala Leu Ala Phe Leu Ala Thr
    670                 675                 680

ggg ggt gtg ctc gtg ttc tta gcg acc aat gtg cat gct taattagttt      3016
Gly Gly Val Leu Val Phe Leu Ala Thr Asn Val His Ala
685                 690                 695

gagcggccgc tcgagcatgc atctagaggg ccctattcta tagtgtcacc taaatgctag   3076

agctcgctga tcagcctcga ctgtgccttc tagttgccag ccatctgttg tttgcccctc   3136

ccccgtgcct tccttgaccc tggaaggtgc cactcccact gtcctttcct aataaaatga   3196

ggaaattgca tcgcattgtc tgagtaggtg tcattctatt ctggggggtg gggtggggca   3256

ggacagcaag ggggaggatt gggaagacaa tagcaggcat gctggggatg cggtgggctc   3316

tatggcttct gaggcggaaa gaaccagctg cattaatgaa tcggccaacg cgcggggaga   3376

ggcggtttgc gtattgggcg ctcttccgct tcctcgctca ctgactcgct gcgctcggtc   3436

gttcggctgc ggcgagcggt atcagctcac tcaaaggcgg taatacggtt atccacagaa   3496

tcaggggata acgcaggaaa gaacatgtga gcaaaaggcc agcaaaaggc caggaaccgt   3556

aaaaaggccg cgttgctggc gtttttccat aggctccgcc cccctgacga gcatcacaaa   3616

aatcgacgct caagtcagag gtggcgaaac ccgacaggac tataaagata ccaggcgttt   3676

ccccctggaa gctccctcgt gcgctctcct gttccgaccc tgccgcttac cggatacctg   3736
```

-continued

```
tccgcctttc tcccttcggg aagcgtggcg ctttctcata gctcacgctg taggtatctc   3796

agttcggtgt aggtcgttcg ctccaagctg ggctgtgtgc acgaaccccc cgttcagccc   3856

gaccgctgcg ccttatccgg taactatcgt cttgagtcca acccggtaag acacgactta   3916

tcgccactgg cagcagccac tggtaacagg attagcagag cgaggtatgt aggcggtgct   3976

acagagttct tgaagtggtg gcctaactac ggctacacta gaagaacagt atttggtatc   4036

tgcgctctgc tgaagccagt taccttcgga aaaagagttg gtagctcttg atccggcaaa   4096

caaaccaccg ctggtagcgg tggttttttt gtttgcaagc agcagattac gcgcagaaaa   4156

aaaggatctc aagaagatcc tttgatcttt tctacggggt ctgacgctca gtggaacgaa   4216

aactcacgtt aagggatttt ggtcatgaga ttatcaaaaa ggatcttcac ctagatcctt   4276

ttaaattaaa aatgaagttt taaatcaatc taaagtatat atgagtaaac ttggtctgac   4336

agttaccaat gcttaatcag tgaggcacct atctcagcga tctgtctatt tcgttcatcc   4396

atagttgcct gactccccgt cgtgtagata actacgatac gggagggctt accatctggc   4456

cccagtgctg caatgatacc gcgagaccca cgctcaccgg ctccagattt atcagcaata   4516

aaccagccag ccggaagggc cgagcgcaga agtggtcctg caactttatc cgcctccatc   4576

cagtctatta attgttgccg ggaagctaga gtaagtagtt cgccagttaa tagtttgcgc   4636

aacgttgttg ccattgctac aggcatcgtg gtgtcacgct cgtcgtttgg tatggcttca   4696

ttcagctccg gttcccaacg atcaaggcga gttacatgat cccccatgtt gtgcaaaaaa   4756

gcggttagct ccttcggtcc tccgatcgtt gtcagaagta agttggccgc agtgttatca   4816

ctcatggtta tggcagcact gcataattct cttactgtca tgccatccgt aagatgcttt   4876

tctgtgactg gtgagtactc aaccaagtca ttctgagaat agtgtatgcg gcgaccgagt   4936

tgctcttgcc cggcgtcaat acgggataat accgcgccac atagcagaac tttaaaagtg   4996

ctcatcattg gaaaacgttc ttcggggcga aaactctcaa ggatcttacc gctgttgaga   5056

tccagttcga tgtaacccac tcgtgcaccc aactgatctt cagcatcttt tactttcacc   5116

agcgtttctg ggtgagcaaa aacaggaagg caaaatgccg caaaaaaggg aataagggcg   5176

acacggaaat gttgaatact catactcttc ctttttcaat attattgaag catttatcag   5236

ggttattgtc tcatgagcgg atacatattt gaatgtattt agaaaaataa acaaataggg   5296

gttccgcgca catttccccg aaaagtgcca cctgacgt                           5334
```

```
<210> SEQ ID NO 18
<211> LENGTH: 697
<212> TYPE: PRT
<213> ORGANISM: Artificial Sequence
<220> FEATURE:
<223> OTHER INFORMATION: Synthetic Construct

<400> SEQUENCE: 18

Met Gly Arg Lys Gln Asn Lys Arg Gly Gly Asn Glu Gly Ser Ile Met
1               5                   10                  15

Trp Leu Ala Ser Leu Ala Val Val Ile Ala Cys Ala Gly Ala Met Lys
            20                  25                  30

Leu Ser Asn Phe Gln Gly Lys Leu Leu Met Thr Ile Asn Asn Thr Asp
        35                  40                  45

Ile Ala Asp Val Ile Val Ile Pro Thr Ser Lys Gly Glu Asn Arg Cys
    50                  55                  60

Trp Val Arg Ala Ile Asp Val Gly Tyr Met Cys Glu Asp Thr Ile Thr
65                  70                  75                  80
```

-continued

```
Tyr Glu Cys Pro Lys Leu Thr Met Gly Asn Asp Pro Glu Asp Val Asp
                85                  90                  95

Cys Trp Cys Asp Asn Gln Glu Val Tyr Val Gln Tyr Gly Arg Cys Thr
            100                 105                 110

Arg Thr Arg His Ser Lys Arg Ser Arg Arg Ser Val Ser Val Gln Thr
        115                 120                 125

His Gly Glu Ser Ser Leu Val Asn Lys Lys Glu Ala Trp Leu Asp Ser
    130                 135                 140

Thr Lys Ala Thr Arg Tyr Leu Met Lys Thr Glu Asn Trp Ile Ile Arg
145                 150                 155                 160

Asn Pro Gly Tyr Ala Phe Leu Ala Ala Val Leu Gly Trp Met Leu Gly
                165                 170                 175

Ser Asn Asn Gly Gln Arg Val Val Phe Thr Ile Leu Leu Leu Leu Val
            180                 185                 190

Ala Pro Ala Tyr Ser Phe Asn Cys Leu Gly Met Gly Asn Arg Asp Phe
        195                 200                 205

Ile Glu Gly Ala Ser Gly Ala Thr Trp Val Asp Leu Val Leu Glu Gly
    210                 215                 220

Asp Ser Cys Leu Thr Ile Met Ala Asn Asp Lys Pro Thr Leu Asp Val
225                 230                 235                 240

Arg Met Ile Asn Ile Glu Ala Ser Gln Leu Ala Glu Val Arg Ser Tyr
                245                 250                 255

Cys Tyr His Ala Ser Val Thr Asp Ile Ser Thr Val Ala Arg Cys Pro
            260                 265                 270

Thr Thr Gly Glu Ala His Asn Glu Lys Arg Ala Asp Ser Ser Tyr Val
        275                 280                 285

Cys Lys Gln Gly Phe Thr Asp Arg Gly Trp Gly Asn Gly Cys Gly Leu
    290                 295                 300

Phe Gly Lys Gly Ser Ile Asp Thr Cys Ala Lys Phe Ser Cys Thr Ser
305                 310                 315                 320

Lys Ala Ile Gly Arg Thr Ile Gln Pro Glu Asn Ile Lys Tyr Glu Val
                325                 330                 335

Gly Ile Phe Val His Gly Thr Thr Thr Ser Glu Asn His Gly Asn Tyr
            340                 345                 350

Ser Ala Gln Val Gly Ala Ser Gln Ala Ala Lys Phe Thr Val Thr Pro
        355                 360                 365

Asn Ala Pro Ser Ile Thr Leu Lys Leu Gly Asp Tyr Gly Glu Val Thr
    370                 375                 380

Leu Asp Cys Glu Pro Arg Ser Gly Leu Asn Thr Glu Ala Phe Tyr Val
385                 390                 395                 400

Met Thr Val Gly Ser Lys Ser Phe Leu Val His Arg Glu Trp Phe His
                405                 410                 415

Asp Leu Ala Leu Pro Trp Thr Ser Pro Ser Ser Thr Ala Trp Arg Asn
            420                 425                 430

Arg Glu Leu Leu Met Glu Phe Glu Glu Ala His Ala Thr Lys Gln Ser
        435                 440                 445

Val Val Ala Leu Gly Ser Gln Glu Gly Gly Leu His Gln Ala Leu Ala
    450                 455                 460

Gly Ala Ile Val Val Glu Tyr Ser Ser Ser Val Lys Leu Thr Ser Gly
465                 470                 475                 480

His Leu Lys Cys Arg Leu Lys Met Asp Lys Leu Ala Leu Lys Gly Thr
                485                 490                 495

Thr Tyr Gly Met Cys Thr Glu Lys Phe Ser Phe Ala Lys Asn Pro Ala
```

-continued

```
            500                 505                 510

Asp Thr Gly His Gly Thr Val Val Ile Glu Leu Ser Tyr Ser Gly Ser
        515                 520                 525

Asp Gly Pro Cys Lys Ile Pro Ile Ala Ser Val Ala Ser Leu Asn Asp
    530                 535                 540

Met Thr Pro Val Gly Arg Leu Val Thr Val Asn Pro Phe Val Ala Thr
545                 550                 555                 560

Ser Ser Ala Ser Ser Lys Val Leu Val Glu Met Glu Pro Pro Phe Gly
                565                 570                 575

Asp Ser Tyr Ile Val Val Gly Arg Gly Asp Lys Gln Ile Asn His His
            580                 585                 590

Trp His Lys Ala Gly Ser Thr Leu Gly Lys Ala Phe Ser Thr Thr Leu
        595                 600                 605

Lys Gly Ala Gln Arg Leu Ala Ala Leu Gly Asp Thr Ala Trp Asp Phe
    610                 615                 620

Gly Ser Ile Gly Gly Val Phe Asn Ser Ile Gly Lys Ala Val His Gln
625                 630                 635                 640

Val Phe Gly Gly Ala Phe Arg Thr Leu Phe Gly Gly Met Ser Trp Ile
                645                 650                 655

Thr Gln Gly Leu Met Gly Ala Leu Leu Leu Trp Met Gly Val Asn Ala
            660                 665                 670

Arg Asp Arg Ser Ile Ala Leu Ala Phe Leu Ala Thr Gly Gly Val Leu
        675                 680                 685

Val Phe Leu Ala Thr Asn Val His Ala
    690                 695


<210> SEQ ID NO 19
<211> LENGTH: 5283
<212> TYPE: DNA
<213> ORGANISM: Artificial Sequence
<220> FEATURE:
<223> OTHER INFORMATION: Description of artificial sequence; note =
      synthetic construct
<220> FEATURE:
<221> NAME/KEY: CDS
<222> LOCATION: (910)..(2964)

<400> SEQUENCE: 19

gacggatcgg gagatctccc gatcccctat ggtcgactct cagtacaatc tgctctgatg      60

ccgcatagtt aagccagtat ctgctccctg cttgtgtgtt ggaggtcgct gagtagtgcg     120

cgagcaaaat ttaagctaca acaaggcaag gcttgaccga caattgcatg aagaatctgc     180

ttagggttag gcgttttgcg ctgcttcgcg atgtacgggc cagatatacg cgttgacatt     240

gattattgac tagttattaa tagtaatcaa ttacggggtc attagttcat agcccatata     300

tggagttccg cgttacataa cttacggtaa atggcccgcc tggctgaccg cccaacgacc     360

cccgcccatt gacgtcaata atgacgtatg ttcccatagt aacgccaata gggactttcc     420

attgacgtca atgggtggac tatttacggt aaactgccca cttggcagta catcaagtgt     480

atcatatgcc aagtacgccc cctattgacg tcaatgacgg taaatggccc gcctggcatt     540

atgcccagta catgacctta tgggactttc ctacttggca gtacatctac gtattagtca     600

tcgctattac catggtgatg cggttttggc agtacatcaa tgggcgtgga tagcggtttg     660

actcacgggg atttccaagt ctccacccca ttgacgtcaa tgggagtttg ttttggcacc     720

aaaatcaacg ggactttcca aaatgtcgta acaactccgc cccattgacg caaatgggcg     780

gtaggcgtgt acggtgggag gtctatataa gcagagctct ctggctaact agagaaccca     840
```

-continued

```
ctgcttactg gcttatcgaa attaatacga ctcactatag ggagacccaa gcttggtacc    900

gccgccgcc atg ggc aag agg tcc gcc ggc tca atc atg tgg ctc gcg agc    951
          Met Gly Lys Arg Ser Ala Gly Ser Ile Met Trp Leu Ala Ser
          1               5                   10

ttg gca gtt gtc ata gct ggt aca agc gct acc acc atc cac cgg gac      999
Leu Ala Val Val Ile Ala Gly Thr Ser Ala Thr Thr Ile His Arg Asp
15                  20                  25                  30

agg gaa gga tac atg gtt atg cgg gcc agt gga agg gac gct gca agc     1047
Arg Glu Gly Tyr Met Val Met Arg Ala Ser Gly Arg Asp Ala Ala Ser
                35                  40                  45

cag gtc agg gta caa aac gga acg tgc gtc atc ctg gca aca gac atg     1095
Gln Val Arg Val Gln Asn Gly Thr Cys Val Ile Leu Ala Thr Asp Met
            50                  55                  60

gga gag tgg tgt gaa gat tca atc acc tac tct tgc gtc acg att gac     1143
Gly Glu Trp Cys Glu Asp Ser Ile Thr Tyr Ser Cys Val Thr Ile Asp
        65                  70                  75

cag gag gaa gaa ccc gtt gac gtg gac tgc ttc tgc cga ggt gtt gat     1191
Gln Glu Glu Glu Pro Val Asp Val Asp Cys Phe Cys Arg Gly Val Asp
    80                  85                  90

agg gtt aag tta gag tat gga cgc tgt gga agg caa gct gga tct agg     1239
Arg Val Lys Leu Glu Tyr Gly Arg Cys Gly Arg Gln Ala Gly Ser Arg
95                  100                 105                 110

ggg aaa agg tct gtg gtc att cca aca cat gca caa aaa gac atg gtc     1287
Gly Lys Arg Ser Val Val Ile Pro Thr His Ala Gln Lys Asp Met Val
                115                 120                 125

ggg cga ggt cat gca tgg ctt aaa ggt gac aat att cga gat cat gtc     1335
Gly Arg Gly His Ala Trp Leu Lys Gly Asp Asn Ile Arg Asp His Val
            130                 135                 140

acc cga gtc gag ggc tgg atg tgg aag aac aag ctt cta act gcc gcc     1383
Thr Arg Val Glu Gly Trp Met Trp Lys Asn Lys Leu Leu Thr Ala Ala
        145                 150                 155

att gtg gcc ttg gct tgg ctc atg gtt gat agt tgg atg gcc aga gtg     1431
Ile Val Ala Leu Ala Trp Leu Met Val Asp Ser Trp Met Ala Arg Val
    160                 165                 170

act gtc atc ctc ttg gcg ttg agt cta ggg cca gtg tac gcc acg agg     1479
Thr Val Ile Leu Leu Ala Leu Ser Leu Gly Pro Val Tyr Ala Thr Arg
175                 180                 185                 190

tgc acg cat ctt gag aac aga gat ttt gtg aca gga act caa ggg acc     1527
Cys Thr His Leu Glu Asn Arg Asp Phe Val Thr Gly Thr Gln Gly Thr
                195                 200                 205

acc aga gtg tcc cta gtt ttg gaa ctt gga ggc tgc gtg acc atc aca     1575
Thr Arg Val Ser Leu Val Leu Glu Leu Gly Gly Cys Val Thr Ile Thr
            210                 215                 220

gct gag ggc aag cca tcc att gat gta tgg ctc gaa gac att ttt cag     1623
Ala Glu Gly Lys Pro Ser Ile Asp Val Trp Leu Glu Asp Ile Phe Gln
        225                 230                 235

gaa agc ccg gct gaa acc aga gaa tac tgc ctg cac gcc aaa ttg acc     1671
Glu Ser Pro Ala Glu Thr Arg Glu Tyr Cys Leu His Ala Lys Leu Thr
    240                 245                 250

aac aca aaa gtg gag gct cgc tgt cca acc act gga ccg gcg aca ctt     1719
Asn Thr Lys Val Glu Ala Arg Cys Pro Thr Thr Gly Pro Ala Thr Leu
255                 260                 265                 270

ccg gag gag cat cag gct aat atg gtg tgc aag aga gac caa agc gac     1767
Pro Glu Glu His Gln Ala Asn Met Val Cys Lys Arg Asp Gln Ser Asp
                275                 280                 285

cgt gga tgg gga aac cac tgc ggg ttt ttt ggg aag ggc agt ata gtg     1815
Arg Gly Trp Gly Asn His Cys Gly Phe Phe Gly Lys Gly Ser Ile Val
            290                 295                 300
```

-continued

```
gct tgt gca aag ttt gaa tgc gag gaa gca aaa aaa gct gtg ggc cac      1863
Ala Cys Ala Lys Phe Glu Cys Glu Glu Ala Lys Lys Ala Val Gly His
        305                 310                 315

gtc tat gac tcc aca aag atc acg tat gtt gtc aag gtt gag ccc cac      1911
Val Tyr Asp Ser Thr Lys Ile Thr Tyr Val Val Lys Val Glu Pro His
    320                 325                 330

aca ggg gat tac ttg gct gca aat gag acc aat tca aac agg aaa tca      1959
Thr Gly Asp Tyr Leu Ala Ala Asn Glu Thr Asn Ser Asn Arg Lys Ser
335                 340                 345                 350

gca cag ttt acg gtg gca tcc gag aaa gtg atc ctg cgg ctc ggc gac      2007
Ala Gln Phe Thr Val Ala Ser Glu Lys Val Ile Leu Arg Leu Gly Asp
                355                 360                 365

tat gga gat gtg tcg ctg acg tgt aaa gtg gca agt ggg att gat gtc      2055
Tyr Gly Asp Val Ser Leu Thr Cys Lys Val Ala Ser Gly Ile Asp Val
            370                 375                 380

gcc caa act gtg gtg atg tca ctc gac agc agc aag gac cac ctg cct      2103
Ala Gln Thr Val Val Met Ser Leu Asp Ser Ser Lys Asp His Leu Pro
        385                 390                 395

tct gca tgg caa gtg cac cgt gac tgg ttt gag gac ttg gcg ctg ccc      2151
Ser Ala Trp Gln Val His Arg Asp Trp Phe Glu Asp Leu Ala Leu Pro
    400                 405                 410

tgg aaa cac aag gac aac caa gat tgg aac agt gtg gag aaa ctt gtg      2199
Trp Lys His Lys Asp Asn Gln Asp Trp Asn Ser Val Glu Lys Leu Val
415                 420                 425                 430

gaa ttt gga cca cca cat gct gtg aaa atg gat gtt ttc aat ctg ggg      2247
Glu Phe Gly Pro Pro His Ala Val Lys Met Asp Val Phe Asn Leu Gly
                435                 440                 445

gac cag acg gct gtg ctg ctc aaa tca ctg gca gga gtt ccg ctg gcc      2295
Asp Gln Thr Ala Val Leu Leu Lys Ser Leu Ala Gly Val Pro Leu Ala
            450                 455                 460

agt gtg gag ggc cag aaa tac cac ctg aaa agc ggc cat gtt act tgt      2343
Ser Val Glu Gly Gln Lys Tyr His Leu Lys Ser Gly His Val Thr Cys
        465                 470                 475

gat gtg gga ctg gaa aag ctg aaa ctg aaa ggc aca acc tac tcc atg      2391
Asp Val Gly Leu Glu Lys Leu Lys Leu Lys Gly Thr Thr Tyr Ser Met
    480                 485                 490

tgt gac aaa gca aag ttc aaa tgg aag aga gtt cct gtg gac agc ggc      2439
Cys Asp Lys Ala Lys Phe Lys Trp Lys Arg Val Pro Val Asp Ser Gly
495                 500                 505                 510

cat gac aca gta gtc atg gag gta tca tac aca gga agc gac aag cca      2487
His Asp Thr Val Val Met Glu Val Ser Tyr Thr Gly Ser Asp Lys Pro
                515                 520                 525

tgt cgg atc ccg gtg cgg gct gtg gca cat ggt gtc cca gcg gtt aat      2535
Cys Arg Ile Pro Val Arg Ala Val Ala His Gly Val Pro Ala Val Asn
            530                 535                 540

gta gcc atg ctc ata acc ccc aat cca acc att gaa aca aat ggt ggc      2583
Val Ala Met Leu Ile Thr Pro Asn Pro Thr Ile Glu Thr Asn Gly Gly
        545                 550                 555

gga ttc ata gaa atg cag ctg cca cca ggg gat aac atc atc tat gtg      2631
Gly Phe Ile Glu Met Gln Leu Pro Pro Gly Asp Asn Ile Ile Tyr Val
    560                 565                 570

gga gac ctt agc cag cag tgg ttt cag aaa ggc agt acc att ggt aga      2679
Gly Asp Leu Ser Gln Gln Trp Phe Gln Lys Gly Ser Thr Ile Gly Arg
575                 580                 585                 590

atg ttt gaa aaa acc cgc agg gga ttg gaa agg ctc tct gtg gtt gga      2727
Met Phe Glu Lys Thr Arg Arg Gly Leu Glu Arg Leu Ser Val Val Gly
                595                 600                 605

gaa cat gca tgg gac ttt ggc tca gta ggc ggg gta ctg tct tct gtg      2775
Glu His Ala Trp Asp Phe Gly Ser Val Gly Gly Val Leu Ser Ser Val
            610                 615                 620
```

-continued

```
ggg aag gca atc cac acg gtg ctg ggg gga gct ttc aac acc ctt ttt     2823
Gly Lys Ala Ile His Thr Val Leu Gly Gly Ala Phe Asn Thr Leu Phe
        625                 630                 635

ggg ggg gtt gga ttc atc cct aag atg ctg ctg ggg gtt gct ctg gtc     2871
Gly Gly Val Gly Phe Ile Pro Lys Met Leu Leu Gly Val Ala Leu Val
    640                 645                 650

tgg ttg gga cta aat gcc agg aat cca acg atg tcc atg acg ttt ctt     2919
Trp Leu Gly Leu Asn Ala Arg Asn Pro Thr Met Ser Met Thr Phe Leu
655                 660                 665                 670

gct gtg ggg gct ttg aca ctg atg atg aca atg gga gtt ggg gca         2964
Ala Val Gly Ala Leu Thr Leu Met Met Thr Met Gly Val Gly Ala
                675                 680                 685

tgagcggccg ctcgagcatg catctagagg gccctattct atagtgtcac ctaaatgcta   3024

gagctcgctg atcagcctcg actgtgcctt ctagttgcca gccatctgtt gtttgcccct   3084

cccccgtgcc ttccttgacc ctggaaggtg ccactcccac tgtcctttcc taataaaatg   3144

aggaaattgc atcgcattgt ctgagtaggt gtcattctat tctggggggt ggggtggggc   3204

aggacagcaa gggggaggat tgggaagaca atagcaggca tgctggggat gcggtgggct   3264

ctatggcttc tgaggcggaa agaacagctg cattaatgaa tcggccaacg cgcggggaga   3324

ggcggtttgc gtattgggcg ctcttccgct tcctcgctca ctgactcgct gcgctcggtc   3384

gttcggctgc ggcgagcggt atcagctcac tcaaaggcgg taatacggtt atccacagaa   3444

tcaggggata acgcaggaaa gaacatgtga gcaaaaggcc agcaaaaggc caggaaccgt   3504

aaaaaggccg cgttgctggc gtttttccat aggctccgcc cccctgacga gcatcacaaa   3564

aatcgacgct caagtcagag gtggcgaaac ccgacaggac tataaagata ccaggcgttt   3624

ccccctggaa gctccctcgt gcgctctcct gttccgaccc tgccgcttac cggatacctg   3684

tccgcctttc tcccttcggg aagcgtggcg ctttctcaat gctcacgctg taggtatctc   3744

agttcggtgt aggtcgttcg ctccaagctg ggctgtgtgc acgaaccccc cgttcagccc   3804

gaccgctgcg ccttatccgg taactatcgt cttgagtcca acccggtaag acacgactta   3864

tcgccactgg cagcagccac tggtaacagg attagcagag cgaggtatgt aggcggtgct   3924

acagagttct tgaagtggtg gcctaactac ggctacacta gaaggacagt atttggtatc   3984

tgcgctctgc tgaagccagt taccttcgga aaaagagttg gtagctcttg atccggcaaa   4044

caaaccaccg ctggtagcgg tggttttttt gtttgcaagc agcagattac gcgcagaaaa   4104

aaaggatctc aagaagatcc tttgatcttt tctacggggt ctgacgctca gtggaacgaa   4164

aactcacgtt aagggatttt ggtcatgaga ttatcaaaaa ggatcttcac ctagatcctt   4224

ttaaattaaa aatgaagttt taaatcaatc taaagtatat atgagtaaac ttggtctgac   4284

agttaccaat gcttaatcag tgaggcacct atctcagcga tctgtctatt tcgttcatcc   4344

atagttgcct gactccccgt cgtgtagata actacgatac gggagggctt accatctggc   4404

cccagtgctg caatgatacc gcgagaccca cgctcaccgg ctccagattt atcagcaata   4464

aaccagccag ccggaagggc cgagcgcaga agtggtcctg caactttatc cgcctccatc   4524

cagtctatta attgttgccg ggaagctaga gtaagtagtt cgccagttaa tagtttgcgc   4584

aacgttgttg ccattgctac aggcatcgtg gtgtcacgct cgtcgtttgg tatggcttca   4644

ttcagctccg gttcccaacg atcaaggcga gttacatgat cccccatgtt gtgcaaaaaa   4704

gcggttagct ccttcggtcc tccgatcgtt gtcagaagta agttggccgc agtgttatca   4764

ctcatggtta tggcagcact gcataattct cttactgtca tgccatccgt aagatgcttt   4824
```

-continued

```
tctgtgactg gtgagtactc aaccaagtca ttctgagaat agtgtatgcg gcgaccgagt   4884

tgctcttgcc cggcgtcaat acgggataat accgcgccac atagcagaac tttaaaagtg   4944

ctcatcattg gaaaacgttc ttcggggcga aaactctcaa ggatcttacc gctgttgaga   5004

tccagttcga tgtaacccac tcgtgcaccc aactgatctt cagcatcttt tactttcacc   5064

agcgtttctg ggtgagcaaa aacaggaagg caaaatgccg caaaaaaggg aataagggcg   5124

acacggaaat gttgaatact catactcttc ctttttcaat attattgaag catttatcag   5184

ggttattgtc tcatgagcgg atacatattt gaatgtattt agaaaaataa acaaataggg   5244

gttccgcgca catttccccg aaaagtgcca cctgacgtc                          5283
```

<210> SEQ ID NO 20
<211> LENGTH: 685
<212> TYPE: PRT
<213> ORGANISM: Artificial Sequence
<220> FEATURE:
<223> OTHER INFORMATION: Synthetic Construct

<400> SEQUENCE: 20

```
Met Gly Lys Arg Ser Ala Gly Ser Ile Met Trp Leu Ala Ser Leu Ala
1               5                   10                  15

Val Val Ile Ala Gly Thr Ser Ala Thr Thr Ile His Arg Asp Arg Glu
            20                  25                  30

Gly Tyr Met Val Met Arg Ala Ser Gly Arg Asp Ala Ala Ser Gln Val
        35                  40                  45

Arg Val Gln Asn Gly Thr Cys Val Ile Leu Ala Thr Asp Met Gly Glu
    50                  55                  60

Trp Cys Glu Asp Ser Ile Thr Tyr Ser Cys Val Thr Ile Asp Gln Glu
65                  70                  75                  80

Glu Glu Pro Val Asp Val Asp Cys Phe Cys Arg Gly Val Asp Arg Val
                85                  90                  95

Lys Leu Glu Tyr Gly Arg Cys Gly Arg Gln Ala Gly Ser Arg Gly Lys
            100                 105                 110

Arg Ser Val Val Ile Pro Thr His Ala Gln Lys Asp Met Val Gly Arg
        115                 120                 125

Gly His Ala Trp Leu Lys Gly Asp Asn Ile Arg Asp His Val Thr Arg
    130                 135                 140

Val Glu Gly Trp Met Trp Lys Asn Lys Leu Leu Thr Ala Ala Ile Val
145                 150                 155                 160

Ala Leu Ala Trp Leu Met Val Asp Ser Trp Met Ala Arg Val Thr Val
                165                 170                 175

Ile Leu Leu Ala Leu Ser Leu Gly Pro Val Tyr Ala Thr Arg Cys Thr
            180                 185                 190

His Leu Glu Asn Arg Asp Phe Val Thr Gly Thr Gln Gly Thr Thr Arg
        195                 200                 205

Val Ser Leu Val Leu Glu Leu Gly Gly Cys Val Thr Ile Thr Ala Glu
    210                 215                 220

Gly Lys Pro Ser Ile Asp Val Trp Leu Glu Asp Ile Phe Gln Glu Ser
225                 230                 235                 240

Pro Ala Glu Thr Arg Glu Tyr Cys Leu His Ala Lys Leu Thr Asn Thr
                245                 250                 255

Lys Val Glu Ala Arg Cys Pro Thr Thr Gly Pro Ala Thr Leu Pro Glu
            260                 265                 270

Glu His Gln Ala Asn Met Val Cys Lys Arg Asp Gln Ser Asp Arg Gly
        275                 280                 285
```

-continued

```
Trp Gly Asn His Cys Gly Phe Phe Gly Lys Gly Ser Ile Val Ala Cys
    290                 295                 300

Ala Lys Phe Glu Cys Glu Glu Ala Lys Lys Ala Val Gly His Val Tyr
305                 310                 315                 320

Asp Ser Thr Lys Ile Thr Tyr Val Val Lys Val Glu Pro His Thr Gly
                325                 330                 335

Asp Tyr Leu Ala Ala Asn Glu Thr Asn Ser Asn Arg Lys Ser Ala Gln
            340                 345                 350

Phe Thr Val Ala Ser Glu Lys Val Ile Leu Arg Leu Gly Asp Tyr Gly
        355                 360                 365

Asp Val Ser Leu Thr Cys Lys Val Ala Ser Gly Ile Asp Val Ala Gln
    370                 375                 380

Thr Val Val Met Ser Leu Asp Ser Ser Lys Asp His Leu Pro Ser Ala
385                 390                 395                 400

Trp Gln Val His Arg Asp Trp Phe Glu Asp Leu Ala Leu Pro Trp Lys
                405                 410                 415

His Lys Asp Asn Gln Asp Trp Asn Ser Val Glu Lys Leu Val Glu Phe
            420                 425                 430

Gly Pro Pro His Ala Val Lys Met Asp Val Phe Asn Leu Gly Asp Gln
        435                 440                 445

Thr Ala Val Leu Leu Lys Ser Leu Ala Gly Val Pro Leu Ala Ser Val
    450                 455                 460

Glu Gly Gln Lys Tyr His Leu Lys Ser Gly His Val Thr Cys Asp Val
465                 470                 475                 480

Gly Leu Glu Lys Leu Lys Leu Lys Gly Thr Thr Tyr Ser Met Cys Asp
                485                 490                 495

Lys Ala Lys Phe Lys Trp Lys Arg Val Pro Val Asp Ser Gly His Asp
            500                 505                 510

Thr Val Val Met Glu Val Ser Tyr Thr Gly Ser Asp Lys Pro Cys Arg
        515                 520                 525

Ile Pro Val Arg Ala Val Ala His Gly Val Pro Ala Val Asn Val Ala
    530                 535                 540

Met Leu Ile Thr Pro Asn Pro Thr Ile Glu Thr Asn Gly Gly Gly Phe
545                 550                 555                 560

Ile Glu Met Gln Leu Pro Pro Gly Asp Asn Ile Ile Tyr Val Gly Asp
                565                 570                 575

Leu Ser Gln Gln Trp Phe Gln Lys Gly Ser Thr Ile Gly Arg Met Phe
            580                 585                 590

Glu Lys Thr Arg Arg Gly Leu Glu Arg Leu Ser Val Val Gly Glu His
        595                 600                 605

Ala Trp Asp Phe Gly Ser Val Gly Gly Val Leu Ser Ser Val Gly Lys
    610                 615                 620

Ala Ile His Thr Val Leu Gly Gly Ala Phe Asn Thr Leu Phe Gly Gly
625                 630                 635                 640

Val Gly Phe Ile Pro Lys Met Leu Leu Gly Val Ala Leu Val Trp Leu
                645                 650                 655

Gly Leu Asn Ala Arg Asn Pro Thr Met Ser Met Thr Phe Leu Ala Val
            660                 665                 670

Gly Ala Leu Thr Leu Met Met Thr Met Gly Val Gly Ala
        675                 680                 685
```

<210> SEQ ID NO 21
<211> LENGTH: 5304

-continued

```
<212> TYPE: DNA
<213> ORGANISM: Artificial Sequence
<220> FEATURE:
<223> OTHER INFORMATION: Description of artificial sequence; note =
      synthetic construct
<220> FEATURE:
<221> NAME/KEY: CDS
<222> LOCATION: (910)..(2985)

<400> SEQUENCE: 21

gacggatcgg gagatctccc gatcccctat ggtcgactct cagtacaatc tgctctgatg      60

ccgcatagtt aagccagtat ctgctccctg cttgtgtgtt ggaggtcgct gagtagtgcg     120

cgagcaaaat ttaagctaca acaaggcaag gcttgaccga caattgcatg aagaatctgc     180

ttagggttag gcgttttgcg ctgcttcgcg atgtacgggc cagatatacg cgttgacatt     240

gattattgac tagttattaa tagtaatcaa ttacggggtc attagttcat agcccatata     300

tggagttccg cgttacataa cttacggtaa atggcccgcc tggctgaccg cccaacgacc     360

cccgcccatt gacgtcaata atgacgtatg ttcccatagt aacgccaata gggactttcc     420

attgacgtca atgggtggac tatttacggt aaactgccca cttggcagta catcaagtgt     480

atcatatgcc aagtacgccc cctattgacg tcaatgacgg taaatggccc gcctggcatt     540

atgcccagta catgacctta tgggactttc ctacttggca gtacatctac gtattagtca     600

tcgctattac catggtgatg cggttttggc agtacatcaa tgggcgtgga tagcggtttg     660

actcacgggg atttccaagt ctccacccca ttgacgtcaa tgggagtttg ttttggcacc     720

aaaatcaacg ggactttcca aaatgtcgta acaactccgc cccattgacg caaatgggcg     780

gtaggcgtgt acggtgggag gtctatataa gcagagctct ctggctaact agagaaccca     840

ctgcttactg gcttatcgaa attaatacga ctcactatag ggagacccaa gcttggtacc     900

gccgccgcc atg ggc aag agg tcc gcc ggc tca atc atg tgg ctc gcg agc      951
          Met Gly Lys Arg Ser Ala Gly Ser Ile Met Trp Leu Ala Ser
          1               5                   10

ttg gca gtt gtc ata gct ggt aca agc gct ttg cag tta tca acc tat       999
Leu Ala Val Val Ile Ala Gly Thr Ser Ala Leu Gln Leu Ser Thr Tyr
15                  20                  25                  30

cag ggg aaa gtg tta atg tca atc aac aag act gac gct caa agc gcc      1047
Gln Gly Lys Val Leu Met Ser Ile Asn Lys Thr Asp Ala Gln Ser Ala
                35                  40                  45

ata aac att cct agt gcc aac gga gca aac act tgc att gtg agg gct      1095
Ile Asn Ile Pro Ser Ala Asn Gly Ala Asn Thr Cys Ile Val Arg Ala
            50                  55                  60

cta gat gtg ggg gtc atg tgc aaa gat gac atc aca tac ctg tgc cca      1143
Leu Asp Val Gly Val Met Cys Lys Asp Asp Ile Thr Tyr Leu Cys Pro
        65                  70                  75

gtg ctt tca gcg gga aat gat ccc gag gac att gac tgt tgg tgt gac      1191
Val Leu Ser Ala Gly Asn Asp Pro Glu Asp Ile Asp Cys Trp Cys Asp
    80                  85                  90

gtc gaa gag gtg tgg gtg cac tac ggc aga tgc acg cgc atg gga cat      1239
Val Glu Glu Val Trp Val His Tyr Gly Arg Cys Thr Arg Met Gly His
95                  100                 105                 110

tcg agg cgt agc cga cgg tca atc tct gtg cag cat cat gga gat tcc      1287
Ser Arg Arg Ser Arg Arg Ser Ile Ser Val Gln His His Gly Asp Ser
                115                 120                 125

aca ctg gca aca aag aac acg cca tgg ttg gac acc gtg aaa acc acc      1335
Thr Leu Ala Thr Lys Asn Thr Pro Trp Leu Asp Thr Val Lys Thr Thr
            130                 135                 140

aaa tac ttg aca aaa gta gaa aac tgg gtt ttg cgc aat cct gga tat      1383
Lys Tyr Leu Thr Lys Val Glu Asn Trp Val Leu Arg Asn Pro Gly Tyr
```

-continued

```
        145                 150                 155

gcc cta gtt gcg ctg gcg att gga tgg atg ctc ggt agc aac aac aca      1431
Ala Leu Val Ala Leu Ala Ile Gly Trp Met Leu Gly Ser Asn Asn Thr
    160                 165                 170

cag aga gtg gtt ttt gtg atc atg ctg atg ctg att gct ccg gca tac      1479
Gln Arg Val Val Phe Val Ile Met Leu Met Leu Ile Ala Pro Ala Tyr
175                 180                 185                 190

agc ttc aac tgt ctg gga aca tca aac agg gac ttt gtc gag gga gcc      1527
Ser Phe Asn Cys Leu Gly Thr Ser Asn Arg Asp Phe Val Glu Gly Ala
                195                 200                 205

agt ggg gca aca tgg att gac ttg gta ctt gaa ggg gga agc tgt gtc      1575
Ser Gly Ala Thr Trp Ile Asp Leu Val Leu Glu Gly Gly Ser Cys Val
            210                 215                 220

aca gtg atg gca cca gag aaa cca aca ctg gac ttc aaa gtg atg aag      1623
Thr Val Met Ala Pro Glu Lys Pro Thr Leu Asp Phe Lys Val Met Lys
        225                 230                 235

atg gag gct acc gag tta gcc act gtg cgt gag tat tgt tac gaa gca      1671
Met Glu Ala Thr Glu Leu Ala Thr Val Arg Glu Tyr Cys Tyr Glu Ala
    240                 245                 250

acc ttg gac acg ctg tca aca gtg gca agg tgc ccc aca aca gga gaa      1719
Thr Leu Asp Thr Leu Ser Thr Val Ala Arg Cys Pro Thr Thr Gly Glu
255                 260                 265                 270

gct cac aac acc aaa agg agt gac cca aca ttt gtc tgc aaa aga gat      1767
Ala His Asn Thr Lys Arg Ser Asp Pro Thr Phe Val Cys Lys Arg Asp
                275                 280                 285

gtt gtg gac cgc gga tgg ggt aac gga tgt ggt ctg ttt gga aaa ggg      1815
Val Val Asp Arg Gly Trp Gly Asn Gly Cys Gly Leu Phe Gly Lys Gly
            290                 295                 300

agc att gac aca tgc gct aag ttc aca tgc aaa aac aag gca aca ggg      1863
Ser Ile Asp Thr Cys Ala Lys Phe Thr Cys Lys Asn Lys Ala Thr Gly
        305                 310                 315

aag acg atc ttg aga gaa aac atc aag tat gag gtt gca atc ttt gtg      1911
Lys Thr Ile Leu Arg Glu Asn Ile Lys Tyr Glu Val Ala Ile Phe Val
    320                 325                 330

cat ggt tca acg gac tct acg tca cat ggc aat tac tct gag cag att      1959
His Gly Ser Thr Asp Ser Thr Ser His Gly Asn Tyr Ser Glu Gln Ile
335                 340                 345                 350

gga aaa aac caa gcg gct aga ttc acc ata agc ccg caa gca ccg tcc      2007
Gly Lys Asn Gln Ala Ala Arg Phe Thr Ile Ser Pro Gln Ala Pro Ser
                355                 360                 365

ttt acg gcc aac atg ggc gag tat gga aca gtt acc att gat tgt gaa      2055
Phe Thr Ala Asn Met Gly Glu Tyr Gly Thr Val Thr Ile Asp Cys Glu
            370                 375                 380

gca aga tca gga atc aac acg gag gat tat tat gtt ttc act gtc aag      2103
Ala Arg Ser Gly Ile Asn Thr Glu Asp Tyr Tyr Val Phe Thr Val Lys
        385                 390                 395

gag aag tca tgg cta gtg aac agg gac tgg ttt cac gac ttg aac ctt      2151
Glu Lys Ser Trp Leu Val Asn Arg Asp Trp Phe His Asp Leu Asn Leu
    400                 405                 410

cca tgg acg agc cct gcc aca act gat tgg cgc aac aga gaa aca ctg      2199
Pro Trp Thr Ser Pro Ala Thr Thr Asp Trp Arg Asn Arg Glu Thr Leu
415                 420                 425                 430

gtg gaa ttt gag gaa ccg cat gcc acc aag caa act gta gta gcc cta      2247
Val Glu Phe Glu Glu Pro His Ala Thr Lys Gln Thr Val Val Ala Leu
                435                 440                 445

gga tcg caa gaa ggt gcc ctg cac aca gca ttg gct gga gcc att cca      2295
Gly Ser Gln Glu Gly Ala Leu His Thr Ala Leu Ala Gly Ala Ile Pro
            450                 455                 460

gcc act gtt agc agc tca acc cta acc ttg caa tca ggg cat ttg aaa      2343
```

-continued

```
Ala Thr Val Ser Ser Ser Thr Leu Thr Leu Gln Ser Gly His Leu Lys
        465                 470                 475

tgc aga gct aag ctt gac aag gtc aaa atc aag gga acg aca tat ggc     2391
Cys Arg Ala Lys Leu Asp Lys Val Lys Ile Lys Gly Thr Thr Tyr Gly
    480                 485                 490

atg tgt gac tct gcc ttc acc ttc agc aag aac cca act gac aca ggg     2439
Met Cys Asp Ser Ala Phe Thr Phe Ser Lys Asn Pro Thr Asp Thr Gly
495                 500                 505                 510

cac ggg aca gtg att gtg gaa ctg cag tat act gga agc aac gga ccc     2487
His Gly Thr Val Ile Val Glu Leu Gln Tyr Thr Gly Ser Asn Gly Pro
                515                 520                 525

tgc cga gtt ccc atc tcc gtg act gca aac ctc atg gat ttg aca ccg     2535
Cys Arg Val Pro Ile Ser Val Thr Ala Asn Leu Met Asp Leu Thr Pro
            530                 535                 540

gtt gga aga ttg gtc acg gtc aat ccc ttt ata agc aca ggg gga gcg     2583
Val Gly Arg Leu Val Thr Val Asn Pro Phe Ile Ser Thr Gly Gly Ala
        545                 550                 555

aac aac aag gtc atg atc gaa gtt gaa cca ccc ttt ggc gat tct tac     2631
Asn Asn Lys Val Met Ile Glu Val Glu Pro Pro Phe Gly Asp Ser Tyr
    560                 565                 570

atc gtc gtc gga aga ggc acc acc cag att aac tac cac tgg cac aaa     2679
Ile Val Val Gly Arg Gly Thr Thr Gln Ile Asn Tyr His Trp His Lys
575                 580                 585                 590

gag gga agc agc att ggg aag gct ttg gcg acc aca tgg aaa gga gcc     2727
Glu Gly Ser Ser Ile Gly Lys Ala Leu Ala Thr Thr Trp Lys Gly Ala
                595                 600                 605

caa cgg cta gcc gtc tta ggg gac aca gcg tgg gac ttt gga tct att     2775
Gln Arg Leu Ala Val Leu Gly Asp Thr Ala Trp Asp Phe Gly Ser Ile
            610                 615                 620

gga gga gtt ttc aat tca att ggc aaa gct gtc cac caa gtt ttc gga     2823
Gly Gly Val Phe Asn Ser Ile Gly Lys Ala Val His Gln Val Phe Gly
        625                 630                 635

gga gcg ttc agg act ctg ttc ggg gga atg tcc tgg atc aca cag ggg     2871
Gly Ala Phe Arg Thr Leu Phe Gly Gly Met Ser Trp Ile Thr Gln Gly
    640                 645                 650

cta ctt gga gct ctt ctc ctg tgg atg ggg ttg cag gcc cgc gac agg     2919
Leu Leu Gly Ala Leu Leu Leu Trp Met Gly Leu Gln Ala Arg Asp Arg
655                 660                 665                 670

agc atc tcg ctg act cta ctg gct gtc gga ggg att ctc atc ttt ctg     2967
Ser Ile Ser Leu Thr Leu Leu Ala Val Gly Gly Ile Leu Ile Phe Leu
                675                 680                 685

gca acc agc gtg caa gcc tgagcggccg ctcgagcatg catctagagg           3015
Ala Thr Ser Val Gln Ala
            690

gccctattct atagtgtcac ctaaatgcta gagctcgctg atcagcctcg actgtgcctt   3075

ctagttgcca gccatctgtt gtttgcccct cccccgtgcc ttccttgacc ctggaaggtg   3135

ccactcccac tgtcctttcc taataaaatg aggaaattgc atcgcattgt ctgagtaggt   3195

gtcattctat tctggggggt ggggtggggc aggacagcaa gggggaggat tgggaagaca   3255

atagcaggca tgctggggat gcggtgggct ctatggcttc tgaggcggaa agaacagctg   3315

cattaatgaa tcggccaacg cgcggggaga ggcggtttgc gtattgggcg ctcttccgct   3375

tcctcgctca ctgactcgct gcgctcggtc gttcggctgc ggcgagcggt atcagctcac   3435

tcaaaggcgg taatacggtt atccacagaa tcaggggata acgcaggaaa gaacatgtga   3495

gcaaaaggcc agcaaaaggc caggaaccgt aaaaaggccg cgttgctggc gtttttccat   3555

aggctccgcc cccctgacga gcatcacaaa aatcgacgct caagtcagag gtggcgaaac   3615
```

-continued

```
ccgacaggac tataaagata ccaggcgttt cccccctggaa gctccctcgt gcgctctcct   3675

gttccgaccc tgccgcttac cggatacctg tccgcctttc tcccttcggg aagcgtggcg   3735

ctttctcaat gctcacgctg taggtatctc agttcggtgt aggtcgttcg ctccaagctg   3795

ggctgtgtgc acgaaccccc cgttcagccc gaccgctgcg ccttatccgg taactatcgt   3855

cttgagtcca acccggtaag acacgactta tcgccactgg cagcagccac tggtaacagg   3915

attagcagag cgaggtatgt aggcggtgct acagagttct tgaagtggtg gcctaactac   3975

ggctacacta gaaggacagt atttggtatc tgcgctctgc tgaagccagt taccttcgga   4035

aaaagagttg gtagctcttg atccggcaaa caaaccaccg ctggtagcgg tggttttttt   4095

gtttgcaagc agcagattac gcgcagaaaa aaaggatctc aagaagatcc tttgatcttt   4155

tctacggggt ctgacgctca gtggaacgaa aactcacgtt aagggatttt ggtcatgaga   4215

ttatcaaaaa ggatcttcac ctagatcctt ttaaattaaa aatgaagttt taaatcaatc   4275

taaagtatat atgagtaaac ttggtctgac agttaccaat gcttaatcag tgaggcacct   4335

atctcagcga tctgtctatt tcgttcatcc atagttgcct gactccccgt cgtgtagata   4395

actacgatac gggagggctt accatctggc cccagtgctg caatgatacc gcgagaccca   4455

cgctcaccgg ctccagattt atcagcaata aaccagccag ccggaagggc cgagcgcaga   4515

agtggtcctg caactttatc cgcctccatc cagtctatta attgttgccg ggaagctaga   4575

gtaagtagtt cgccagttaa tagtttgcgc aacgttgttg ccattgctac aggcatcgtg   4635

gtgtcacgct cgtcgtttgg tatggcttca ttcagctccg gttcccaacg atcaaggcga   4695

gttacatgat cccccatgtt gtgcaaaaaa gcggttagct ccttcggtcc tccgatcgtt   4755

gtcagaagta agttggccgc agtgttatca ctcatggtta tggcagcact gcataattct   4815

cttactgtca tgccatccgt aagatgcttt tctgtgactg gtgagtactc aaccaagtca   4875

ttctgagaat agtgtatgcg gcgaccgagt tgctcttgcc cggcgtcaat acgggataat   4935

accgcgccac atagcagaac tttaaaagtg ctcatcattg gaaaacgttc ttcggggcga   4995

aaactctcaa ggatcttacc gctgttgaga tccagttcga tgtaacccac tcgtgcaccc   5055

aactgatctt cagcatcttt tactttcacc agcgtttctg ggtgagcaaa aacaggaagg   5115

caaaatgccg caaaaaaggg aataagggcg acacggaaat gttgaatact catactcttc   5175

ctttttcaat attattgaag catttatcag ggttattgtc tcatgagcgg atacatattt   5235

gaatgtattt agaaaaataa acaaataggg gttccgcgca catttccccg aaaagtgcca   5295

cctgacgtc                                                             5304
```

<210> SEQ ID NO 22
<211> LENGTH: 692
<212> TYPE: PRT
<213> ORGANISM: Artificial Sequence
<220> FEATURE:
<223> OTHER INFORMATION: Synthetic Construct

<400> SEQUENCE: 22

```
Met Gly Lys Arg Ser Ala Gly Ser Ile Met Trp Leu Ala Ser Leu Ala
1               5                   10                  15

Val Val Ile Ala Gly Thr Ser Ala Leu Gln Leu Ser Thr Tyr Gln Gly
            20                  25                  30

Lys Val Leu Met Ser Ile Asn Lys Thr Asp Ala Gln Ser Ala Ile Asn
        35                  40                  45

Ile Pro Ser Ala Asn Gly Ala Asn Thr Cys Ile Val Arg Ala Leu Asp
    50                  55                  60
```

-continued

```
Val Gly Val Met Cys Lys Asp Asp Ile Thr Tyr Leu Cys Pro Val Leu
65                  70                  75                  80

Ser Ala Gly Asn Asp Pro Glu Asp Ile Asp Cys Trp Cys Asp Val Glu
                85                  90                  95

Glu Val Trp Val His Tyr Gly Arg Cys Thr Arg Met Gly His Ser Arg
            100                 105                 110

Arg Ser Arg Arg Ser Ile Ser Val Gln His His Gly Asp Ser Thr Leu
        115                 120                 125

Ala Thr Lys Asn Thr Pro Trp Leu Asp Thr Val Lys Thr Thr Lys Tyr
    130                 135                 140

Leu Thr Lys Val Glu Asn Trp Val Leu Arg Asn Pro Gly Tyr Ala Leu
145                 150                 155                 160

Val Ala Leu Ala Ile Gly Trp Met Leu Gly Ser Asn Asn Thr Gln Arg
                165                 170                 175

Val Val Phe Val Ile Met Leu Met Leu Ile Ala Pro Ala Tyr Ser Phe
            180                 185                 190

Asn Cys Leu Gly Thr Ser Asn Arg Asp Phe Val Glu Gly Ala Ser Gly
        195                 200                 205

Ala Thr Trp Ile Asp Leu Val Leu Glu Gly Gly Ser Cys Val Thr Val
    210                 215                 220

Met Ala Pro Glu Lys Pro Thr Leu Asp Phe Lys Val Met Lys Met Glu
225                 230                 235                 240

Ala Thr Glu Leu Ala Thr Val Arg Glu Tyr Cys Tyr Glu Ala Thr Leu
                245                 250                 255

Asp Thr Leu Ser Thr Val Ala Arg Cys Pro Thr Thr Gly Glu Ala His
            260                 265                 270

Asn Thr Lys Arg Ser Asp Pro Thr Phe Val Cys Lys Arg Asp Val Val
        275                 280                 285

Asp Arg Gly Trp Gly Asn Gly Cys Gly Leu Phe Gly Lys Gly Ser Ile
    290                 295                 300

Asp Thr Cys Ala Lys Phe Thr Cys Lys Asn Lys Ala Thr Gly Lys Thr
305                 310                 315                 320

Ile Leu Arg Glu Asn Ile Lys Tyr Glu Val Ala Ile Phe Val His Gly
                325                 330                 335

Ser Thr Asp Ser Thr Ser His Gly Asn Tyr Ser Glu Gln Ile Gly Lys
            340                 345                 350

Asn Gln Ala Ala Arg Phe Thr Ile Ser Pro Gln Ala Pro Ser Phe Thr
        355                 360                 365

Ala Asn Met Gly Glu Tyr Gly Thr Val Thr Ile Asp Cys Glu Ala Arg
    370                 375                 380

Ser Gly Ile Asn Thr Glu Asp Tyr Tyr Val Phe Thr Val Lys Glu Lys
385                 390                 395                 400

Ser Trp Leu Val Asn Arg Asp Trp Phe His Asp Leu Asn Leu Pro Trp
                405                 410                 415

Thr Ser Pro Ala Thr Thr Asp Trp Arg Asn Arg Glu Thr Leu Val Glu
            420                 425                 430

Phe Glu Glu Pro His Ala Thr Lys Gln Thr Val Val Ala Leu Gly Ser
        435                 440                 445

Gln Glu Gly Ala Leu His Thr Ala Leu Ala Gly Ala Ile Pro Ala Thr
    450                 455                 460

Val Ser Ser Ser Thr Leu Thr Leu Gln Ser Gly His Leu Lys Cys Arg
465                 470                 475                 480
```

-continued

```
Ala Lys Leu Asp Lys Val Lys Ile Lys Gly Thr Thr Tyr Gly Met Cys
                485                 490                 495

Asp Ser Ala Phe Thr Phe Ser Lys Asn Pro Thr Asp Thr Gly His Gly
            500                 505                 510

Thr Val Ile Val Glu Leu Gln Tyr Thr Gly Ser Asn Gly Pro Cys Arg
        515                 520                 525

Val Pro Ile Ser Val Thr Ala Asn Leu Met Asp Leu Thr Pro Val Gly
    530                 535                 540

Arg Leu Val Thr Val Asn Pro Phe Ile Ser Thr Gly Gly Ala Asn Asn
545                 550                 555                 560

Lys Val Met Ile Glu Val Glu Pro Pro Phe Gly Asp Ser Tyr Ile Val
                565                 570                 575

Val Gly Arg Gly Thr Thr Gln Ile Asn Tyr His Trp His Lys Glu Gly
            580                 585                 590

Ser Ser Ile Gly Lys Ala Leu Ala Thr Thr Trp Lys Gly Ala Gln Arg
        595                 600                 605

Leu Ala Val Leu Gly Asp Thr Ala Trp Asp Phe Gly Ser Ile Gly Gly
    610                 615                 620

Val Phe Asn Ser Ile Gly Lys Ala Val His Gln Val Phe Gly Gly Ala
625                 630                 635                 640

Phe Arg Thr Leu Phe Gly Gly Met Ser Trp Ile Thr Gln Gly Leu Leu
                645                 650                 655

Gly Ala Leu Leu Leu Trp Met Gly Leu Gln Ala Arg Asp Arg Ser Ile
            660                 665                 670

Ser Leu Thr Leu Leu Ala Val Gly Gly Ile Leu Ile Phe Leu Ala Thr
        675                 680                 685

Ser Val Gln Ala
    690
```

<210> SEQ ID NO 23
<211> LENGTH: 5271
<212> TYPE: DNA
<213> ORGANISM: Artificial Sequence
<220> FEATURE:
<223> OTHER INFORMATION: Description of artificial sequence; note =
synthetic construct
<220> FEATURE:
<221> NAME/KEY: CDS
<222> LOCATION: (910)..(2952)

<400> SEQUENCE: 23

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720
```

-continued

```
aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttggtacc    900

gccgccgcc atg ggc aag agg tcc gcc ggc tca atc atg tgg ctc gcg agc    951
          Met Gly Lys Arg Ser Ala Gly Ser Ile Met Trp Leu Ala Ser
          1               5                   10

ttg gca gtt gtc ata gct ggt aca agc gct gtg acc ttg gtg cgg aaa      999
Leu Ala Val Val Ile Ala Gly Thr Ser Ala Val Thr Leu Val Arg Lys
15                  20                  25                  30

aac aga tgg ttg ctc cta aat gtg aca tct gag gac ctc ggg aaa aca     1047
Asn Arg Trp Leu Leu Leu Asn Val Thr Ser Glu Asp Leu Gly Lys Thr
                35                  40                  45

ttc tct gtg ggc aca ggc aac tgc aca aca aac att ttg gaa gcc aag     1095
Phe Ser Val Gly Thr Gly Asn Cys Thr Thr Asn Ile Leu Glu Ala Lys
            50                  55                  60

tac tgg tgc cca gac tca atg gaa tac aac tgt ccc aat ctc agt cca     1143
Tyr Trp Cys Pro Asp Ser Met Glu Tyr Asn Cys Pro Asn Leu Ser Pro
        65                  70                  75

aga gag gag cca gat gac att gat tgc tgg tgc tat ggg gtg gaa aac     1191
Arg Glu Glu Pro Asp Asp Ile Asp Cys Trp Cys Tyr Gly Val Glu Asn
    80                  85                  90

gtt aga gtc gca tat ggt aag tgt gac tca gca ggc agg tct agg agg     1239
Val Arg Val Ala Tyr Gly Lys Cys Asp Ser Ala Gly Arg Ser Arg Arg
95                  100                 105                 110

tca aga agg gcc att gac ttg cct acg cat gaa aac cat ggt ttg aag     1287
Ser Arg Arg Ala Ile Asp Leu Pro Thr His Glu Asn His Gly Leu Lys
                115                 120                 125

acc cgg caa gaa aaa tgg atg act gga aga atg ggt gaa agg caa ctc     1335
Thr Arg Gln Glu Lys Trp Met Thr Gly Arg Met Gly Glu Arg Gln Leu
            130                 135                 140

caa aag att gag aga tgg ttc gtg agg aac ccc ttt ttt gca gtg acg     1383
Gln Lys Ile Glu Arg Trp Phe Val Arg Asn Pro Phe Phe Ala Val Thr
        145                 150                 155

gct ctg acc att gcc tac ctt gtg gga agc aac atg acg caa cga gtc     1431
Ala Leu Thr Ile Ala Tyr Leu Val Gly Ser Asn Met Thr Gln Arg Val
    160                 165                 170

gtg att gcc cta ctg gtc ttg gct gtt ggt ccg gcc tac tca gct cac     1479
Val Ile Ala Leu Leu Val Leu Ala Val Gly Pro Ala Tyr Ser Ala His
175                 180                 185                 190

tgc att gga att act gac agg gat ttc att gag ggg gtg cat gga gga     1527
Cys Ile Gly Ile Thr Asp Arg Asp Phe Ile Glu Gly Val His Gly Gly
                195                 200                 205

act tgg gtt tca gct acc ctg gag caa gac aag tgt gtc act gtt atg     1575
Thr Trp Val Ser Ala Thr Leu Glu Gln Asp Lys Cys Val Thr Val Met
            210                 215                 220

gcc cct gac aag cct tca ttg gac atc tca cta gag aca gta gcc att     1623
Ala Pro Asp Lys Pro Ser Leu Asp Ile Ser Leu Glu Thr Val Ala Ile
        225                 230                 235

gat aga cct gct gag gtg agg aaa gtg tgt tac aat gca gtt ctc act     1671
Asp Arg Pro Ala Glu Val Arg Lys Val Cys Tyr Asn Ala Val Leu Thr
    240                 245                 250

cat gtg aag att aat gac aag tgc ccc agc act gga gag gcc cac cta     1719
His Val Lys Ile Asn Asp Lys Cys Pro Ser Thr Gly Glu Ala His Leu
255                 260                 265                 270

gct gaa gag aac gaa ggg gac aat gcg tgc aag cgc act tat tct gat     1767
Ala Glu Glu Asn Glu Gly Asp Asn Ala Cys Lys Arg Thr Tyr Ser Asp
                275                 280                 285
```

-continued

```
aga ggc tgg ggc aat ggc tgt ggc cta ttt ggg aaa ggg agc att gtg      1815
Arg Gly Trp Gly Asn Gly Cys Gly Leu Phe Gly Lys Gly Ser Ile Val
            290                 295                 300

gca tgc gcc aaa ttc act tgt gcc aaa tcc atg agt ttg ttt gag gtt      1863
Ala Cys Ala Lys Phe Thr Cys Ala Lys Ser Met Ser Leu Phe Glu Val
        305                 310                 315

gat cag acc aaa att cag tat gtc atc aga gca caa ttg cat gta ggg      1911
Asp Gln Thr Lys Ile Gln Tyr Val Ile Arg Ala Gln Leu His Val Gly
    320                 325                 330

gcc aag cag gaa aat tgg act acc gac att aag act ctc aag ttt gat      1959
Ala Lys Gln Glu Asn Trp Thr Thr Asp Ile Lys Thr Leu Lys Phe Asp
335                 340                 345                 350

gcc ctg tca ggc tcc cag gaa gtc gag ttc att ggg tat gga aaa gct      2007
Ala Leu Ser Gly Ser Gln Glu Val Glu Phe Ile Gly Tyr Gly Lys Ala
                355                 360                 365

aca ctg gaa tgc cag gtg caa act gcg gtg gac ttt ggt aac agt tac      2055
Thr Leu Glu Cys Gln Val Gln Thr Ala Val Asp Phe Gly Asn Ser Tyr
            370                 375                 380

atc gct gag atg gaa aca gag agc tgg ata gtg gac aga cag tgg gcc      2103
Ile Ala Glu Met Glu Thr Glu Ser Trp Ile Val Asp Arg Gln Trp Ala
        385                 390                 395

cag gac ttg acc ctg cca tgg cag agt gga agt ggc ggg gtg tgg aga      2151
Gln Asp Leu Thr Leu Pro Trp Gln Ser Gly Ser Gly Gly Val Trp Arg
    400                 405                 410

gag atg cat cat ctt gtc gaa ttt gaa cct ccg cat gcc gcc act atc      2199
Glu Met His His Leu Val Glu Phe Glu Pro Pro His Ala Ala Thr Ile
415                 420                 425                 430

aga gta ctg gcc ctg gga aac cag gaa ggc tcc ttg aaa aca gct ctt      2247
Arg Val Leu Ala Leu Gly Asn Gln Glu Gly Ser Leu Lys Thr Ala Leu
                435                 440                 445

act ggc gca atg agg gtt aca aag gac aca aat gac aac aac ctt tac      2295
Thr Gly Ala Met Arg Val Thr Lys Asp Thr Asn Asp Asn Asn Leu Tyr
            450                 455                 460

aaa cta cat ggt gga cat gtt tct tgc aga gtg aaa ttg tca gct ttg      2343
Lys Leu His Gly Gly His Val Ser Cys Arg Val Lys Leu Ser Ala Leu
        465                 470                 475

aca ctc aag ggg aca tcc tac aaa ata tgc act gac aaa atg ttt ttt      2391
Thr Leu Lys Gly Thr Ser Tyr Lys Ile Cys Thr Asp Lys Met Phe Phe
    480                 485                 490

gtc aag aac cca act gac act ggc cat ggc act gtt gtg atg cag gtg      2439
Val Lys Asn Pro Thr Asp Thr Gly His Gly Thr Val Val Met Gln Val
495                 500                 505                 510

aaa gtg tca aaa gga gcc ccc tgc agg att cca gtg ata gta gct gat      2487
Lys Val Ser Lys Gly Ala Pro Cys Arg Ile Pro Val Ile Val Ala Asp
                515                 520                 525

gat ctt aca gcg gca atc aat aaa ggc att ttg gtt aca gtt aac ccc      2535
Asp Leu Thr Ala Ala Ile Asn Lys Gly Ile Leu Val Thr Val Asn Pro
            530                 535                 540

atc gcc tca acc aat gat gat gaa gtg ctg att gag gtg aac cca cct      2583
Ile Ala Ser Thr Asn Asp Asp Glu Val Leu Ile Glu Val Asn Pro Pro
        545                 550                 555

ttt gga gac agc tac att atc gtt ggg aga gga gat tca cgt ctc act      2631
Phe Gly Asp Ser Tyr Ile Ile Val Gly Arg Gly Asp Ser Arg Leu Thr
    560                 565                 570

tac cag tgg cac aaa gag gga agc tca ata gga aag ttg ttc act cag      2679
Tyr Gln Trp His Lys Glu Gly Ser Ser Ile Gly Lys Leu Phe Thr Gln
575                 580                 585                 590

acc atg aaa ggc gtg gaa cgc ctg gcc gtc atg gga gac acc gcc tgg      2727
Thr Met Lys Gly Val Glu Arg Leu Ala Val Met Gly Asp Thr Ala Trp
                595                 600                 605
```

-continued

```
gat ttc agc tcc gct gga ggg ttc ttc act tcg gtt ggg aaa gga att     2775
Asp Phe Ser Ser Ala Gly Gly Phe Phe Thr Ser Val Gly Lys Gly Ile
            610                 615                 620

cat acg gtg ttt ggc tct gcc ttt cag ggg cta ttt ggc ggc ttg aac     2823
His Thr Val Phe Gly Ser Ala Phe Gln Gly Leu Phe Gly Gly Leu Asn
        625                 630                 635

tgg ata aca aag gtc atc atg ggg gcg gta ctt ata tgg gtt ggc atc     2871
Trp Ile Thr Lys Val Ile Met Gly Ala Val Leu Ile Trp Val Gly Ile
    640                 645                 650

aac aca aga aac atg aca atg tcc atg agc atg atc ttg gta gga gtg     2919
Asn Thr Arg Asn Met Thr Met Ser Met Ser Met Ile Leu Val Gly Val
655                 660                 665                 670

atc atg atg ttt ttg tct cta gga gtt ggg gcg tgagcggccg ctcgagcatg   2972
Ile Met Met Phe Leu Ser Leu Gly Val Gly Ala
                675                 680

catctagagg gccctattct atagtgtcac ctaaatgcta gagctcgctg atcagcctcg   3032

actgtgcctt ctagttgcca gccatctgtt gtttgcccct cccccgtgcc ttccttgacc   3092

ctggaaggtg ccactcccac tgtcctttcc taataaaatg aggaaattgc atcgcattgt   3152

ctgagtaggt gtcattctat tctggggggt ggggtggggc aggacagcaa gggggaggat   3212

tgggaagaca atagcaggca tgctggggat gcggtgggct ctatggcttc tgaggcggaa   3272

agaacagctg cattaatgaa tcggccaacg cgcggggaga ggcggtttgc gtattgggcg   3332

ctcttccgct tcctcgctca ctgactcgct gcgctcggtc gttcggctgc ggcgagcggt   3392

atcagctcac tcaaaggcgg taatacggtt atccacagaa tcaggggata acgcaggaaa   3452

gaacatgtga gcaaaaggcc agcaaaaggc caggaaccgt aaaaaggccg cgttgctggc   3512

gtttttccat aggctccgcc cccctgacga gcatcacaaa aatcgacgct caagtcagag   3572

gtggcgaaac ccgacaggac tataaagata ccaggcgttt ccccctggaa gctccctcgt   3632

gcgctctcct gttccgaccc tgccgcttac cggatacctg tccgcctttc tcccttcggg   3692

aagcgtggcg ctttctcaat gctcacgctg taggtatctc agttcggtgt aggtcgttcg   3752

ctccaagctg ggctgtgtgc acgaaccccc cgttcagccc gaccgctgcg ccttatccgg   3812

taactatcgt cttgagtcca acccggtaag acacgactta tcgccactgg cagcagccac   3872

tggtaacagg attagcagag cgaggtatgt aggcggtgct acagagttct tgaagtggtg   3932

gcctaactac ggctacacta gaaggacagt atttggtatc tgcgctctgc tgaagccagt   3992

taccttcgga aaaagagttg gtagctcttg atccggcaaa caaaccaccg ctggtagcgg   4052

tggttttttt gtttgcaagc agcagattac gcgcagaaaa aaaggatctc aagaagatcc   4112

tttgatcttt tctacggggt ctgacgctca gtggaacgaa aactcacgtt aagggatttt   4172

ggtcatgaga ttatcaaaaa ggatcttcac ctagatcctt ttaaattaaa aatgaagttt   4232

taaatcaatc taaagtatat atgagtaaac ttggtctgac agttaccaat gcttaatcag   4292

tgaggcacct atctcagcga tctgtctatt tcgttcatcc atagttgcct gactccccgt   4352

cgtgtagata actacgatac gggagggctt accatctggc cccagtgctg caatgatacc   4412

gcgagaccca cgctcaccgg ctccagattt atcagcaata aaccagccag ccggaagggc   4472

cgagcgcaga agtggtcctg caactttatc cgcctccatc cagtctatta attgttgccg   4532

ggaagctaga gtaagtagtt cgccagttaa tagtttgcgc aacgttgttg ccattgctac   4592

aggcatcgtg gtgtcacgct cgtcgtttgg tatggcttca ttcagctccg gttcccaacg   4652

atcaaggcga gttacatgat cccccatgtt gtgcaaaaaa gcggttagct ccttcggtcc   4712
```

-continued

```
tccgatcgtt gtcagaagta agttggccgc agtgttatca ctcatggtta tggcagcact   4772

gcataattct cttactgtca tgccatccgt aagatgcttt tctgtgactg gtgagtactc   4832

aaccaagtca ttctgagaat agtgtatgcg gcgaccgagt tgctcttgcc cggcgtcaat   4892

acgggataat accgcgccac atagcagaac tttaaaagtg ctcatcattg gaaaacgttc   4952

ttcggggcga aaactctcaa ggatcttacc gctgttgaga tccagttcga tgtaacccac   5012

tcgtgcaccc aactgatctt cagcatcttt tactttcacc agcgtttctg ggtgagcaaa   5072

aacaggaagg caaaatgccg caaaaaaggg aataagggcg acacggaaat gttgaatact   5132

catactcttc ctttttcaat attattgaag catttatcag ggttattgtc tcatgagcgg   5192

atacatattt gaatgtattt agaaaaataa acaaataggg gttccgcgca catttccccg   5252

aaaagtgcca cctgacgtc                                                5271
```

<210> SEQ ID NO 24
<211> LENGTH: 681
<212> TYPE: PRT
<213> ORGANISM: Artificial Sequence
<220> FEATURE:
<223> OTHER INFORMATION: Synthetic Construct

<400> SEQUENCE: 24

```
Met Gly Lys Arg Ser Ala Gly Ser Ile Met Trp Leu Ala Ser Leu Ala
1               5                   10                  15

Val Val Ile Ala Gly Thr Ser Ala Val Thr Leu Val Arg Lys Asn Arg
            20                  25                  30

Trp Leu Leu Leu Asn Val Thr Ser Glu Asp Leu Gly Lys Thr Phe Ser
        35                  40                  45

Val Gly Thr Gly Asn Cys Thr Thr Asn Ile Leu Glu Ala Lys Tyr Trp
    50                  55                  60

Cys Pro Asp Ser Met Glu Tyr Asn Cys Pro Asn Leu Ser Pro Arg Glu
65                  70                  75                  80

Glu Pro Asp Asp Ile Asp Cys Trp Cys Tyr Gly Val Glu Asn Val Arg
                85                  90                  95

Val Ala Tyr Gly Lys Cys Asp Ser Ala Gly Arg Ser Arg Arg Ser Arg
            100                 105                 110

Arg Ala Ile Asp Leu Pro Thr His Glu Asn His Gly Leu Lys Thr Arg
        115                 120                 125

Gln Glu Lys Trp Met Thr Gly Arg Met Gly Glu Arg Gln Leu Gln Lys
    130                 135                 140

Ile Glu Arg Trp Phe Val Arg Asn Pro Phe Phe Ala Val Thr Ala Leu
145                 150                 155                 160

Thr Ile Ala Tyr Leu Val Gly Ser Asn Met Thr Gln Arg Val Val Ile
                165                 170                 175

Ala Leu Leu Val Leu Ala Val Gly Pro Ala Tyr Ser Ala His Cys Ile
            180                 185                 190

Gly Ile Thr Asp Arg Asp Phe Ile Glu Gly Val His Gly Gly Thr Trp
        195                 200                 205

Val Ser Ala Thr Leu Glu Gln Asp Lys Cys Val Thr Val Met Ala Pro
    210                 215                 220

Asp Lys Pro Ser Leu Asp Ile Ser Leu Glu Thr Val Ala Ile Asp Arg
225                 230                 235                 240

Pro Ala Glu Val Arg Lys Val Cys Tyr Asn Ala Val Leu Thr His Val
                245                 250                 255

Lys Ile Asn Asp Lys Cys Pro Ser Thr Gly Glu Ala His Leu Ala Glu
```

-continued

```
            260                 265                 270

Glu Asn Glu Gly Asp Asn Ala Cys Lys Arg Thr Tyr Ser Asp Arg Gly
        275                 280                 285

Trp Gly Asn Gly Cys Gly Leu Phe Gly Lys Gly Ser Ile Val Ala Cys
    290                 295                 300

Ala Lys Phe Thr Cys Ala Lys Ser Met Ser Leu Phe Glu Val Asp Gln
305                 310                 315                 320

Thr Lys Ile Gln Tyr Val Ile Arg Ala Gln Leu His Val Gly Ala Lys
                325                 330                 335

Gln Glu Asn Trp Thr Thr Asp Ile Lys Thr Leu Lys Phe Asp Ala Leu
            340                 345                 350

Ser Gly Ser Gln Glu Val Glu Phe Ile Gly Tyr Gly Lys Ala Thr Leu
        355                 360                 365

Glu Cys Gln Val Gln Thr Ala Val Asp Phe Gly Asn Ser Tyr Ile Ala
    370                 375                 380

Glu Met Glu Thr Glu Ser Trp Ile Val Asp Arg Gln Trp Ala Gln Asp
385                 390                 395                 400

Leu Thr Leu Pro Trp Gln Ser Gly Ser Gly Gly Val Trp Arg Glu Met
                405                 410                 415

His His Leu Val Glu Phe Glu Pro Pro His Ala Ala Thr Ile Arg Val
            420                 425                 430

Leu Ala Leu Gly Asn Gln Glu Gly Ser Leu Lys Thr Ala Leu Thr Gly
        435                 440                 445

Ala Met Arg Val Thr Lys Asp Thr Asn Asp Asn Asn Leu Tyr Lys Leu
    450                 455                 460

His Gly Gly His Val Ser Cys Arg Val Lys Leu Ser Ala Leu Thr Leu
465                 470                 475                 480

Lys Gly Thr Ser Tyr Lys Ile Cys Thr Asp Lys Met Phe Phe Val Lys
                485                 490                 495

Asn Pro Thr Asp Thr Gly His Gly Thr Val Val Met Gln Val Lys Val
            500                 505                 510

Ser Lys Gly Ala Pro Cys Arg Ile Pro Val Ile Val Ala Asp Asp Leu
        515                 520                 525

Thr Ala Ala Ile Asn Lys Gly Ile Leu Val Thr Val Asn Pro Ile Ala
    530                 535                 540

Ser Thr Asn Asp Asp Glu Val Leu Ile Glu Val Asn Pro Pro Phe Gly
545                 550                 555                 560

Asp Ser Tyr Ile Ile Val Gly Arg Gly Asp Ser Arg Leu Thr Tyr Gln
                565                 570                 575

Trp His Lys Glu Gly Ser Ser Ile Gly Lys Leu Phe Thr Gln Thr Met
            580                 585                 590

Lys Gly Val Glu Arg Leu Ala Val Met Gly Asp Thr Ala Trp Asp Phe
        595                 600                 605

Ser Ser Ala Gly Gly Phe Phe Thr Ser Val Gly Lys Gly Ile His Thr
    610                 615                 620

Val Phe Gly Ser Ala Phe Gln Gly Leu Phe Gly Gly Leu Asn Trp Ile
625                 630                 635                 640

Thr Lys Val Ile Met Gly Ala Val Leu Ile Trp Val Gly Ile Asn Thr
                645                 650                 655

Arg Asn Met Thr Met Ser Met Ser Met Ile Leu Val Gly Val Ile Met
            660                 665                 670

Met Phe Leu Ser Leu Gly Val Gly Ala
        675                 680
```

-continued

<210> SEQ ID NO 25
<211> LENGTH: 35
<212> TYPE: DNA
<213> ORGANISM: Artificial Sequence
<220> FEATURE:
<223> OTHER INFORMATION: Description of artificial sequence; note =
synthetic construct
<220> FEATURE:
<221> NAME/KEY: misc_feature
<222> LOCATION: (1)..(35)
<223> OTHER INFORMATION: POW 454

<400> SEQUENCE: 25
aaaagaaaaa gcgctaccac catccaccgg gacag 35

<210> SEQ ID NO 26
<211> LENGTH: 41
<212> TYPE: DNA
<213> ORGANISM: Artificial Sequence
<220> FEATURE:
<223> OTHER INFORMATION: Description of artificial sequence; note =
synthetic construct
<220> FEATURE:
<221> NAME/KEY: misc_feature
<222> LOCATION: (1)..(41)
<223> OTHER INFORMATION: CPOW 2417

<400> SEQUENCE: 26
actgttaccc tcaaccccgt actcgccggc gaaaaagaaa a 41

<210> SEQ ID NO 27
<211> LENGTH: 24
<212> TYPE: PRT
<213> ORGANISM: Artificial Sequence
<220> FEATURE:
<223> OTHER INFORMATION: Description of artificial sequence; note =
synthetic construct
<220> FEATURE:
<221> NAME/KEY: misc_feature
<223> OTHER INFORMATION: Modified JE Signal

<400> SEQUENCE: 27

Met Gly Lys Arg Ser Ala Gly Ser Ile Met Trp Leu Ala Ser Leu Ala
1 5 10 15

Val Val Ile Ala Gly Thr Ser Ala
20

<210> SEQ ID NO 28
<211> LENGTH: 36
<212> TYPE: DNA
<213> ORGANISM: Artificial Sequence
<220> FEATURE:
<223> OTHER INFORMATION: Description of artificial sequence; note =
synthetic construct
<220> FEATURE:
<221> NAME/KEY: misc_feature
<222> LOCATION: (1)..(36)
<223> OTHER INFORMATION: YF 482

<400> SEQUENCE: 28
aaaagaaaaa gcgctgtgac cttggtgcgg aaaaac 36

<210> SEQ ID NO 29
<211> LENGTH: 41
<212> TYPE: DNA
<213> ORGANISM: Artificial Sequence
<220> FEATURE:
<223> OTHER INFORMATION: Description of artificial sequence; note =

-continued

```
      synthetic construct
<220> FEATURE:
<221> NAME/KEY: misc_feature
<222> LOCATION: (1)..(41)
<223> OTHER INFORMATION: CYF 2433

<400> SEQUENCE: 29

acagagatcc tcaaccccgc actcgccggc gaaaaagaaa a                          41


<210> SEQ ID NO 30
<211> LENGTH: 41
<212> TYPE: DNA
<213> ORGANISM: Artificial Sequence
<220> FEATURE:
<223> OTHER INFORMATION: Description of artificial sequence; note =
      synthetic construct
<220> FEATURE:
<221> NAME/KEY: misc_feature
<222> LOCATION: (1)..(41)
<223> OTHER INFORMATION: SLE 463

<400> SEQUENCE: 30

aaaagaaaaa gcgctttgca gttatcaacc tatcagggga a                          41


<210> SEQ ID NO 31
<211> LENGTH: 40
<212> TYPE: DNA
<213> ORGANISM: Artificial Sequence
<220> FEATURE:
<223> OTHER INFORMATION: Description of artificial sequence; note =
      synthetic construct
<220> FEATURE:
<221> NAME/KEY: misc_feature
<222> LOCATION: (1)..(40)
<223> OTHER INFORMATION: CSLE 2477

<400> SEQUENCE: 31

accgttggtc gcacgttcgg actcgccggc gaaaaagaaa                            40


<210> SEQ ID NO 32
<211> LENGTH: 39
<212> TYPE: PRT
<213> ORGANISM: Artificial Sequence
<220> FEATURE:
<223> OTHER INFORMATION: Description of artificial sequence; note =
      synthetic construct

<400> SEQUENCE: 32

Leu Asp Thr Ile Asn Arg Arg Pro Ser Lys Lys Arg Gly Gly Thr Arg
1               5                   10                  15

Ser Leu Leu Gly Leu Ala Ala Leu Ile Gly Leu Ala Ser Ser Leu Gln
            20                  25                  30

Leu Leu Ser Thr Tyr Gln Gly
        35


<210> SEQ ID NO 33
<211> LENGTH: 24
<212> TYPE: PRT
<213> ORGANISM: Artificial Sequence
<220> FEATURE:
<223> OTHER INFORMATION: Description of artificial sequence; note =
      synthetic construct

<400> SEQUENCE: 33

Met Trp Leu Ala Ser Leu Ala Val Val Ile Ala Cys Ala Gly Ala Met
1               5                   10                  15

Lys Leu Ser Asn Phe Gln Gly Lys
```

-continued

20

<210> SEQ ID NO 34
<211> LENGTH: 30
<212> TYPE: PRT
<213> ORGANISM: Artificial Sequence
<220> FEATURE:
<223> OTHER INFORMATION: Description of artificial sequence; note = synthetic construct

<400> SEQUENCE: 34

```
Met Asn Glu Gly Ser Ile Met Trp Leu Ala Ser Leu Ala Val Val Ile
1               5                   10                  15

Ala Cys Ala Gly Ala Met Lys Leu Ser Asn Phe Gln Gly Lys
            20                  25                  30
```

<210> SEQ ID NO 35
<211> LENGTH: 39
<212> TYPE: PRT
<213> ORGANISM: Artificial Sequence
<220> FEATURE:
<223> OTHER INFORMATION: Description of artificial sequence; note = synthetic construct

<400> SEQUENCE: 35

```
Met Gly Arg Lys Gln Asn Lys Arg Gly Gly Asn Glu Gly Ser Ile Met
1               5                   10                  15

Trp Leu Ala Ser Leu Ala Val Val Ile Ala Cys Ala Gly Ala Met Lys
            20                  25                  30

Leu Ser Asn Phe Gln Gly Lys
        35
```

<210> SEQ ID NO 36
<211> LENGTH: 34
<212> TYPE: PRT
<213> ORGANISM: Artificial Sequence
<220> FEATURE:
<223> OTHER INFORMATION: Description of artificial sequence; note = synthetic construct

<400> SEQUENCE: 36

```
Met Ser Lys Lys Arg Gly Gly Ser Glu Thr Ser Val Leu Met Val Ile
1               5                   10                  15

Phe Met Leu Ile Gly Phe Ala Ala Ala Leu Lys Leu Ser Asn Phe Gln
            20                  25                  30

Gly Lys
```

<210> SEQ ID NO 37
<211> LENGTH: 33
<212> TYPE: PRT
<213> ORGANISM: Artificial Sequence
<220> FEATURE:
<223> OTHER INFORMATION: Description of artificial sequence; note = synthetic construct

<400> SEQUENCE: 37

```
Met Gly Lys Arg Ser Ala Gly Ser Ile Met Trp Leu Ala Ser Leu Ala
1               5                   10                  15

Val Val Ile Ala Cys Ala Gly Ala Val Thr Leu Ser Asn Phe Gln Gly
            20                  25                  30

Lys
```

<210> SEQ ID NO 38

-continued

<211> LENGTH: 46
<212> TYPE: PRT
<213> ORGANISM: Artificial Sequence
<220> FEATURE:
<223> OTHER INFORMATION: Description of artificial sequence; note =
synthetic construct

<400> SEQUENCE: 38

```
Met Asn Val Leu Arg Gly Phe Arg Lys Glu Ile Gly Arg Met Leu Asn
1               5                   10                  15

Ile Leu Asn Arg Arg Arg Arg Thr Ala Gly Met Ile Ile Met Leu Ile
            20                  25                  30

Pro Thr Val Met Ala Phe His Leu Thr Thr Arg Asn Gly Glu
        35                  40                  45
```

<210> SEQ ID NO 39
<211> LENGTH: 40
<212> TYPE: PRT
<213> ORGANISM: Artificial Sequence
<220> FEATURE:
<223> OTHER INFORMATION: Description of artificial sequence; note =
synthetic construct

<400> SEQUENCE: 39

```
Met Val Gly Leu Gln Lys Arg Gly Lys Arg Arg Ser Ala Thr Asp Trp
1               5                   10                  15

Met Ser Trp Leu Leu Val Ile Thr Leu Leu Gly Met Thr Leu Ala Ala
            20                  25                  30

Thr Val Arg Lys Glu Arg Gly Asp
        35                  40
```

<210> SEQ ID NO 40
<211> LENGTH: 24
<212> TYPE: PRT
<213> ORGANISM: Artificial Sequence
<220> FEATURE:
<223> OTHER INFORMATION: Description of artificial sequence; note =
synthetic construct

<400> SEQUENCE: 40

```
Met Gly Trp Leu Leu Val Val Val Leu Leu Gly Val Thr Leu Ala Ala
1               5                   10                  15

Thr Val Arg Lys Glu Arg Gly Asp
            20
```

<210> SEQ ID NO 41
<211> LENGTH: 24
<212> TYPE: PRT
<213> ORGANISM: Artificial Sequence
<220> FEATURE:
<223> OTHER INFORMATION: Description of artificial sequence; note =
synthetic construct

<400> SEQUENCE: 41

```
Met Ser Trp Leu Leu Val Ile Thr Leu Leu Gly Met Thr Ile Ala Ala
1               5                   10                  15

Thr Val Arg Lys Glu Arg Gly Asp
            20
```

<210> SEQ ID NO 42
<211> LENGTH: 5292
<212> TYPE: DNA
<213> ORGANISM: Artificial Sequence
<220> FEATURE:
<223> OTHER INFORMATION: Description of artificial sequence; note =

-continued

```
      synthetic construct
<220> FEATURE:
<221> NAME/KEY: CDS
<222> LOCATION: (910)..(2964)

<400> SEQUENCE: 42

gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttggtacc    900

gccgccgcc atg ggc aag agg tcc gcc ggc tca atc atg tgg ctc gcg agc    951
          Met Gly Lys Arg Ser Ala Gly Ser Ile Met Trp Leu Ala Ser
          1               5                   10

ttg gca gtt gtc ata gct tgt gca ggc gcc ttc cat tta acc aca cgt      999
Leu Ala Val Val Ile Ala Cys Ala Gly Ala Phe His Leu Thr Thr Arg
15                  20                  25                  30

aac gga gaa cca cac atg atc gtc agc aga caa gag aaa ggg aaa agt     1047
Asn Gly Glu Pro His Met Ile Val Ser Arg Gln Glu Lys Gly Lys Ser
                35                  40                  45

ctt ctg ttt aaa aca gag gat ggc gtg aac atg tgt acc ctc atg gcc     1095
Leu Leu Phe Lys Thr Glu Asp Gly Val Asn Met Cys Thr Leu Met Ala
            50                  55                  60

atg gac ctt ggt gaa ttg tgt gaa gac aca atc acg tac aag tgt ccc     1143
Met Asp Leu Gly Glu Leu Cys Glu Asp Thr Ile Thr Tyr Lys Cys Pro
        65                  70                  75

ctt ctc agg cag aat gag cca gaa gac ata gac tgt tgg tgc aac tct     1191
Leu Leu Arg Gln Asn Glu Pro Glu Asp Ile Asp Cys Trp Cys Asn Ser
    80                  85                  90

acg tcc acg tgg gta act tat ggg acg tgt acc acc atg gga gaa cat     1239
Thr Ser Thr Trp Val Thr Tyr Gly Thr Cys Thr Thr Met Gly Glu His
95                  100                 105                 110

aga aga gaa aaa aga tca gtg gca ctc gtt cca cat gtg gga atg gga     1287
Arg Arg Glu Lys Arg Ser Val Ala Leu Val Pro His Val Gly Met Gly
                115                 120                 125

ctg gag aca cga act gaa aca tgg atg tca tca gaa ggg gcc tgg aaa     1335
Leu Glu Thr Arg Thr Glu Thr Trp Met Ser Ser Glu Gly Ala Trp Lys
            130                 135                 140

cat gtc cag aga att gaa act tgg atc ttg aga cat cca ggc ttc acc     1383
His Val Gln Arg Ile Glu Thr Trp Ile Leu Arg His Pro Gly Phe Thr
        145                 150                 155

atg atg gca gca atc ctg gca tac acc ata gga acg aca cat ttc caa     1431
Met Met Ala Ala Ile Leu Ala Tyr Thr Ile Gly Thr Thr His Phe Gln
```

-continued

```
    160                 165                 170

aga gcc ctg att ttc atc tta ctg aca gct gtc act cct tca atg aca      1479
Arg Ala Leu Ile Phe Ile Leu Leu Thr Ala Val Thr Pro Ser Met Thr
175                 180                 185                 190

atg cgt tgc ata gga atg tca aat aga gac ttt gtg gaa ggg gtt tca      1527
Met Arg Cys Ile Gly Met Ser Asn Arg Asp Phe Val Glu Gly Val Ser
                195                 200                 205

gga gga agc tgg gtt gac ata gtc tta gaa cat gga agc tgt gtg acg      1575
Gly Gly Ser Trp Val Asp Ile Val Leu Glu His Gly Ser Cys Val Thr
            210                 215                 220

acg atg gca aaa aac aaa cca aca ttg gat ttt gaa ctg ata aaa aca      1623
Thr Met Ala Lys Asn Lys Pro Thr Leu Asp Phe Glu Leu Ile Lys Thr
        225                 230                 235

gaa gcc aaa cag cct gcc acc cta agg aag tac tgt ata gag gca aag      1671
Glu Ala Lys Gln Pro Ala Thr Leu Arg Lys Tyr Cys Ile Glu Ala Lys
    240                 245                 250

cta acc aac aca aca aca gaa tct cgc tgc cca aca caa ggg gaa ccc      1719
Leu Thr Asn Thr Thr Thr Glu Ser Arg Cys Pro Thr Gln Gly Glu Pro
255                 260                 265                 270

agc cta aat gaa gag cag gac aaa agg ttc gtc tgc aaa cac tcc atg      1767
Ser Leu Asn Glu Glu Gln Asp Lys Arg Phe Val Cys Lys His Ser Met
                275                 280                 285

gta gac aga gga tgg gga aat gga tgt gga cta ttt gga aag gga ggc      1815
Val Asp Arg Gly Trp Gly Asn Gly Cys Gly Leu Phe Gly Lys Gly Gly
            290                 295                 300

att gtg acc tgt gct atg ttc aga tgc aaa aag aac atg gaa gga aaa      1863
Ile Val Thr Cys Ala Met Phe Arg Cys Lys Lys Asn Met Glu Gly Lys
        305                 310                 315

gtt gtg caa cca gaa aac ttg gaa tac acc att gtg ata aca cct cac      1911
Val Val Gln Pro Glu Asn Leu Glu Tyr Thr Ile Val Ile Thr Pro His
    320                 325                 330

tca ggg gaa gag cat gca gtc gga aat gac aca gga aaa cat ggc aag      1959
Ser Gly Glu Glu His Ala Val Gly Asn Asp Thr Gly Lys His Gly Lys
335                 340                 345                 350

gaa atc aaa ata aca cca cag agt tcc atc aca gaa gca gaa ttg aca      2007
Glu Ile Lys Ile Thr Pro Gln Ser Ser Ile Thr Glu Ala Glu Leu Thr
                355                 360                 365

ggt tat ggc act gtc aca atg gag tgc tct cca aga acg ggc ctc gac      2055
Gly Tyr Gly Thr Val Thr Met Glu Cys Ser Pro Arg Thr Gly Leu Asp
            370                 375                 380

ttc aat gag atg gtg ttg ttg cag atg gaa aat aaa gct tgg ctg gtg      2103
Phe Asn Glu Met Val Leu Leu Gln Met Glu Asn Lys Ala Trp Leu Val
        385                 390                 395

cac agg caa tgg ttc cta gac ctg ccg tta cca tgg ttg ccc gga gcg      2151
His Arg Gln Trp Phe Leu Asp Leu Pro Leu Pro Trp Leu Pro Gly Ala
    400                 405                 410

gac aca caa ggg tca aat tgg ata cag aaa gag aca ttg gtc act ttc      2199
Asp Thr Gln Gly Ser Asn Trp Ile Gln Lys Glu Thr Leu Val Thr Phe
415                 420                 425                 430

aaa aat ccc cat gcg aag aaa cag gat gtt gtt gtt tta gga tcc caa      2247
Lys Asn Pro His Ala Lys Lys Gln Asp Val Val Val Leu Gly Ser Gln
                435                 440                 445

gaa ggg gcc atg cac aca gca ctt aca ggg gcc aca gaa atc caa atg      2295
Glu Gly Ala Met His Thr Ala Leu Thr Gly Ala Thr Glu Ile Gln Met
            450                 455                 460

tca tca gga aac tta ctc ttc aca gga cat ctc aag tgc agg ctg aga      2343
Ser Ser Gly Asn Leu Leu Phe Thr Gly His Leu Lys Cys Arg Leu Arg
        465                 470                 475

atg gac aag cta cag ctc aaa gga atg tca tac tct atg tgc aca gga      2391
```

-continued

```
Met Asp Lys Leu Gln Leu Lys Gly Met Ser Tyr Ser Met Cys Thr Gly
    480                 485                 490

aag ttt aaa gtt gtg aag gaa ata gca gaa aca caa cat gga aca ata      2439
Lys Phe Lys Val Val Lys Glu Ile Ala Glu Thr Gln His Gly Thr Ile
495                 500                 505                 510

gtt atc aga gtg caa tat gaa ggg gac ggc tct cca tgc aag atc cct      2487
Val Ile Arg Val Gln Tyr Glu Gly Asp Gly Ser Pro Cys Lys Ile Pro
                515                 520                 525

ttt gag ata atg gat ttg gaa aaa aga cat gtc tta ggt cgc ctg att      2535
Phe Glu Ile Met Asp Leu Glu Lys Arg His Val Leu Gly Arg Leu Ile
            530                 535                 540

aca gtc aac cca att gtg aca gaa aaa gat agc cca gtc aac ata gaa      2583
Thr Val Asn Pro Ile Val Thr Glu Lys Asp Ser Pro Val Asn Ile Glu
        545                 550                 555

gca gaa cct cca ttc gga gac agc tac atc atc ata gga gta gag ccg      2631
Ala Glu Pro Pro Phe Gly Asp Ser Tyr Ile Ile Ile Gly Val Glu Pro
    560                 565                 570

gga caa ctg aag ctc aac tgg ttt aag aaa gga agt tct atc ggc caa      2679
Gly Gln Leu Lys Leu Asn Trp Phe Lys Lys Gly Ser Ser Ile Gly Gln
575                 580                 585                 590

atg ttt gag aca aca atg agg ggg gcg aag aga atg gcc att tta ggt      2727
Met Phe Glu Thr Thr Met Arg Gly Ala Lys Arg Met Ala Ile Leu Gly
                595                 600                 605

gac aca gcc tgg gat ttt gga tcc ttg gga gga gtg ttt aca tct ata      2775
Asp Thr Ala Trp Asp Phe Gly Ser Leu Gly Gly Val Phe Thr Ser Ile
            610                 615                 620

gga aag gct ctc cac caa gtc ttt gga gca atc tat gga gct gcc ttc      2823
Gly Lys Ala Leu His Gln Val Phe Gly Ala Ile Tyr Gly Ala Ala Phe
        625                 630                 635

agt ggg gtt tca tgg act atg aaa atc ctc ata gga gtc att atc aca      2871
Ser Gly Val Ser Trp Thr Met Lys Ile Leu Ile Gly Val Ile Ile Thr
    640                 645                 650

tgg ata gga atg aat tca cgc agc acc tca ctg tct gtg aca cta gta      2919
Trp Ile Gly Met Asn Ser Arg Ser Thr Ser Leu Ser Val Thr Leu Val
655                 660                 665                 670

ttg gtg gga att gtg aca ctg tat ttg gga gtc atg gtg cag gcc          2964
Leu Val Gly Ile Val Thr Leu Tyr Leu Gly Val Met Val Gln Ala
                675                 680                 685

taattagttg agcggccgct cgagcatgca tctagagggc cctattctat agtgtcacct   3024

aaatgctaga gctcgctgat cagcctcgac tgtgccttct agttgccagc catctgttgt   3084

ttgcccctcc cccgtgcctt ccttgaccct ggaaggtgcc actcccactg tcctttccta   3144

ataaaatgag gaaattgcat cgcattgtct gagtaggtgt cattctattc tggggggtgg   3204

ggtggggcag gacagcaagg gggaggattg ggaagacaat agcaggcatg ctggggatgc   3264

ggtgggctct atggcttctg aggcggaaag aaccagctgc attaatgaat cggccaacgc   3324

gcggggagag gcggtttgcg tattgggcgc tcttccgctt cctcgctcac tgactcgctg   3384

cgctcggtcg ttcggctgcg gcgagcggta tcagctcact caaaggcggt aatacggtta   3444

tccacagaat caggggataa cgcaggaaag aacatgtgag caaaaggcca gcaaaaggcc   3504

aggaaccgta aaaaggccgc gttgctggcg tttttccata ggctccgccc ccctgacgag   3564

catcacaaaa atcgacgctc aagtcagagg tggcgaaacc cgacaggact ataaagatac   3624

caggcgtttc cccctggaag ctccctcgtg cgctctcctg ttccgaccct gccgcttacc   3684

ggatacctgt ccgcctttct cccttcggga agcgtggcgc tttctcatag ctcacgctgt   3744

aggtatctca gttcggtgta ggtcgttcgc tccaagctgg gctgtgtgca cgaacccccc   3804
```

-continued

```
gttcagcccg accgctgcgc cttatccggt aactatcgtc ttgagtccaa cccggtaaga   3864

cacgacttat cgccactggc agcagccact ggtaacagga ttagcagagc gaggtatgta   3924

ggcggtgcta cagagttctt gaagtggtgg cctaactacg gctacactag aagaacagta   3984

tttggtatct gcgctctgct gaagccagtt accttcggaa aaagagttgg tagctcttga   4044

tccggcaaac aaaccaccgc tggtagcggt ggtttttttg tttgcaagca gcagattacg   4104

cgcagaaaaa aaggatctca agaagatcct ttgatctttt ctacggggtc tgacgctcag   4164

tggaacgaaa actcacgtta agggattttg gtcatgagat tatcaaaaag gatcttcacc   4224

tagatccttt taaattaaaa atgaagtttt aaatcaatct aaagtatata tgagtaaact   4284

tggtctgaca gttaccaatg cttaatcagt gaggcaccta tctcagcgat ctgtctattt   4344

cgttcatcca tagttgcctg actccccgtc gtgtagataa ctacgatacg ggagggctta   4404

ccatctggcc ccagtgctgc aatgataccg cgagacccac gctcaccggc tccagattta   4464

tcagcaataa accagccagc cggaagggcc gagcgcagaa gtggtcctgc aactttatcc   4524

gcctccatcc agtctattaa ttgttgccgg gaagctagag taagtagttc gccagttaat   4584

agtttgcgca acgttgttgc cattgctaca ggcatcgtgg tgtcacgctc gtcgtttggt   4644

atggcttcat tcagctccgg ttcccaacga tcaaggcgag ttacatgatc ccccatgttg   4704

tgcaaaaaag cggttagctc cttcggtcct ccgatcgttg tcagaagtaa gttggccgca   4764

gtgttatcac tcatggttat ggcagcactg cataattctc ttactgtcat gccatccgta   4824

agatgctttt ctgtgactgg tgagtactca accaagtcat tctgagaata gtgtatgcgg   4884

cgaccgagtt gctcttgccc ggcgtcaata cgggataata ccgcgccaca tagcagaact   4944

ttaaaagtgc tcatcattgg aaaacgttct tcggggcgaa aactctcaag gatcttaccg   5004

ctgttgagat ccagttcgat gtaacccact cgtgcaccca actgatcttc agcatctttt   5064

actttcacca gcgtttctgg gtgagcaaaa acaggaaggc aaaatgccgc aaaaaaggga   5124

ataagggcga cacggaaatg ttgaatactc atactcttcc tttttcaata ttattgaagc   5184

atttatcagg gttattgtct catgagcgga tacatatttg aatgtattta gaaaaataaa   5244

caaatagggg ttccgcgcac atttccccga aaagtgccac ctgacgtc                5292
```

<210> SEQ ID NO 43
<211> LENGTH: 685
<212> TYPE: PRT
<213> ORGANISM: Artificial Sequence
<220> FEATURE:
<223> OTHER INFORMATION: Synthetic Construct

<400> SEQUENCE: 43

```
Met Gly Lys Arg Ser Ala Gly Ser Ile Met Trp Leu Ala Ser Leu Ala
1               5                   10                  15

Val Val Ile Ala Cys Ala Gly Ala Phe His Leu Thr Thr Arg Asn Gly
            20                  25                  30

Glu Pro His Met Ile Val Ser Arg Gln Glu Lys Gly Lys Ser Leu Leu
        35                  40                  45

Phe Lys Thr Glu Asp Gly Val Asn Met Cys Thr Leu Met Ala Met Asp
    50                  55                  60

Leu Gly Glu Leu Cys Glu Asp Thr Ile Thr Tyr Lys Cys Pro Leu Leu
65                  70                  75                  80

Arg Gln Asn Glu Pro Glu Asp Ile Asp Cys Trp Cys Asn Ser Thr Ser
                85                  90                  95

Thr Trp Val Thr Tyr Gly Thr Cys Thr Thr Met Gly Glu His Arg Arg
```

-continued

```
            100                 105                 110

Glu Lys Arg Ser Val Ala Leu Val Pro His Val Gly Met Gly Leu Glu
        115                 120                 125

Thr Arg Thr Glu Thr Trp Met Ser Ser Glu Gly Ala Trp Lys His Val
    130                 135                 140

Gln Arg Ile Glu Thr Trp Ile Leu Arg His Pro Gly Phe Thr Met Met
145                 150                 155                 160

Ala Ala Ile Leu Ala Tyr Thr Ile Gly Thr Thr His Phe Gln Arg Ala
                165                 170                 175

Leu Ile Phe Ile Leu Leu Thr Ala Val Thr Pro Ser Met Thr Met Arg
            180                 185                 190

Cys Ile Gly Met Ser Asn Arg Asp Phe Val Glu Gly Val Ser Gly Gly
        195                 200                 205

Ser Trp Val Asp Ile Val Leu Glu His Gly Ser Cys Val Thr Thr Met
    210                 215                 220

Ala Lys Asn Lys Pro Thr Leu Asp Phe Glu Leu Ile Lys Thr Glu Ala
225                 230                 235                 240

Lys Gln Pro Ala Thr Leu Arg Lys Tyr Cys Ile Glu Ala Lys Leu Thr
                245                 250                 255

Asn Thr Thr Thr Glu Ser Arg Cys Pro Thr Gln Gly Glu Pro Ser Leu
            260                 265                 270

Asn Glu Glu Gln Asp Lys Arg Phe Val Cys Lys His Ser Met Val Asp
        275                 280                 285

Arg Gly Trp Gly Asn Gly Cys Gly Leu Phe Gly Lys Gly Gly Ile Val
    290                 295                 300

Thr Cys Ala Met Phe Arg Cys Lys Lys Asn Met Glu Gly Lys Val Val
305                 310                 315                 320

Gln Pro Glu Asn Leu Glu Tyr Thr Ile Val Ile Thr Pro His Ser Gly
                325                 330                 335

Glu Glu His Ala Val Gly Asn Asp Thr Gly Lys His Gly Lys Glu Ile
            340                 345                 350

Lys Ile Thr Pro Gln Ser Ser Ile Thr Glu Ala Glu Leu Thr Gly Tyr
        355                 360                 365

Gly Thr Val Thr Met Glu Cys Ser Pro Arg Thr Gly Leu Asp Phe Asn
    370                 375                 380

Glu Met Val Leu Leu Gln Met Glu Asn Lys Ala Trp Leu Val His Arg
385                 390                 395                 400

Gln Trp Phe Leu Asp Leu Pro Leu Pro Trp Leu Pro Gly Ala Asp Thr
                405                 410                 415

Gln Gly Ser Asn Trp Ile Gln Lys Glu Thr Leu Val Thr Phe Lys Asn
            420                 425                 430

Pro His Ala Lys Lys Gln Asp Val Val Val Leu Gly Ser Gln Glu Gly
        435                 440                 445

Ala Met His Thr Ala Leu Thr Gly Ala Thr Glu Ile Gln Met Ser Ser
    450                 455                 460

Gly Asn Leu Leu Phe Thr Gly His Leu Lys Cys Arg Leu Arg Met Asp
465                 470                 475                 480

Lys Leu Gln Leu Lys Gly Met Ser Tyr Ser Met Cys Thr Gly Lys Phe
                485                 490                 495

Lys Val Val Lys Glu Ile Ala Glu Thr Gln His Gly Thr Ile Val Ile
            500                 505                 510

Arg Val Gln Tyr Glu Gly Asp Gly Ser Pro Cys Lys Ile Pro Phe Glu
        515                 520                 525
```

-continued

```
Ile Met Asp Leu Glu Lys Arg His Val Leu Gly Arg Leu Ile Thr Val
    530                 535                 540

Asn Pro Ile Val Thr Glu Lys Asp Ser Pro Val Asn Ile Glu Ala Glu
545                 550                 555                 560

Pro Pro Phe Gly Asp Ser Tyr Ile Ile Ile Gly Val Glu Pro Gly Gln
                565                 570                 575

Leu Lys Leu Asn Trp Phe Lys Lys Gly Ser Ser Ile Gly Gln Met Phe
            580                 585                 590

Glu Thr Thr Met Arg Gly Ala Lys Arg Met Ala Ile Leu Gly Asp Thr
        595                 600                 605

Ala Trp Asp Phe Gly Ser Leu Gly Gly Val Phe Thr Ser Ile Gly Lys
    610                 615                 620

Ala Leu His Gln Val Phe Gly Ala Ile Tyr Gly Ala Ala Phe Ser Gly
625                 630                 635                 640

Val Ser Trp Thr Met Lys Ile Leu Ile Gly Val Ile Ile Thr Trp Ile
                645                 650                 655

Gly Met Asn Ser Arg Ser Thr Ser Leu Ser Val Thr Leu Val Leu Val
            660                 665                 670

Gly Ile Val Thr Leu Tyr Leu Gly Val Met Val Gln Ala
        675                 680                 685


<210> SEQ ID NO 44
<211> LENGTH: 5293
<212> TYPE: DNA
<213> ORGANISM: Artificial Sequence
<220> FEATURE:
<223> OTHER INFORMATION: Description of artificial sequence; note =
      synthetic construct
<220> FEATURE:
<221> NAME/KEY: CDS
<222> LOCATION: (910)..(2964)

<400> SEQUENCE: 44

gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttggtacc    900

gccgccgcc atg ggc aag agg tcc gcc ggc tca atc atg tgg ctc gcg agc    951
          Met Gly Lys Arg Ser Ala Gly Ser Ile Met Trp Leu Ala Ser
          1               5                   10
```

-continued

```
ttg gca gtt gtc ata gct tgt gca ggc gcc ttc cat tta acc aca cgt      999
Leu Ala Val Val Ile Ala Cys Ala Gly Ala Phe His Leu Thr Thr Arg
15                  20                  25                  30

aac gga gaa cca cac atg atc gtc agc aga caa gag aaa ggg aaa agt     1047
Asn Gly Glu Pro His Met Ile Val Ser Arg Gln Glu Lys Gly Lys Ser
                35                  40                  45

ctt ctg ttt aaa aca gag gat ggc gtg aac atg tgt acc ctc atg gcc     1095
Leu Leu Phe Lys Thr Glu Asp Gly Val Asn Met Cys Thr Leu Met Ala
            50                  55                  60

atg gac ctt ggt gaa ttg tgt gaa gac aca atc acg tac aag tgt ccc     1143
Met Asp Leu Gly Glu Leu Cys Glu Asp Thr Ile Thr Tyr Lys Cys Pro
        65                  70                  75

ctt ctc agg cag aat gag cca gaa gac ata gac tgt tgg tgc aac tct     1191
Leu Leu Arg Gln Asn Glu Pro Glu Asp Ile Asp Cys Trp Cys Asn Ser
    80                  85                  90

acg tcc acg tgg gta act tat ggg acg tgt acc acc atg gga gaa cat     1239
Thr Ser Thr Trp Val Thr Tyr Gly Thr Cys Thr Thr Met Gly Glu His
95                  100                 105                 110

aga aga gaa aaa aga tca gtg gca ctc gtt cca cat gtg gga atg gga     1287
Arg Arg Glu Lys Arg Ser Val Ala Leu Val Pro His Val Gly Met Gly
                115                 120                 125

ctg gag aca cga act gaa aca tgg atg tca tca gaa ggg gcc tgg aaa     1335
Leu Glu Thr Arg Thr Glu Thr Trp Met Ser Ser Glu Gly Ala Trp Lys
            130                 135                 140

cat gtc cag aga att gaa act tgg atc ttg aga cat cca ggc ttc acc     1383
His Val Gln Arg Ile Glu Thr Trp Ile Leu Arg His Pro Gly Phe Thr
        145                 150                 155

atg atg gca gca atc ctg gca tac acc ata gga acg aca cat ttc caa     1431
Met Met Ala Ala Ile Leu Ala Tyr Thr Ile Gly Thr Thr His Phe Gln
    160                 165                 170

aga gcc ctg att ttc atc tta ctg aca gct gtc act cct tca atg aca     1479
Arg Ala Leu Ile Phe Ile Leu Leu Thr Ala Val Thr Pro Ser Met Thr
175                 180                 185                 190

atg cgt tgc ata gga atg tca aat aga gac ttt gtg gaa ggg gtt tca     1527
Met Arg Cys Ile Gly Met Ser Asn Arg Asp Phe Val Glu Gly Val Ser
                195                 200                 205

gga gga agc tgg gtt gac ata gtc tta gaa cat gga agc tgt gtg acg     1575
Gly Gly Ser Trp Val Asp Ile Val Leu Glu His Gly Ser Cys Val Thr
            210                 215                 220

acg atg gca aaa aac aaa cca aca ttg gat ttt gaa ctg ata aaa aca     1623
Thr Met Ala Lys Asn Lys Pro Thr Leu Asp Phe Glu Leu Ile Lys Thr
        225                 230                 235

gaa gcc aaa cag cct gcc acc cta agg aag tac tgt ata gag gca aag     1671
Glu Ala Lys Gln Pro Ala Thr Leu Arg Lys Tyr Cys Ile Glu Ala Lys
    240                 245                 250

cta acc aac aca aca aca gaa tct cgc tgc cca aca caa ggg gaa ccc     1719
Leu Thr Asn Thr Thr Thr Glu Ser Arg Cys Pro Thr Gln Gly Glu Pro
255                 260                 265                 270

agc cta aat gaa gag cag gac aaa agg ttc gtc tgc aaa cac tcc atg     1767
Ser Leu Asn Glu Glu Gln Asp Lys Arg Phe Val Cys Lys His Ser Met
                275                 280                 285

gta gac aga gga tgg gga aat gga tgt gga cta ttt gga aag gga ggc     1815
Val Asp Arg Gly Trp Gly Asn Gly Cys Gly Leu Phe Gly Lys Gly Gly
            290                 295                 300

att gtg acc tgt gct atg ttc aga tgc aaa aag aac atg gaa gga aaa     1863
Ile Val Thr Cys Ala Met Phe Arg Cys Lys Lys Asn Met Glu Gly Lys
        305                 310                 315

gtt gtg caa cca gaa aac ttg gaa tac acc att gtg ata aca cct cac     1911
Val Val Gln Pro Glu Asn Leu Glu Tyr Thr Ile Val Ile Thr Pro His
    320                 325                 330
```

-continued

```
tca ggg gaa gag cat gca gtc gga aat gac aca gga aaa cat ggc aag     1959
Ser Gly Glu Glu His Ala Val Gly Asn Asp Thr Gly Lys His Gly Lys
335                 340                 345                 350

gaa atc aaa ata aca cca cag agt tcc atc aca gaa gca gaa ttg aca     2007
Glu Ile Lys Ile Thr Pro Gln Ser Ser Ile Thr Glu Ala Glu Leu Thr
                355                 360                 365

ggt tat ggc act gtc aca atg gag tgc tct cca aga acg ggc ctc gac     2055
Gly Tyr Gly Thr Val Thr Met Glu Cys Ser Pro Arg Thr Gly Leu Asp
            370                 375                 380

ttc aat gag atg gtg ttg ttg cag atg gaa aat aaa gct tgg ctg gtg     2103
Phe Asn Glu Met Val Leu Leu Gln Met Glu Asn Lys Ala Trp Leu Val
        385                 390                 395

cac agg caa tgg ttc cta gac ctg ccg tta cca tgg ttg ccc gga gcg     2151
His Arg Gln Trp Phe Leu Asp Leu Pro Leu Pro Trp Leu Pro Gly Ala
    400                 405                 410

gac aca caa ggg tca aat tgg ata cag aaa gag aca ttg gtc act ttc     2199
Asp Thr Gln Gly Ser Asn Trp Ile Gln Lys Glu Thr Leu Val Thr Phe
415                 420                 425                 430

aaa aat ccc cat gcg aag aaa cag gat gtt gtt gtt tta gga tcc caa     2247
Lys Asn Pro His Ala Lys Lys Gln Asp Val Val Val Leu Gly Ser Gln
                435                 440                 445

gaa ggg gcc atg cac aca gca ctt aca ggg gcc aca gaa atc caa atg     2295
Glu Gly Ala Met His Thr Ala Leu Thr Gly Ala Thr Glu Ile Gln Met
            450                 455                 460

tca tca gga aac tta ctc ttc aca gga cat ctc aag tgc agg ctg aga     2343
Ser Ser Gly Asn Leu Leu Phe Thr Gly His Leu Lys Cys Arg Leu Arg
        465                 470                 475

atg gac aag cta cag ctc aaa gga atg tca tac tct atg tgc aca gga     2391
Met Asp Lys Leu Gln Leu Lys Gly Met Ser Tyr Ser Met Cys Thr Gly
    480                 485                 490

aag ttt aaa gtt gtg aag gaa ata gca gaa aca caa cat gga aca ata     2439
Lys Phe Lys Val Val Lys Glu Ile Ala Glu Thr Gln His Gly Thr Ile
495                 500                 505                 510

gtt atc aga gtg caa tat gaa ggg gac ggc tct cca tgc aag atc cct     2487
Val Ile Arg Val Gln Tyr Glu Gly Asp Gly Ser Pro Cys Lys Ile Pro
                515                 520                 525

ttt gag ata atg gat ttg gaa aaa aga cat gtc tta ggt cgc ctg att     2535
Phe Glu Ile Met Asp Leu Glu Lys Arg His Val Leu Gly Arg Leu Ile
            530                 535                 540

aca gtc aac cca att gtg aca gaa aaa gat agc cca gtc aac ata gaa     2583
Thr Val Asn Pro Ile Val Thr Glu Lys Asp Ser Pro Val Asn Ile Glu
        545                 550                 555

gca gaa cct cca ttc gga gac agc cac atc atc ata gga gta gag ccg     2631
Ala Glu Pro Pro Phe Gly Asp Ser His Ile Ile Ile Gly Val Glu Pro
    560                 565                 570

gga caa ctg aag ctc aac tgg ttt aag aaa gga agt tct atc ggc caa     2679
Gly Gln Leu Lys Leu Asn Trp Phe Lys Lys Gly Ser Ser Ile Gly Gln
575                 580                 585                 590

atg ttt gag aca aca atg agg ggg gcg aag aga atg gcc att tta ggt     2727
Met Phe Glu Thr Thr Met Arg Gly Ala Lys Arg Met Ala Ile Leu Gly
                595                 600                 605

gac aca gcc tgg gat ttt gga tcc ttg gga gga gtg ttt aca tct ata     2775
Asp Thr Ala Trp Asp Phe Gly Ser Leu Gly Gly Val Phe Thr Ser Ile
            610                 615                 620

gga aag gct ctc cac caa gtg ttt ggt ggt gcc ttc aga aca ctc ttt     2823
Gly Lys Ala Leu His Gln Val Phe Gly Gly Ala Phe Arg Thr Leu Phe
        625                 630                 635

ggg gga atg tct tgg atc aca caa ggg cta atg ggt gcc cta ctg ctc     2871
Gly Gly Met Ser Trp Ile Thr Gln Gly Leu Met Gly Ala Leu Leu Leu
```

-continued

```
    640                 645                 650

tgg atg ggc gtc aac gca cga gac cga tca att gct ttg gcc ttc tta     2919
Trp Met Gly Val Asn Ala Arg Asp Arg Ser Ile Ala Leu Ala Phe Leu
655                 660                 665                 670

gcc aca ggg ggt gtg ctc gtg ttc tta gcg acc aat gtg cat gct         2964
Ala Thr Gly Gly Val Leu Val Phe Leu Ala Thr Asn Val His Ala
                675                 680                 685

taattagttt gggcggccgc tcgagcatgc atctagaggg ccctattcta tagtgtcacc   3024

taaatgctag agctcgctga tcagcctcga ctgtgccttc tagttgccag ccatctgttg   3084

tttgcccctc ccccgtgcct tccttgaccc tggaaggtgc cactcccact gtcctttcct   3144

aataaaatga ggaaattgca tcgcattgtc tgagtaggtg tcattctatt ctggggggtg   3204

gggtggggca ggacagcaag ggggaggatt gggaagacaa tagcaggcat gctggggatg   3264

cggtgggctc tatggcttct gaggcggaaa gaaccagctg cattaatgaa tcggccaacg   3324

cgcggggaga ggcggtttgc gtattgggcg ctcttccgct tcctcgctca ctgactcgct   3384

gcgctcggtc gttcggctgc ggcgagcggt atcagctcac tcaaaggcgg taatacggtt   3444

atccacagaa tcaggggata acgcaggaaa gaacatgtga gcaaaaggcc agcaaaaggc   3504

caggaaccgt aaaaaggccg cgttgctggc gtttttccat aggctccgcc cccctgacga   3564

gcatcacaaa aatcgacgct caagtcagag gtggcgaaac ccgacaggac tataaagata   3624

ccaggcgttt ccccctggaa gctccctcgt gcgctctcct gttccgaccc tgccgcttac   3684

cggatacctg tccgcctttc tcccttcggg aagcgtggcg ctttctcata gctcacgctg   3744

taggtatctc agttcggtgt aggtcgttcg ctccaagctg ggctgtgtgc acgaaccccc   3804

cgttcagccc gaccgctgcg ccttatccgg taactatcgt cttgagtcca acccggtaag   3864

acacgactta tcgccactgg cagcagccac tggtaacagg attagcagag cgaggtatgt   3924

aggcggtgct acagagttct tgaagtggtg gcctaactac ggctacacta gaagaacagt   3984

atttggtatc tgcgctctgc tgaagccagt taccttcgga aaaagagttg gtagctcttg   4044

atccggcaaa caaaccaccg ctggtagcgg tggttttttt gtttgcaagc agcagattac   4104

gcgcagaaaa aaaggatctc aagaagatcc tttgatcttt tctacggggt ctgacgctca   4164

gtggaacgaa aactcacgtt aagggatttt ggtcatgaga ttatcaaaaa ggatcttcac   4224

ctagatcctt ttaaattaaa aatgaagttt taaatcaatc taaagtatat atgagtaaac   4284

ttggtctgac agttaccaat gcttaatcag tgaggcacct atctcagcga tctgtctatt   4344

tcgttcatcc atagttgcct gactccccgt cgtgtagata actacgatac gggagggctt   4404

accatctggc cccagtgctg caatgatacc gcgagaccca cgctcaccgg ctccagattt   4464

atcagcaata aaccagccag ccggaagggc cgagcgcaga agtggtcctg caactttatc   4524

cgcctccatc cagtctatta attgttgccg ggaagctaga gtaagtagtt cgccagttaa   4584

tagtttgcgc aacgttgttg ccattgctac aggcatcgtg gtgtcacgct cgtcgtttgg   4644

tatggcttca ttcagctccg gttcccaacg atcaaggcga gttacatgat cccccatgtt   4704

gtgcaaaaaa gcggttagct ccttcggtcc tccgatcgtt gtcagaagta agttggccgc   4764

agtgttatca ctcatggtta tggcagcact gcataattct cttactgtca tgccatccgt   4824

aagatgcttt tctgtgactg gtgagtactc aaccaagtca ttctgagaat agtgtatgcg   4884

gcgaccgagt tgctcttgcc cggcgtcaat acgggataat accgcgccac atagcagaac   4944

tttaaaagtg ctcatcattg gaaaacgttc ttcggggcga aaactctcaa ggatcttacc   5004

gctgttgaga tccagttcga tgtaacccac tcgtgcaccc aactgatctt cagcatcttt   5064
```

-continued

```
tactttcacc agcgtttctg ggtgagcaaa aacaggaagg caaaatgccg caaaaaaggg   5124

aataagggcg acacggaaat gttgaatact catactcttc ctttttcaat attattgaag   5184

catttatcag ggttattgtc tcatgagcgg atacatattt gaatgtattt agaaaaataa   5244

acaaataggg gttccgcgca catttccccg aaaagtgcca cctgacgtc               5293


<210> SEQ ID NO 45
<211> LENGTH: 685
<212> TYPE: PRT
<213> ORGANISM: Artificial Sequence
<220> FEATURE:
<223> OTHER INFORMATION: Synthetic Construct

<400> SEQUENCE: 45

Met Gly Lys Arg Ser Ala Gly Ser Ile Met Trp Leu Ala Ser Leu Ala
1               5                   10                  15

Val Val Ile Ala Cys Ala Gly Ala Phe His Leu Thr Thr Arg Asn Gly
            20                  25                  30

Glu Pro His Met Ile Val Ser Arg Gln Glu Lys Gly Lys Ser Leu Leu
        35                  40                  45

Phe Lys Thr Glu Asp Gly Val Asn Met Cys Thr Leu Met Ala Met Asp
    50                  55                  60

Leu Gly Glu Leu Cys Glu Asp Thr Ile Thr Tyr Lys Cys Pro Leu Leu
65                  70                  75                  80

Arg Gln Asn Glu Pro Glu Asp Ile Asp Cys Trp Cys Asn Ser Thr Ser
                85                  90                  95

Thr Trp Val Thr Tyr Gly Thr Cys Thr Thr Met Gly Glu His Arg Arg
            100                 105                 110

Glu Lys Arg Ser Val Ala Leu Val Pro His Val Gly Met Gly Leu Glu
        115                 120                 125

Thr Arg Thr Glu Thr Trp Met Ser Ser Glu Gly Ala Trp Lys His Val
    130                 135                 140

Gln Arg Ile Glu Thr Trp Ile Leu Arg His Pro Gly Phe Thr Met Met
145                 150                 155                 160

Ala Ala Ile Leu Ala Tyr Thr Ile Gly Thr Thr His Phe Gln Arg Ala
                165                 170                 175

Leu Ile Phe Ile Leu Leu Thr Ala Val Thr Pro Ser Met Thr Met Arg
            180                 185                 190

Cys Ile Gly Met Ser Asn Arg Asp Phe Val Glu Gly Val Ser Gly Gly
        195                 200                 205

Ser Trp Val Asp Ile Val Leu Glu His Gly Ser Cys Val Thr Thr Met
    210                 215                 220

Ala Lys Asn Lys Pro Thr Leu Asp Phe Glu Leu Ile Lys Thr Glu Ala
225                 230                 235                 240

Lys Gln Pro Ala Thr Leu Arg Lys Tyr Cys Ile Glu Ala Lys Leu Thr
                245                 250                 255

Asn Thr Thr Thr Glu Ser Arg Cys Pro Thr Gln Gly Glu Pro Ser Leu
            260                 265                 270

Asn Glu Glu Gln Asp Lys Arg Phe Val Cys Lys His Ser Met Val Asp
        275                 280                 285

Arg Gly Trp Gly Asn Gly Cys Gly Leu Phe Gly Lys Gly Gly Ile Val
    290                 295                 300

Thr Cys Ala Met Phe Arg Cys Lys Lys Asn Met Glu Gly Lys Val Val
305                 310                 315                 320
```

-continued

```
Gln Pro Glu Asn Leu Glu Tyr Thr Ile Val Ile Thr Pro His Ser Gly
                325                 330                 335

Glu Glu His Ala Val Gly Asn Asp Thr Gly Lys His Gly Lys Glu Ile
            340                 345                 350

Lys Ile Thr Pro Gln Ser Ser Ile Thr Glu Ala Glu Leu Thr Gly Tyr
        355                 360                 365

Gly Thr Val Thr Met Glu Cys Ser Pro Arg Thr Gly Leu Asp Phe Asn
    370                 375                 380

Glu Met Val Leu Leu Gln Met Glu Asn Lys Ala Trp Leu Val His Arg
385                 390                 395                 400

Gln Trp Phe Leu Asp Leu Pro Leu Pro Trp Leu Pro Gly Ala Asp Thr
                405                 410                 415

Gln Gly Ser Asn Trp Ile Gln Lys Glu Thr Leu Val Thr Phe Lys Asn
            420                 425                 430

Pro His Ala Lys Lys Gln Asp Val Val Val Leu Gly Ser Gln Glu Gly
        435                 440                 445

Ala Met His Thr Ala Leu Thr Gly Ala Thr Glu Ile Gln Met Ser Ser
    450                 455                 460

Gly Asn Leu Leu Phe Thr Gly His Leu Lys Cys Arg Leu Arg Met Asp
465                 470                 475                 480

Lys Leu Gln Leu Lys Gly Met Ser Tyr Ser Met Cys Thr Gly Lys Phe
                485                 490                 495

Lys Val Val Lys Glu Ile Ala Glu Thr Gln His Gly Thr Ile Val Ile
            500                 505                 510

Arg Val Gln Tyr Glu Gly Asp Gly Ser Pro Cys Lys Ile Pro Phe Glu
        515                 520                 525

Ile Met Asp Leu Glu Lys Arg His Val Leu Gly Arg Leu Ile Thr Val
    530                 535                 540

Asn Pro Ile Val Thr Glu Lys Asp Ser Pro Val Asn Ile Glu Ala Glu
545                 550                 555                 560

Pro Pro Phe Gly Asp Ser His Ile Ile Ile Gly Val Glu Pro Gly Gln
                565                 570                 575

Leu Lys Leu Asn Trp Phe Lys Lys Gly Ser Ser Ile Gly Gln Met Phe
            580                 585                 590

Glu Thr Thr Met Arg Gly Ala Lys Arg Met Ala Ile Leu Gly Asp Thr
        595                 600                 605

Ala Trp Asp Phe Gly Ser Leu Gly Gly Val Phe Thr Ser Ile Gly Lys
    610                 615                 620

Ala Leu His Gln Val Phe Gly Gly Ala Phe Arg Thr Leu Phe Gly Gly
625                 630                 635                 640

Met Ser Trp Ile Thr Gln Gly Leu Met Gly Ala Leu Leu Leu Trp Met
                645                 650                 655

Gly Val Asn Ala Arg Asp Arg Ser Ile Ala Leu Ala Phe Leu Ala Thr
            660                 665                 670

Gly Gly Val Leu Val Phe Leu Ala Thr Asn Val His Ala
        675                 680                 685
```

<210> SEQ ID NO 46
<211> LENGTH: 5293
<212> TYPE: DNA
<213> ORGANISM: Artificial Sequence
<220> FEATURE:
<223> OTHER INFORMATION: Description of artificial sequence; note =
synthetic construct
<220> FEATURE:
<221> NAME/KEY: CDS -continued

<222> LOCATION: (910)..(2964)

<400> SEQUENCE: 46

```
gacggatcgg gagatctccc gatcccctat ggtcgactct cagtacaatc tgctctgatg      60

ccgcatagtt aagccagtat ctgctccctg cttgtgtgtt ggaggtcgct gagtagtgcg     120

cgagcaaaat ttaagctaca acaaggcaag gcttgaccga caattgcatg aagaatctgc     180

ttagggttag gcgttttgcg ctgcttcgcg atgtacgggc cagatatacg cgttgacatt     240

gattattgac tagttattaa tagtaatcaa ttacggggtc attagttcat agcccatata     300

tggagttccg cgttacataa cttacggtaa atggcccgcc tggctgaccg cccaacgacc     360

cccgcccatt gacgtcaata atgacgtatg ttcccatagt aacgccaata gggactttcc     420

attgacgtca atgggtggac tatttacggt aaactgccca cttggcagta catcaagtgt     480

atcatatgcc aagtacgccc cctattgacg tcaatgacgg taaatggccc gcctggcatt     540

atgcccagta catgacctta tgggactttc ctacttggca gtacatctac gtattagtca     600

tcgctattac catggtgatg cggttttggc agtacatcaa tgggcgtgga tagcggtttg     660

actcacgggg atttccaagt ctccacccca ttgacgtcaa tgggagtttg ttttggcacc     720

aaaatcaacg ggactttcca aaatgtcgta acaactccgc cccattgacg caaatgggcg     780

gtaggcgtgt acggtgggag gtctatataa gcagagctct ctggctaact agagaaccca     840

ctgcttactg gcttatcgaa attaatacga ctcactatag ggagacccaa gcttggtacc     900

gccgccgcc atg ggc aag agg tcc gcc ggc tca atc atg tgg ctc gcg agc     951
          Met Gly Lys Arg Ser Ala Gly Ser Ile Met Trp Leu Ala Ser
          1               5                   10

ttg gca gtt gtc ata gct tgt gca ggc gcc ttc cat tta acc aca cgt      999
Leu Ala Val Val Ile Ala Cys Ala Gly Ala Phe His Leu Thr Thr Arg
15                  20                  25                  30

aac gga gaa cca cac atg atc gtc agc aga caa gag aaa ggg aaa agt     1047
Asn Gly Glu Pro His Met Ile Val Ser Arg Gln Glu Lys Gly Lys Ser
                35                  40                  45

ctt ctg ttt aaa aca gag gat ggc gtg aac atg tgt acc ctc atg gcc     1095
Leu Leu Phe Lys Thr Glu Asp Gly Val Asn Met Cys Thr Leu Met Ala
            50                  55                  60

atg gac ctt ggt gaa ttg tgt gaa gac aca atc acg tac aag tgt ccc     1143
Met Asp Leu Gly Glu Leu Cys Glu Asp Thr Ile Thr Tyr Lys Cys Pro
        65                  70                  75

ctt ctc agg cag aat gag cca gaa gac ata gac tgt tgg tgc aac tct     1191
Leu Leu Arg Gln Asn Glu Pro Glu Asp Ile Asp Cys Trp Cys Asn Ser
    80                  85                  90

acg tcc acg tgg gta act tat ggg acg tgt acc acc atg gga gaa cat     1239
Thr Ser Thr Trp Val Thr Tyr Gly Thr Cys Thr Thr Met Gly Glu His
95                  100                 105                 110

aga aga gaa aaa aga tca gtg gca ctc gtt cca cat gtg gga atg gga     1287
Arg Arg Glu Lys Arg Ser Val Ala Leu Val Pro His Val Gly Met Gly
                115                 120                 125

ctg gag aca cga act gaa aca tgg atg tca tca gaa ggg gcc tgg aaa     1335
Leu Glu Thr Arg Thr Glu Thr Trp Met Ser Ser Glu Gly Ala Trp Lys
            130                 135                 140

cat gtc cag aga att gaa act tgg atc ttg aga cat cca ggc ttc acc     1383
His Val Gln Arg Ile Glu Thr Trp Ile Leu Arg His Pro Gly Phe Thr
        145                 150                 155

atg atg gca gca atc ctg gca tac acc ata gga acg aca cat ttc caa     1431
Met Met Ala Ala Ile Leu Ala Tyr Thr Ile Gly Thr Thr His Phe Gln
    160                 165                 170

aga gcc ctg att ttc atc tta ctg aca gct gtc act cct tca atg aca     1479
```

-continued

```
Arg Ala Leu Ile Phe Ile Leu Leu Thr Ala Val Thr Pro Ser Met Thr
175                 180                 185                 190

atg cgt tgc ata gga atg tca aat aga gac ttt gtg gaa ggg gtt tca      1527
Met Arg Cys Ile Gly Met Ser Asn Arg Asp Phe Val Glu Gly Val Ser
                195                 200                 205

gga gga agc tgg gtt gac ata gtc tta gaa cat ggg agc tgt gtg acg      1575
Gly Gly Ser Trp Val Asp Ile Val Leu Glu His Gly Ser Cys Val Thr
            210                 215                 220

acg atg gca aaa aac aaa cca aca ttg gat ttt gaa ctg ata aaa aca      1623
Thr Met Ala Lys Asn Lys Pro Thr Leu Asp Phe Glu Leu Ile Lys Thr
        225                 230                 235

gaa gcc aaa cag cct gcc acc cta agg aag tac tgt ata gag gca aag      1671
Glu Ala Lys Gln Pro Ala Thr Leu Arg Lys Tyr Cys Ile Glu Ala Lys
    240                 245                 250

cta acc aac aca aca aca gaa tct cgc tgc cca aca caa ggg gaa ccc      1719
Leu Thr Asn Thr Thr Thr Glu Ser Arg Cys Pro Thr Gln Gly Glu Pro
255                 260                 265                 270

agc cta aat gaa gag cag gac aaa agg ttc gtc tgc aaa cac tcc atg      1767
Ser Leu Asn Glu Glu Gln Asp Lys Arg Phe Val Cys Lys His Ser Met
                275                 280                 285

gta gac aga gga tgg gga aat gga tgt gga cta ttt gga aag gga ggc      1815
Val Asp Arg Gly Trp Gly Asn Gly Cys Gly Leu Phe Gly Lys Gly Gly
            290                 295                 300

att gtg acc tgt gct atg ttc aga tgc aaa aag aac atg gaa gga aaa      1863
Ile Val Thr Cys Ala Met Phe Arg Cys Lys Lys Asn Met Glu Gly Lys
        305                 310                 315

gtt gtg caa cca gaa aac ttg gaa tac acc att gtg ata aca cct cac      1911
Val Val Gln Pro Glu Asn Leu Glu Tyr Thr Ile Val Ile Thr Pro His
    320                 325                 330

tca ggg gaa gag cat gca gtc gga aat gac aca gga aaa cat ggc aag      1959
Ser Gly Glu Glu His Ala Val Gly Asn Asp Thr Gly Lys His Gly Lys
335                 340                 345                 350

gaa atc aaa ata aca cca cag agt tcc atc aca gaa gca gaa ttg aca      2007
Glu Ile Lys Ile Thr Pro Gln Ser Ser Ile Thr Glu Ala Glu Leu Thr
                355                 360                 365

ggt tat ggc act gtc aca atg gag tgc tct cca aga acg ggc ctc gac      2055
Gly Tyr Gly Thr Val Thr Met Glu Cys Ser Pro Arg Thr Gly Leu Asp
            370                 375                 380

ttc aat gag atg gtg ttg ttg cag atg gaa aat aaa gct tgg ctg gtg      2103
Phe Asn Glu Met Val Leu Leu Gln Met Glu Asn Lys Ala Trp Leu Val
        385                 390                 395

cac agg caa tgg ttc cta gac ctg ccg tta cca tgg ttg ccc gga gcg      2151
His Arg Gln Trp Phe Leu Asp Leu Pro Leu Pro Trp Leu Pro Gly Ala
    400                 405                 410

gac aca caa ggg tca aat tgg ata cag aaa gag aca ttg gtc act ttc      2199
Asp Thr Gln Gly Ser Asn Trp Ile Gln Lys Glu Thr Leu Val Thr Phe
415                 420                 425                 430

aaa aat ccc cat gcg aag aaa cag gat gtt gtt gtt tta gga tcc caa      2247
Lys Asn Pro His Ala Lys Lys Gln Asp Val Val Val Leu Gly Ser Gln
                435                 440                 445

gaa ggg gcc atg cac aca gca ctt aca ggg gcc aca gaa atc caa atg      2295
Glu Gly Ala Met His Thr Ala Leu Thr Gly Ala Thr Glu Ile Gln Met
            450                 455                 460

tca tca gga aac tta ctc ttc aca gga cat ctc aag tgc agg ctg aga      2343
Ser Ser Gly Asn Leu Leu Phe Thr Gly His Leu Lys Cys Arg Leu Arg
        465                 470                 475

atg gac aag cta cag ctc aaa gga atg tca tac tct atg tgc aca gga      2391
Met Asp Lys Leu Gln Leu Lys Gly Met Ser Tyr Ser Met Cys Thr Gly
    480                 485                 490
```

-continued

```
aag ttt aaa gtt gtg aag gaa ata gca gaa aca caa cat gga aca ata      2439
Lys Phe Lys Val Val Lys Glu Ile Ala Glu Thr Gln His Gly Thr Ile
495                 500                 505                 510

gtt atc aga gtg caa tat gaa ggg gac ggc tct cca tgc aag atc cct      2487
Val Ile Arg Val Gln Tyr Glu Gly Asp Gly Ser Pro Cys Lys Ile Pro
                515                 520                 525

ttt gag ata atg gat ttg gaa aaa aga cat gtc tta ggt cgc ctg att      2535
Phe Glu Ile Met Asp Leu Glu Lys Arg His Val Leu Gly Arg Leu Ile
            530                 535                 540

aca gtc aac cca att gtg aca gaa aaa gat agc cca gtc aac ata gaa      2583
Thr Val Asn Pro Ile Val Thr Glu Lys Asp Ser Pro Val Asn Ile Glu
        545                 550                 555

gca gaa cct cca ttc gga gac agc tac atc atc ata gga gta gag ccg      2631
Ala Glu Pro Pro Phe Gly Asp Ser Tyr Ile Ile Ile Gly Val Glu Pro
    560                 565                 570

gga caa ctg aag ctc aac tgg ttt aag aaa gga agc acg ctg ggc aag      2679
Gly Gln Leu Lys Leu Asn Trp Phe Lys Lys Gly Ser Thr Leu Gly Lys
575                 580                 585                 590

gcc ttt tca aca act ttg aag gga gct caa aga ctg gca gcg ttg ggc      2727
Ala Phe Ser Thr Thr Leu Lys Gly Ala Gln Arg Leu Ala Ala Leu Gly
                595                 600                 605

gac aca gcc tgg gac ttt ggc tct att gga ggg gtc ttc aac tcc ata      2775
Asp Thr Ala Trp Asp Phe Gly Ser Ile Gly Gly Val Phe Asn Ser Ile
            610                 615                 620

gga aaa gcc gtt cac caa gtg ttt ggt ggt gcc ttc aga aca ctc ttt      2823
Gly Lys Ala Val His Gln Val Phe Gly Gly Ala Phe Arg Thr Leu Phe
        625                 630                 635

ggg gga atg tct tgg atc aca caa ggg cta atg ggt gcc cta ctg ctc      2871
Gly Gly Met Ser Trp Ile Thr Gln Gly Leu Met Gly Ala Leu Leu Leu
    640                 645                 650

tgg atg ggc gtc aac gca cga gac cga tca att gct ttg gcc ttc tta      2919
Trp Met Gly Val Asn Ala Arg Asp Arg Ser Ile Ala Leu Ala Phe Leu
655                 660                 665                 670

gcc aca ggg ggt gtg ctc gtg ttc tta gcg acc aat gtg cat gct          2964
Ala Thr Gly Gly Val Leu Val Phe Leu Ala Thr Asn Val His Ala
                675                 680                 685

taattagttt gagcggccgc tcgagcatgc atctagaggg ccctattcta tagtgtcacc   3024

taaatgctag agctcgctga tcagcctcga ctgtgccttc tagttgccag ccatctgttg   3084

tttgcccctc ccccgtgcct tccttgaccc tggaaggtgc cactcccact gtcctttcct   3144

aataaaatga ggaaattgca tcgcattgtc tgagtaggtg tcattctatt ctggggggtg   3204

gggtggggca ggacagcaag ggggaggatt gggaagacaa tagcaggcat gctggggatg   3264

cggtgggctc tatggcttct gaggcggaaa gaaccagctg cattaatgaa tcggccaacg   3324

cgcggggaga ggcggtttgc gtattgggcg ctcttccgct tcctcgctca ctgactcgct   3384

gcgctcggtc gttcggctgc ggcgagcggt atcagctcac tcaaaggcgg taatacggtt   3444

atccacagaa tcaggggata acgcaggaaa gaacatgtga gcaaaaggcc agcaaaaggc   3504

caggaaccgt aaaaaggccg cgttgctggc gtttttccat aggctccgcc cccctgacga   3564

gcatcacaaa aatcgacgct caagtcagag gtggcgaaac ccgacaggac tataaagata   3624

ccaggcgttt ccccctggaa gctccctcgt gcgctctcct gttccgaccc tgccgcttac   3684

cggatacctg tccgcctttc tcccttcggg aagcgtggcg ctttctcaat gctcacgctg   3744

taggtatctc agttcggtgt aggtcgttcg ctccaagctg ggctgtgtgc acgaaccccc   3804

cgttcagccc gaccgctgcg ccttatccgg taactatcgt cttgagtcca acccggtaag   3864

acacgactta tcgccactgg cagcagccac tggtaacagg attagcagag cgaggtatgt   3924
```

-continued

```
aggcggtgct acagagttct tgaagtggtg gcctaactac ggctacacta gaaggacagt   3984

atttggtatc tgcgctctgc tgaagccagt taccttcgga aaaagagttg gtagctcttg   4044

atccggcaaa caaaccaccg ctggtagcgg tggttttttt gtttgcaagc agcagattac   4104

gcgcagaaaa aaaggatctc aagaagatcc tttgatcttt tctacggggt ctgacgctca   4164

gtggaacgaa aactcacgtt aagggatttt ggtcatgaga ttatcaaaaa ggatcttcac   4224

ctagatcctt ttaaattaaa aatgaagttt taaatcaatc taaagtatat atgagtaaac   4284

ttggtctgac agttaccaat gcttaatcag tgaggcacct atctcagcga tctgtctatt   4344

tcgttcatcc atagttgcct gactccccgt cgtgtagata actacgatac gggagggctt   4404

accatctggc cccagtgctg caatgatacc gcgagaccca cgctcaccgg ctccagattt   4464

atcagcaata aaccagccag ccggaagggc cgagcgcaga agtggtcctg caactttatc   4524

cgcctccatc cagtctatta attgttgccg ggaagctaga gtaagtagtt cgccagttaa   4584

tagtttgcgc aacgttgttg ccattgctac aggcatcgtg gtgtcacgct cgtcgtttgg   4644

tatggcttca ttcagctccg gttcccaacg atcaaggcga gttacatgat cccccatgtt   4704

gtgcaaaaaa gcggttagct ccttcggtcc tccgatcgtt gtcagaagta agttggccgc   4764

agtgttatca ctcatggtta tggcagcact gcataattct cttactgtca tgccatccgt   4824

aagatgcttt tctgtgactg gtgagtactc aaccaagtca ttctgagaat agtgtatgcg   4884

gcgaccgagt tgctcttgcc cggcgtcaat acgggataat accgcgccac atagcagaac   4944

tttaaaagtg ctcatcattg gaaaacgttc ttcggggcga aaactctcaa ggatcttacc   5004

gctgttgaga tccagttcga tgtaacccac tcgtgcaccc aactgatctt cagcatcttt   5064

tactttcacc agcgtttctg ggtgagcaaa aacaggaagg caaaatgccg caaaaaaggg   5124

aataagggcg acacggaaat gttgaatact catactcttc ctttttcaat attattgaag   5184

catttatcag ggttattgtc tcatgagcgg atacatattt gaatgtattt agaaaaataa   5244

acaaataggg gttccgcgca catttccccg aaaagtgcca cctgacgtc              5293
```

```
<210> SEQ ID NO 47
<211> LENGTH: 685
<212> TYPE: PRT
<213> ORGANISM: Artificial Sequence
<220> FEATURE:
<223> OTHER INFORMATION: Synthetic Construct

<400> SEQUENCE: 47

Met Gly Lys Arg Ser Ala Gly Ser Ile Met Trp Leu Ala Ser Leu Ala
1               5                   10                  15

Val Val Ile Ala Cys Ala Gly Ala Phe His Leu Thr Thr Arg Asn Gly
            20                  25                  30

Glu Pro His Met Ile Val Ser Arg Gln Glu Lys Gly Lys Ser Leu Leu
        35                  40                  45

Phe Lys Thr Glu Asp Gly Val Asn Met Cys Thr Leu Met Ala Met Asp
    50                  55                  60

Leu Gly Glu Leu Cys Glu Asp Thr Ile Thr Tyr Lys Cys Pro Leu Leu
65                  70                  75                  80

Arg Gln Asn Glu Pro Glu Asp Ile Asp Cys Trp Cys Asn Ser Thr Ser
                85                  90                  95

Thr Trp Val Thr Tyr Gly Thr Cys Thr Thr Met Gly Glu His Arg Arg
            100                 105                 110

Glu Lys Arg Ser Val Ala Leu Val Pro His Val Gly Met Gly Leu Glu
```

-continued

```
        115                 120                 125

Thr Arg Thr Glu Thr Trp Met Ser Ser Glu Gly Ala Trp Lys His Val
    130                 135                 140

Gln Arg Ile Glu Thr Trp Ile Leu Arg His Pro Gly Phe Thr Met Met
145                 150                 155                 160

Ala Ala Ile Leu Ala Tyr Thr Ile Gly Thr Thr His Phe Gln Arg Ala
                165                 170                 175

Leu Ile Phe Ile Leu Leu Thr Ala Val Thr Pro Ser Met Thr Met Arg
            180                 185                 190

Cys Ile Gly Met Ser Asn Arg Asp Phe Val Glu Gly Val Ser Gly Gly
        195                 200                 205

Ser Trp Val Asp Ile Val Leu Glu His Gly Ser Cys Val Thr Thr Met
    210                 215                 220

Ala Lys Asn Lys Pro Thr Leu Asp Phe Glu Leu Ile Lys Thr Glu Ala
225                 230                 235                 240

Lys Gln Pro Ala Thr Leu Arg Lys Tyr Cys Ile Glu Ala Lys Leu Thr
                245                 250                 255

Asn Thr Thr Thr Glu Ser Arg Cys Pro Thr Gln Gly Glu Pro Ser Leu
            260                 265                 270

Asn Glu Glu Gln Asp Lys Arg Phe Val Cys Lys His Ser Met Val Asp
        275                 280                 285

Arg Gly Trp Gly Asn Gly Cys Gly Leu Phe Gly Lys Gly Gly Ile Val
    290                 295                 300

Thr Cys Ala Met Phe Arg Cys Lys Lys Asn Met Glu Gly Lys Val Val
305                 310                 315                 320

Gln Pro Glu Asn Leu Glu Tyr Thr Ile Val Ile Thr Pro His Ser Gly
                325                 330                 335

Glu Glu His Ala Val Gly Asn Asp Thr Gly Lys His Gly Lys Glu Ile
            340                 345                 350

Lys Ile Thr Pro Gln Ser Ser Ile Thr Glu Ala Glu Leu Thr Gly Tyr
        355                 360                 365

Gly Thr Val Thr Met Glu Cys Ser Pro Arg Thr Gly Leu Asp Phe Asn
    370                 375                 380

Glu Met Val Leu Leu Gln Met Glu Asn Lys Ala Trp Leu Val His Arg
385                 390                 395                 400

Gln Trp Phe Leu Asp Leu Pro Leu Pro Trp Leu Pro Gly Ala Asp Thr
                405                 410                 415

Gln Gly Ser Asn Trp Ile Gln Lys Glu Thr Leu Val Thr Phe Lys Asn
            420                 425                 430

Pro His Ala Lys Lys Gln Asp Val Val Val Leu Gly Ser Gln Glu Gly
        435                 440                 445

Ala Met His Thr Ala Leu Thr Gly Ala Thr Glu Ile Gln Met Ser Ser
    450                 455                 460

Gly Asn Leu Leu Phe Thr Gly His Leu Lys Cys Arg Leu Arg Met Asp
465                 470                 475                 480

Lys Leu Gln Leu Lys Gly Met Ser Tyr Ser Met Cys Thr Gly Lys Phe
                485                 490                 495

Lys Val Val Lys Glu Ile Ala Glu Thr Gln His Gly Thr Ile Val Ile
            500                 505                 510

Arg Val Gln Tyr Glu Gly Asp Gly Ser Pro Cys Lys Ile Pro Phe Glu
        515                 520                 525

Ile Met Asp Leu Glu Lys Arg His Val Leu Gly Arg Leu Ile Thr Val
    530                 535                 540
```

-continued

Asn Pro Ile Val Thr Glu Lys Asp Ser Pro Val Asn Ile Glu Ala Glu
545 550 555 560

Pro Pro Phe Gly Asp Ser Tyr Ile Ile Ile Gly Val Glu Pro Gly Gln
565 570 575

Leu Lys Leu Asn Trp Phe Lys Lys Gly Ser Thr Leu Gly Lys Ala Phe
580 585 590

Ser Thr Thr Leu Lys Gly Ala Gln Arg Leu Ala Ala Leu Gly Asp Thr
595 600 605

Ala Trp Asp Phe Gly Ser Ile Gly Gly Val Phe Asn Ser Ile Gly Lys
610 615 620

Ala Val His Gln Val Phe Gly Gly Ala Phe Arg Thr Leu Phe Gly Gly
625 630 635 640

Met Ser Trp Ile Thr Gln Gly Leu Met Gly Ala Leu Leu Leu Trp Met
645 650 655

Gly Val Asn Ala Arg Asp Arg Ser Ile Ala Leu Ala Phe Leu Ala Thr
660 665 670

Gly Gly Val Leu Val Phe Leu Ala Thr Asn Val His Ala
675 680 685

<210> SEQ ID NO 48
<211> LENGTH: 34
<212> TYPE: DNA
<213> ORGANISM: Artificial Sequence
<220> FEATURE:
<223> OTHER INFORMATION: Description of artificial sequence; note = synthetic construct

<400> SEQUENCE: 48
tgtgcaggcg ccttccattt aaccacacgt aacg 34

<210> SEQ ID NO 49
<211> LENGTH: 40
<212> TYPE: DNA
<213> ORGANISM: Artificial Sequence
<220> FEATURE:
<223> OTHER INFORMATION: Description of artificial sequence; note = synthetic construct

<400> SEQUENCE: 49
tcgagcggcc gctcaactaa ttaggcctgc accatgactc 40

<210> SEQ ID NO 50
<211> LENGTH: 30
<212> TYPE: DNA
<213> ORGANISM: Artificial Sequence
<220> FEATURE:
<223> OTHER INFORMATION: Description of artificial sequence; note = synthetic construct

<400> SEQUENCE: 50
cttatcgaaa ttaatacgac tcactatagg 30

<210> SEQ ID NO 51
<211> LENGTH: 25
<212> TYPE: DNA
<213> ORGANISM: Artificial Sequence
<220> FEATURE:
<223> OTHER INFORMATION: Description of artificial sequence; note = synthetic construct

<400> SEQUENCE: 51
atagattgct ccaaacactt ggtgg 25

-continued

<210> SEQ ID NO 52
<211> LENGTH: 24
<212> TYPE: DNA
<213> ORGANISM: Artificial Sequence
<220> FEATURE:
<223> OTHER INFORMATION: Description of artificial sequence; note = synthetic construct

<400> SEQUENCE: 52
actccatagg aaaagccgtt cacc 24

<210> SEQ ID NO 53
<211> LENGTH: 30
<212> TYPE: DNA
<213> ORGANISM: Artificial Sequence
<220> FEATURE:
<223> OTHER INFORMATION: Description of artificial sequence; note = synthetic construct

<400> SEQUENCE: 53
gcgagctcta gcatttaggt gacactatag 30

<210> SEQ ID NO 54
<211> LENGTH: 33
<212> TYPE: DNA
<213> ORGANISM: Artificial Sequence
<220> FEATURE:
<223> OTHER INFORMATION: Description of artificial sequence; note = synthetic construct

<400> SEQUENCE: 54
ctccaccaag tgtttggtgg tgccttcaga aca 33

<210> SEQ ID NO 55
<211> LENGTH: 11
<212> TYPE: PRT
<213> ORGANISM: Artificial Sequence
<220> FEATURE:
<223> OTHER INFORMATION: Description of artificial sequence; note = synthetic construct

<400> SEQUENCE: 55

Leu His Gln Val Phe Gly Gly Ala Phe Arg Thr
1 5 10

<210> SEQ ID NO 56
<211> LENGTH: 30
<212> TYPE: DNA
<213> ORGANISM: Artificial Sequence
<220> FEATURE:
<223> OTHER INFORMATION: Description of artificial sequence; note = synthetic construct

<400> SEQUENCE: 56
cttatcgaaa ttaatacgac tcactatagg 30

<210> SEQ ID NO 57
<211> LENGTH: 39
<212> TYPE: DNA
<213> ORGANISM: Artificial Sequence
<220> FEATURE:
<223> OTHER INFORMATION: Description of artificial sequence; note = synthetic construct

<400> SEQUENCE: 57
gaattcgtct cacttccttt cttaaaccag ttgagcttc 39

-continued

<210> SEQ ID NO 58
<211> LENGTH: 31
<212> TYPE: DNA
<213> ORGANISM: Artificial Sequence
<220> FEATURE:
<223> OTHER INFORMATION: Description of artificial sequence; note = synthetic construct

<400> SEQUENCE: 58
ggaattcgtc tcggaagcac gctgggcaag g 31

<210> SEQ ID NO 59
<211> LENGTH: 30
<212> TYPE: DNA
<213> ORGANISM: Artificial Sequence
<220> FEATURE:
<223> OTHER INFORMATION: Description of artificial sequence; note = synthetic construct

<400> SEQUENCE: 59
gcgagctcta gcatttaggt gacactatag 30

<210> SEQ ID NO 60
<211> LENGTH: 33
<212> TYPE: DNA
<213> ORGANISM: Artificial Sequence
<220> FEATURE:
<223> OTHER INFORMATION: Description of artificial sequence; note = synthetic construct

<400> SEQUENCE: 60
aactggttta agaaaggaag cacgctgggc gcc 33

<210> SEQ ID NO 61
<211> LENGTH: 11
<212> TYPE: PRT
<213> ORGANISM: Artificial Sequence
<220> FEATURE:
<223> OTHER INFORMATION: Description of artificial sequence; note = synthetic construct

<400> SEQUENCE: 61

```
Asn Trp Lys Lys Gly Ser Thr Leu Gly Lys Ala
1               5                   10
```

<210> SEQ ID NO 62
<211> LENGTH: 33
<212> TYPE: PRT
<213> ORGANISM: Artificial Sequence
<220> FEATURE:
<223> OTHER INFORMATION: Synthetic construct

<400> SEQUENCE: 62

```
Met Gly Lys Arg Ser Ala Gly Ser Ile Met Trp Leu Ala Ser Leu Ala
1               5                   10                  15

Val Val Ile Ala Cys Ala Gly Ala Met Lys Leu Ser Asn Phe Gln Gly
            20                  25                  30

Lys
```

<210> SEQ ID NO 63
<211> LENGTH: 39
<212> TYPE: PRT
<213> ORGANISM: Artificial Sequence
<220> FEATURE:
<223> OTHER INFORMATION: Synthetic construct -continued

```
<400> SEQUENCE: 63

Met Gly Arg Lys Gln Asn Lys Arg Gly Gly Asn Glu Gly Ser Ile Met
1               5                   10                  15

Trp Leu Ala Ser Leu Ala Val Val Ile Ala Gly Thr Ser Ala Met Lys
            20                  25                  30

Leu Ser Asn Phe Gln Gly Lys
        35


<210> SEQ ID NO 64
<211> LENGTH: 33
<212> TYPE: PRT
<213> ORGANISM: Artificial Sequence
<220> FEATURE:
<223> OTHER INFORMATION: Synthetic construct

<400> SEQUENCE: 64

Met Gly Lys Arg Ser Ala Gly Ser Ile Met Trp Leu Ala Ser Leu Ala
1               5                   10                  15

Val Val Ile Ala Gly Thr Ser Ala Met Lys Leu Ser Asn Phe Gln Gly
            20                  25                  30

Lys
```

NUCLEIC ACIDS ENCODING CHIMERIC *FLAVIVIRUS* IMMUNOGENS COMPRISING THE JAPANESE ENCEPHALITIS VIRUS (JEV) PRM SIGNAL SEQUENCE

CROSS REFERENCE TO RELATED APPLICATIONS

This is a §371 U.S. national stage of PCT/US02/10764, filed Apr. 4, 2002, which was published in English under PCT Article 2(2), which is a continuation-in-part of, and claims the benefit of U.S. patent application Ser. No. 09/826,115, filed Apr. 4, 2001, and issued as U.S. Pat. No. 7,227,011.

U.S. application Ser. No. 09/826,115 is a continuation-in-part of, and claims the benefit of U.S. application Ser. No. 09/701,536, filed Nov. 29, 2000, which status is pending. U.S. application Ser. No. 09/701,536 is a national stage application of international application Ser. No. PCT/US99/12298, filed Jun. 3, 1999, which claims the benefit of U.S. provisional application Ser. No. 60/087,908, filed Jun. 4. 1998. Each of the above-referenced applications is hereby incorporated by reference herein in its entirety.

FIELD OF THE INVENTION

This invention relates to novel vaccines, diagnostics and methods of using both in the treatment and prevention of the diseases caused by flaviviruses. In particular, the vaccines are recombinant nucleic acids which contain genes for structural proteins of flaviviruses, such as Japanese encephalitis virus (JEV), West Nile virus (WNV) or related flaviviruses. These vaccines serve as a transcriptional unit for the biosynthesis of the virus protein antigens when administered in vivo. The diagnostics are compositions containing antigens produced from the recombinant nucleic acids that can be used to detect *flavivirus* infection.

BACKGROUND OF THE INVENTION flaviviruses are members of the genus *Flavivirus*, which is classified within the family Flaviviridae. The flaviviruses are largely pathogenic to humans and other mammals. Flaviviruses that inflict disease upon humans and animals include Alfuy, Apoi, Aroa, Bagaza, Banzi, Batu Cave, Bouboui, Bukalasa bat, Bussuquara, Cacipacore, Carey Island, Cowbone Ridge, Dakar bat, Dengue (serotypes 1, 2, 3 and 4), Edge Hill, Entebbe bat, Gadgets Gully, Iguape, Ilheus, Israel turkey meningoencephalitis, Japanese encephalitis, Jugra, Jutiapa, Kadam, Karshi, Kedougou, Kokobera, Koutango, Kunjin, Kyasanur Forest disease, Langat, Meaban, Modoc, Montana myotis leukoencephalitis, Murray Valley encephalitis, Naranjal, Negishi, Ntaya, Omsk hemorrhagic fever, Phnom Penh bat, Potiskum, Powassan, Rio Bravo, Rocio, Royal Farm, Russian spring summer encephalitis, Saboya, Sal Vieja, San Perlita, Saumarez Reef, Sepik, Sokuluk, Spondweni, St. Louis encephalitis, Stratford, Tick-borne encephalitis—central European subtype, Tick-borne encephalititis—far eastern subtype, Tembusu, THCAr, Tyuleniy, Uganda S, Usutu, West Nile, Yaounde, Yellow fever, Yokose, Ziki, Cell fusing agent and other related flaviviruses, as listed in Kuno et al. (*J. Virol.* 72: 73-83 (1998)).

The flaviviruses contain the following three structural proteins: prM/M, the premembrane and membrane protein; E, the envelope protein; and C, the capsid protein. (Monath, in *Virology* (Fields, ed.), Raven Press, New York, 1990, pp. 763-814; Heinz and Roehrig, in *Immunochemistry of Viruses II: The Basis for Serodiagnosis and Vaccines* (van Regenmortel and Neurath, eds.), Elsevier, Amsterdam, 1990, pp. 289-305). M has a molecular weight (MW) of about 7-8 kilodaltons (kDa) and E has a MW of about 55-60 kDa. M is synthesized as a larger precursor termed prM. The pr portion of prM is removed when prM is processed to form M protein in mature virions. M and E are located in the membrane of the *flavivirus* particle, and so have long been considered to constitute important immunogenic components of the viruses.

The flaviviruses are RNA viruses comprising single stranded RNA having a length, among the various species, of about 10 kilobases (kb). The C protein, with a MW of 12-14 kDa, complexes with the RNA to form a nucleocapsid complex. Several nonstructural proteins are also encoded by the RNA genome which are termed NS1, NS2A, NS2B, NS3, NS4A, NS4B and NS5. The genome is translated within the host cell as a polyprotein, then processed co- or post-translationally into the individual gene products by viral- or host-specific proteases (FIG. 1).

The nucleotide sequences of the genomes of several flaviviruses are known, as summarized in U.S. Pat. No. 5,494,671. That for JEV is provided by Sumiyoshi et al. (*Virology* 161: 497-510 (1987)) and Hashimoto et al. (*Virus Genes* 1: 305-317 (1988)). The nucleotide sequences of the virulent strain SA-14 of JEV and the attenuated strain SA-14-14-2, used as a vaccine in the People's Republic of China, are compared in the work of Nitayaphan et al. (*Virology* 177: 541-552 (1990)).

Nucleotide sequences encoding the structural proteins of other *flavivirus* species are also known. In many cases, the sequences for the complete genomes have been reported. The sequences available include dengue serotype 1 virus, dengue serotype 2 virus (Deubel et al., *Virology* 155: 365-377 (1986); Gruenberg et al., *J. Gen. Virol.* 69: 1391-1398 (1988); Hahn et al. *Virology* 162: 167-180 (1988)), dengue serotype 3 virus (Osatomi et al., *Virus Genes* 2: 99-108 (1988)), dengue serotype 4 virus (Mackow et al., *Virology* 159: 217-228 (1987), Zhao et al., *Virology* 155: 77-88 (1986)), West Nile virus (Lanciotti et al., *Science* 286: 2331-2333 (1999)), Powassan virus (Mandl et al., *Virology* 194: 173-184 (1993)) and yellow fever virus (YFV) (Rice et al., *Science* 229: 726-733 (1985)).

Many flaviviruses, including St. Louis encephalitis virus (SLEV), WNV and JEV, are transmitted to humans and other host animals by mosquitoes. They therefore occur over widespread areas and their transmission is not easily interrupted or prevented.

West Nile fever is a mosquito-borne flaviviral infection that is transmitted to vertebrates primarily by various species of *Culex* mosquitoes. Like other members of the Japanese encephalitis (JE) antigenic complex of flaviviruses, including JE, SLE and Murray Valley encephalitis (MVE) viruses, WNV is maintained in a natural cycle between arthropod vectors and birds. The virus was first isolated from a febrile human in the West Nile district of Uganda in 1937 (Smithburn et al., *Am. J. Trop. Med. Hyg.* 20: 471-492 (1940)). It was soon recognized as one of the most widely distributed flaviviruses, with its geographic range including Africa, the Middle East, Western Asia, Europe and Australia (Hubalek et al., *Emerg. Infect. Dis.* 5: 643-50 (1999)). Clinically, West Nile fever in humans is a self-limited acute febrile illness accompanied by headache, myalgia, polyarthropathy, rash and lymphadenopathy (Monath and Tsai, in *Clinical Virology*, (Richman, Whitley and Hayden eds.), Churchill-Livingtone, New York, 1997, pp. 1133-1186). Acute hepatitis or pancreatis has been reported on occasion and cases of WNV infection in elderly patients are sometimes complicated by encephalitis or meningitis (Asnis et al., *Clin. Infect Dis.* 30: 413418 (2000)). Thus, infection by WNV is a serious health concern in many regions of the world.

The geographical spread of the disease, particularly the introduction of WNV into the U.S. in 1999, has greatly increased awareness of the human and animal health concerns of this disease. Between late August and early September 1999, New York City and surrounding areas experienced an outbreak of viral encephalitis, with 62 confirmed cases, resulting in seven deaths. Concurrent with this outbreak, local health officials observed increased mortality among birds (especially crows) and horses. The outbreak was subsequently shown to be caused by WNV, based on monoclonal antibody (Mab) mapping and detection of genomic sequences in human, avian and mosquito specimens (Anderson et al., *Science* 286: 2331-2333 (1999); Jia et al., *Lancet* 354: 1971-1972 (1999); Lanciotti et al., *Science* 286: 2333-2337 (1999)). Virus activity detected during the ensuing winter months indicated that the virus had established itself in North America (*Morb. Mortal. Wkly. Rep.* 49: 178-179 (2000); Asnis et al., *Clin. Infect. Dis.* 30: 413-418 (2000); Garmendia et al., *J. Clin. Micro.* 38: 3110-3111 (2000)). Surveillance data reported from the northeastern and mid-Atlantic states during the year 2000 confirmed an intensified epizootic/epidemic transmission and a geographic expansion of the virus with documentation of numerous cases of infection in birds, mosquitoes and horses, as well as cases in humans (*Morb. Mortal. Wkly. Rep.* 49: 820-822 (2000)).

Currently, no human or veterinary vaccine is available to prevent WNV infection and mosquito control is the only practical strategy to combat the spread of the disease.

Japanese encephalitis virus (JEV) infects adults and children and there is a high mortality rate among infants, children and the elderly in areas of tropical and subtropical Asia (Tsai et al., in *Vaccines* (Plotkin, ed.) W.B. Saunders, Philadelphia, Pa., 1999, pp. 672-710). Among survivors, there are serious neurological consequences, related to the symptoms of encephalitis, that persist after infection. In more developed countries of this region, such as Japan, the Republic of China (Taiwan) and Korea, JEV has been largely controlled by use of a vaccine of inactivated JEV. Nevertheless, it is still prevalent in other countries of the region.

Vaccines available for use against JEV infection include live virus inactivated by such methods as formalin treatment, as well as attenuated virus (Tsai et al., in *Vaccines* (Plotkin, ed.) W.B. Saunders, Philadelphia, Pa., 1994, pp. 671-713). Whole virus vaccines, although effective, do have certain problems and/or disadvantages. The viruses are cultivated in mouse brain or in cell culture using mammalian cells as the host. Such culture methods are cumbersome and expensive. Furthermore, there is the attendant risk of incorporating antigens from the host cells, i.e., the brain or other host, into the final vaccine product, potentially leading to unintended and undesired allergic responses in the vaccine recipients. There is also the risk of inadvertent infection among workers involved in vaccine production. Finally, there is the risk that the virus may not be fully or completely inactivated or attenuated and thus, the vaccine may actually cause disease.

Dengue fever and dengue hemorrhagic fever (DF/DHF) are caused by dengue virus, which is also a mosquito-borne *flavivirus*. There are four antigenically related, but distinct, dengue virus serotypes, (DEN-1, DEN-2, DEN-3 and DEN-4), all of which can cause DF/DHF. Symptoms of DF, the mild form of dengue-related disease, include fever, rash, severe headache and joint pain. Mortality among those subjects suffering from DF is low; however, among those subjects suffering from DHF, mortality can be as high as 5%. From available evidence, more than 3 million cases of DHF and 58,000 deaths have been attributed to DHF over the past 40 years, making DHF a major emerging disease (Halstead, in Dengue and Dengue Hemorrhagic Fever (Gubler and Kuno, eds.) CAB International, New York, N.Y., (1997) pp 23-44). Nevertheless, despite decades of effort, safe and effective vaccines to protect against dengue virus infection are not yet available.

Yellow fever is prevalent in tropical regions of South America and sub-Saharan Africa and is transmitted by mosquitos. Infection leads to fever, chills, severe headache and other pains, anorexia, nausea and vomiting, with the emergence of jaundice. A live virus vaccine, 17D, grown in infected chicken embryos, is considered safe and effective. Nevertheless, there remains a need for a vaccine that is stable under adverse conditions, such as are commonly encountered in the tropical regions of Africa and the Americas where the vaccine is most needed.

A recombinant *flavivirus* which is a chimera between two flaviviruses is disclosed in PCT publication WO 93/06214. The chimera is a construct fusing non-structural proteins from one "type," or serotype, of dengue virus or a *flavivirus*, with structural proteins from a different "type," or serotype, of dengue virus or other *flavivirus.*

Several recombinant subunit and viral vaccines have been devised in recent years. U.S. Pat. No. 4,810,492 describes the production of the E glycoprotein of JEV for use as the antigen in a vaccine. The corresponding DNA is cloned into an expression system in order to express the antigen protein in a suitable host cell such as *E. coli*, yeast, or a higher organism cell culture. U.S. Pat. No. 5,229,293 discloses recombinant baculovirus harboring the gene for JEV E protein. The virus is used to infect insect cells in culture such that the E protein is produced and recovered for use as a vaccine.

U.S. Pat. No. 5,021,347 discloses a recombinant vaccinia virus genome into which the gene for JEV E protein has been incorporated. The live recombinant vaccinia virus is used as the vaccine to immunize against JEV. Recombinant vaccinia viruses and baculoviruses in which the viruses incorporate a gene for a C-terminal truncation of the E protein of dengue serotype 2, dengue serotype 4 and JEV are disclosed in U.S. Pat. No. 5,494,671. U.S. Pat. No. 5,514,375 discloses various recombinant vaccinia viruses which express portions of the JEV open reading frame extending from prM to NS2B. These pox viruses induced formation of extracellular particles that contain the processed M protein and the E protein. Two recombinant viruses encoding these JEV proteins produced high titers of neutralizing and hemagglutinin-inhibiting antibodies, and protective immunity, in mice. The extent of these effects was greater after two immunization treatments than after only one. Recombinant vaccinia virus containing genes for the prM/M and E proteins of JEV conferred protective immunity when administered to mice (Konishi et al., *Virology* 180: 401-410 (1991)). HeLa cells infected with recombinant vaccinia virus bearing genes for prM and E from JEV were shown to produce subviral particles (Konishi et al., *Virology* 188: 714-720 (1992)). Dmitriev et al. reported immunization of mice with a recombinant vaccinia virus encoding structural and certain nonstructural proteins from tick-borne encephalitis virus (*J. Biotechnology* 44: 97-103 (1996)).

Recombinant virus vectors have also been prepared to serve as virus vaccines for dengue fever. Zhao et al. (*J. Virol.* 61: 4019-4022 (1987)) prepared recombinant vaccinia virus bearing structural proteins and NS1 from dengue serotype 4 and achieved expression after infecting mammalian cells with the recombinant virus. Similar expression was obtained using recombinant baculovirus to infect target insect cells (Zhang et al., *J. Virol.* 62: 3027-3031(1988)). Bray et al. (*J. Virol.* 63: 2853-2856 (1989)) also reported a recombinant vaccinia dengue vaccine based on the E protein gene that confers protective immunity to mice against dengue encephalitis when challenged. Falgout et al. (*J. Virol* 63: 1852-1860 (1989)) and Falgout et al. (*J. Virol.* 64: 4356-4363 (1990)) reported similar results. Zhang et al. (*J. Virol* 62: 3027-3031 (1988)) showed that recombinant baculovirus encoding dengue E and NS1 proteins likewise protected mice against dengue encephalitis when challenged. Other combinations in which structural and nonstructural genes were incorporated into recombinant virus vaccines failed to produce significant immunity (Bray et al., *J. Virol.* 63: 2853-2856 (1989)). Also, monkeys failed to develop fully protective immunity to dengue virus challenge when immunized with recombinant baculovirus expressing the E protein (Lai et al. (1990) pp. 119-124 in F. Brown, R. M. Chancock, H. S. Ginsberg and R. Lerner (eds.) *Vaccines* 90: Modern approaches to new vaccines including prevention of AIDS, Cold Spring Harbor Laboratory, Cold Spring Harbor, N.Y.).

Immunization using recombinant DNA preparations has been reported for SLEV and dengue-2 virus, using weanling mice as the model (Phillpotts et al., *Arch. Virol.* 141: 743-749 (1996); Kochel et al., *Vaccine* 15: 547-552 (1997)). Plasmid DNA encoding the prM and E genes of SLEV provided partial protection against SLEV challenge with a single or double dose of DNA immunization. In these experiments, control mice exhibited about 25% survival and no protective antibody was detected in the DNA-immunized mice (Phillpotts et al., *Arch. Virol.* 141: 743-749 (1996)). In mice that received three intradermal injections of recombinant dengue-2 plasmid DNA containing prM, 100% developed anti-dengue-2 neutralizing antibodies and 92% of those receiving the corresponding E gene likewise developed neutralizing antibodies (Kochel et al., *Vaccine* 15: 547-552 (1997)). Challenge experiments using a two-dose schedule, however, failed to protect mice against lethal dengue-2 virus challenge.

The vaccines developed to date for immunizing against infection by JEV, SLEV, dengue virus and other flaviviruses have a number of disadvantages and problems attending their use. Inactivated vaccine is costly and inconvenient to prepare. In addition, any such vaccine entails the risk of allergic reaction originating from proteins of the host cell used in preparing the virus. Furthermore, such vaccines present considerable risk to the workers employed in their production. Candidate attenuated JEV vaccines are undergoing clinical trials, but as of 1996 have not found wide acceptance outside of the People's Republic of China (Hennessy et al., *Lancet* 347: 1583-1586 (1996)).

Recombinant vaccines based on the use of only certain proteins of flaviviruses, such as JEV, produced by biosynthetic expression in cell culture with subsequent purification or treatment of antigens, do not induce high antibody titers. Also, like the whole virus preparations, these vaccines carry the risk of adverse allergic reaction to antigens from the host or to the vector. Vaccine development against dengue virus and WNV is less advanced and such virus-based or recombinant protein-based vaccines face problems similar to those alluded to above.

There is therefore a need for vaccines or improved vaccines directed against flaviviruses such as yellow fever virus, dengue virus, JEV, SLEV and WNV which are inexpensive to prepare, present little risk to workers involved in their manufacture, carry minimal risk of adverse immunological reactions due to impurities or adventitious immunogenic components and are highly effective in eliciting neutralizing antibodies and protective immunity. There is furthermore a need for a vaccine against JEV, WNV and related flaviviruses that minimizes the number of immunizing doses required.

Many of the shortcomings of the current art as described in detail for the production of vaccines also apply to the production of antigens and antibodies to be used for the production of immunodiagnostics. Particularly, the concurrent risks and costs involved in the production of antigens from viruses and the failure of most currently available recombinantly expressed antigens to elicit effective immune responses are paralleled in the field of immunodiagnostics by the same risks, high costs and a corresponding lack of sensitivity. Thus, because of the high costs, risk of accidental infection with live virus and the lower than desired levels of sensitivity of the previously available tests, there exists a need for rapid, simple and highly sensitive diagnostic tests for detecting *flavivirus* infection and/or contamination.

The present invention meets these needs by providing highly immunogenic recombinant antigens for use in diagnostic assays for the detection of antibodies to selected flaviviruses. The present invention further provides for the use of recombinant antigens derived from flaviviruses, *flavivirus* genes or mimetics thereof in immunodiagnostic assays for the detection of antibodies to *flavivirus* proteins.

SUMMARY OF THE INVENTION

The present invention provides a nucleic acid molecule which contains a transcriptional unit (TU) for an immunogenic *flavivirus* antigen. The TU directs a host cell, after being incorporated within the cell, to synthesize the antigen. In an important aspect of the invention, the *flavivirus* can be yellow fever virus (YFV), dengue serotype 1 virus (DEN-1), dengue serotype 2 virus (DEN-2), dengue serotype 3 virus (DEN-3), dengue serotype 4 virus (DEN4), St. Louis encephalitis virus (SLEV), Japanese encephalitis virus (JEV), West Nile virus (WNV), Powassan virus or any other *flavivirus*. In important embodiments of the present invention, the antigen can be the *flavivirus* prM/M protein, the E protein, or both. In important embodiments of the present invention, the antigen can be a chimeric *flavivirus* protein. In particular, when the TU includes both the prM/M and E proteins, the host cell secretes subviral particles containing the prM/M and E antigens. In a further important aspect of the invention, the nucleic acid is a DNA molecule. In additional significant embodiments, the nucleic acid TU includes a control sequence disposed appropriately such that it operably controls the expression of the prM/M and E antigens and this control sequence can be the cytomegalovirus immediate early promoter. In an additional embodiment, the nucleotide sequence of the TU is engineered to optimize eukaryotic translation by minimizing large hairpin structures in the 5'-end untranslated region of an mRNA produced by the TU and/or the inclusion of a Kozak consensus sequence at the translational start site of an mRNA produced by the TU. In an additional embodiment, the transcriptional unit also includes a poly-A terminator.

The present invention further provides a host cell comprising a nucleic acid molecule which includes a transcriptional unit for an immunogenic *flavivirus* antigen that directs the host cell to synthesize the immunogenic antigen. The *flavivirus* may be YFV, DEN-1, DEN-2, DEN-3, DEN-4, SLEV, JEV, WNV, Powassan virus or other *flavivirus*. In important embodiments, the antigen may be the prM/M protein, the E protein, or both the prM/M and the E proteins. In the latter case, the cell secretes subviral particles containing the prM/M and E antigens.

Additionally, the invention provides a composition for vaccinating a subject against a *flavivirus* containing a nucleic acid molecule that includes a transcriptional unit for an immunogenic flaviviral antigen. The transcriptional unit directs a cell within the body of the subject, after being incorporated therein, to synthesize the immunogenic antigen. The composition further includes a pharmaceutically acceptable carrier. In significant embodiments, the *flavivirus* may be YFV, DEN-1, DEN-2, DEN-3, DEN-4, SLEV, JEV, WNV, Powassan virus or other *flavivirus*. Furthermore, the antigen may be the prM/M protein, the E protein, or both the prM/M and the E proteins. In the latter instance, the cell secretes subviral particles comprising the *flavivirus* prM/M and E antigens. These subviral particles are also referred to as noninfectious recombinant antigen (NRA). In important embodiments, the nucleic acid molecule is a DNA molecule. In further significant embodiments, the transcriptional unit additionally contains a control sequence disposed appropriately such that it operably controls the synthesis of the prM/M and E antigens when the nucleic acid is introduced into the cell of the subject. This control sequence can be the cytomegalovirus immediate early promoter. In a still further embodiment, the transcriptional unit can also include a poly-A terminator.

The compositions provided by the present invention for vaccinating a subject against a *flavivirus* can include a nucleic acid molecule, or molecules, that include transcriptional units for more than one immunogenic flaviviral antigen. The more than one immunogenic flaviviral antigen can be from different *flavivirus* species, strains or isolates in any combination. In significant embodiments, the flaviviruses included can be two or more, three or more, four or more, five or more, or seven or more flaviviruses. Examples of such flaviviruses include, but are not limited to YFV, DEN-1, DEN-2, DEN-3, DEN-4, SLEV, JEV, WNV, Powassan virus or other flaviviruses. Combination vaccines can be formulated to confer immunity to *flavivirus* disease common to particular geographical regions. In a particular embodiment directed toward tropical and subtropical Asia, DEN-1, DEN-2, DEN-3, DEN-4, WN, and JE viruses can be selected. In a particular embodiment directed to Africa, DEN-1, DEN-2, DEN-3, DEN-4, WN and YF can be selected. In a particular embodiment directed to Latin America, DEN-1, DEN-2, DEN-3, DEN-4, Rocio and YF viruses can be selected.

The invention provides still further a method of immunizing a subject against infection by a *flavivirus*. The method involves administering to the subject an effective amount of a vaccinating composition that contains a nucleic acid molecule which includes a transcriptional unit for an immunogenic *flavivirus* antigen. The transcriptional unit directs a cell within the body of the subject, after being taken up by the cell, to synthesize the immunogenic antigen. The composition additionally includes a pharmaceutically acceptable carrier. In significant embodiments of the method, the *flavivirus* may be YFV, DEN-1, DEN-2, DEN-3, DEN-4, SLEV, JEV, WNV, Powassan virus or other *flavivirus*. In yet other important aspects of the method, the antigen may be the prM/M protein, the E protein, or both the prM/M and the E proteins. When the antigen is both the prM/M and the E proteins, the cell within the body of the subject, after incorporating the nucleic acid within it, secretes subviral particles comprising the flaviviral prM/M and E antigens. Additionally, in significant embodiments of the method, the vaccinating composition is administered to the subject in a single dose, via a parenteral route. In yet a further aspect of the method, the nucleic acid is a DNA molecule. In yet additional embodiments of the method, the transcriptional unit further includes a control sequence disposed appropriately such that it operably controls the synthesis of the prM/M and E antigens and in a significant aspect of this embodiment, the control sequence is the cytomegalovirus immediate early promoter. Furthermore, the transcriptional unit may include a poly-A terminator.

These aspects and embodiments of the invention are the basis for its distinct attributes and advantages. Being a nucleic acid construct involving only portions of the *flavivirus* genome rather than the sequence encompassing the complete genome, the nucleic acid TU-containing vaccine is completely nonviable. It therefore poses no danger of infection by the *flavivirus* to those involved in its manufacture or to subjects receiving the vaccine. The nucleic acid vaccine is easy to prepare and easy to administer and is stable in storage prior to use. Unexpectedly it has been found that the nucleic acid vaccine of the invention is essentially 100% successful in conferring protective immunity in mammals after administering only a single dose. A further unexpected result is that the nucleic acid TU is able to engender immunity to a *flavivirus* in a female mammal which can be transmitted to its progeny through the milk. Without wishing to be limited by theory, the inventor believes that a possible mechanism for the success of the nucleic acid in conferring protective immunity is that a host cell harboring the nucleic acid, such as the cell of a subject to whom the vaccine is administered, produces subviral particles containing the flaviviral prM/M and E antigens. These particles mimic the immunogenic attributes of native *flavivirus* virions.

The present invention also provides noninfectious antigenic polypeptides, antigenic polypeptide fragments and NRA comprising the prM/M and/or E proteins of flaviviruses, wherein the transmembrane signal sequence is derived from a first *flavivirus* and the M and/or E proteins are derived from a second *flavivirus*. Further, the prM/M protein can comprise amino acid sequences from both the first and the second flaviviruses. Further, the E protein can comprise amino acid sequences from both the first and second flaviviruses. "Chimeric" as used herein means any protein or nucleic acid comprising sequence from more than one *flavivirus*. As used herein, "non-virulent" means the antigen or vaccine of this invention is incapable of causing disease. More particularly, the recombinant protein antigens are free of contaminating genomic material from flaviviruses that is necessary for *flavivirus* infection, replication and pathogenesis.

The polypeptides of the present invention can comprise the amino acid sequences defined herein, or that are known in the art, of the prM, M and/or E proteins of selected flaviviruses. The nucleic acids of this invention can comprise nucleotide sequence that encodes the prM, M and/or E proteins of selected flaviviruses.

The antigens of the present invention can be unconjugated, or they can be conjugated to a carrier molecule that facilitates placement of the antigen on a solid phase. A carrier molecule is one to which antigens can be conjugated and which will not react with antibodies in human serum. An example of such a carrier is bovine serum albumin (BSA).

The antigens of the present invention can also be recombinant proteins obtained by expressing nucleic acids encoding the antigen in an expression system capable of producing the antigen.

The amino acid sequences of the present antigens can contain an immunoreactive portion of the prM, M and/or E antigen. These antigens may further be attached to sequences designed to provide for some additional property, such as to remove/add amino acids capable of disulfide bonding to increase the reactivity of an epitope by providing a more rigid secondary structure, to increase its bio-longevity or to alter its cytotoxicity or to prevent infection. In any case, the antigen must possess immunoreactivity and/or immunogenicity.

DETAILED DESCRIPTION OF THE INVENTION

Figure 1:
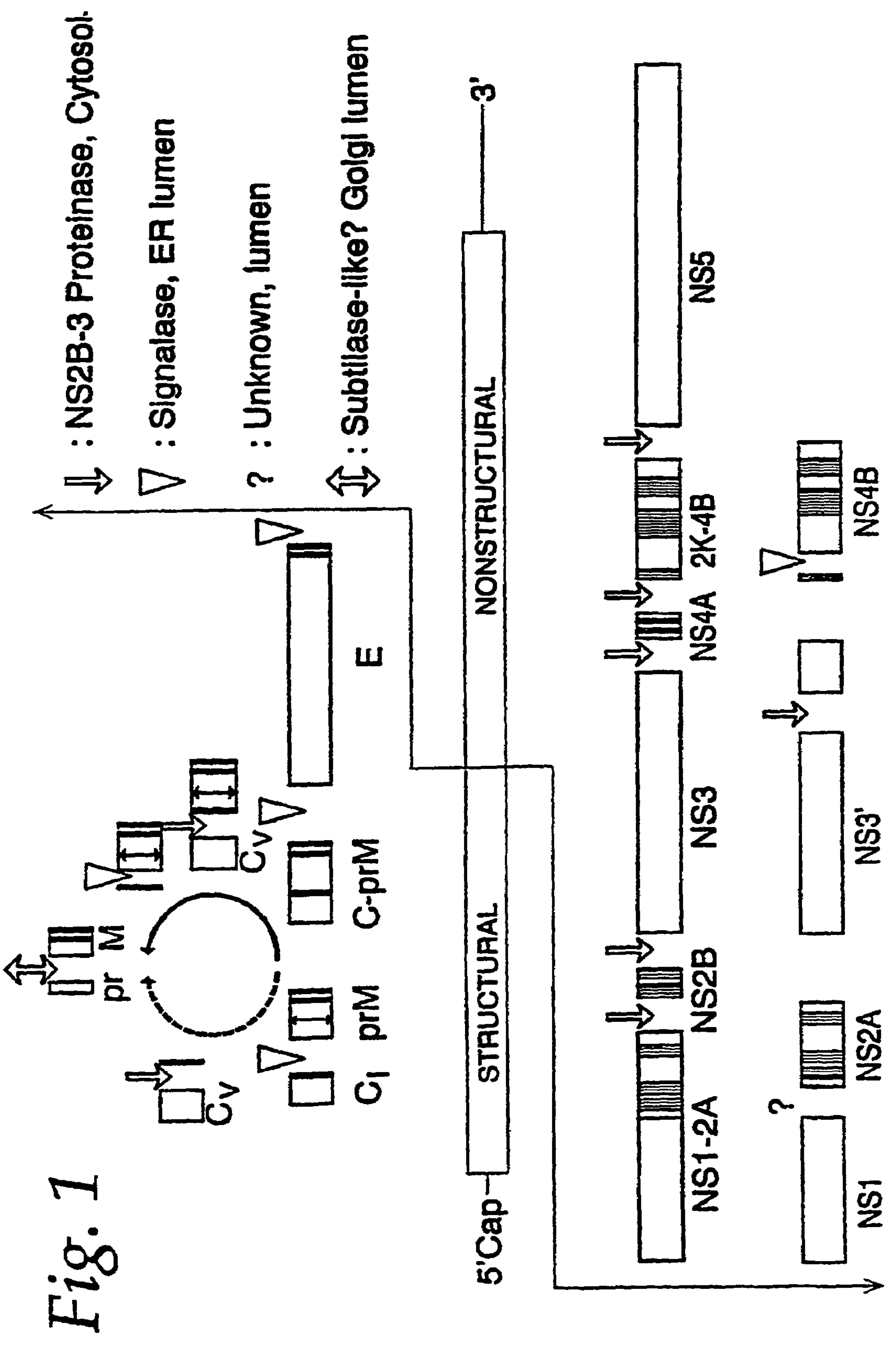
FIG. 1 is a schematic representation of flaviviral polyprotein processing. The central horizontal region provides a schematic representation of the viral genome. The lines denote the 5' and 3' non-translated regions and the boxed regions represent the open reading frame for structural (left and top) and non-structural (right and bottom) proteins. Cleavage by host cell signalase occurs simultaneously with translation at the E protein C-terminus, separating structural and non-structural regions. A subtilase-like cellular enzyme, furin, may be responsible for prM cleavage. Potential transmembrane domains of viral polyprotein are indicated by shaded areas.

The invention encompasses nucleic acid transcriptional units which encode flaviviral antigenic proteins, such as the prM/M and E protein antigens. The nucleic acids function to express the prM/M and E protein antigens when the nucleic acid is taken up by an appropriate cell, especially when the cell is the cell of a subject. The invention also encompasses a vaccine whose active agent is the nucleic acid transcriptional unit (TU). The invention further encompasses cells containing a TU. The invention in addition encompasses a method of immunizing a subject against flaviviral infection by administering to the subject an effective amount of a vaccine containing the nucleic acid TU molecules.

The invention provides an isolated nucleic acid comprising a transcriptional unit encoding a signal sequence of a structural protein of a first *flavivirus* and an immunogenic *flavivirus* antigen of a second *flavivirus*, wherein the transcriptional unit directs the synthesis of the antigen. The invention further encompasses the use of the nucleic acid transcriptional unit (TU) to generate flaviviral antigens and the flaviviral antigens produced by the nucleic acid TU. The flaviviral antigens encompassed by the present invention include chimeric *flavivirus* antigens incorporating amino acid sequence from a first *flavivirus* and at least one further *flavivirus*. The invention still further encompasses the use of the flaviviral antigens encoded by the TU of the invention to produce *flavivirus*-specific antibodies and to detect the presence of *flavivirus*-specific antibodies.

In one embodiment, the isolated nucleic acid of this invention can comprise a transcriptional unit encoding a Japanese encephalitis virus signal sequence.

In another embodiment, the transcriptional unit of this invention can encode an immunogenic *flavivirus* antigen which can be from one or more of the following flaviviruses: yellow fever virus, dengue serotype 1 virus, dengue serotype 2 virus, dengue serotype 3 virus, dengue serotype 4 virus, Japanese encephalitis virus, Powassan virus and West Nile virus.

In another embodiment, the transcriptional unit of this invention can encode an immunogenic chimeric *flavivirus* antigen which can include sequence from more than one of the following flaviviruses: yellow fever virus, dengue serotype 1 virus, dengue serotype 2 virus, dengue serotype 3 virus, dengue serotype 4 virus, Japanese encephalitis virus, Powassan virus and West Nile virus.

In a particular embodiment, the nucleic acid of this invention can encode a signal sequence of Japanese encephalitis virus and an M protein and an E protein of West Nile virus, SLEV, YFV and/or Powassan virus. The nucleic acid can also encode an immunogenic antigen which can be an M protein of a *flavivirus*, an E protein of a *flavivirus*, both an M protein and an E protein of a *flavivirus*, a portion of an M protein of a *flavivirus*, a portion of an E protein of a *flavivirus* and/or both a portion of an M protein of a *flavivirus* and a portion of an E protein of a *flavivirus*. In a preferred embodiment, the isolated nucleic acid encodes both the M protein and the E protein of the *flavivirus*. Further, the nucleic acid of the invention can be DNA and can comprise nucleotide sequence SEQ ID NO:15, SEQ ID NO:19, SEQ ID NO:21, SEQ ID NO:23 or SEQ ID NO: 42.

In another particular embodiment, the nucleic acid of this invention can encode a signal sequence of Japanese encephalitis virus, an M protein of a second virus and a chimeric E protein formed by from substitution of a portion of the nucleic acid encoding the second virus' E protein with nucleic acid encoding the corresponding portion of the JEV E protein. Alternatively, the portion of sequence corresponding to the deleted portion of the second virus' E protein can be substituted by other sequence selected from a third virus or it can be a non-viral sequence. The second protein can be West Nile virus, SLEV, YFV, Powassan and/or a serotype of Dengue virus. Chimeric E proteins can include those where the carboxy terminal portion can be from one *flavivirus* and the remainder of the chimeric E protein is from another *flavivirus*. The carboxy terminal portion can be, for example, 5, 10, 15, 20, 25, 30, 35, 40, 45, 50, 60, or 75% of the chimeric E protein. The nucleic acid of the invention can be DNA and can comprise the protein-encoding sequence from nucleotide sequence SEQ ID NO:44 or SEQ ID NO:46. The nucleic acid of the invention can comprise nucleotide sequence SEQ ID NO:44 or SEQ ID NO:46.

The transcriptional unit of this invention can also comprise a control sequence disposed appropriately so that it operably controls the synthesis of the antigen. The control sequence can be, for example, the cytomegalovirus immediate early promoter. The nucleic acid of this invention can also comprise a Kozak consensus sequence located at a translational start site for a polypeptide comprising the antigen encoded by the transcriptional unit. The transcriptional unit of this invention can also comprise a poly-A terminator.

The present invention further provides a cell comprising the nucleic acid of this invention.

Also provided is a composition comprising a pharmaceutically acceptable carrier and nucleic acid or cell or antigen of this invention. The present invention additionally provides a method of immunizing a subject against infection by a *flavivirus*, comprising administering to the subject an effective amount of a composition of this invention. In a particular embodiment, the composition used to immunize a subject directs the synthesis of both the M protein and the E protein of a *flavivirus* and a cell within the body of the subject, after incorporating the nucleic acid within it, secretes subviral particles comprising the M protein and the E protein. Alternatively, the composition can comprise an M protein and/or E protein of a *flavivirus* or subviral particles comprising the M protein and E protein. In the methods of this invention, the immunizing composition can be administered to the subject in a single dose and can be administered via a parenteral route.

This invention further provides the antigens produced from the isolated nucleic acids of this invention. As an example, the antigen from the second *flavivirus* encoded by the nucleotide sequence of TU can be the M protein which can be, for example, from West Nile virus. The antigen can also be protein from dengue virus, St. Louis encephalitis virus, Japanese encephalitis virus, Powassan virus and/or yellow fever virus.

In a further embodiment, the antigen comprises a prM/M protein comprising the transmembrane signal sequence from a first *flavivirus* and further amino acid sequence comprising the remainder of the prM/M protein from a second *flavivirus*, which can be from SLEV, JEV, YFV, WNV and/or Powassan virus. The transmembrane signal sequence from a first *flavivirus* can be an improved or modified signal sequence wherein the signal sequence imparts desired characteristics such as a high signal sequence probability. Accomplishing these goals by design or selection can be with the use of machine-learning computer programs including, but not limited to, those using a hidden Markov model.

The antigen encoded by the nucleotide sequence of the TU can be West Nile virus antigen, dengue virus antigen, St. Louis encephalitis virus antigen, Japanese encephalitis virus antigen, Powassan virus antigen and/or yellow fever virus antigen.

The antigen encoded by the nucleotide sequence of the TU can also be the E protein, which can be the E protein from West Nile virus, dengue virus, St. Louis encephalitis virus, Japanese encephalitis virus, Powassan virus and/or yellow fever virus. The antigen encoded can also be a chimeric E protein comprising amino acid sequence selected from more than one *flavivirus*.

Additionally, the antigen encoded by the nucleotide sequence of the TU can be the M protein and the E protein, which can be from West Nile virus, dengue virus, St. Louis encephalitis virus, Japanese encephalitis virus, Powassan virus and/or yellow fever virus.

As used herein, "M protein" or "pr/M protein" or "prM/M protein" means a *flavivirus* M protein or *flavivirus* prM protein. Examples include, but are not limited to, prM proteins comprising amino acid sequence from one or more *flavivirus* prM proteins, M proteins comprising no additional amino acid sequence and proteins comprising additional amino acid sequences which are processed in vitro or in vivo to generate the mature M protein.

As used herein, "nucleic acid transcriptional unit" or "nucleic acid transcriptional unit molecule" means a nucleic acid encoding one or more specified proteins. The TU has biological activity such that, after having been introduced into a suitable cell, the nucleic acid induces the synthesis of one or more specified gene products encoded by the nucleic acid. The gene product(s) is(are) other biological macromolecules, such as proteins, not chemically related to the TU. The nucleic acid TU induces the cell to employ its cellular components to produce the specific gene product or products encoded by the nucleic acid of the TU. Although any nucleic acid may serve as a TU, in a preferred embodiment, the TU is the DNA of a plasmid or similar vector, wherein the plasmid or vector comprises coding sequences of marker genes or other sequence constructions that facilitate use of the TU for experimentation and biosynthesis.

As used herein, a "control sequence" is a regulatory nucleotide sequence incorporated within a TU which interacts with appropriate cellular components of the cell and leads to enhanced or activated biosynthesis of the gene products encoded by the TU. Thus a suitable control sequence is one with which the components of the cell have the capability to interact, resulting in synthesis of the gene product. When operably disposed in a nucleic acid with respect to a specified coding sequence, a control sequence effectively controls expression of the specified nucleic acid to produce the gene product.

As used herein, a "promoter" is a nucleotide sequence in a TU which serves as a control sequence.

As used herein, a "Kozak sequence" or "Kozak consensus sequence" is a nucleotide sequence at the translational start site which optimizes translation of eukaryotic mRNAs (Kozak, *Mol. Cell. Biology* 9: 5134-5142 (1989)).

As used herein, a "terminator" is an extended nucleotide sequence which acts to induce polyadenylation at the 3' end of a mature mRNA. A terminator sequence is found after, or downstream from, a particular coding sequence.

As used herein, a "cell" is a prokaryotic or eukaryotic cell comprising a TU coding for one or more gene products, or into which such a TU has been introduced. Thus, a cell harbors a foreign or heterologous substance, the TU, which is not naturally or endogenously found in the cell as a component. A suitable cell is one which has the capability for the biosynthesis of the gene products as a consequence of the introduction of the TU. In particular, a suitable cell is one which responds to a control sequence and to a terminator sequence, if any, that may be included within the TU. In important embodiments of the present invention, the cell is a mammalian cell. In particularly important embodiments of this invention, the cell is a naturally occurring cell in the body of a human or nonhuman subject to whom (which) the TU has been administered as a component of a vaccine. Alternatively, in analytical, or diagnostic applications, including preparation of antigen for use as a vaccine or in immunodiagnostic assays, or for demonstrative purposes, the cell may be a human or nonhuman cell cultured in vitro.

As used herein, a "vaccine" or a "composition for vaccinating a subject" specific for a particular pathogen means a preparation, which, when administered to a subject, leads to an immunogenic response in a subject. As used herein, an "immunogenic" response is one that confers upon the subject protective immunity against the pathogen. Without wishing to be bound by theory, it is believed that an immunogenic response may arise from the generation of neutralizing antibodies (i.e., a humoral immune response) or from cytotoxic cells of the immune system (i.e., a cellular immune response) or both. As used herein, an "immunogenic antigen" is an antigen which induces an immunogenic response when it is introduced into a subject, or when it is synthesized within the cells of a host or a subject. As used herein, an "effective amount" of a vaccine or vaccinating composition is an amount which, when administered to a subject, is sufficient to confer protective immunity upon the subject. Historically, a vaccine has been understood to contain as an active principle one or more specific molecular components or structures which comprise the pathogen, especially its surface. Such structures may include surface components such as proteins, complex carbohydrates, and/or complex lipids which commonly are found in pathogenic organisms.

As used herein, however, it is to be stressed that the terms "vaccine" or "composition for vaccinating a subject" extend the conventional meaning summarized in the preceding paragraph. As used herein, these terms also relate to the TU of the instant invention or to compositions containing the TU. The TU induces the biosynthesis of one or more specified gene products encoded by the TU within the cells of the subject, wherein the gene products are specified antigens of a pathogen. The biosynthetic antigens then serve as an immunogen. As already noted, the TU, and hence the vaccine, may be any nucleic acid that encodes the specified immunogenic antigens. In a preferred embodiment of this invention, the TU of the vaccine is DNA. The TU can include a plasmid or vector incorporating additional genes or particular sequences for the convenience of the skilled worker in the fields of molecular biology, cell biology and viral immunology (See *Molecular Cloning: A Laboratory Manual,* 2nd Ed., Sambrook, Fritsch and Maniatis, Cold Spring Harbor Laboratory, Cold Spring Harbor, N.Y., 1989; and *Current Protocols in Molecular Biology*, Ausubel et al., John Wiley and Sons, New York 1987 (updated quarterly), which are incorporated herein by reference).

The TU molecules of the instant invention comprise nucleic acids, or derivatives of nucleic acids, having nucleotide sequences that encode specific gene products related to antigens of flaviviruses such as, but not limited to, WNV, JEV, dengue virus, yellow fever virus and SLEV. Although any nucleic acid may serve as a TU, in an important embodiment, the TU is DNA. Alternatively, the nucleic acids may be RNA molecules. They may also be any one of several derivatives of DNA or RNA having a backbone of phosphodiester bonds that have been chemically modified to increase the stability of the TU as a pharmaceutical agent. Modifications so envisioned include, but are not limited to, phosphorothioate derivatives or phosphonate derivatives. These and other examples of derivatives are well known to persons skilled in the field of nucleic acid chemistry.

Figure 2:
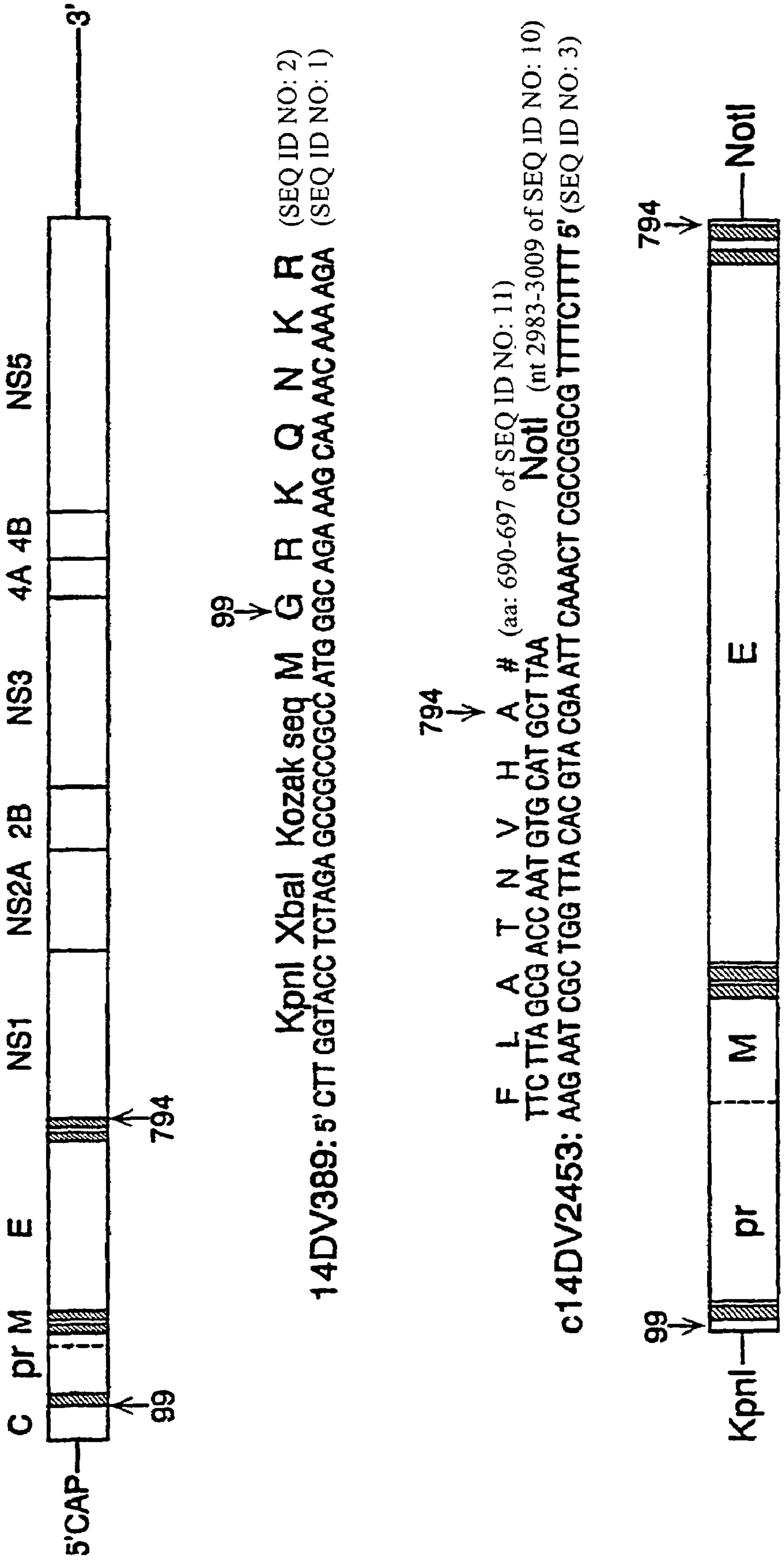
FIG. 2 is a map of the JEV genome (top) and the DNA sequence of oligonucleotides used in a reverse transcriptase-polymerase chain reaction (RT-PCR) (center) to construct the transcription unit for the expression of prM-E protein coding regions (bottom). Potential transmembrane domains of viral polyprotein are indicated by shaded areas.

The genome of JEV has been characterized and sequenced (FIGS. 1 and 2). The M structural protein is expressed as a portion of the polyprotein which includes a pre-M sequence (pr). This pr sequence, immediately amino terminal to the M protein sequence, prevents conformational problems in the processing of the polyprotein. In particular, the presence of the pr sequence is important in preventing misfolding of the E protein. Thus, the presence of prM allows for assembly of JEV particles. Once the virion or particle is formed, the pr sequence can be cleaved from the prM protein to yield mature virus particles containing M proteins, although cleavage of the prM protein to yield M protein is not necessary to produce infectious particles. The prM sequences from many different, related flaviviruses are cleaved to but a low extent, but the flaviviruses themselves are nonetheless, infectious. Examples of such related flaviviruses with similar genomic structures and functions include, but are not limited to WNV, YFV, dengue virus and SLEV.

In one embodiment, the TU encoding flaviviral M and E proteins in the instant invention is DNA. In accord with the discussion in the preceding paragraph, this DNA comprises a nucleotide sequence which encodes the M protein, comprising the pre-M sequence, and a nucleotide sequence encoding the E protein. In this way, the intended gene products are enabled to form subviral particles within the cell. The pre-M sequence can then be cleaved in a fashion analogous to that which occurs with respect to replete virions.

In order to function effectively in vivo as a vaccine, it is advantageous to include within the TU a control sequence that has the effect of enhancing or promoting the transcription of the nucleotide sequences encoding the antigens. Use of such promoters is well known to those of skill in the fields of molecular biology, cell biology and viral immunology (See *Molecular Cloning: A Laboratory Manual,* 2nd Ed., Sambrook, Fritsch and Maniatis, Cold Spring Harbor Laboratory, Cold Spring Harbor, N.Y., 1989; and *Current Protocols in Molecular Biology*, Ausubel et al., John Wiley and Sons, New York 1987 (updated quarterly)). When the TU is used as a vaccine in a mammalian host, the promoter to be employed is preferably one which operates effectively in mammalian cells. Such a promoter is disposed with respect to the coding sequences from which transcription is to be promoted, at a position at which it may operably promote such transcription. In a significant embodiment of the instant invention, this promoter is the cytomegalovirus early promoter. In addition, in a further preferred embodiment of the invention, the coding sequences are followed, in the TU nucleic acid, by a terminator sequence (Sambrook et al.). Particular embodiments of the invention relate to both prokaryotic and eukaryotic cells. Many promoter sequences are known that are useful in either prokaryotic or eukaryotic cells. (See Sambrook et al.)

The nucleic acids of the invention may further include DNA sequences known to those of skill in the art to act as immunostimulatory elements. Examples of such elements include, but are not limited to, certain CpG motifs in bacterial DNA (Sato et al., *Science* 273: 352-354 (1996); Klinman et al., *Vaccine* 17: 19-25 (1998)).

Preparation of the TU of the invention is readily accomplished by methods well known to workers of skill in the field of molecular biology. Procedures involved are set forth, for example, in *Molecular Cloning: A Laboratory Manual,* 2nd Ed., Sambrook, Fritsch and Maniatis, Cold Spring Harbor Laboratory, Cold Spring Harbor, N.Y., 1989 and *Current Protocols in Molecular Biology*, Ausubel et al., John Wiley and Sons, New York 1987 (updated quarterly). The flaviviral RNA molecule may be isolated from a sample of live virus by methods widely known among virologists familiar with flaviviruses, for example, and with other groups of viruses as well. Methods used with JEV are summarized in Kuno et al. (*J. Virol.* 72: 73-83 (1998)). The RNA is used as a template for the synthesis of cDNA using reverse transcriptase. From the cDNA, a fragment containing the pre-M through E coding region (FIG. 2) is obtained by digestion with restriction nucleases known to cleave the cDNA appropriately to provide such fragments. Examples of restriction digestion of JEV are provided in Nitayaphan et al. (1990) and Konishi et al. (1991). Incorporation of promoters, such as the cytomegalovirus promoter, sequences to promote efficient translation, such as the Kozak sequence, and of the polyadenylation signal, is likewise well known to skilled practitioners in molecular biology and recombinant DNA engineering (Kozak, *Mol. Cell. Biology* 9: 5134-5142 (1989); Azevedo et al., *Braz. J. Med. Biol. Res.* 32: 147-153 (1999)). When a nucleic acid comprising a TU containing the desired coding sequences and control sequences is prepared, it may be obtained in larger quantities by methods that amplify nucleic acids. Such methods are widely known to workers skilled in molecular biology and recombinant DNA engineering. Examples of these methods include incorporation of the nucleic acid into a plasmid for replication by culturing in a cell such as a prokaryotic cell and harvesting the plasmid after completing the culture, as well as amplification of the nucleic acid by methods such as PCR and other amplification protocols, as are well known in the art. These examples are not intended to limit the ways in which the nucleic acid containing the TU may be obtained.

The TU-containing nucleic acid molecules of the instant invention may be introduced into appropriate cells in many ways well known to skilled workers in the fields of molecular biology and viral immunology. By way of example, these include, but are not limited to, incorporation into a plasmid or similar nucleic acid vector which is taken up by the cells, or encapsulation within vesicular lipid structures such as liposomes, especially liposomes comprising cationic lipids, or adsorption to particles that are incorporated into the cell by endocytosis.

In general, a cell of this invention is a prokaryotic or eukaryotic cell comprising a TU, or into which a TU has been introduced. The TU of the present invention induces the intracellular biosynthesis of the encoded prM/M and E antigens. A suitable cell is one which has the capability for the biosynthesis of the gene products as a consequence of the introduction of the nucleic acid. In particular embodiments of the invention, a suitable cell is one which responds to a control sequence and to a terminator sequence, if any, which may be included within the TU. In order to respond in this fashion, such a cell contains within it components which interact with a control sequence and with a terminator and act to carry out the respective promoting and terminating functions. When the cell is cultured in vitro, it may be a prokaryote, a single-cell eukaryote or a multicellular eukaryote cell. In particular embodiments of the present invention, the cell is a mammalian cell. In these cases, the synthesized prM/M and E protein gene products are available for use in analytical, or diagnostic applications, including preparation of antigen for use as a vaccine or in immunodiagnostic assays, or for demonstrative purposes.

In some circumstances, such as when the cell is a cultured mammalian cell, the prM/M and E antigens are secreted in the form of subviral particles. These are aggregates of prM/M and E proteins resembling live virus in surface ultrastructural morphology and immunogenic properties. Since the TU of the invention does not include the remainder of the flaviviral genome, however, there is no capsid incorporated, and most importantly, no infectious viral RNA.

In another important embodiment of this invention, the cell is a natural cellular component of the subject to whom the TU has been administered as a vaccine. The TU, when administered to the subject, is taken up by the cells of the subject. The subject's cells have the capability of responding to any promoter sequences, and terminator, if present. In any case, the TU induces the subject's cells to synthesize flaviviral prM/M and E gene products. Without wishing to be constrained by theoretical considerations, it is believed that the subject's cells produce subviral particles in vivo consisting of the prM/M and E antigens, just as has been found to occur with cultured mammalian cells in vitro. Such subviral particles, it is believed, then serve as the in vivo immunogen, stimulating the immune system of the subject to generate immunological responses which confer protective immunity on the subject. Again without wishing to be limited by theory, the resulting protective immunity may arise via either humoral or cellular immunity, i.e., via either an MHC class II— or class I-restricted mechanism, respectively, or by both mechanisms.

According to the invention, subjects are immunized against infection by flaviviruses, such as JEV, YFV, dengue virus, SLEV, WNV or other flaviviruses by administering to them an effective amount of a TU comprising nucleic acid which encodes the prM and/or E antigens. The nucleic acid, after being incorporated into the cells of the subject, leads to the synthesis of the flaviviral prM/M and/or E antigens.

In order to administer the TU to the subject, it is incorporated into a composition which comprises a pharmaceutically acceptable carrier. The term "pharmaceutically acceptable" means a material that is not biologically or otherwise undesirable, i.e., the material may be administered to an subject along with the immunogenic material (i.e., recombinant *flavivirus* protein antigens or portions thereof) without causing any undesirable biological effects or interacting in a deleterious manner with any of the other components of the vaccine in which it is contained. Examples of pharmaceutically acceptable carriers, or components thereof, include water, physiological saline and common physiological buffers (for further examples, see Arnon, R. (Ed.) *Synthetic Vaccines I*: pp. 83-92, CRC Press, Inc., Boca Raton, Fla., 1987).

It is understood by those skilled in the art that the critical value in describing a vaccination dose is the total amount of immunogen needed to elicit a protective response in a host which is subject to infectious disease caused by virulent or wild-type *flavivirus* infection. The number and volume of doses used can be varied and are determined by the practitioner based on such parameters as, age, weight, gender, species, type of vaccine to be administered, mode of administration, overall condition of the subject, et cetera, as well as other important factors recognized by those of skill in the art.

The TU may be administered to a subject orally, parenterally (e.g., intravenously), by intramuscular injection, by intraperitoneal injection, transdermally, extracorporeally, intranasally, topically or the like. Delivery can also be directly to any area of the respiratory system (e.g., lungs) via intubation. The exact amount of the TU required will vary from subject to subject, depending on the species, age, weight and general condition of the subject, the immunogenicity of the vaccine used, the strain or species of *flavivirus* against which the subject is being immunized, the mode of administration and the like. Thus, it is not possible to specify an exact amount for every embodiment of the present invention. However, an appropriate amount can be determined by one of ordinary skill in the art using only routine experimentation given the teachings herein and what is available in the art.

Parenteral administration of the vaccine of the present invention, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences* (Martin, E. W. (ed.), latest edition, Mack Publishing Co., Easton, Pa.).

In one embodiment, the TU of this invention can be administered to the subject by the use of electrotransfer mediated in vivo gene delivery, wherein immediately following administration of the TU to the subject, transcutaneous electric pulses are applied to the subject, providing greater efficiency and reproducibility of in vivo nucleic acid transfer to tissue in the subject (Mir et al., *Proc. Nat. Acad. Sci USA* 96: 4262-4267 (1999)).

In the methods of the present invention which describe the immunization of a subject by administering a vaccine of this invention to a subject, the efficacy of the immunization can be monitored according the clinical protocols well known in the art for monitoring the immune status of a subject.

An effective amount of a vaccinating composition is readily determined by those of skill in the art to be an amount which, when administered to a subject, confers protective immunity upon the subject. In order to undertake such a determination, the skilled artisan can assess the ability to induce flaviviral prM/M- and E-specific antibodies and/or flaviviral prM/M- and E-specific cytotoxic T lymphocytes present in the blood of a subject to whom the vaccine has been administered. One can also determine the level of protective immunity conferred upon an experimental subject by challenge with live *flavivirus* corresponding to the antigenic composition used to immunize the experimental subject. Such challenge experiments are well known to those of skill in the art.

In general, in order to immunize a subject against infection by WNV, JEV, YFV, dengue virus, SLEV, or other flaviviruses according to the present invention, and recognizing that the TUs employed in such methods may have differing overall sizes, doses ranging from about 0.1 μg/kg body weight to about 50 μg/kg body weight can be used.

It has unexpectedly been found that a TU of the present invention which is a DNA confers protective immunity at a level of effectiveness approximating 100% after administration of only a single effective dose of the TU by i.m. injection or by electrotransfer. This is in contrast to many immunization methods carried out using conventional vaccines (as described above), which require one or more booster vaccinations and which may not confer protective immunity to an effectiveness near 100%.

It has further been found unexpectedly that protective immunity may be transmitted from a vaccinated female subject to the offspring of the subject. A significant proportion of neonatal mice was shown to be protected against viral challenge after the mothers were vaccinated using the TU DNA of the invention. Without wishing to be limited by theory, it is known that passive immunity may be conferred on neonatal mammals due to the presence in maternal milk of neutralizing antibodies specific for various pathogens. It is possible that the protective immunity against JEV found within the neonates was transmitted to them in this way.

In another embodiment of the invention, the TU encodes a signal sequence of a structural protein of a first *flavivirus* and an immunogenic *flavivirus* antigen of a second *flavivirus*. Thus, in one embodiment, for example, the signal sequence of structural protein of a first *flavivirus* is replaced by a signal sequence of structural protein of a second *flavivirus*, which results in proper folding of the nascent polypeptide, proper processing in a host, and/or proper folding of the processed protein.

In another embodiment of the invention, the TU may encode an immunogenic *flavivirus* antigen wherein the antigen comprises sequence from one or more than one *flavivirus*. The signal sequence can be an improved signal peptide. Improvement of signal sequences, or selection of more optimal signal sequences, can be accomplished by application of the principles and techniques taught in Example 18 and references cited therein, each of which are incorporated herein by reference for the express teachings in each related to the selection, identification and design of signal sequences with desired properties and functions. Generally, these desired properties and functions will include a high signal sequence probability.

In another embodiment of the invention, more than one TU or a TU encoding an immunogenic *flavivirus* antigen from more than one *flavivirus* are included in a single composition. Thus, in one embodiment, for example, a TU can encode a nascent polypeptide or polypeptides that are processed into proteins from more than one *flavivirus*. Preferably, the processed proteins form subviral particles that elicit an immunological response against the proteins. The subviral particles can be formed from processed proteins derived from the sequence of the same *flavivirus*, a combination of flaviviruses, or chimeric *flavivirus* proteins. Combination vaccines, comprising more than one TU or a TU encoding an immunogenic *flavivirus* antigen from more than one *flavivirus* can be tailored for use in particular geographical regions by inclusion of proteins from flaviviruses endemic to the region or otherwise likely to be encountered. For example, a vaccine for tropical and subtropical Asia can include TU(s) that encode proteins from the four serotypes of DEN, WN and JE virus vaccines. Similarly useful vaccines for Africa and Latin America could include TU(s) that encode proteins from the four serotypes of DEN, WN and YF viruses and the four serotypes of DEN, Rocio and YF viruses, respectively.

In another embodiment, the TU encodes a signal sequence of a structural protein of a first *flavivirus* and an immunogenic chimeric *flavivirus* antigen that includes amino acid sequence from more than one *flavivirus*. The signal sequence can be a Japanese encephalitis virus signal sequence. The chimeric *flavivirus* antigen can include sequence from a Japanese encephalitis virus antigen. In certain embodiments, the chimeric antigen is an E protein. The carboxy terminal portion of the E protein can be E protein sequence from the Japanese encephalitis virus. The carboxy terminal portion can be, for example, 5, 10, 15, 20, 25, 30, 40, 50 or 75% of the chimeric E protein. In a preferred embodiment, the TU encodes a signal sequence of a structural protein of Japanese encephalitis virus, a prM protein of a Dengue virus and a chimeric E protein containing sequence from both the Japanese encephalitis virus and the Dengue virus. The chimeric protein can be an E protein wherein the carboxy terminal portion comprises Japanese encephalitis virus sequence. Examples of TUs include nucleic acid sequences shown in SEQ ID NO:44 and SEQ ID NO:46 that can direct the synthesis of *flavivirus* antigens such as those shown in SEQ ID NO:45 and SEQ ID NO:47.

The present invention further provides immunogenic compositions comprising the polypeptides of this invention in a pharmaceutical acceptable carrier for use as a protein vaccine. Antigens produced from the transcriptional units of the present invention can be used to elicit effective immune responses in a subject. Antigens for this purpose can comprise *flavivirus* prM protein, *flavivirus* M protein, *flavivirus* E protein or any combination thereof, including immunogenic fragments of the proteins. A particularly preferred embodiment is the use of the NRA described herein. A further preferred embodiment is a chimeric protein comprising the signal sequence of one *flavivirus* and the structural protein(s) of one or more different flaviviruses. In a particularly preferred embodiment, the signal sequence of the antigen is the Japanese encephalitis virus signal sequence. In other preferred embodiments, the signal sequence is a an improved signal peptide. Improvement of signal sequences, or selection of more optimal signal sequences, can be accomplished by application of the principles and techniques taught in Example 18 and references cited therein each of which are incorporated herein by reference for the express teachings in each related to the selection, identification and design of signal sequences with desired properties and function. Generally, these desired properties and function will include a high signal sequence probability.

In other embodiments, the protein vaccine of this invention further comprises a suitable adjuvant. As used herein, an "adjuvant" is a potentiator or enhancer of the immune response. The term "suitable" is meant to include any substance which can be used in combination with the vaccine immunogen (i.e., *flavivirus* prM protein, *flavivirus* M protein, *flavivirus* E protein, or any combination thereof) to augment the immune response, without producing adverse reactions in the vaccinated subject. Effective amounts of a specific adjuvant may be readily determined so as to optimize the potentiation effect of the adjuvant on the immune response of a vaccinated subject. In a preferred embodiment, adjuvanting of the vaccines of this invention is a 2-stage process, utilizing first a 2% aluminum hydroxide solution and then a mineral oil. In specific embodiments, suitable adjuvants can be chosen from the following group: mineral, vegetable or fish oil with water emulsions, incomplete Freund's adjuvant, *E. coli* J5, dextran sulfate, iron oxide, sodium alginate, Bacto-Adjuvant, certain synthetic polymers such as Carbopol (BF Goodrich Company, Cleveland, Ohio), poly-amino acids and copolymers of amino acids, saponin, carrageenan, REGRESSIN (Vetrepharm, Athens, Ga.), AVRIDINE (N,N-dioctadecyl-N',N'-bis(2-hydroxyethyl)-propanediamine), long chain polydispersed β (1,4) linked mannan polymers interspersed with O-acetylated groups (e.g. ACEMANNAN), deproteinized highly purified cell wall extracts derived from non-pathogenic strain of *Mycobacterium* species (e.g. EQUIMUNE, Vetrepharm Research Inc., Athens Ga.), Mannite monooleate, paraffin oil and muramyl dipeptide.

In another aspect, this invention provides a method for immunizing subjects with immunogenic amounts of the protein vaccine of the invention to elicit an effective immune response in the subject. Immunization can be carried out orally, parenterally, intranasally, intratracheally, intramuscularly, intramammarily, subcutaneously, intravenously and/or intradermally. The vaccine containing the *flavivirus* prM protein, *flavivirus* M protein and/or the *flavivirus* E protein can be administered by injection, by inhalation, by ingestion, or by infusion. A single dose can be given and/or repeated doses of the vaccine preparations, i.e. "boosters," can be administered at periodic time intervals to enhance the initial immune response or after a long period of time since the last dose. The time interval between vaccinations can vary, depending on the age and condition of the subject.

The term "immunogenic amount" means an amount of an immunogen, or a portion thereof, which is sufficient to induce an immune response in a vaccinated subject and which protects the subject against disease caused by wild-type or virulent *flavivirus* infections upon exposure thereto or which has a therapeutic or commercially beneficial effect that lessens the effect of *flavivirus* infection on the vaccinated subject.

The invention further provides an antibody produced in response to immunization by the antigen of this invention. The antibodies of the present invention can include polyclonal and monoclonal antibodies which can be intact immunoglobulin molecules, chimeric immunoglobulin molecules, "humanized antibodies," or Fab or $F(ab')_2$ fragments. Such antibodies and antibody fragments can be produced by techniques well known in the art which include those described in Harlow and Lane (*Antibodies: A Laboratory Manual.* Cold Spring Harbor Laboratory, Cold Spring Harbor, N.Y., 1989) and Kohler et al. (*Nature* 256: 495-97, 1975) and U.S. Pat. Nos. 5,545,806, 5,569,825 and 5,625,126, incorporated herein by reference. The antibodies can be of any isotype IgG, IgA, IgD, IgE and IgM.

The present invention can also include single chain antibodies (ScFv), comprising linked $V_H$ and $V_L$ domains and which retain the conformation and specific binding activity of the native idiotype of the antibody. Such single chain antibodies are well known in the art and can be produced by standard methods. (see, e.g., Alvarez et al., *Hum. Gene Ther.* 8: 229-242 (1997)).

Antibodies can be produced against the antigens of this invention which are synthesized from nucleic acid sequences encoding immunogenic amino acid sequences of the prM, M and/or E antigens of one or more flaviviruses and the signal sequence of a different *flavivirus* (e.g., JEV). Immunogenic peptides synthesized from the use of these chimeric constructs can easily be identified by use of methods well known in the art for identifying immunogenic regions in an amino acid sequence and used to produce the antibodies of this invention.

Conditions whereby an antigen/antibody complex can form, as well as assays for the detection of the formation of an antigen/antibody complex and quantitation of the detected protein, are standard in the art. Such assays can include, but are not limited to, Western blotting, immunoprecipitation, immunofluorescence, immunocytochemistry, immunohistochemistry, fluorescence activated cell sorting (FACS), fluorescence in situ hybridization (FISH), immunomagnetic assays, ELISA, ELISPOT (Coligan et al., eds. 1995. *Current Protocols in Immunology*. Wiley, New York.), agglutination assays, flocculation assays, cell panning, etc., as are well known to the artisan.

As used herein, the term "bind" means the well characterized binding of antibody to antigen as well as other nonrandom association with an antigen. "Specifically bind" as used herein describes an antibody or other ligand that does not cross react substantially with any antigen other than the one specified, which in this case, is an antigen of this invention.

The antibody or ligand of this invention can be bound to a substrate (e.g., beads, tubes, slides, plates, nitrocellulose sheets, etc.) or conjugated with a detectable moiety or both bound and conjugated. The detectable moieties contemplated for the present invention can include, but are not limited to, an immunofluorescent moiety (e.g., fluorescein, rhodamine), a radioactive moiety (e.g., $^{32}P$, $^{125}I$, $^{35}S$), an enzyme moiety (e.g., horseradish peroxidase, alkaline phosphatase), a colloidal gold moiety and a biotin moiety. Such conjugation techniques are standard in the art (for example, Harlow and Lane, *Antibodies: A Laboratory Manual*. Cold Spring Harbor Laboratory, Cold Spring Harbor, N.Y. (1989); Yang et al., *Nature* 382: 319-324 (1996)).

The present invention further provides a method of detecting *flavivirus* antibody in a sample, comprising contacting the sample with the *flavivirus* antigen of the present invention, under conditions whereby an antigen/antibody complex can form; and detecting formation of the complex, thereby detecting *flavivirus* antibody in the sample.

The present invention further provides a method of detecting *flavivirus* antigen in a sample, comprising contacting the sample with an antibody of this invention under conditions whereby an antigen/antibody complex can form; and detecting formation of the complex, thereby detecting *flavivirus* antigen in the sample.

The method of detecting *flavivirus* antigen in a sample can be performed, for example, by contacting a fluid or tissue sample from a subject with an antibody of this invention and detecting binding of the antibody to the antigen. It is contemplated that the antigen will be on an intact *flavivirus* virion, will be a *flavivirus*-encoded protein displayed on the surface of a *flavivirus*-infected cell expressing the antigen, or will be a fragment of the antigen. A fluid sample of this method can comprise any biological fluid which could contain the antigen or a cell containing the antigen, such as cerebrospinal fluid, blood, bile, plasma, serum, saliva and urine. Other possible examples of body fluids include sputum, mucus and the like.

The method of detecting *flavivirus* antibody in a sample can be performed, for example, by contacting a fluid or tissue sample from a subject with an antigen of this invention and detecting the binding of the antigen to the antibody. A fluid sample of this method can comprise any biological fluid which could contain the antibody, such as cerebrospinal fluid, blood, bile, plasma, serum, saliva and urine. Other possible examples of body fluids include sputum, mucus and the like.

Enzyme immunoassays such as immunofluorescence assays (IFA), enzyme linked immunosorbent assays (ELISA) and immunoblotting can be readily adapted to accomplish the detection of *flavivirus* antibodies according to the methods of this invention. An ELISA method effective for the detection of the antibodies can, for example, be as follows: (1) bind the antigen to a substrate; (2) contact the bound antigen with a fluid or tissue sample containing the antibody; (3) contact the above with a secondary antibody bound to a detectable moiety which is reactive with the bound antibody (e.g., horseradish peroxidase enzyme or alkaline phosphatase enzyme); (4) contact the above with the substrate for the enzyme; (5) contact the above with a color reagent; and (6) observe/measure color change or development.

Another immunologic technique that can be useful in the detection of *flavivirus* antibodies uses monoclonal antibodies (MAbs) for detection of antibodies specifically reactive with *flavivirus* antigens in a competitive inhibition assay. Briefly, sample is contacted with an antigen of this invention which is bound to a substrate (e.g., an ELISA 96-well plate). Excess sample is thoroughly washed away. A labeled (e.g., enzyme-linked, fluorescent, radioactive, etc.) monoclonal antibody is then contacted with any previously formed antigen-antibody complexes and the amount of monoclonal antibody binding is measured. The amount of inhibition of monoclonal antibody binding is measured relative to a control (no antibody), allowing for detection and measurement of antibody in the sample. The degree of monoclonal antibody inhibition can be a very specific assay for detecting a particular *flavivirus* variety or strain, when based on monoclonal antibody binding specificity for a particular variety or strain of *flavivirus*. MAbs can also be used for direct detection of *flavivirus* antigens in cells by, for example, immunofluorescence assay (IFA) according to standard methods.

As a further example, a micro-agglutination test can be used to detect the presence of *flavivirus* antibodies in a sample. Briefly, latex beads, red blood cells or other agglutinable particles are coated with the antigen of this invention and mixed with a sample, such that antibodies in the sample that are specifically reactive with the antigen crosslink with the antigen, causing agglutination. The agglutinated antigen-antibody complexes form a precipitate, visible with the naked eye or measurable by spectrophotometer. In a modification of the above test, antibodies of this invention can be bound to the agglutinable particles and antigen in the sample thereby detected.

The present invention further provides a method of diagnosing a *flavivirus* infection in a subject, comprising contacting a sample from the subject with the antigen of this invention under conditions whereby an antigen/antibody complex can form; and detecting antigen/antibody complex formation, thereby diagnosing a *flavivirus* infection in a subject.

The present invention further provides a method of diagnosing a *flavivirus* infection in a subject, comprising contacting a sample from the subject with the antibody of this invention under conditions whereby an antigen/antibody complex can form; and detecting antigen/antibody complex formation, thereby diagnosing a *flavivirus* infection in a subject.

In the diagnostic methods taught herein, the antigen of this invention can be bound to a substrate and contacted with a fluid sample such as blood, serum, urine or saliva. This sample can be taken directly from the patient or in a partially purified form. In this manner, antibodies specific for the antigen (the primary antibody) will specifically react with the bound antigen. Thereafter, a secondary antibody bound to, or labeled with, a detectable moiety can be added to enhance the detection of the primary antibody. Generally, the secondary antibody or other ligand, which is reactive, either specifically with a different epitope of the antigen or nonspecifically with the ligand or reacted antibody, will be selected for its ability to react with multiple sites on the primary antibody. Thus, for example, several molecules of the secondary antibody can react with each primary antibody, making the primary antibody more detectable.

The detectable moiety allows for visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change).

Particular embodiments of the present invention are set forth in the examples which follow. These examples are not intended to limit the scope of the invention as disclosed in this specification.

EXAMPLES

General methods utilizing molecular biology and recombinant DNA techniques related to preparing and expressing the nucleic acid TU molecules of the invention are set forth in, for example, *Current Protocols in Molecular Biology*, Ausubel et al., John Wiley and Sons, New York 1987 (updated quarterly), and *Molecular Cloning: A Laboratory Manual* 2nd Ed., Sambrook, Fritsch and Maniatis, Cold Spring Harbor Laboratory, Cold Spring Harbor, N.Y., 1989.

Example 1

Preparation of Recombinant Plasmids Containing the Transcriptional Unit Encoding JEV prM and E Antigens Genomic RNA was extracted from 150 μL of JEV strain SA 14 virus seed grown from mouse brain using a QIAamp™ Viral RNA Kit (Qiagen, Santa Clarita, Calif.). RNA, adsorbed on a silica membrane, was eluted in 80 μL of nuclease-free water, and used as a template for the amplification of JEV prM and E gene coding sequences. Primer sequences were obtained from the work of Nitayaphan et al. (*Virology* 177: 541-552 (1990)). A single cDNA fragment containing the genomic nucleotide region 389-2478 was amplified by the reverse transcriptase-polymerase chain reaction (RT-PCR). Restriction sites KpnI and XbaI, the consensus Kozak ribosomal binding sequence, and the translation initiation site were engineered at the 5' terminus of the cDNA by amplimer 14DV389 (nucleotide sequence, SEQ ID NO:1; amino acid sequence, SEQ ID NO:2). An in-frame translation termination codon, followed by a NotI restriction site, was introduced at the 3' terminus of the cDNA by amplimer c14DV2453 (SEQ ID NO:3) (FIG. 2). One-tube RT-PCR was performed using a Titan RT-PCR Kit (Boehringer Mannheim, Indianapolis, Ind.). 10 μL of viral RNA was mixed with 1 μL each of 14DV389 (50 μM) and c14DV2453 (50 μM) and 18 μL of nuclease-free water and the mixture was heated at 85° C. for 5 min and then cooled to 4° C. 75 μL of reaction mix [20 μL 5× buffer, 2 μL of dNTP mixture (10 mM each), 5 μL of dithiothreitol (0.1 mM), 0.5 μL of RNasin™ (40 U/1L, Boehringer Mannheim), 2 μL of polymerase mixture, and 45.5 μL of nuclease-free water] was added and RT-PCR performed as follows: 1 cycle (50° C. for 30 min, 94° C. for 3 min, 50° C. for 30 s, 68° C. for 2.5 min), 9 cycles (94° C. for 30 s, 50° C. for 30 s, 68° C. for 2.5 min), 20 cycles (94° C. for 30 s, 50° C. for 30 s, 68° C. for 2.5 min in the first cycle, with an increment of 5 s per cycle thereafter), and a final extension at 68° C. for 15 min. The RT-PCR product was purified by a QIAquick™ PCR Purification Kit (Qiagen) and eluted with 50 μL of 1 mM Tris-HCl, pH 7.5.

All vector constructions and analyses were carried out by using standard techniques (Sambrook et al., 1989). RT-PCR amplified cDNA, digested with KpnI and NotI nucleases, was inserted into the KpnI-NotI site of eukaryotic expression plasmid vector (pCDNA3, Invitrogen, Carlsbad, Calif.). Electroporation-competent *Escherichia coli* XL1-Blue cells (Stratagene, La Jolla, Calif.) were transformed by electroporation (Gene Pulser™, Bio-Rad, Hercules, Calif.) and plated onto LB agar plates containing 100 μg/mL carbenicillin (Sigma Chemical Co., St. Louis, Mo.). Clones were picked and inoculated into 3 mL LB broth containing 100 μg/mL carbenicillin. Plasmid DNA was extracted from a 14 h culture using a QIAprep™ Spin Miniprep Kit (Qiagen). Automated DNA sequencing was performed as recommended (Applied Biosystems/Perkin Elmer, Foster City, Calif.). Both strands of the cDNA were sequenced and shown to be identical to the sequence for the original SA14 strain (Nitayaphan et al., 1990).

Figure 3:
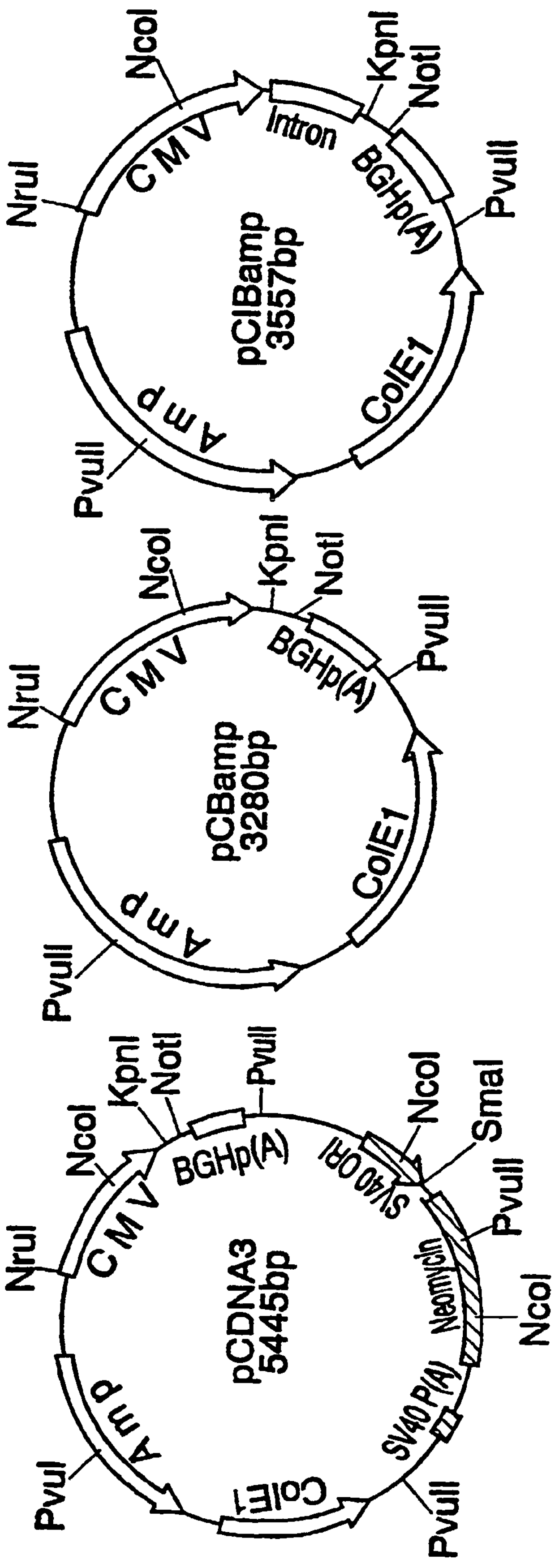
FIG. 3 shows a schematic representation of the plasmid vectors, pCDNA3, pCBamp, and pCIBamp, and the relationship between them. These plasmids include the CMV (cytomegalovirus) promoter/enhancer element, BGHp(A) (bovine growth hormone polyadenylation signal and transcription termination sequence), ampicillin resistance gene and ColE1 origin of replication for selection and maintenance in *E. coli*. The f1 origin of replication for single-stranded rescue in *E. coli* cells, SV40 origin of replication (SV40 ORI), neomycin resistance coding region and SV40p (A) sequences were deleted from pCDNA3 to generate pCBamp. An intron sequence was inserted in the NcoI-KpnI site of pCBamp to generate plasmid pCIBamp.

The fragment of plasmid pCDNA3 (Invitrogen, Carlsbad, Calif.) from nucleotide (nt) 1289 to nt 3455, containing f1 ori, SV40 ori, the neomycin resistance gene, and SV40 poly(A) elements was deleted by PvII digestion and then ligated to generate the pCBamp plasmid. The vector pCIBamp, containing a chimeric intron insertion at the NcoI/KpnI site of the pCBamp was constructed by excising the intron sequence from pCI (Promega, Madison, Wis.) by digestion with NcoI and KpnI. The resulting 566-bp fragment was cloned into pCBamp by digesting with NcoI-KpnI to replace its 289-bp fragment. FIG. 3 presents the relationships between the plasmids pCDA3, pCBamp, and pCIBamp.

Plasmids containing the transcriptional unit encoding JEV prM and E proteins were prepared from these plasmids. The cDNA fragment containing the JEV prM and E coding regions in the recombinant plasmid pCDJE2-7 (nucleotide sequence, SEQ ID NO:10; amino acid sequence, SEQ ID NO:11), derived from the pCDNA3 vector, was excised by digestion with NotI and KpnI or XbaI and cloned into the KpnI-NotI site of pCBamp, pCIBamp, pCEP4 (Invitrogen, Carlsbad, Calif.), or pREP4 (Invitrogen, Carlsbad, Calif.), or into the SpeI-NotI site of pRc/RSV (Invitrogen, Carlsbad, Calif.) expression vector to create pCBJE1-14 (nucleotide sequence, SEQ ID NO:17; amino acid sequence, SEQ ID NO:18), pCIBJES14, pCEJE, pREFE, and pRCJE, respectively. Both strands of the cDNA from clones of each plasmid were sequenced and recombinant clones with the correct nucleotide sequence were identified. Plasmid DNA for use in the in vitro transformation of mammalian cells or mouse immunization experiments was purified by anion exchange chromatography using an EndoFree™ Plasmid Maxi Kit (Qiagen).

Example 2

Evaluation of JEV prM and E Proteins Expressed by Various Recombinant Plasmids using an Indirect Immunofluorescent Antibody Assay The expression of JEV specific gene products by the various recombinant expression plasmids was evaluated in transiently transfected cell lines of COS-1, COS-7 and SV-T2 (ATCC, Rockville Md.; 1650-CRL, 1651-CRL, and 163.1-

CCL, respectively) by indirect immunofluorescent antibody assay (IFA). The SV-T2 cell line was excluded from further testing since a preliminary result showed only 1-2% of transformed SV-T2 cells were JEV antigen positive. For transformation, cells were grown to 75% confluence in 150 $cm^2$ culture flasks, trypsinized, and resuspended at 4° C. in phosphate buffered saline (PBS) to a final cell count $5\times10^6$ per mL. 10 μg of plasmid DNA was electroporated into 300 μL of cell suspension using a BioRad Gene Pulse™ (Bio-Rad) set at 150 V, 960 μF and 100 Ω resistance. Five minutes after electroporation, cells were diluted with 25 mL fresh medium and seeded into a 75 $cm^2$ flask. 48 h after transformation the medium was removed from the cells, and the cells were trypsinized and resuspended in 5 mL PBS with 3% normal goat serum. 10 μL aliquots were spotted onto slides, air dried and fixed with acetone at −20° C. for 20 min. IFA was performed with acetone-fixed plasmid-transformed cells using fluorescein isothiocyanate-conjugated goat anti-mouse immunoglobulin G (Sigma Chemical Co.) and JEV HIAF.

To determine the influence of various promoter and poly (A) elements on the JEV prM and E protein expression, COS-1 and COS-7 cell lines were transiently transformed by an equal amount of pCDJE2-7 (SEQ ID NO:10), pCEJE, pREJE, or pRCJE plasmid DNA. JEV antigens were expressed in both cell lines transformed by all four recombinant plasmids, thus confirming that the CMV or RSV (rous sarcoma virus) promoter and BGH or SV40 poly(A) elements were functionally active. However, the percentage of transformed cells and the level of JEV antigens expressed, as determined by the number of IFA positive cells and IFA intensity, respectively, differed greatly among the various plasmids (Table 1). A significantly high percentage of COS-1 cells transformed by pCDJE2-7 (SEQ ID NO:10), pCBJE1-14 (SEQ ID NO:17) and pCIBJES14 expressed the JEV antigens, and the level of the expressed proteins was compatible with JEV-infected cells. Cells transfected with pCEJE, pREJE, or pRCJE vectors, on the other hand, had a low percentage of antigen-expressing cells, as well as a low intensity of fluorescence, indicating weak expression of the antigens.

In order to ascertain whether the enhanced expression of JEV proteins by pCDJE2-7 (SEQ ID NO:10) was influenced by the SV40-encoded eukaryotic origin of replication, the plasmid pCBJE1-14 (SEQ ID NO:17) was constructed so that a 2166-bp fragment, containing f1 ori, SV40 ori, the neomycin resistance gene and SV40 poly(a) elements from pCDJE2-7, was deleted. A chimeric intron was then inserted into pCBJE1-14 to generate pCIBJES14. The pCIBJES14 plasmid was used to determine if the expression of JEV proteins could be enhanced by the intron sequence. Following transformation, cells harboring both pCBJE1-14 and pCIBJES14 vectors expressed a level of JEV antigens similar to that observed with pCDJE2-7 (Table 1). This result indicates that expression of JEV prM and E antigens by recombinant vectors is influenced only by the transcriptional regulatory elements. Neither the eukaryotic origin of replication nor the intron sequence enhanced JEV antigen expression in the cells used. Vectors containing the CMV promoter and BGH poly(A) (FIG. 3) were selected for further analysis.

Example 3

Selection of an In Vitro Transformed, Stable Cell Line Constitutively Expressing JEV Specific Gene Products COS-1 cells were transformed with 10 μg of pCDJE2-7 DNA by electroporation as described in the previous example. After a 24 hr incubation in non-selective culture medium, cells were treated with neomycin (0.5 mg/mL, Sigma Chemical Co.). Neomycin-resistant colonies, which became visible after 2-3 weeks, were cloned by limited dilution in neomycin-containing medium. Expression of vector-encoded JEV gene products was initially screened by IFA using JEV HIAF. One JEV-IFA positive clone (JE-4B) and one negative clone (JE-SA) were selected for further analysis and maintained in medium containing 200 μg/mL neomycin.

Authenticity of the JEV E protein expressed by the JE-4B clone was demonstrated by epitope mapping by IFA using a panel of JEV E-specific murine monoclonal antibodies (Mab) (Kimura-Kuroda et al., *J. Virol.* 45: 124-132 (1983); Kimura-Kuroda et al., *J. Gen. Virol.* 67: 2663-2672 (1986); Zhang et al., *J. Med. Virol.* 29: 133-138 (1989); and Roehrig et al., *Virol.* 128: 118-126 (1983)). JEV HIAF and normal mouse serum were used as positive and negative antibody controls, respectively. Four JEV-specific, six *flavivirus*-subgroup specific, and two *flavivirus*-group reactive Mabs reacted similarly with the 4B clone or JEV-infected COS-1 cells (Table 2).

Example 4

Figure 4:
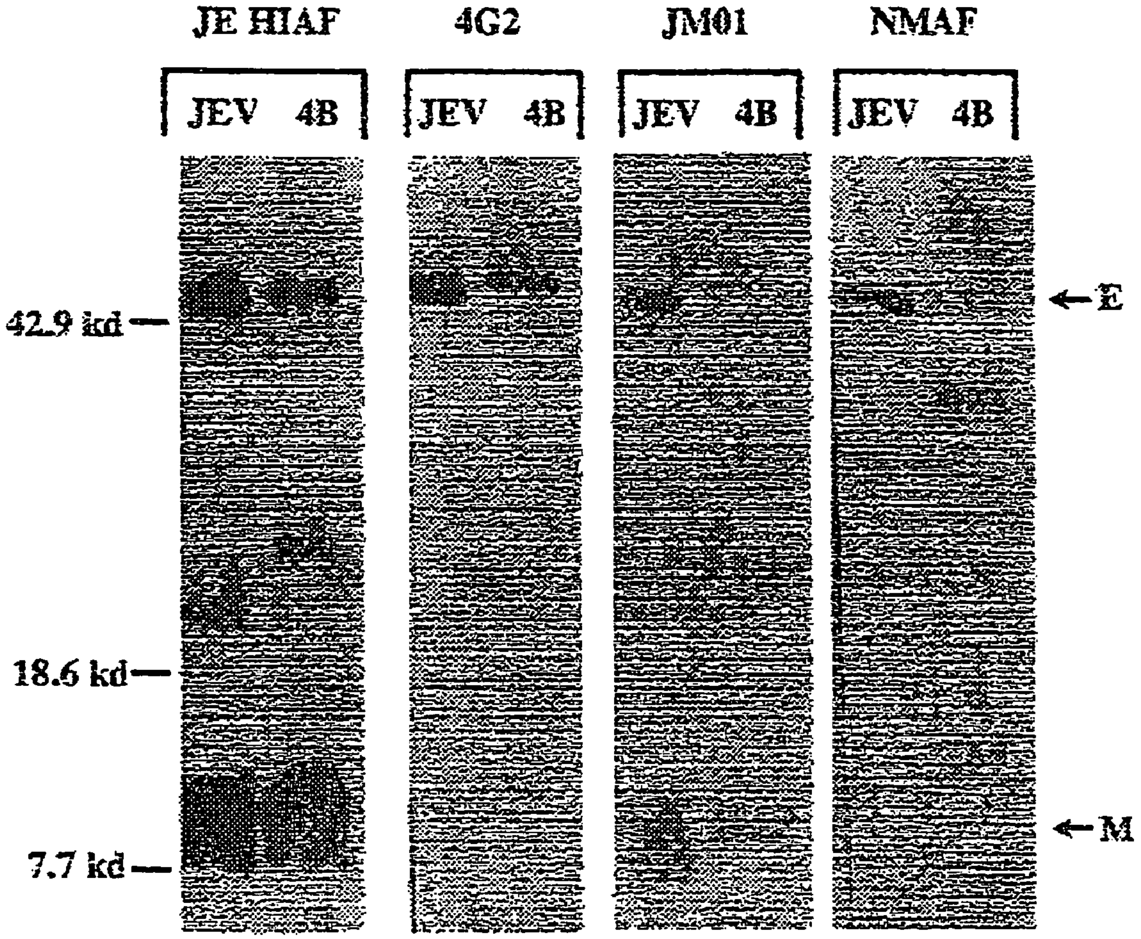
FIG. 4 shows SDS-PAGE-immunoblot analyses of the sucrose gradient purified subviral particles from JE-4B COS-1 culture fluid (4B, right lane of each pair). The density gradient purified JE virion from JEV infected C6/36 cell culture was used as a positive control (JEV, left lane of each pair). JE HIAF (hyperimmune ascitic fluid); 4G2, anti-E monoclonal antibody; JM01, anti-M monoclonal antibody; NMAF (normal mouse ascitic fluid).

Antigenic Properties and Immunological Detection of Subviral Particles Secreted by the JE-4B COS-1 Cell Line a. Preparation of subviral particles. JE-4B COS-1 cells were grown and maintained in medium containing 200 μg/mL of neomycin. The cultured medium was routinely harvested and stored at 4° C., and replenished twice weekly, and the cells were split 1:5 every 7-10 days. Culture medium was clarified by centrifugation at 10,000 rpm for 30 min in a Sorvall F16/250 rotor at 4° C., and centrifuged further for 4 hr at 39,000 rpm in a Sorvall TH641 rotor at 4° C. through a 5% sucrose cushion (w/w, prepared with 10 mM Tris HCl, pH 7.5, 100 mM NaCl (TN buffer)). The pellet containing subviral particles was resuspended in TN buffer and stored at 4° C. Alternatively, 7% or 10% PEG-8000 (w/v) was added to the clarified culture medium. The mixture was stirred at 4° C. for at least 2 hr, and the precipitated particles were collected by centrifugation at 10,000 rpm for 30 min. The precipitate was resuspended in TN buffer and stored at 4° C. The subviral particles were purified from both pelleted and PEG-precipitated preparations by rate zonal centrifugation in a 5-25% continuous sucrose gradient in TN at 38,000 rpm at 4° C. for 90 min. 1-mL fractions were collected from the top of the gradient, tested by antigen capture ELISA (see below), and the positive fractions loaded onto a 25-50% sucrose gradient in TN. This was centrifuged overnight in an equilibrium density centrifugation at 35,000 rpm at 4° C. 0.9-mL fractions from the equilibrium gradients were collected from the bottom. They were tested by antigen-capture ELISA and assessed for hemagglutination (HA) activity at pH 6.6. An aliquot of 100 μL of each fraction was weighed precisely to determine its density. The ELISA-positive fractions were pooled and pelleted at 39,000 rpm at 4° C. for 3-4 hr and the pellet resuspended in TN buffer. Antigen-capture ELISA and HA titers were determined on the pelleted samples. JEV-infected COS-1 cell supernatant was also subjected to similar purification protocols as detailed above and used as a positive control for the gradient analysis. JE virions were also purified from infected C6/36 cells 5-6 days postinfection by sedimentation in a glycerol/tartrate equilibrium gradient.

b. Western blots of subviral particles. Gradient-purified samples of the subviral particles were mixed with electrophoresis sample buffer and run on 10 or 12.5% sodium dodecyl sulfate-containing polyacrylamide gels (SDS-PAGE) as described by Laemmli (*Nature* 277: 680-685 (1970)). Proteins were transferred to a nitrocellulose membrane and immunochemically detected with polyclonal JEV HIAF, *flavivirus* cross-reactive anti-E Mab 4G2 (Henchal et al., *Amer. J. Trop. Med. Hyg.* 31: 830-836 (1982)), or mouse anti-prM peptide hyperimmune serum (JM101). FIG. 4 shows a comparison of the M and E proteins produced by JEV infected C6/36 and J-4B COS-1 cells. Some nonspecific reactivity to E protein was observed in the normal mouse ascitic fluid and Jmol anti-peptide serum. Proteins identical in size to M and E were secreted in the subviral particles and could be detected by E-specific Mab 4G2 and prM-specific JM01 antiserum, respectively.

c. Density gradient detection of JEV subviral particles in culture medium. For ELISA, antigen-capture antibody (4G2) was diluted in 0.1 M sodium carbonate buffer, pH 9.6, and used to coat 96-well microtiter plates (Immulon II, Dynatech, Chantilly, Va.) by overnight incubation at 4° C. After blocking with 3% normal goat serum in PBS, two-fold serially-diluted samples were added to the 402-coated plate and incubated 1.5 hours at 37° C. Captured antigen was detected by horseradish peroxidase-conjugated 6B6C-1 Mag, and incubated for 1 hour at 37° C. The enzyme activity on the solid phase was then detected with TMB (3,3',5,5'-tetramethylbenzidine)-ELISA (Life Technologies, Grand Island, N.Y.).

Figure 5:
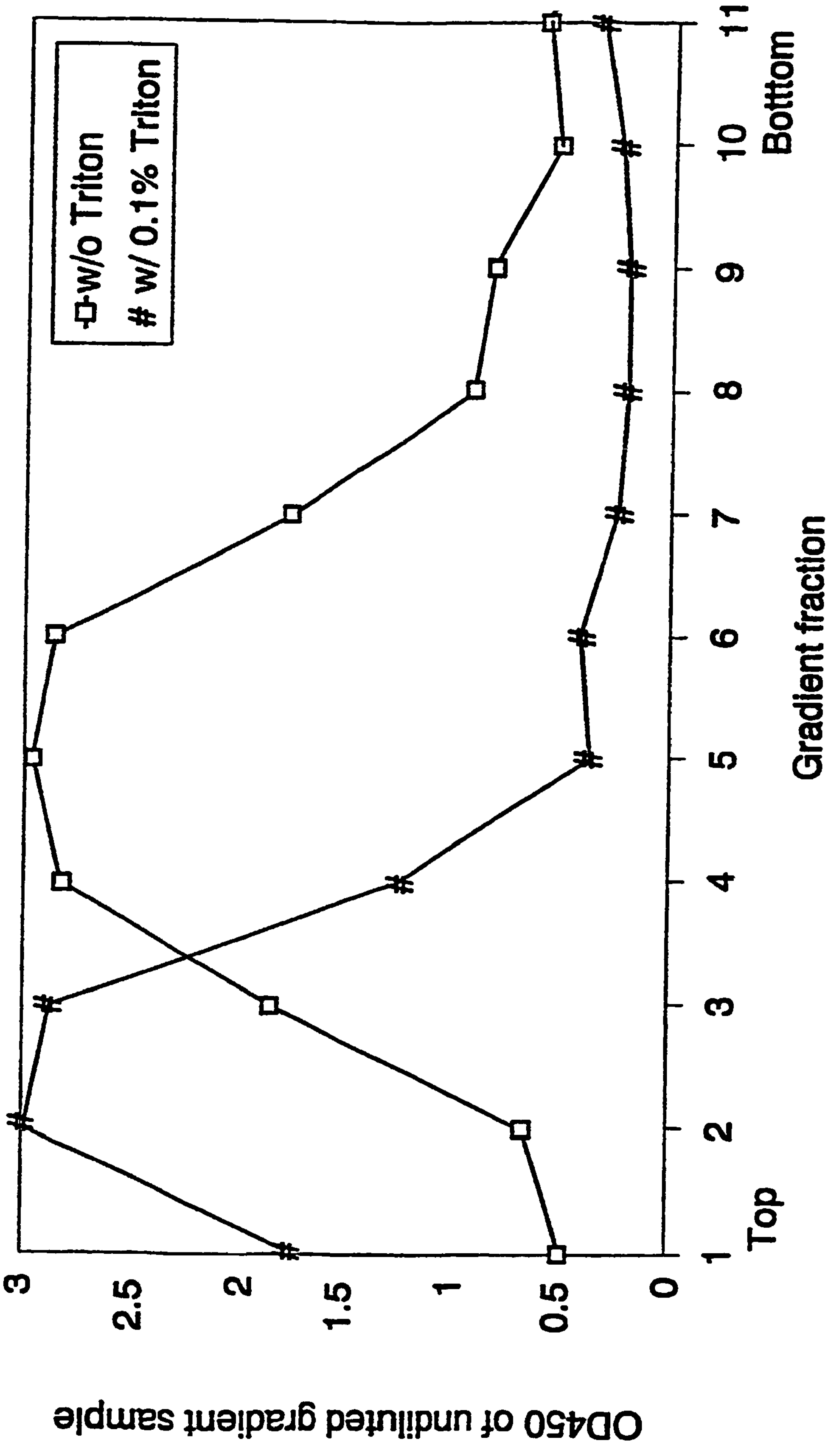
FIG. 5 shows a profile of the E antigen in a rate zonal sucrose gradient analysis prepared from the PEG precipitate of JE4B cell culture medium with or without Triton X-100 treatment.

Approximately 500 mL of cell culture medium from 15×150 $cm^2$ flasks of JE-4B cells was collected four days after cells were seeded. PEG-precipitated subviral particles were resuspended in 2 mL of TN buffer, pH 7.5; a 0.7 mL aliquot of this resuspended pellet was loaded onto a 5-25% sucrose gradient. Triton X-100, which disrupts subviral particles, was added to another 0.7 mL aliquot to a final concentration of 0.1% and this was loaded onto a 5-25% sucrose gradient prepared in TN buffer containing 0.1% Triton X-100. A definite opaque band was observed approximately 2.5 cm from the top of the gradient containing Triton X-100, but not in the gradient without detergent. Fractions (1 mL) were collected from top to bottom for each gradient (FIG. 5). Each collected fraction was analyzed by antigen capture ELISA. Antigen was detected in fractions 4-6, indicating relatively rapid sedimentation characteristic of subviral particles. Treatment of the PEG precipitate from JE-4B culture medium with Triton X-100 shifted the position of ELISA-reactive material to the top of the gradient. Thus treatment with Triton X-100 produces only slow-sedimenting molecules. A similar finding was reported by Konishi et al. (*Virol.* 188: 714-720 (1992)). These results show that rapidly sedimenting subviral particles containing prM/M and E could be disrupted by detergent treatment.

Hemagglutination (HA) activity was determined in the pH range from 6.1 to 7.0 by the method of Clarke and Casals (*Amer. J. Trop. Med. Hyg.* 7: 561-573 (1958)). The subviral particle secreted by JE-4B cells and the virion particle produced by JEV infected COS-1 cells had a similar HA profile with the optimum pH determined to be 6.6.

Example 5

Comparison of the Immune Response in Mice Vaccinated with pCDJE2-7 Nucleic Acid Vaccine of the Invention and Commercial JEV Vaccine Groups of five 3-week-old female, ICR outbred mice were injected intramuscularly in the left and right quadriceps with 100 μg of pCDJE2-7 plasmid in 100 μL of $dH_2O$ or were given doses of JE-VAX (manufactured by the Research Foundation for Microbial Disease of Osaka University and distributed by Connaught Laboratories, Swiftwater, Pa.) subcutaneously that are one-fifth the dose given to humans. The plasmid pCDNA3/CAT (Invitrogen), which encodes and expresses an unrelated protein, was used as the negative vaccination control. Except for one group of pCDJE2-7-vaccinated mice, all animals were boosted 3 weeks later with an additional dose of plasmid or JE-VAX. Mice were bled from the retroorbital sinus at 3, 6, 9, 23, 40 and 60 weeks after inoculation. JEV antibody titers were determined by enzyme-linked imunosorbent assay (ELISA) against purified JEV or by plaque reduction neutralization tests (PRNT) (Roehrig et al., *Virol.* 171: 49-60 (1989); and Hunt and Calisher, *Amer. J. Trop. Med. Hyg.* 28: 740-749 (1979)).

The pCDJE2-7 nucleic acid vaccine and JE-VAX provided 100% seroconversion within three weeks after the first vaccination in all three groups of mice (Table 3). The JEV ELISA and PRNT antibody titers reached the highest level at week 6 and week 9, respectively, after immunization. Mice receiving 1 dose of DNA vaccine had similar antibody responses as those receiving 2 doses. Comparable ELISA antibody titers were maintained in DNA-vaccinated groups up to 60 weeks, after which the experiment was terminated. However, only one of four mice in the JE-VAX group was JEV antibody positive at 60 weeks post-inoculation. The pCDNA3/CAT control group did not have any measurable JEV antibody. These results demonstrate that a single dose of JEV-specific nucleic acid vaccine is more effective in maintaining JEV antibody in mice than the commercial, FDA-approved JE-VAX vaccine.

Example 6

Comparison of Various Nucleic Acid Vaccine Constructs of the Invention and Commercial JEV Vaccine for Effectiveness of Vaccination at Different Ages A similar level of JEV protein was expressed by COS-1 cells transformed by either pCDJE2-7, pCBJE1-14, or pCIBJES14. JEV antibody induction by these nucleic acid constructs was compared to JE-VAX commercial vaccine at two different ages at vaccination. Three-day (mixed sex) or 3-week-old (female) ICR outbred mice, 10 per group, were vaccinated intramuscularly with 50 or 100 μg of plasmid DNA, or subcutaneously with doses of JE-VAX that are one-tenth or one-fifth the dose given to humans. Serum specimens were collected at 3 and 7 weeks after immunization and tested at a 1:1600 dilution by ELISA using purified JEV as an antigen. Results are shown in Table 4.

Plasmid pCBJE1-14 provided the highest extent of seroconversion, i.e., antibody titer greater than 1:1600, achieving 80-100% at both ages of vaccination. Administration of pCDJE2-7 or pCIBJES14 provided moderate seroconversion by 7 weeks when 3-day old mice were vaccinated (60% for each), but weaker seroconversion (40% and 10%, respectively) when measured 3 weeks after vaccination. When these plasmids were administered at the age of 3 weeks, however, seroconversions of 90% or 100% were attained at both 3 weeks and 7 weeks after vaccination. In contrast, the commercial vaccine, JE-VAX, conferred no seroconversion when administered at 3 days of age, and 100% when given at 3 weeks of age. Thus the nucleic acid TU's for JEV prM and E provided an extent of seroconversion better than a very high dose of the commercial vaccine, and unexpectedly high seroconversion in both young and more mature animals.

Example 7

Protective Immunity Conferred by the Nucleic Acid Vaccine of the Invention

Three-day old vaccinated groups from Example 6 were challenged 7 weeks after vaccination by intraperitoneal injection of 50,000 pfu/100 μL of the mouse-adapted JEV strain SA14 and observed for 3 weeks. 100% protection was achieved in groups that received various nucleic acid TU-containing vaccine constructs for up to 21 days (Table 5). In contrast, 60% of the JE-VAX-vaccinated mice, as well as 70% of the pCDNA3/CAT-vaccinated negative controls, did not survive virus challenge by 21 days. These results indicate that the nucleic acid TU's of the invention confer unexpectedly effective protection on vaccinated mice. This suggests the possibility of employing the nucleic acid vaccine of the invention as an early childhood vaccine for humans. In contrast, JE-VAX, the inactivated human vaccine currently used, does not appear to be effective in young animals.

Example 8

Passive Protection of Neonatal Mice Correlated with the Maternal Antibody Titer

Female ICR mice at the age of 3 weeks were vaccinated with either one dose or two doses spaced two days apart of pCDJE2-7 plasmid DNA, at 100 μg/100 μL, or with two doses of JE-VAX that were one-fifth the dose given to humans. The negative control group received two doses of 100 μg/100 μL of pCDNA-3/CAT plasmid. Passive protection by maternal antibody was evaluated in pups resulting from matings of experimental females with non-immunized male mice that occurred nine weeks following the first vaccination or 6 weeks following the second vaccination. Pups were challenged between 3-15 days after birth by intraperitoneal administration of 5,000 pfu/100 μL of mouse-adapted SA14 virus and observed daily for 3 weeks (Table 6). The survival rates correlated with the maternal neutralizing antibody titers. 100% of pups nursed by mothers with a PRNT of 1:80 survived viral infection, whereas none of the pups from the control mother survived (Table 6). Partial protection of 45% and 75% was observed in older pups that were nursed by mothers with a PRNT titer of 1:20 and 1:40, respectively. The survival rates also correlated with the length of time that pups were nursed by the immune mother. As just indicated, 13-15 day old pups had high survival rates. None of the 34 day old pups, however, survived virus challenge when the mother had a PRNT titer of 1:20 or 1:40. Thus maternal antibody provides partial to complete protective immunity to the offspring. In addition, JEV antibody was detected by ELISA in the sera of 97% (29/30) of the post-challenge pups.

Mice were inoculated intramuscularly with 1 or 2, 100 μg doses of plasmid DNA, or subcutaneously with two, ⅕ human doses of JE-VAX vaccine. Sera were collected 9 weeks post-vaccination for PRNT testing prior to mating with non-immune male.

Example 9

Preparation of Recombinant Plasmids Containing the Transcriptional Unit Encoding WNV prM and E Antigens Genomic RNA was extracted from 150 μL of Vero cell culture medium infected with NY 99-6480 strain, an strain isolated from the outbreak in New York 1999, using the QIAamp™ Viral RNA Kit (Qiagen, Santa Clarita, Calif.). Extracted RNA was eluted and suspended in 80 μl of nuclease-free water, and used as a template for the amplification of WNV prM and E gene coding sequences. Primer sequences were obtained from the work of Lanciotti et al. (*Science* 286: 2333-2337 (1999)). A cDNA fragment containing the genomic nucleotide region was amplified by the reverse transcriptase-polymerase chain reaction (RT-PCR). Restriction sites BsmBI and KasI were engineered at the 5' terminus of the cDNA by using amplimer WN466 (nucleotide sequence, SEQ ID NO:12). An in-frame translation termination codon, followed by a NotI restriction site was introduced at the 3' terminus of the cDNA by using amplimer cWN2444 (SEQ ID NO:13). The RT-PCR product was purified by a QIAquick™ PCR Purification Kit (Qiagen).

The double-stranded amplicon produced by use of the two amplimers above (SEQ ID NO:12 and SEQ ID NO:13) was digested with KasI and NotI enzymes to generate a 998 bp (nt-1470 to 2468) fragment of DNA was inserted into the KasI and NotI sites of a pCBJESS vector to form an intermediate plasmid, pCBINT. The pCBJESS was derived from the pCBamp plasmid, that contained the cytomegalovirus early gene promoter and translational control element and an engineered JE signal sequence element (Chang et al., *J. Virol.* 74: 4244-4252 (2000)). The JE signal sequence element comprises the JE signal sequence (SEQ ID NO:14).

The cDNA amplicon was subsequently digested with BsmBI and Kas I enzymes and the remaining 1003 bp fragment (nt-466 to 1470) was inserted in to the KasI site of pCBINT to form pCBWN (nucleic acid sequence, SEQ ID NO:15; amino acid sequence, SEQ ID NO:16). Automated DNA sequencing using an ABI prism 377 Sequencer (Applied Biosystems/Perkin Elmer, Foster City, Calif.) was used to confirm that the recombinant plasmid had a correct prM and E sequence as defined by Lanciotti et al. (*Science* 286: 2333-2337 (1999)).

Plasmid DNA for use in the in vitro transformation of mammalian cells or mouse immunization experiments was purified by anion exchange chromatography as described in Example 1.

Example 10

Immunochemical Characterization and Evaluation of WNV prM and E Proteins Expressed by pCBWN WNV specific gene products encoded by the pCBWN plasmid were expressed in COS-1 cells. Cells were electroporated and transformed with pCBWN plasmid according to Chang et al. (*J. Virol.* 74: 4244-4252 (2000)). Electroporated cells were seeded onto 75 $cm^2$ culture flasks or a 12-well tissue culture dish containing one sterile coverslip/well. All flasks and 12-well plates were kept at 37° C., 5% $CO_2$ incubator. Forty hours following electroporation, coverslips containing adherent cells were removed from the wells, washed briefly with PBS, fixed with acetone for 2 minutes at room temperature, and allowed to air dry.

Protein expression was detected using indirect immunofluorescence antibody assay (IFA), as described in Example 2. *Flavivirus* E-protein specific monoclonal antibody (Mab) 4G2, WNV mouse hyperimmune ascitic fluid (HIAF) and normal mouse serum (NMS) at 1:200 dilution in PBS were used as the primary antibody to detect protein expression (Henchal et al., *Am. J. Trop. Med. Hyg.* 31: 830-836 (1982)).

Tissue culture medium was harvested 40 and 80 hours following electroporation. Antigen-capture (Ag-capture) ELISA was used to detect secreted WN virus antigen in the culture medium of transiently transformed COS-1 cells. The Mab 4G2 and horseradish peroxidase-conjugated Mab 6B6C-1 were used to capture the WN virus antigens and detect captured antigen, respectively (Chang et al., *J. Virol.* 74: 4244-4452 (2000); Henchal et al., *Am. J. Trop. Med. Hyg.* 31: 830-836 (1983); Roehrig et al., *Virology* 128: 118-126 (1983)).

WN virus antigen in the medium was concentrated by precipitation with 10% polyethylene glycol (PEG)-8000. The precipitant was resuspended in TNE buffer (50 mM Tris, 100 mM NaCl, 10 mM EDTA, pH 7.5), clarified by centrifugation, and stored at 4° C. Alternatively, the precipitant was resuspended in a lyophilization buffer (0.1 M TRIZMA and 0.4% bovine serum albumin in borate saline buffer, pH 9.0), lyophilized and stored at 4° C. Lyophilized preparations were used as antigen for the evaluation in MAC— and indirect IgG ELISAs.

WN virus-specific protein was detected by IFA on the transiently transformed COS-1 cells. E, prM and M proteins expressed in these cells were secreted into the culture medium. WN virus antigen concentrated by PEG precipitation was extracted with 7.0% ethanol to remove residual PEG (Aizawa et al., *Appl. Enviro. Micro.* 39: 54-57 (1980)). Ethanol extracted antigens and gradient-purified WN virions were analyzed on a NuPAGE, 4-12% gradient Bis-Tris Gel in a Excel Plus Electrophoresis Apparatus (Invitrogen Corp., Carlsbad, Calif.) and followed by electroblotting onto nitrocellulose membranes using a Excel Plus Blot Unit (Invitrogen Corp.). WN virus-specific proteins produced by the transiently transformed COS-1 cells were detected by WN virus specific mouse HIAF or *flavivirus* E protein reactive Mab 4G2 in a Western blot analysis, using NMS as a negative serum control. The proteins displayed similar reactivity and identical molecular weights to the corresponding gradient purified virion E, prM and M protein derived from WN virus infected suckling mouse brain (SMB).

In analysis of the NRA as an antigen for diagnostic ELISA, one vial of lyophilized NRA, representing antigen harvested from 40 ml of tissue culture fluid, was reconstituted in 1.0 ml of distilled water and compared with the reconstituted WN virus infected suckling mouse brain (SMB) antigen provided as lyophilized as β-propiolactone-inactivated sucrose-acetone extracts (Clarke et al., *Am. J. Trop. Med. Hyg.* 7: 561-573 (1958)). All recombinant proteins, prM, M and E, had a similar reactivity to that of the gradient-purified virion E, prM and M proteins.

Coded human specimens were tested concurrently with antigens in the same test at the developmental stage. The MAC- and IgG ELISA protocols employed were identical to the published methods (Johnson et al., *J. Clin. Microbiol.* 38: 1827-1831 (2000); Martin et al., *J. Clin. Microbiol.* 38: 1823-1826. (2000)). Human serum specimens were obtained from the serum bank in our facility, which consists of specimens sent to the DVBID for WN virus confirmation testing during the 1999 outbreak In these tests, a screening MAC— and IgG ELISA were performed on a 1:400 specimen dilution. Specimens yielding positive/negative (P/N) OD ratios between 2 and 3 were considered suspect positives. Suspect serum specimens were subject to confirmation as positives by both ELISA end-point titration and plaque-reduction neutralization test (PRNT). All specimens yielding P/N OD ratios greater than 3.0 were considered positives without further confirmatory testing.

An Ag-capture ELISA employing *flavivirus*-group reactive, anti-E Mab, 4G2 and 6B6C-1, was used to detect NRA secreted into culture fluid of pCBWN transformed COS-1 cells. The antigen could be detected in the medium one day following transformation; and the maximum ELISA titer (1:32-1:64) in the culture fluid without further concentration was observed between day two and day four. NRA was concentrated by PEG precipitation, resuspended in a lyophilization buffer, and lyophilized for preservation. For diagnostic test development, one vial of lyophilized NRA was reconstituted with 1.0 ml distilled water and titrated in the MAC— or indirect IgG ELISA using WN virus positive and negative reference human sera (Johnson et al., *J. Clin. Microbiol.* 38: 1827-1831 (2000); Martin et al., *J. Clin. Microbiol.* 38: 1823-1826 (2000)). Dilutions 1:320 and 1:160 of the NRA were found to be the optimal concentrations for use in MAC— and IgG ELISA, respectively. These dilutions resulted in a P/N $OD_{450}$ ratio of 4.19 and 4.54, respectively, for MAC— and IgG test. The WN virus SMB antigens produced by NY-6480 and Eg101 strains were used at 1:320 and 1:640 dilution for MAC-ELISA, and 1:120 and 1:320 for IgG ELISA, respectively. The negative control antigens, PEG precipitates of the culture medium of normal COS-1 cells and normal SMB antigen, were used at the same dilutions as for the respective NRA and SMB antigen. Human serum specimens, diluted at 1:400, were tested concurrently in triplicate with virus-specific and negative control antigens. For the positive test result to be valid, the $OD_{450}$ for the test serum reacted with viral antigen (P) had to be at least two-fold greater than the corresponding optical density value of the same serum reacted with negative control antigen (N).

The reactivity of NRA and NY-06480, Eg101 and SLE virus SMBs were compared by the MAC— and IgG ELISAs using 21 coded human serum specimens. Of the 21 specimens, 19 had similar results on all three antigens (8 negatives and 11 suspect positives or positives). Eighteen specimens were also tested separately using SLE SMB antigen. Only three of 13 Eg-101-SMB positive specimens were positive in the SLE MAC-ELISA (Table 1). None of WN antigen negative specimens was positive by SLE MAC-ELISA. This result confirmed a previous observation that anti-WN virus IgM did not cross-react significantly with other flaviviruses (Tardei et al., *J. Clin. Microbiol.* 38: 2232-2239 (1940)) and was specific to diagnose acute WN virus infection regardless of whether NRA or SMB antigen was used in the test. All of the specimens were also tested concurrently by indirect IgG ELISA. Ten of 21 specimens were positive using any of the three antigens.

The two discrepant serum specimens (7 and 9) both from the same patient, collected on day-4 and 44 after onset of disease, respectively, were IgM-negative with NRA and SMB NY antigen and IgM-positive using Eg-101 SMB antigen in the initial test. To investigate these two discordant specimens further, six sequentially collected specimens from this patient were retested by end-point MAC— and IgG ELISAs. A greater than 32-fold serial increase shown in the MAC-ELISA titer between day-3 and day-15 could be demonstrated with all antigens used. Cerebrospinal fluid collected on day-9 after onset of disease also confirmed that this patient indeed was infected by WN shortly prior to taking the sample. The cerebrospinal fluid had IgM P/N reading of 13.71 and 2.04 against Eg-101- and SLE-SMB antigens, respectively. Day-31 and day-44 specimens were negative (<1:400) by using NY-SMB antigen but positive by using NRA and Eg101-SMB. Compatible IgG titers were observed with all three antigens used in the test.

Example 11

Evaluation of the Immune Response in Animals Vaccinated with pCBWN

Groups of ten, three-wk-old female ICR mice were used in the study. Mice were injected intramuscularly (i.m.) with a single dose of pCBWN or a green fluorescent protein expressing plasmid (pEGFP) DNA (Clonetech, San Francisco, Calif.). The pCBWN plasmid DNA was purified from XL-1 blue cells with EndoFree Plasmid Giga Kits (Qiagen) and resuspended in PBS, pH 7.5, at a concentration of 1.0 μg/μl. Mice that received 100 μg of pEGFP were used as unvaccinated controls. Mice were injected with the pCBWN plasmid at a dose of 100, 10, 1.0, or 0.1 μg in a volume of 100 μl. Groups that received 10, 1.0, or 0.1 μg of pCBWN were vaccinated by the electrotransfer mediated in vivo gene delivery protocol using the EMC-830 square wave electroporator (Genetronics Inc. San Diego, Calif.). The electrotransfer protocol was based on the method of Mir et al., (*Proc. Natl. Acad. Sci. USA* 96: 4262-4267.(1999)). Immediately following DNA injection, transcutaneous electric pulses were applied by two stainless steel plate electrodes, placed 4.5-5.5 mm apart, at each side of the leg. Electrical contact with the leg skin was ensured by completely wetting the leg with PBS. Two sets of four pulses of 40 volts/mm of 25 msec duration with a 200 msec interval between pulses were applied. The polarity of the electrode was reversed between the set of pulses to enhance electrotransfer efficiency.

Mice were bled every 3 wks following injection. The WN virus specific antibody response was evaluated by Ag-capture ELISA and plaque reduction neutralization test (PRNT). Individual sera were tested by IgG-ELISA, and pooled sera from 10 mice of each group were assayed by PRNT. All the mice vaccinated with pCBWN had IgG ELISA titers ranging from 1:640 to 1:1280 three wks after vaccination. The pooled sera collected at three and six wks had a Nt antibody titer of 1:80. None of the serum specimens from pEGFP control mice displayed any ELISA or Nt titer to WN virus.

To determine if the single i.m. vaccination of pCBWN could protect mice from WN virus infection, mice were challenged with NY-6480 virus either by intraperitoneal injection or by exposure to the bite of virus-infected *Culex* mosquitoes. Half of the mouse groups were challenged intraperitoneally (ip) at 6 wks post vaccination with 1,000 $LD_{50}$ (1,025 PFU/100 μl) of NY99-6480 virus. The remaining mice were each exposed to the bites of three *Culex tritaeniorhynchus* mosquitoes that has been infected with NY99-6480 virus 7 days prior to the challenge experiment. Mosquitoes were allowed to feed on mice until they were fully engorged. Mice were observed twice daily for three wks after challenge.

It was evident that the presence of Nt antibodies correlated with protective immunity, since all mice immunized with WN virus DNA remained healthy after virus challenge while all control mice developed symptoms of CNS infection 4-6 days following virus challenge and died on an average of 6.9 and 7.4 days after intraperitoneal or infective mosquito challenge, respectively. In the vaccinated group, the pooled sera collected three wks after virus challenge (9-wk post immunization) had Nt antibody titers of 1:640 or 1:320. Pooled vaccinated mouse sera reacted only with E protein in the Western blot analysis.

Groups of ten mice were immunized with 10.0 to 0.1 μg of pCBWN per animal by use of electrotransfer. All groups that received pCBWN were completely protected from virus challenge. At 6 wks after immunization all groups of electrotransfer mice had Nt titer less than four-fold different than animals receiving 100 μg of pCBWN by conventional i.m. injection without electrotransfer. Both these results evidencing effective immunization suggest that the electrotransfer protocol enhances the immunogenicity and protective efficacy of the DNA vaccine of the invention (when carried out as described in (Mir et al., *Proc. Natl. Acad. Sci. USA.* 96: 4262-4267. (1999))).

Mixed-bred mares and geldings of various ages used in this study were shown to be WN virus and SLE virus antibody-negative by ELISA and PRNT. Four horses were injected i.m. with a single dose (1,000 g/11,000 μl in PBS, pH 7.5) of pCBWN plasmid. Serum specimens were collected every other day for 38 days prior to virus challenge, and the WN virus specific antibody response was evaluated by MAC— or IgG ELISA and PRNT.

Two days prior to virus challenge, 12 horses (4 vaccinated and 8 control) were relocated into a bio-safety level (BSL)-3 containment building at the Colorado State University. The eight unvaccinated control horses were the subset of a study that was designed to investigate WN virus induced pathogenesis in horses and the potential of horses to serve as amplifying hosts. Horses were each challenged by the bite of 14 or 15 *Aedes albopictus* mosquitoes that had been infected by NY99-6425 or BC787 virus 12 days prior to horse challenge. Mosquitoes were allowed to feed on horses for a period of 10 min. Horses were examined for signs of disease twice daily. Body temperature was recorded, and serum specimens collected twice daily from days 0 (day of infection) to 10, then once daily through day 14. Pulse and respiration were recorded daily after challenge. The collected serum samples were tested by plaque titration for detection of viremia, and by MAC— or IgG ELISA and PRNT for antibody response.

No systemic or local reaction was observed in any vaccinated horse. Individual horse sera were tested by PRNT. Vaccinated horses developed Nt antibody greater than or equal to 1:5 between days 14 and 31. End point titers for vaccinated horses, #5, #6, #7, and #8, on day-37 (two days prior to mosquito challenge) were 1:40, 1:5, 1:20, and 1:20, respectively. Horses vaccinated with the pCBWN plasmid remained healthy after virus challenge. None of them developed a detectible viremia or fever from days 1 to 14. All unvaccinated control horses became infected with WN virus after exposure to infected mosquito bites. Seven of the eight unvaccinated horses developed viremia that appeared during the first 6 days after virus challenge. Viremic horses developed Nt antibody between day-7 and day-9 after virus challenge. The only horse from the entire study to display clinical signs of disease was horse #11, which became febrile and showed neurologic signs beginning 8 days after infection. This horse progressed to severe clinical disease within 24 hours and was euthanized on day 9. Four representing horses, #9, 10, 14 and 15, presenting viremia for 0, 2, 4, or 6 days, were selected and used as examples in this example. Virus titers ranged from $10^{1.0}$ PFU/ml of serum (in horse #10), the lowest level detectable in our assay, to $10^{2.4}$/ml (in horse #9). Horse #14 did not develop a detectible viremia during the test period. However, this horse was infected by the virus, as evidenced by Nt antibody detected after day 12.

Anamnestic Nt antibody response was not observed in vaccinated horses as evidenced by the gradual increase in Nt titer during the experiment. Pre-existing Nt antibody in the vaccinated horse prior to mosquito challenge could suppress initial virus infection and replication. Without virus replication, the challenge virus antigen provided by infected mosquitoes may not contain a sufficient antigen mass to stimulate anamnestic immune response in the vaccinated horse. All vaccinated horses were euthanized at 14 days after virus challenge. Gross pathological and histopathological lesions indicative of WN viral infection were not observed.

Example 12

Preparation of Recombinant Plasmids Containing Coding Sequences for Yellow Fever Virus (YFV) or St. Louis Encephalitis Virus (SLEV) prM and E Proteins A strategy similar to constructing the pCDJE2-7 recombinant plasmid was used to prepare YFV and SLEV recombinant plasmids. Genomic RNA was extracted from 150 μL of YFV strain TRI-788379 or SLE strain 78V-6507 virus seeds using Q1Aamp™ Viral RNA Kit (Qiagen, Santa Clarita, Calif.). The viral RNA was used as a template for amplification of YFV or SLEV prM and E gene coding regions. Primers YFDV389 (nucleotide sequence, SEQ ID NO:4; amino acid sequence, SEQ ID NO:5), cYFDV2452 (SEQ ID NO:6), SLEDV410 (nucleotide sequence, SEQ ID NO:7; amino acid sequence, SEQ ID NO:8) and cSLEDV2449 (SEQ ID NO:9) were used to generate the corresponding recombinant nucleic acids as described above for the preparation of the JEV and WNV recombinant plasmids. RT-PCR amplified cDNA, digested with KpnI and NotI enzymes, was inserted into the KpnI-NotI site of a eukaryotic expression plasmid vector, pCDNA3 (Invitrogen). Both strands of the cDNA were sequenced and verified for identity to sequences from YFV strain TRI-788379 or SLEV strain 78V-6507. Recombinant plasmids pCDYF2 and pCDSLE4-3, which contained the nucleotide sequences of the prM and E coding regions for YFV or SLEV, respectively, were purified using an EndoFree™ Plasmid Maxi Kit (Qiagen), and used for in vitro transformation or mouse immunization.

YFV or SLEV specific antigens were expressed in COS-1 cells transformed by pCDYF2 or pCDSLE4-3, respectively. The level of expressed proteins was similar to a YFV- or SLEV-infected COS-1 cell control. As in the JEV model, COS-1 cell lines transformed by vectors bearing genes for the viral antigens were obtained which constitutively express YFV or SLEV antigenic proteins. Epitope mapping by IFA using a panel of YFV or SLEV E-specific Mabs indicated that the authentic E protein was expressed by the pCDYF2— or pCDSLE4-3-transformed COS-1 cells. A preliminary study indicated that 100% of three week-old female, ICR mice seroconverted after intramuscular inoculation with a single dose of 100 μg/100 μL of pCDSLE4-3 plasmid in deionized water.

Example 13

Preparation of Recombinant Plasmids Containing Coding Sequences for St. Louis Encephalitis Virus prM and E Antigens with JEV Signal Sequence.

Genomic RNA was extracted from 150 μL of Vero cell culture medium infected with MSI-7 strain of St. Louis encephalitis virus using the QIAamp™ Viral RNA Kit (Qiagen, Santa Clarita, Calif.). Extracted RNA was eluted and suspended in 80 μl of nuclease-free water, and used as a template for the amplification of St. Louis encephalitis virus prM and E gene coding sequences. Primer sequences were obtained from the work of Trent et al. (*Virology* 156: 293-304 (1987)). A cDNA fragment containing the genomic nucleotide region was amplified by the reverse transcriptase-polymerase chain reaction (RT-PCR). Restriction site AfeI was engineered at the 5' terminus of the cDNA by using amplimer SLE463 (SEQ ID NO:30). An in-frame translation termination codon, followed by a NotI restriction site was introduced at the 3' terminus of the cDNA by using amplimer cSLE2447 (SEQ ID NO:31). The RT-PCR product was purified by a QIAquick™ PCR Purification Kit (Qiagen).

The double-stranded amplicon, produced by use of the two amplimers above (SEQ ID NO:30 and SEQ ID NO:31), was digested with AfeI and NotI enzymes to generate a 2004 fragment of DNA (463 to 2466 nt), and inserted into the AfeI and NotI sites of a pCBJESS-M vector to form pCBSLE (nucleotide sequence, SEQ ID NO:21; amino acid sequence, SEQ ID NO:22). The pCBJESS-M was derived from the pCBamp plasmid, that contained the cytomegalovirus early gene promoter and translational control element and an engineered, modified JE signal sequence element (SEQ ID NO:27). The JE signal sequence element comprises the modified JE signal sequence at −4 (Cys to Gly) and −2 (Gly to Ser) position in the original pCBJESS plasmid.

Automated DNA sequencing using an ABI prism 377 Sequencer (Applied Biosystems/Perkin Elmer, Foster City, Calif.) was used to confirm that the recombinant plasmid had a correct prM and E sequence as defined by Trent et al., (*Virology* 156: 293-304 (1987)).

Example 14

Preparation of Recombinant Plasmids Containing Coding Sequences for Yellow Fever Virus (YFV) prM and E Proteins with JEV Signal Sequence Genomic RNA was extracted from 150 μL of Vero cell culture medium infected with 17D-213 strain of yellow fever virus using the QIAamp™ Viral RNA Kit (Qiagen, Santa Clarita, Calif.). Extracted RNA was eluted and suspended in 80 μl of nuclease-free water, and used as a template for the amplification of yellow fever virus prM and E gene coding sequences. Primer sequences were obtained from the work of dos Santos et al. (*Virus Research* 35: 3541 (1995)). A cDNA fragment containing the genomic nucleotide region was amplified by the reverse transcriptase-polymerase chain reaction (RT-PCR). Restriction site AfeI was engineered at the 5' terminus of the cDNA by using amplimer YF482 (SEQ ID NO:28). An in-frame translation termination codon, followed by a NotI restriction site was introduced at the 3' terminus of the cDNA by using amplimer cYF2433 (SEQ ID NO:29). The RT-PCR product was purified by a QIAquick™ PCR Purification Kit (Qiagen).

The double-stranded amplicon, produced by use of the two amplimers above (SEQ ID NO:28 and SEQ ID NO:29), was digested with AfeI and NotI enzymes to generate a 1971 fragment of DNA (482 to 2452 nt), and inserted into the AfeI and NotI sites of a pCBJESS-M vector to form pCBYF (nucleotide sequence, SEQ ID NO:23; amino acid sequence, SEQ ID NO:24). The pCBJESS-M was derived from the pCBamp plasmid, that contained the cytomegalovirus early gene promoter and translational control element and an engineered JE signal sequence element (SEQ ID NO:27). The JE signal sequence element comprises the modified JE signal sequence at −4 (Cys to Gly) and −2 (Gly to Ser) position of JESS in the pCBJESS plasmid.

Automated DNA sequencing using an ABI prism 377 Sequencer (Applied Biosystems/Perkin Elmer, Foster City, Calif.) was used to confirm that the recombinant plasmid had a correct prM and E sequence as defined by dos Santos et al. (*Virus Research* 35: 35-41 (1995)).

Example 15

Preparation of Recombinant Plasmids Containing Coding Sequences for Powassan Virus prM and E Antigens with JEV Signal Sequence Genomic RNA was extracted from 150 μL of Vero cell culture medium infected with LB strain of Powassan virus using the QIAamp™ Viral RNA Kit (Qiagen, Santa Clarita, Calif.). Extracted RNA was eluted and suspended in 80 μl of nuclease-free water, and used as a template for the amplification of Powassan virus prM and E gene coding sequences. Primer sequences were obtained from the work of Mandl et al. (*Virology* 194: 173-184 (1993)). A cDNA fragment containing the genomic nucleotide region was amplified by the reverse transcriptase-polymerase chain reaction (RT-PCR). Restriction site AfeI was engineered at the 5' terminus of the cDNA by using amplimer POW454 (SEQ ID NO:25). An in-frame translation termination codon, followed by a NotI restriction site was introduced at the 3' terminus of the cDNA by using amplimer cPOW2417 (SEQ ID NO:26). The RT-PCR product was purified by a QIAquick™ PCR Purification Kit (Qiagen).

The double-stranded amplicon, produced by use of the two amplimers above (SEQ ID NO:25 and SEQ ID NO:26), was digested with AfeI and NotI enzymes to generate a 1983 bp fragment of DNA (454 to 2436 nt), and inserted into the AfeI and NotI sites of a pCBJESS-M vector to form pCBPOW (nucleotide sequence, SEQ ID NO:19; amino acid sequence, SEQ ID NO:20). The pCBJESS-M was derived from the pCBamp plasmid, that contained the cytomegalovirus early gene promoter and translational control element and an engineered JE signal sequence element (SEQ ID NO:27). The JE signal sequence element comprises the modified JE signal sequence at −4 (Cys to Gly) and −2 (Gly to Ser) position of JESS in the pCBJESS plasmid.

Automated DNA sequencing using an ABI prism 377 Sequencer (Applied Biosystems/Perkin Elmer, Foster City, Calif.) was used to confirm that the recombinant plasmid had a correct prM and E sequence as defined by Mandl et al. (*Virology* 194:173-184, (1993)).

Example 16

Preparation of Plasmids Containing Coding Sequences for Dengue Serotype 2 Structural Proteins.

Procedures such as those carried out for other flaviviruses (see Examples 1, 9 and 12-15) are to be followed to prepare vectors including nucleic acid TU's for dengue serotype 2 antigens. According to the examples, the amplimers used for construction of the vectors may be chosen to engineer the normal dengue virus signal sequence or they may be chosen so as to engineer a signal sequence from another *flavivirus*, such as a modified Japanese encephalitis virus signal sequence.

A plasmid containing the dengue serotype 2 gene region from prM to E is to be constructed. The dengue serotype 2 prM and E genes (Deubel et al., *Virology* 155:365-377 (1986); Gruenberg et al., *J. Gen. Virol.* 69: 1301-1398 (1988); Hahn et al., *Virology* 162:167-180 (1988)) are to be ligated into a plasmid such as pCDNA3, and then excised and cloned into vectors such as pCBamp, pCEP4, pREP4, or pRc/RSV (supplied by Invitrogen, Carlsbad, Calif.) to enable expression. If necessary, a dengue serotype 2 virus-specific sequence encoded in a cDNA sequence may be amplified using a procedure such as the polymerase chain reaction (PCR). Alternatively, if the viral RNA is the source of the gene region, a DNA sequence may be amplified by a RT-PCR procedure. A DNA fragment including an initiation codon at the 5' end, and a termination codon at the 3' end is to be cloned into an expression vector at an appropriate restriction nuclease-specific site, in such a way that the cytomegalovirus (CMV) immediate early (IE) promoter, an initiation codon, and a terminator, are operably linked to the dengue serotype 2 virus sequence.

Example 17

Vaccination of Mice Using a Dengue Serotype 2 DNA Vaccine

The dengue serotype 2 nucleic TU vaccine encoding the gene region from prM to E prepared in Example 16 is to be suspended in a suitable pharmaceutical carrier, such as water for injection or buffered physiological saline, and injected intramuscularly into groups of weanling mice. Control groups receive a comparable plasmid preparation lacking the dengue serotype 2 specific genes. The generation of dengue serotype 2-specific antibodies, and/or of dengue serotype 2-specific immune system cytotoxic cells, is to be assessed at fixed intervals thereafter, for example at weekly intervals. At about two to four months after administration of the nucleic acid TU vaccine, mice are to be challenged with dengue serotype 2 virus. Levels of viremia are to be assessed at appropriate intervals thereafter, such as every second day. Passive protection by maternal antibody is to be assessed as indicated in Example 8.

Example 18

Design and Construction of Improved Signal Peptides

Signal peptides can determine the translocation and orientation of inserted protein, hence, the topology of prM and E proteins. The most common feature of signal peptides of eukaryotes consists of an 8 to 12 stretch of hydrophobic amino acids called the h-region (von Heijne, "Signal sequences. The limits of variation" *J. Mol. Biol.* 184: 99-105 (1985)). The region between the initiator Met and the h-region, which is known as the n-region, usually has one to five amino acids, and normally carries positively charged amino acids. Between the h-region and the cleavage site is the c-region, which consists of three to seven polar but mostly uncharged amino acid residues. During viral polyprotein synthesis, modulation of the signalase cleavage site from a cryptic to cleavable conformation at the junction of C and prM proteins depends on prior removal of the C protein by the viral protease complex, NS2B/NS3 (Lobigs, "*flavivirus* premembrane protein cleavage and spike heterodimer secretion require the function of the viral proteinase NS3," *Proc. Natl. Acad. Sci. USA.* 90: 6218-6222 (1993)). Thus, it is critical to consider the effectiveness of the viral signal sequence when prM and E proteins are to be expressed alone by an expression plasmid.

Signal peptide differences in various plasmid constructs can account, at least in part, for the difference in protein translocation, cleavage site presentation and correct topology, thus, prM and E secretion and VLP formation. The modulation or optimization of these attributes can be improved by selection or use of signal sequences with properties that impart the desired characteristics. This can be accomplished by use of machine-learning computer programs using, for example, a hidden Markov model (HMM) trained on eukaryotes (see Henrik Nielsen et al., "Prediction of signal peptides and signal anchors by a hidden Markov model," In Proceedings of the Sixth International Conference on Intelligent Systems for Molecular Biology (ISMB 6), AAAI Press, Menlo Park, Calif., pp. 122-130 (1998); Nielsen et al., "Machine learning approaches to the prediction of signal peptides and other protein sorting signals," *Protein Engineering* 12: 3-9 (1999); Nielsen et al., "A neural network method for identification of prokaryotic and eukaryotic signal peptides and prediction of their cleavage sites," *Int. J. Neural Sys.* 8: 581-599 (1997); "From sequence to sorting: Prediction of signal peptides," Henrik Nielsen, Ph.D. thesis. Defended at Department of Biochemistry, Stockholm University, Sweden (May 25, 1999); each of which is incorporated herein by reference, particularly for the teaching related to the optimization of signal sequences using computer-enabled algorithms).

An example of the type of program used is that found at http://www.cbs.dtu.dk/services/SignalP-2.0/as of Apr. 3, 2002. The HMM described in the referred to and incorporated references was applied to calculate the signal peptide probability of the prM signal peptide sequences in different plasmid constructs (Table 7). SignalP-HMM searches correctly predicted the signal peptidase cleavage sites in all constructs. However, considerable differences in cleavage probability (ranging between 0.164 and 1.000) and in signal peptide probability (ranging between 0.165 to 1.00) were observed (Table 7). This is not surprising, as the cleavage site and signal peptide probability are known to also be influenced by the positively charged amino acids in the n-region, the length of the hydrophobic amino acid in the h-region and amino acid composition in the c-region in the constructs (Chang et al., "*Flavivirus* DNA vaccines: current status and potential," *Annals of NY Acad. Sci.* 951: 272-285 (2001); Sakaguchi et al., "Functions of Signal and Signal-Anchor Sequences are Determined by the Balance Between the Hydrophobic Segment and the N-Terminal Charge," *Proc. Natl. Acad. Sci. USA* 89: 16-19 (1992)).

Three JE virus plasmid constructs, each derived from different strain of JE virus, showed different vaccine potentials (Lin et al., "DNA immunization with Japanese encephalitis virus nonstructural protein NS1 elicits protective immunity in mice," *J. Virol.* 72: 191-200 (1998); Konishi et al., "Induction of protective immunity against Japanese encephalitis in mice by immunization with a plasmid encoding Japanese encephalitis virus premembrane and envelope genes," *J. Virol.* 72: 4925-4930 (1998); Chang et al., "A single intramuscular injection of recombinant plasmid DNA induces protective immunity and prevents Japanese encephalitis in mice," *J. Virol.* 74: 4244-4252 (2000)). The signal peptide sequences in these constructs are different in the length of n-region which may or may not contain charged amino acids (Table 7). The n-region containing positively charged amino acids forms a short loop in the cytoplasmic side that causes the h-region (transmembrane helix) to be inserted in a tail orientation, exposing the signalase cleavage site. In our study, secreted VLPs containing prM/M and E proteins could be purified from culture medium of the pCDJE2-7 transformed cell line, JE4B, or pCBJE1-14 transiently transformed COS-1 cells. The gradient-purified VLPs and virions have identical immunological and biochemical properties. Processing efficiency from prM to mature M protein, the hallmark of *flavivirus* morphogenesis, is also similar between VLPs and virion particles. Thus, prM and E proteins expressed by pCDJE2-7 and pCBJE1-14 can be expressed as type I transmembrane proteins in the orientation similar to that of virion prM and E (Chang et al., "A single intramuscular injection of recombinant plasmid DNA induces protective immunity and prevents Japanese encephalitis in mice," *J. Virol.* 74: 4244-4252 (2000)). In contrast, the prM protein of pCDNA3JEME could be expressed as a type II membrane protein with its transmembrane h-region inserted in a head orientation because of the absence of positively charged amino acids in its n-region (Konishi et al., "Induction of protective immunity against Japanese encephalitis in mice by immunization with a plasmid encoding Japanese encephalitis virus premembrane and envelope genes," *J. Virol.* 72: 4925-4930 (1998)). Efficient protein synthesis in combination with the expressed protein having the correct topology, particularly of the expressed prM and E, can enhance VLP formation and secretion, and thus promote the immunogenicity of the DNA vaccine (Chang et al., "A single intramuscular injection of recombinant plasmid DNA induces protective immunity and prevents Japanese encephalitis in mice," *J. Virol.* 74: 4244-4252 (2000)).

The use of computer-based computations, as described above, has been applied to optimize the design of expression plasmid. In particular, the predictive power of the SignalP-HMM program was applied to design the WN virus expression plasmid (Table 2) (Davis et al., "West Nile virus recombinant DNA vaccine protects mouse and horse from virus challenge and expresses in vitro a noninfectious recombinant antigen that can be used in enzyme-linked immunosorbent assays," *J. Virol.* 75: 4040-4047 (2001)). The pCBWN plasmid consists of a short version of JE virus signal peptide followed by WN virus prM-E gene sequence. Vaccine potential of this construct was amply demonstrated, as a single i.m. injection of pCBWN DNA not only induced a protective immunity but also prevented WN virus infection in mice and horses.

Figure 6:
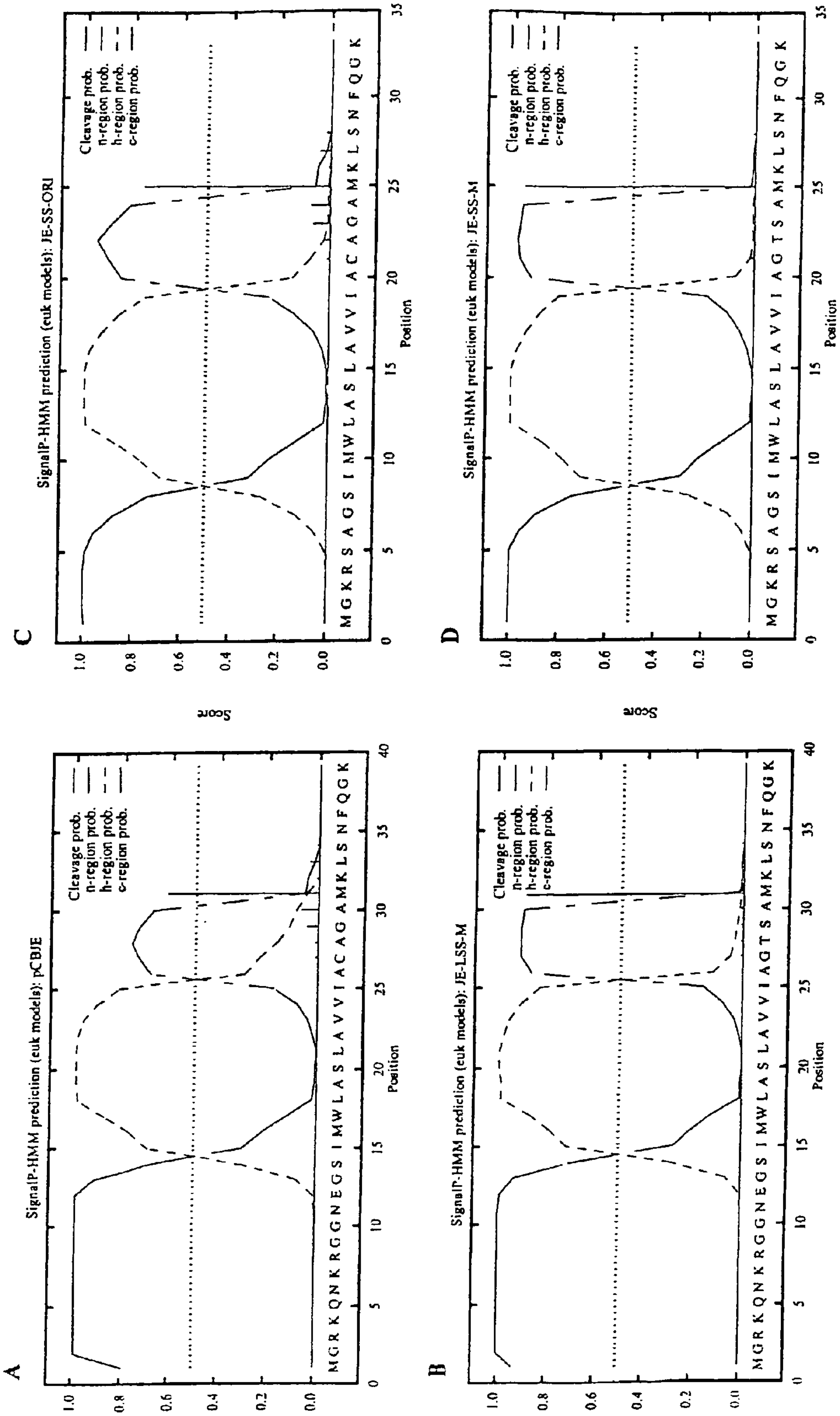
FIG. 6 shows signal peptide probability of the pCBJE1-14 (pCBJE) predicted by the SignalP-HMM program (panel A; amino acids 1-39 of SEQ ID NO: 18). The signal peptide probability is improved by altering the c-region sequence at −4 and −2 positions (C-4G and G-2S) (panel B, JE-LSS-M; SEQ ID NO: 62), by shortening the n-region (panel C, JE-SS-ORI; SEQ ID NO: 63), or by a combination of both modifications (panel D, JE-SS-M; SEQ ID NO: 64).

As discussed earlier, and as demonstrated in Examples 13-15, virus-encoded signal sequence from the same virus as the antigen-coding regions is not necessarily the optimal signal peptide available. Further, non-modified signal sequence is not necessarily optimal. For example, the signal peptide encoded in the pCBJE1-14 plasmid can be improved, as measured by the signal sequence probability by shortening n-region, by altering c-region sequence, or by the combination of both modifications (FIG. 6). By way of illustration, a shortened version of JE virus signal peptide has been used for the expression of WN virus prM and E genes as described herein and in papers incorporated herein by reference for the teaching (Davis et al., "West Nile virus recombinant DNA vaccine protects mouse and horse from virus challenge and expresses in vitro a noninfectious recombinant antigen that can be used in enzyme-linked immunosorbent assays," *J. Virol.* 75: 4040-4047 (2001)). Dose titration studies by single i.m. inoculation indicated that the pCBWN was at least 2-4 fold more immunogenic than pCBJE1-14 in mice.

Example 19

Multivalent Vaccines

Multivalent and/or combination vaccines designed to immunize against multiple flaviviruses can also be produced. In preparation of a multivalent vaccine, monovalent vaccine components are prepared that include elements related to pathogens of interest, such as YF, different serotypes of DEN, JE, WN, SLE and TBE (RSSE and CEE) viruses or any other combination of flaviviruses. Design and production of DNA constructs as described in the other examples and in the specification are carried out as described. Combinations of appropriate vaccines can be made to provide multivalent or combination vaccines protective against multiple pathogens. Preliminary data from our group has demonstrated that i.m. injection of the combined pCBJE1-14 and pCBWN DNA vaccines induced JE virus- and WN virus-specific Nt antibodies in mice (Table 8). Each monovalent component, even if constructed using identical transcriptional and translational regulators, should preferably be tested in an analogous model system to ensure its vaccine potential. A combination vaccine cocktail can then be formulated. These vaccine cocktails can be tailored specifically for particular geographic regions. For example, a vaccine cocktail for tropical and subtropical Asia should include four serotypes of DEN, WN and JE virus vaccines. Similarly useful vaccine cocktails for Africa and Latin America should include four serotypes of DEN, WN and YF virus vaccines and four serotypes of DEN, Rocio and YF virus vaccines, respectively.

Example 20

Preparation and Testing of Recombinant Dengue Virus Type 2 Vaccines a. Summary of example. A series of plasmids that encode the premembrane (prM) and envelope (E) proteins of the dengue virus type 2 (DEN-2) were constructed. These plasmids included an authentic DEN-2 prM-E construct (pCBD2-14-6)(SEQ ID NO:42) encoding the protein described by SEQ ID NO:43, a 90% DEN-2 E-10% Japanese encephalitis (JE) virus E chimeric construct (pCB9D2-1J-4-3)(SEQ ID NO:44) that encodes the protein described by SEQ ID NO:45 and an 80% DEN-2 E-20% JE E chimeric construct (pCB8D2-2J-2-9-1)(SEQ ID NO:46) that encodes the protein described by SEQ ID NO:47. Monoclonal antibody (MAb) reactivity indicated that all three plasmids expressed E protein epitopes that reacted with a panel of domain 1, 2 and 3 antibodies. However, only the pCB8D2-2J-2-9-1 construct (SEQ ID NO:46) secreted high levels of prM, M (matured prM) and E into the media of the plasmid-transformed COS-1 cells. The major portion of the prM and E protein expressed by COS-1 cells transformed with pCBD2-14-6 plasmid (SEQ ID NO:42) and by COS-1 cells transformed with pCB9D2-4-3 plasmid (SEQ ID NO:44) remained membrane-bound. Replacement of 20% of the sequence encoding the E protein of DEN-2 E with sequence encoding the corresponding JE E protein sequence had no effect on MAbs reactivity.

In testing, groups of mice received two intramuscular immunization of selected plasmids at 0 and 3-wks, and the immune response was evaluated by determining specific neutralizing and ELISA antibody. The plasmid expressing secreted prM and E, which can form subviral-particles (SVPs), was superior to other constructs in stimulating an antibody response. Ninety percent neutralization titers ranging from 1:40 to >1:1000 were observed from the 7 of 9 serum specimens of pCB8D2-2J-2-9-1 immunized mice.

b. Importance of DEN-2 virus and vaccines. Dengue (DEN) fever is an acute infection that occurs in subtropical and tropical areas. It is one of the most important flaviviral diseases of humans. As noted earlier, there are four distinct DEN serotypes (DEN-1, DEN-2, DEN-3 and DEN-4) of dengue virus. Infection with any of these is usually either asymptomatic or only causes a self-limited febrile illness known as dengue fever (DF). However, in a small percentage of cases, dengue virus infection results in a much more serious disease, life-threatening dengue hemorrhage fever or dengue shock syndrome (DHF/DSS). Thus, while there are approximately 100 million cases of the relatively mild DF world-wide annually which are of limited concern, there are also an estimated 500,000 hospitalized DHF/DSS cases reported annually. To protect against this disease, a safe and effective DEN vaccine effective against all four serotypes is required for administration to children and non-immune adults in the DEN endemic and epidemic regions.

Safe vaccines must minimize the potential risk of serious infection by virulent viruses. Such virulent viruses can arise by gene reversion or recombination of some types of vaccines derived from attenuated vaccine viruses. Such occurrences did arise in the poliovirus eradication campaign (Guillot et al., "Natural Genetic Exchanges between Vaccine and Wild *Poliovirus* Strains in Humans," *J. Virol.* 74: 8434-8443 (2000); Liu et al., "Molecular Evolution of a Type 1 Wild-Vaccine *Poliovirus* Recombinant during Widespread Circulation in China," *J. Virol.* 74: 11153-11161 (2000)). Further, genomic sequencing of an American strain of yellow fever virus, TRINID79A, demonstrates that there is extensive similarity between this strain and the attenuated yellow fever vaccine virus, FNV (Chang et al., "Nucleotide sequence variation of the envelope protein gene identifies two distinct genotypes of yellow fever virus," *J. Virol.* 69: 5773-5780 (1995); Pisano et al., "Complete nucleotide sequence and phylogeny of an American strain of yellow fever virus, TRINID79A," *Arch. Virol.* 144: 1837-1843 (1999)). While not conclusive in and of itself, the similarity strongly suggests that TRINID 79A is derived from the FNV vaccine virus.

The use of DNA-based vaccines is a novel and promising immunization approach for the development of *flavivirus* vaccines (as described herein, in Chang et al., "*Flavivirus* DNA vaccines: current status and potential," *Ann. NY Acad. Sci.* 951: 272-285 (2001), and in references cited therein). In this example, a number of DEN-2 vaccines were produced and the immune response in mice after i.m. immunization of DEN-2 constructs were correlated with the efficiency of prM/M and E secretion. One construct that led to the secretion of significant amounts of prM/M and E antigens was shown to be capable of stimulating high titers of neutralizing antibodies in plasmid-vaccinated mice.

c. Materials and Methods.

i. Cell culture and virus strains. COS-1 cells (ATCC, Manassas, Va.; 1650-CRL) were grown at 37° C. with 5% $CO_2$ in Dulbecco's modified Eagle minimal essential medium (DMEM, GIBCO, Grand Island, N.Y.) supplemented with 10% heat-inactivated fetal bovine serum (FBS, Hyclone Laboratories, Inc., Logan, Utah), 1 mM sodium pyruvate, 1 mM non-essential amino acids, 30 ml/liter 7.5% $NaHCO_3$, 100 units/ml of penicillin, and 100 μg/ml of streptomycin. Vero and C6/36 cells were grown under the same conditions used for COS-1 cells. DEN-2 virus, strain-16681, was used for cDNA cloning, IgG ELISA and the plaque reduction neutralization test (PRNT). Virus was propagated in the C6/36 cell culture. Virus used for immunological or biochemical studies was purified by precipitation with 7% polyethylene glycol (PEG-8000; Fisher Scientific, Fair Lawn, N.J.) followed by ultracentrifugation on 30% glycerol-45% potassium-tartrate gradients (Obijeski et al., "Segmented genome and nucleocapsid of La Crosse virus," *J. Virol.* 20:664-675 (1976)).

ii. Plasmid construction. Genomic RNA was extracted from 150 μl of C6/36 cell culture medium infected with DEN-2 16681 strain using the QIAamp™ Viral RNA Kit (Qiagen, Santa Clarita, Calif.). Extracted RNA was resuspended in 80 μl of diethyl pyrocarbonate-treated water (DEPC, Sigma, ST. Louis, Mo.) and then used as a template in reverse transcriptase-PCR (RT-PCR) amplification of DEN-2 virus prM and E genes. Primer sequences (Table 9) were designed based on published sequences (Gadkari et al., "Critical evaluation of Kyasanur Forest disease virus neutralizing antibodies found in bats (a preliminary report)," *Indian J. Med. Res.* 64: 64-67 (1976); Kinney et al., "Construction of infectious cDNA clones for dengue 2 virus: strain 16681 and its attenuated vaccine derivative, strain PDK-53," Virology 230: 300-308 (1997)). The recognition and cleavage site for restriction enzyme KasI was incorporated at the 5' terminus of the cDNA amplicon. An in-frame termination codon, followed by a NotI restriction site, was introduced at the 3' terminus of the cDNA amplicon. The DEN-2 virus cDNA amplicon was digested with KasI and NotI enzymes, and was then inserted into the KasI and NotI sites of a pCBJESS vector to form the 100% DEN-2 E plasmid, pCBD2-14-6 (SEQ ID NO:42).

Figure 7:
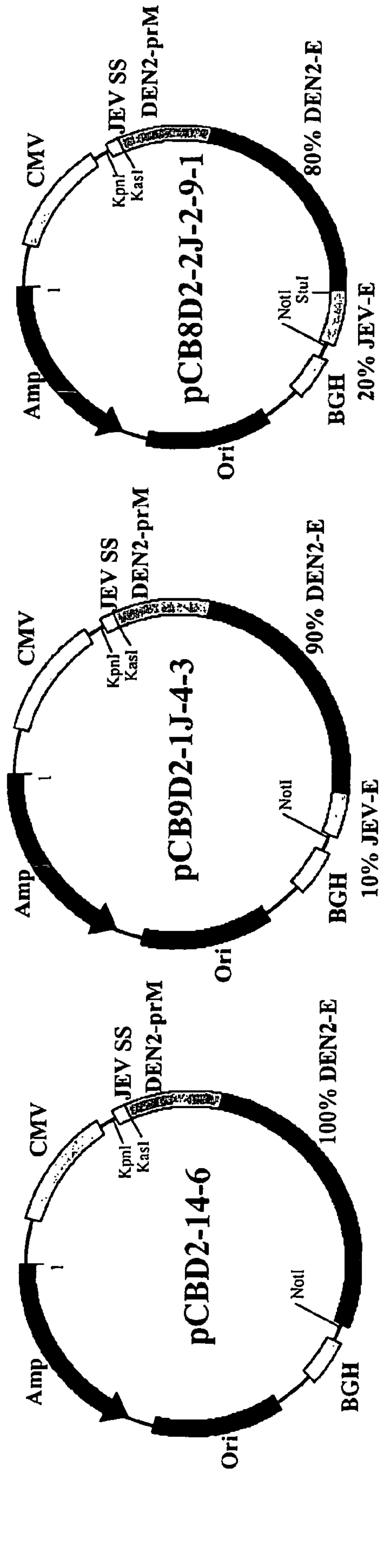
FIG. 7 shows schematic representations of plasmid vectors pCBD2-14-16 (100% DEN-2 E), pCBD2-1J-4-3 (90% DEN-2 E: 10% JEV E), and pCB8D2-2J-2-9-1 (80% DEN-2 E: 20% JEV E). These plasmids include the human cytomegalovirus (CMV) early gene promoter; JE virus signal sequence; DEN-2 virus prM and E gene region (amino terminal 100%, 90%, or 80%, respectively); JE virus E gene region (none, 10% or 20%, respectively); and bovine growth hormone poly A signal (BGH).

To construct the 90% and 80% DEN-2 E plasmids, the 100% DEN-2 plasmid, pCBD2-14-6 (SEQ ID NO:42), and the JE plasmid, pCBJE1-14 (SEQ ID NO:17), were used as the PCR templates to amplify DEN-2 and JE DNA sequence, respectively. Sets of primers used in amplification reactions to obtain the DEN-2 and JE gene fragments are listed in Table 9. T7 and SP6 priming sites are found in the pCBamp plasmid, derived from original pCDNA-3 plasmid (Invitrogen, Carlsbad, Calif.), and can be utilized as desired or as required. PCR amplified DNA fragments for the 90% DEN-2-10% JE E protein gene were digested with BxtXI restriction endonuclease, ligated using T4 DNA ligase, digested with KasI and NotI enzyme, and inserted into the KasI and NotI sites of the pCBJESS vector to obtain the plasmid, pCB9D2-1J-4-3 (SEQ ID NO:44). PCR amplified DNA fragments for the 80% DEN-2-20% JE E gene were digested with BsmBI, ligated with T4 DNA ligase, digested with KasI and NotI enzyme, and inserted into the KasI and NotI sites of the pCBJESS vector to obtain the plasmid, pCB8D2-2J-2-9-1 (SEQ ID NO:46). Schematic representations of the three plasmid constructs are shown in FIG. 7. The 90% DEN-2-10% JE E and the 80% DEN-2-20% JE E protein junction regions, respectively, are shown in Table 9.

Automated DNA sequencing was performed on an ABI Prism 377 Sequencer (Applied Biosystems/Perkin Elmer, Foster City, Calif.) according to the manufacture's recommended procedures. Recombinant plasmids with the correct prM and E sequences were identified using sequence analysis.

iii. Transient expression of DEN-2 recombinant antigen in COS-1 cells by electroporation. COS-1 cells were electroporated separately with each DEN-2 plasmid or green fluorescent protein expression plasmid control (pEGFP, Clonetech, San Francisco, Calif.) using the protocol described elsewhere in the examples and in Chang et al., ("A single intramuscular injection of recombinant plasmid DNA induces protective immunity and prevents Japanese encephalitis in mice," *J. Virol.* 74: 4244-4252 (2000)). Electroporated cells were seeded onto 75 $cm^2$ culture flasks, and kept at 37° C. and 5% $CO_2$. Six hours following electroporation the growth media were replaced with a maintenance media containing 2% fetal bovine serum. Tissue culture medium and cells were harvested separately 48 hours following electroporation for antigen characterization.

iv. Epitope mapping using DEN-2 E-specific monoclonal antibodies. Forty-eight hours following electroporation, adherent cells were trypsinized, resuspended in PBS containing 5% goat serum, spotted on a 12 well spot-slide and air dried. Cells adhered to the spot-slide were fixed with acetone for 10 minutes at −20° C. and allowed to air dry. E-protein specific monoclonal antibodies (MAb) were used to detect protein expression by the indirect immunofluorescence antibody assay (IFA), as described previously (Table 10; Chang et al., "A single intramuscular injection of recombinant plasmid DNA induces protective immunity and prevents Japanese encephalitis in mice," *J. Virol.* 74: 4244-4252 (2000)).

v. Characterization of the recombinant DEN-2 virus antigen. Tissue culture medium was harvested 48 hours following electroporation. Antigen-capture (Ag-capture) ELISA was used to detect secreted DEN-2 virus antigen in the culture medium of transiently transformed COS-1 cells. The MAb 4G2 and horseradish peroxidase-conjugated MAb 6B6C-1 were used to capture the DEN virus antigens and detect captured antigen, respectively (Chang et al., "A single intramuscular injection of recombinant plasmid DNA induces protective immunity and prevents Japanese encephalitis in mice," *J. Virol.* 74: 4244-4252 (2000); Hunt et al., "A recombinant particulate antigen of Japanese encephalitis virus produced in stably-transformed cells is an effective noninfectious antigen and subunit immunogen," *J. Virol. Methods.* 97: 133-149 (2001)).

Forty-eight hours following electroporation, transformed cells for each plasmid were trypsinized and resuspended in PBS as aliquots containing $5\times10^6$ cells. These cell samples were processed for membrane protein extraction using the Mem-PER mammalian membrane protein extraction reagent kit (Pierce, Rockford, Ill.) following the manufacturer's suggested protocol. Both hydrophobic and hydrophilic proteins are isolated. This procedure was developed for enrichment of integral membrane protein found in the hydrophobic phase. Both hydrophobic and hydrophilic fractions were analyzed by Ag-capture ELISA for DEN-2 recombinant antigen.

Recombinant antigen in the medium was concentrated by precipitation with 10% polyethylene glycol (PEG)-8000. The precipitant was resuspended in TNE buffer (50 mM Tris, 100 mM NaCl, 10 mM EDTA, pH 7.5) to $1/100^{th}$ of the original volume, clarified by centrifugation, and stored at 4° C. Recombinant antigen concentrated by PEG precipitation and resuspended in TNE buffer was extracted with 4.0% ethanol to remove residual PEG (Hunt et al., "A recombinant particulate antigen of Japanese encephalitis virus produced in stably-transformed cells is an effective noninfectious antigen and subunit immunogen," *J. Virol. Methods.* 97: 133-149 (2001)). Ethanol-extracted antigens, hydrophobic membrane proteins from the transformed cells and gradient-purified DEN-2 virions were analyzed on a NuPAGE, 4-12% Bis-Tris gradient gel in an Excel Plus Electrophoresis Apparatus™ (Invitrogen Corp., Carlsbad, Calif.), followed by electroblotting onto nitrocellulose membranes using a Excel Plus Blot Unit (Invitrogen Corp.). DEN-2 virus-specific protein was detected by western blot using DEN-2 virus specific MAbs 1A6A-8 (E specific) and 1A2A-1 (capsid specific), as well as rabbit antiserum specific for DEN-2 prM and mouse serum specific for a peptide composed of amino acid 1-34 of the DEN-2 M protein, and normal mouse ascitic fluid was used as negative control (Murray et al., "Processing of the dengue virus type 2 proteins prM and C-prM," *J. Gen. Virol.* 74 (Pt 2): 175-182 (1993); Roehrig et al., "Monoclonal antibody mapping of the envelope glycoprotein of the dengue 2 virus, Jamaica," *Virology* 246: 317-328 (1998)).

vi. Mouse vaccination. Groups of ten, three-wk-old female ICR out-bred mice were used in the study. Mice were i.m. injected with pCBD2-14-6, pCB9D2-1J-4-3, pCB8D2-2J-2-

9-1 or pEGFP on week-0 and week-3 at a dose of 100 μg in a volume of 100 μl per mouse. The plasmid DNA was purified from XL-1 blue cells with EndoFree Plasmid Giga Kits™ (Qiagen) and resuspended in PBS, pH 7.5, at a concentration of 1.0 μg/l. Mice that received 100 μg of pEGFP were used as plasmid-vaccinated controls. Mice were bled every 3 wks following injection, and the DEN-2 virus specific antibody response was evaluated by use of indirect ELISA and PRNT.

vii. Serological tests. Pre- and post-vaccination serum specimens were tested for antibody binding ability to purified DEN-2 virion by ELISA, for neutralizing (Nt) antibody by PRNT, and for antibodies that recognize purified DEN-2 virus proteins by Western blotting. PRNT was performed with Vero cells, as previously described (Chang et al., "A single intramuscular injection of recombinant plasmid DNA induces protective immunity and prevents Japanese encephalitis in mice," *J. Virol.* 74: 4244-4252 (2000)), using DEN-2 (strain-16681) and JE (strain-Nakayama) virus. Endpoints were determined at a 90% plaque-reduction level (Hunt et al., "A recombinant particulate antigen of Japanese encephalitis virus produced in stably-transformed cells is an effective noninfectious antigen and subunit immunogen," *J. Virol. Methods.* 97: 133-149 (2001)).

d. Results.

i. Transient expression of DEN-2 virus recombinant antigen. Expression of the prM and E genes of DEN-2 virus or a chimeric E gene from a combination of DEN-2 and JE virus sequences (80% DEN-20% JE or 90% DEN-10% JE) was accomplished by separate transformations of each of the three recombinant DEN-2 DNA plasmids into COS-1 cells. The basic plasmid design was based on results from previous studies with JE virus and WN virus recombinant plasmids in which plasmid-transformed cells expressed, and secreted authentic viral proteins into the cell culture fluid (Chang et al., "A single intramuscular injection of recombinant plasmid DNA induces protective immunity and prevents Japanese encephalitis in mice," *J. Virol.* 74: 4244-4252 (2000); Davis et al., "West Nile virus recombinant DNA vaccine protects mouse and horse from virus challenge and expresses in vitro a noninfectious recombinant antigen that can be used in enzyme-linked immunosorbent assays," *J. Virol.* 75: 40404047 (2001)). Transient expression of DEN-2 recombinant proteins was initially assessed by Ag-capture ELISA of cell culture supernatants and by IFA of acetone-fixed, transformed COS-1 cells (Chang et al., "A single intramuscular injection of recombinant plasmid DNA induces protective immunity and prevents Japanese encephalitis in mice," *J. Virol.* 74: 4244-4252 (2000)). The point of optimum antigen expression was determined to be 48 hours following electroporation.

ii. Epitope mapping of the E protein expressed by transiently-transformed COS-1 cells. The DEN-2 protein expressed by each of the recombinant plasmids was evaluated by IFA using a panel of murine MAbs with known reactivity to DEN-2 virus (Table 10; Henchal et al., "Epitopic analysis of antigenic determinants on the surface of dengue-2 virions using monoclonal antibodies," *Am. J. Trop. Med. Hyg.* 34: 162-169 (1985); Roehrig et al., "Monoclonal antibody mapping of the envelope glycoprotein of the dengue 2 virus, Jamaica," *Virology* 246: 317-328 (1998)). The MAb panel included antibodies reactive with each of the three antigenic domains of the E protein of flaviviruses as well as prM and C proteins. (Mandl et al., "Antigenic structure of the *flavivirus* envelope protein E at the molecular level, using tick-borne encephalitis virus as a model," *J. Virol.* 63: 564-571 (1989); Rey et al., "The envelope glycoprotein from tick-borne encephalitis virus at 2 Å resolution," *Nature* 375: 291-298 (1995)). The MAbs specific for *flavivirus* antigenic Domains 2 and 3 showed nearly identical qualitative reactivity with DEN-2 virus and each of the three plasmid-expressed proteins. One of the Domain 1-specific MAbs, 1B4C-2, also showed a similar reactivity pattern with all expressed proteins. However, two of the Domain 1-specific MAbs, 2B3A-1 and 9A4D-1, were much less reactive with E protein expressed by plasmids pCBD2-14-6 and pCB9D2-1J4-3 as shown by endpoint titration (values in parentheses, Table 10). Comparison of the endpoint titers revealed the apparent poor expression of epitopes C3 and C4 in constructs containing 100% DEN-2 E and 90% DEN-2 E-10% JE E. MAb 2H2, specific for prM, had the same reactivity with antigen expressed by all three plasmids. Anti-C MAb 1A2A-1 reacted well with DEN-2 virus and had low level, non-specific reactivity with the plasmid-expressed viral proteins, which included prM and E, but not C.

iii. Comparison of secreted protein and membrane-bound protein produced by each of the three DEN-2 recombinant plasmids. Similar amounts of cell culture fluid were harvested from COS-1 cells 48 hours post-transformation for each recombinant DEN-2 plasmid. Secreted recombinant antigen found in the culture fluid was concentrated 100-fold by PEG precipitation, followed by ethanol extraction to remove PEG which interfered with subsequent analysis by polyacrylamide gel electrophoresis. The relative amount of secreted antigen expressed by each plasmid was determined by Ag-capture ELISA analysis of both PEG-precipitated and ethanol-extracted cell culture fluid preparations (Table 11). Secreted antigen was detected only from cells transfected with pCB8D2-2J-2-9-1 (SEQ ID NO:34), which contained 80% DEN-2 E and 20% JE E genes. The recombinant plasmids containing either 100% DEN-2 E or 90% DEN-2 E-10% JE E genes produced no ELISA-detectable antigen in the culture fluid, despite efforts to concentrate expressed protein.

Figure 8:
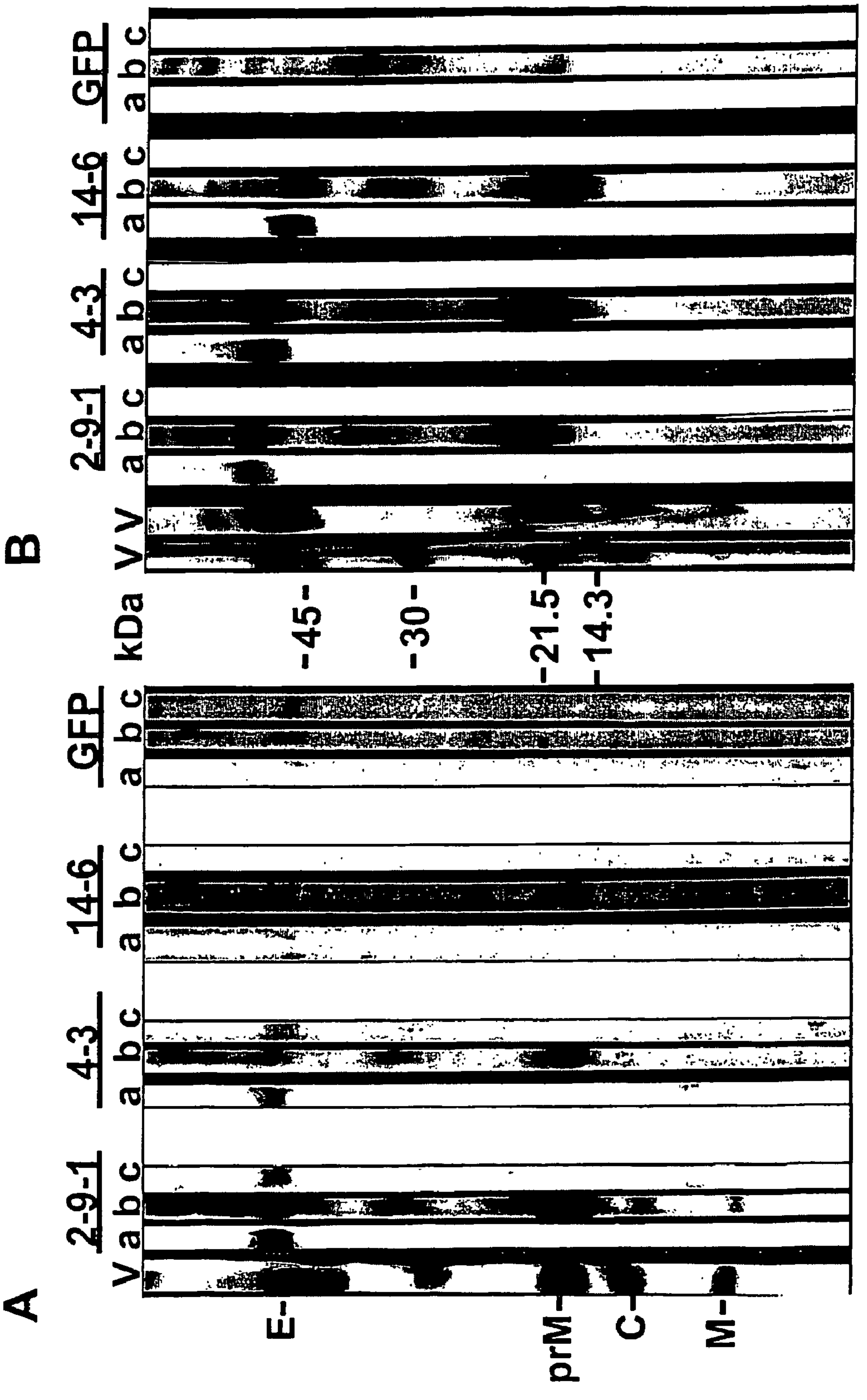
FIG. 8 shows a comparison of secreted and membrane-bound recombinant protein by western blot. (A) Analysis of secreted recombinant antigen following PEG-precipitation and ethanol extraction of culture fluid for DEN-2 plasmids pCB8D2-2J-2-9-1, pCB9D2-1J-4-3, pCBD2-14-16, and control plasmid pEGFP. Lane 1(V), purified DEN-2 virus stained by Gold Blot (Owl Separation Systems, Portsmouth, N. H.). Reactivity of secreted, recombinant antigen from each plasmid with a, anti-envelope (E) specific Mab 1A6A-8; b, a mixture of MAB 1A6A-8, anti-capsid (C) specific Mab 1A2A-1, anti-serum specific for DEN-2 virus premembrane (prM) protein; and c, normal mouse ascites. (B) Analysis of recombinant plasmid-transformed cell hydrophobic membrane proteins. Lane 1 (V), purified DEN-2 virus stained by Gold Blot; lane 2 (V), reactivity of purified DEN-2 virus with a mixture of Mab 1A6A-8, Mab 1A2A-1, anti-serum specific for DEN-2 virus M protein, and anti-serum for DEN-2 virus prM protein. Reactivity of isolated hydrophobic membrane proteins from each plasmid-transformed cell line with a, Mab 1A6A-8; b, a mixture of Mab 1A6A-8, Mab 1A2A-1, anti-serum specific for DEN-2 virus M protein, and anti-serum for DEN-2 virus prM protein; and c, normal mouse ascites.

Western blot analysis was also used to evaluate the production of secreted antigen by each of the DEN-2 recombinant plasmids. For comparison purposes, equivalent volumes of PEG-precipitated, ethanol-extracted cell culture supernatant were run on NuPAGE gradient gels, electroblotted to nitrocellulose, and analyzed using MAbs or polyclonal antisera capable of reacting with all DEN-2 structural proteins (FIG. 8A). Western blot analysis showed greater sensitivity in detecting recombinant antigen than Ag-capture ELISA since DEN-2-specific proteins were detected in the culture fluid from two of the plasmids, pCB8D2-2J-2-9-1 and pCB9D2-1J4-3 (SEQ ID NOS:46 and 44, respectively). Plasmid pCB8D2-2J-2-9-1 (SEQ ID NO:46) expressed the greatest amount of secreted antigen which was shown to be composed of E, prM, and M proteins. Relatively less secreted antigen was produced by pCB9D2-1J4-3 (SEQ ID NO:44) and barely detectable levels were found for the pCBD2-14-6 (SEQ ID NO:42) preparation, which appeared to contain relatively less expressed E protein, especially if the non-specific reactivity of the E-specific MAb, 1A6A-8, on the control pEGFP was taken into consideration (FIG. 8A, lanes a, b for 14-6 and GFP).

Since E, prM, and M are membrane-associated proteins throughout their intracellular synthesis, any assessment of the expression of these proteins by the three recombinant DEN-2 plasmids should include an evaluation of cell membrane preparations from plasmid-transformed cells. The Mem-PER Mammalian Membrane Protein Extraction Reagent kit (Pierce) was used to isolate the integral membrane proteins from equivalent numbers of cells transformed by each of the recombinant plasmids. Hydrophobic proteins were separated from hydrophilic proteins by phase partitioning. Preliminary analysis by Ag-capture ELISA indicated that the hydrophilic protein fraction was non-reactive; however, the hydrophobic protein fractions from COS-1 cells transformed with each of the recombinant DEN-2 plasmids had similar titers in ELISA tests (Table 11). These results indicated that recombinant antigen encoded by all three plasmids was expressed following transformation, but that the recombinant antigens expressed were not all secreted at the same level.

Confirmation of the Ag-capture results for the hydrophobic protein fractions was accomplished by western blot (FIG. 8B). Equivalent volumes of hydrophobic protein fractions from each of the plasmid-transformed cells were diluted according to the manufacturer's recommendations for SDS-polyacrylamide gel electrophoresis in order to reduce band and lane distortion. Immunoblotting with E-, prM-, C-, and M-specific MAbs or polyclonal antisera demonstrated that all three recombinant DEN-2 plasmids induced the production of similar amounts of recombinant antigen composed of E and prM. No M protein was detected, either because it was not processed from prM or because the levels were too low to be detected. Despite efforts to reduce band distortion, high levels of detergent in the hydrophobic protein samples apparently caused E and prM to run in a slightly aberrant manner (slower migration) compared to samples without such high concentrations of detergents (compare E and prM migration in FIGS. 8A and 8B).

iv. Comparison of the immune response in mice vaccinated with three different DEN-2 recombinant DNA plasmids. Three-week old ICR mice were immunized by i.m. injection with 100 μg of pCB8D2-2J-2-9-1 (SEQ ID NO:46), pCB9D2-1J-4-3 (SEQ ID NO:44), pCBD2-14-6 (SEQ ID NO:42), or pEGFP on weeks 0 and 3. Mice were bled 3, 6, and 9 weeks after the primary immunization. Individual and pooled sera were tested by indirect ELISA, using screening dilutions of 1:100 and 1:400 at 3 and 6 weeks post-vaccination and endpoint titrations at 9 weeks post-vaccination. Nine-week sera were also tested by PRNT with both DEN-2 and JE viruses. The ELISA results showed that after one immunization (3-week sera), all mice given pCB8D2-2J-2-9-1 had seroconverted, whereas only 50% of pCB9D2-1J-4-3 and 20% of pCBD2-14-6-vaccinated mice reacted with DEN-2 virus (Table 12). By 9 weeks post-vaccination, all mice vaccinated with either pCB8D2-2J-2-9-1 or pCBD2-1J4-3 demonstrated anti-DEN-2 ELISA reactivity; however, the geometric mean titers differed significantly (titers of 1:20,000 versus 1:708, respectively). Only 40% of pCBD2-14-6-immunized mice had anti-DEN-2 ELISA titers greater than 1:100. A western blot of pooled 9-week sera from pCB8D2-2J-2-9-1-immunized mice on purified DEN-2 virus showed that the immunodominant response was to the E glycoprotein. Slight reactivity reactivity to prM and M were also detected.

More significantly, in terms of evaluating the vaccine potential of the three DEN-2 plasmids, the induction of virus-neutralizing antibody in 7 of 9 mice immunized with pCB8D2-2J-2-9-1 (SEQ ID NO:46) was observed based on a 90% plaque-reduction endpoint (Table 10). However, if a 50% neutralization endpoint is used, then all 9 of 9 sera have PRNT titers of $^3$ 1:40. Ninety percent neutralization titers ranged from 1:40 to >1:1000 for the 7 sera with neutralizing activity. None of the mice immunized with pCB9D2-1J-4-3 produced neutralizing antibody, and only 1 of 10 sera from pCBD2-14-6-vaccinated mice neutralized virus, but at a titer of only 1:8.

Since two of the recombinant plasmids, namely pCB9D2-IJ-4-3 (SEQ ID NO:44) and pCB8D2-2J-2-9-1 (SEQ ID NO:46) contained JE virus E-gene sequences, all sera were also evaluated for the presence of JE virus neutralizing activity. However, no such activity was detected at the 90% neutralization endpoint for mice in any of the immunization groups. Not surprisingly, mice immunized with the control plasmid pEGFP exhibited no reactivity to either DEN-2 or JE viruses.

e. Discussion. The same steps used earlier for the JE and WN vaccines was initially used to construct a recombinant DEN-2 plasmid, pCBD2-14-6 (SEQ ID NO:42), consisting of the authentic DEN-2 prM and E gene region. Antigenic mapping of DEN-2 proteins expressed by COS-1 cells transformed by this plasmid, using a panel of MAb by IFA, indicated the prM and E protein had a compatible fluorescent intensity and a similar MAb reactivity as virus infected cells (Table 10). However, these COS-1 cells transformed by the plasmid encoding an authentic DEN-2 prM and E region failed to secrete detectable DEN-2 antigen into the culture fluid (as measured by antigen-capture ELISA). In addition, vaccination using the plasmid encoding an authentic DEN-2 prM and E region failed to stimulate anti-DEN-2 virus neutralizing antibody in i.m. immunized-mice (Table 13). Interestingly, transformation of cells by pCBD2-14-6 resulted in a punctuated-globular fluorescent staining that suggested that the C-terminus of the E protein of DEN-2 may contribute to that protein's membrane retention signal. This IFA staining pattern was not observed in either the JE or WN construct-transformed cells (Chang et al., "A single intramuscular injection of recombinant plasmid DNA induces protective immunity and prevents Japanese encephalitis in mice," *J. Virol.* 74: 4244-4252 (2000); Davis et al., "West Nile virus recombinant DNA vaccine protects mouse and horse from virus challenge and expresses in vitro a noninfectious recombinant antigen that can be used in enzyme-linked immunosorbent assays," *J. Virol.* 75: 4040-4047 (2001)). Therefore, in light of the observation made in accordance with the teachings of the present application, two additional plasmids, pCB9D2-1J-4-3 (SEQ ID NO:44) and pCB8D2-2J-2-9-1 (SEQ ID NO:46), in which appropriate manipulation of the DNA sequence was made for 10% or 20% of C-terminal E of DEN-2 to be replaced with the corresponding region of JE virus E protein, respectively. Relative effectiveness of the different constructs in stimulating detectable anti-DEN-2 ELISA antibody in vaccinated mice is shown in Table 13.

These results are consistent with the model that interactions between prM and E can influence the processes of particle assembly and secretion. Support for this model can be found in a study of tick-borne encephalitis virus that putatively suggests that interactions between prM and the ectodomain of E are involved in prM-mediated intracellular transport of prM-E, thus, secretion of virus-like particle (Allison et al., "Mapping of functional elements in the stem-anchor region of tick-borne encephalitis virus envelope protein E," *J. Virol.* 73: 5605-5612 (1999)).

In the present example, replacing a C-terminal portion of DEN-2 E protein with JE E protein, corresponding to TBE $H1^{pred}$ to TM2, resulted in DEN-2 prM protein and chimeric E protein secretion. However, in contrast, replacement of TM1 and TM2, in TBE, caused only a minor improvement in antigen secretion. The major portion of the prM and E protein expressed by either COS-1 transformed pCBD2-14-6 and pCB9D2-4-3 plasmid remained membrane-bound (Table 13). These results indicated that an unidentified membrane retention sequence is located in the C-terminal stem region of DEN-2 E protein. Substitution of this C-terminal stem region with sequence from the JE virus removes or renders ineffective this retention sequence.

It has been asserted by others that the prM protein is essential for maintaining proper conformation and secretion of E protein during prM-E maturation (Aberle et al., "A DNA immunization model study with constructs expressing the tick-borne encephalitis virus envelope protein E in different physical forms," *J. Immunol.* 163: 6756-6761 (1999), Allison et al., "Synthesis and secretion of recombinant tick-borne encephalitis virus protein E in soluble and particulate form," *J. Virol.* 69: 5816-5820 (1995)). Further, it has also been demonstrated that the ectodomain of the E protein interacts with prM. This interaction has been estimated to involve amino acid sequence within amino acid residues 200-327 of E in the Murray Valley encephalitis virus (Guirakhoo et al., "The Murray Valley encephalitis virus prM protein confers acid resistance to virus particles and alters the expression of epitopes within the R2 domain of E glycoprotein," *Virology* 191: 921-931 (1992)).

Proper prM and E interactions and retained integrity of the E protein's structure are likely maintained in the protein expressed by all three DEN-2 constructs, at least insofar as they are required for immunoreactivity. Furthermore, the replacement of the C-terminus 20% E in the pCB8D2-2J-2-9-1 resulted in a protein that maintained 395 amino acids of authentic DEN-2 E. Any such modification is expected to have minimal influence on E and prM-E interactions and their influence on the antigenic nature of the chimeric E protein. As replacing the C-terminus region of DEN-2 E with JE stem-anchor sequence had no effect on MAbs reactivity (Table 10), retention of the DEN-2 sequence so replaced can only be optional in attaining a DEN-2 specific immunological response.

Previously, it has been shown that a plasmid construct encoding a secreted subviral particle of tick-borne encephalitis virus prM and E protein was superior, in terms of the extent and functionality of the antibody response and in terms of response to virus challenge, to other constructs that encoded C-terminally truncated soluble E-dimer that was secreted, full-length E that was not secreted, or a truncated E that was not efficiently secreted (Aberle et al., "A DNA immunization model study with constructs expressing the tick-borne encephalitis virus envelope protein E in different physical forms," *J. Immunol.* 163: 6756-6761 (1999)). However, here we have demonstrated that the vaccine potency of DEN-2 DNA is correlated with the secretion of prM/M and E (Table 13). The morphology and physical character of secreted prM and E were not demonstrated in this study. However, the prM and E, secreted by the pCB8D2-2J-2-9-1 construct, does likely form a viral-like particle. It is believed that the presentation of multiple protective antigens on the particle surface improves vaccine potency of this construct.

Previous attempts for the development of DEN-2 virus DNA vaccine has resulted in varying degrees of success (Kochel et al., "Inoculation of plasmids expressing the dengue-2 envelope gene elicit neutralizing antibodies in mice," Vaccine 15: 547-552 (1997); Konishi et al., "A DNA vaccine expressing dengue type 2 virus premembrane and envelope genes induces neutralizing antibody and memory B cells in mice," *Vaccine* 18: 1133-1139 (2000)). To improve the level of effectiveness, differing strategies have been adopted. For example, coimmunization of the immuno-stimulatory CpG motif containing pUC19 plasmid, plasmid expressing murine GM-CSF in the vaccine regimen, or replacing C-terminus 43 amino acid of E with lysosome-associated membrane retention sequence improved the antibody response to the DEN-2 vaccine has been used (Porter et al., "Protective efficacy of a dengue 2 DNA vaccine in mice and the effect of CpG immuno-stimulatory motifs on antibody responses," *Arch. Virol.* 143: 997-1003 (1998); Raviprakash et al., "Synergistic Neutralizing Antibody Response to a Dengue Virus Type 2 DNA Vaccine by Incorporation of *Lysosome*-Associated Membrane Protein Sequences and Use of Plasmid Expressing GM-CSF," Virology 290: 74-82 (2001)). Unmethylated CpG motifs directly activates macrophages, natural killer cells and lymphocytes to secrete cytokines and chemokines, and supports the development of immune responses mediated by Th1 cytokines (Manders et al., "Immunology of DNA vaccines: CpG motifs and antigen presentation," *Inflamm. Res.* 49: 199-205 (2000)). However, inclusion of the CpG might bias the host's cytokine profile and thereby contribute to the both the development of Th-1-mediated organ-specific autoimmune disorders and interfere with immune homeostasis (Smith et al., "The regulation of DNA vaccines," *Curr. Opin. Biotech.* 12: 299-303 (2001)). There is also evidence in mice that excess levels of cytokine, although increasing the response of certain T-helper cells, can decrease or shutdown the response of other actors in the immune response, leading to generalized immunosuppression or chronic inflammation (Robertson et al., "Assuring the quality, safety, and efficacy of DNA vaccines," *Mol. Biotechnol.* 17: 143-149 (2001)). Correspondingly, the safety and efficacy of *flavivirus* DNA immunization could be benefited by manipulation of an expression plasmid to enhance transcription and translation and targeting prM and E proteins for secretion that promote correct polyprotein processing and assembly (Chang et al., "*Flavivirus* DNA vaccines: current status and potential," *Ann. NY Acad. Sci.* 951: 272-285 (2001)). Future improvements could be focused on enhancing DNA uptake by antigen presenting cells or by muscle cells (Rodriguez et al., "Enhancing DNA immunization," *Virology* 268: 233-238 (2000)).

TABLE 1

Transient expression of JE prM and E proteins by various recombinant plasmids in two transferred cell lines.

| | Vector | | | | Recombinant | IFA intensity/ percentage of antigen-positive cells* | |
|---|---|---|---|---|---|---|---|
| | Promotor | Intron | Poly (A) | ORI | Plasmid | COS-1 | COS-7 |
| pCDNA3 | CMV | No | BGH | SV40 | pCDJE2-7 | 3+/40 | 3+/35 |
| pCBamp | CMV | No | BGH | No | pCBJE1-14 | 3+/45 | nd |
| pC1Bamp | CMV | Yes | BGH | No | pC1BJES14 | 3+/39 | nd |
| pCEP4 | CMV | No | SV40 | OriP | pCEJE | 2+/4 | 2+/3 |
| pREP4 | RSV | No | SV40 | OriP | pREJE | 1+/3 | 1+/2 |

TABLE 1-continued

Transient expression of JE prM and E proteins by various recombinant plasmids in two transferred cell lines.

| Vector | | | | | Recombinant | IFA intensity/ percentage of antigen-positive cells* | |
|---|---|---|---|---|---|---|---|
| | Promotor | Intron | Poly (A) | ORI | Plasmid | COS-1 | COS-7 |
| pRe/RSV | RSV | No | BGH | SV40 | pRCJE | 1+/3 | 1+/3 |
| pCDNA3 | CMV | No | BGH | SV40 | pCDNA3/CAT | — | — |

*Various cell lines were transformed with pCDNA3/CAT (negative control), pCDJE2-7, pCBJE1-14, pC1BJES14, pCEJEm pREJE, or pRCJE, Cells ere trypsinized 48 hours later and tested by an indirect immunofluorescent antibody assay (IFA) with JE virus-specific HIAF. Data are presented as the intensity (scale of 1+ to 4+) and the percentage of IFA positive cells. The pCDNA3/CAT transformed cells were used as the negative control.

TABLE 2

Characterization of proteins expressed by a pCDJE2-7 stably transformed clone (JE-4B) of COS-1 cells with JE virus-reactive antibodies.

| Mab or antiserum | Biological Activity of Mab: Specificity | Biological Function | Immunofluorescent intensity of cells: JEV infected | 4B |
|---|---|---|---|---|
| Mab: | | | | |
| MC3 | JEV Specific | | 2+ | 2+ |
| 2F2 | JEV Specific | HI, N | 4+ | 4+ |
| 112 | JEV Specific | | 4+ | 4+ |
| 503 | JEV Specific | N | 4+ | 3+ |
| 109 | Subgroup | HI | 2+ | 1+ |
| N.04 | Subgroup | HI, N | 3+ | 4+ |
| 201 | Subgroup | | 1+ | 1+ |
| 203 | Subgroup | | 4+ | 3+ |
| 204 | Subgroup | | 2+ | 2+ |
| 301 | Subgroup | HI | 2+ | 2+ |
| 504 | Flavivirus | | 4+ | 4+ |
| 6B6C-1 | Flavivirus | | 2+ | 2+ |
| 3B4C-4 | VEE | | — | — |
| H1AF: | | | | |
| Anti-JEV | | | 4+ | 3+ |
| Anti-WEE | | | — | — |
| PBS | | | — | — |

TABLE 4

The age-dependent percent seropositive rate in mice following vaccination with various JEV vaccines.

| | 3-day old | | 3-week old | |
|---|---|---|---|---|
| | 3 weeks PV | 7 weeks PV | 3 weeks PV | 7 weeks PV |
| JE-VAX | 0 | 0 | 100 | 100 |
| pCDNA3/CAT | 0 | 0 | 0 | 0 |
| pCDJE2-7 | 40 | 60 | 90 | 90 |
| pC1BJES14 | 10 | 60 | 80 | 100 |
| pCBJE1-14 | 80 | 100 | 100 | 100 |

TABLE 5

Protection from JEV challenge in 8 week old mice following vaccination at 3 days old with various JEV vaccines.

| Vaccine | Pre-challenge JEV seroconversion | Days post-challenge survival rate (%): 6 | 7 | 8 | 9 | 21 |
|---|---|---|---|---|---|---|
| JE-VAX | 0 | 100 | 100 | 60 | 40 | 40 |
| pCDNA3/CAT | 0 | 100 | 80 | 30 | 30 | 30 |
| pCDJE2-7 | 60 | 100 | 100 | 100 | 100 | 100 |
| pC1BJES14 | 60 | 100 | 100 | 100 | 100 | 100 |
| pCBJE1-14 | 100 | 100 | 100 | 100 | 100 | 100 |

TABLE 3

Persistence of the immune response in mice immunized with pCDJE2-7 or JE-VEX vaccine.

| | ELISA Titer ($log_{10}$) | | | | | | $PRNT_{90\%}$ Titer | | |
|---|---|---|---|---|---|---|---|---|---|
| | 3 wks | 6 wks | 9 wks | 23 wks | 40 wks | 60 wks* | 3 wks | 6 wks | 9 wks |
| 1 × pCDJE2-7 | 2.6-3.2 | 3.8-5.0 | 3.8-4.4 | >3.2 | >3.2 | 2.4, 2.4, 3.8, 4.4 | <20 | 20 | 40-160 |
| 2 × pCDJE2-7 | 2.6-3.8 | 4.4 | 3.8-4.4 | >3.2 | >3.2 | 2.6, 3.8, 3.8 | <20 | 20-40 | 40-160 |
| 2 × JE-VAX | 2.6-3.8 | 4.4-5.0 | 3.8-5.6 | >3.2 | >3.2 | <2, <2, <2, 4.4 | <20 | 20-40 | 20-160 |
| 2 × pCDNA3/CAT | <2 | <2 | <2 | ND | ND | <2 | <20 | <20 | <20 |

Mice were inoculated with 1 or 2, 100 μg/dose plasmid DNA, or 1/5 human dose of JE-VAX vaccine. Sera were collected for testing prior to the second immunization.
*Individual serum titers.

TABLE 6

Evaluation of the ability of maternal antibody from JEV-nucleic acid-vaccinated female mice to protect their pups from fatal JEV encephalitis.

| Vaccinated mother | | JEV challenged pups | | |
|---|---|---|---|---|
| | | Challenge age | | |
| Vaccine | $PRNT_{90\%}$ | (days) | No. survival[1] | ELISA[2] |
| 1 × pCDJE2-7 | 40 | 4 | 0/11 | |
| 2 × pCDJE2-7 | 80 | 4 | 12/12 | 12/12 |
| 2 × JE-VAX | 20 | 3 | 0/16 | |
| 2 × pCDNA-3/CAT | <10 | 5 | 0/14 | |
| 1 × pCDJE2-7 | 20 | 15 | 5/11 | 5/5 |
| 2 × pCDJE2-7 | 40 | 14 | 8/12 | 7/8 |

TABLE 6-continued

Evaluation of the ability of maternal antibody from JEV-nucleic acid-vaccinated female mice to protect their pups from fatal JEV encephalitis.

| Vaccinated mother | | JEV challenged pups | | |
|---|---|---|---|---|
| | | Challenge age | | |
| Vaccine | $PRNT_{90\%}$ | (days) | No. survival[1] | ELISA[2] |
| 2 × JE-VAX | 80 | 13 | 5/5 | 5/5 |
| 2 × pCDNA-3/CAT | <10 | 14 | 0/14 | |

Mice were inoculated intramuscularly with 1 or 2, 100 μg dose of plasmid DNA, or subcutaneously with two, 1/5 human dose of JE-VAX vaccine. Sera were collected 9 weeks post-vaccination for PRNT testing prior to mating with non-immune male.

[1]No Survivors/total for each litter.

[2]Number of JEV ELISA-antibody-positive animals (titer ≧ 1:400)/No. of survivors; sera were collected for testing 12 weeks after challenge.

TABLE 7

Characteristic of the signal peptides and their vaccine of potentials among flavivirus DNA vaccine constructs

| | | | Signal peptide probability[a] | | | Immuni-zation protocol/ |
|---|---|---|---|---|---|---|
| Plasmid | Signal peptide sequence preceding prM protein | | SP | AP | Csite | protection |
| pSLE1 | ?L**D**TIN**RR**PS**KKR**GGT**R**SLLGLAALIGLASS/LQLLSTYQG | (SEQ ID NO: 32) | 0.702 | 0.292 | 0.352 | im × 2/ Partial |
| pJME | MWLASLAVVIACAGA/M**K**LSNFQG**K** | (SEQ ID NO: 33) | 0.998 | 0.000 | 0.778 | im × 2/ Partial |
| pCJEME | MN**E**GSIMWLASLAVVIACAGA/M**K**LSNFQG**K** | (SEQ ID NO: 34) | 0.985 | 0.012 | 0.785 | im × 2/ 100% |
| pCBJE1-14 | MG**RK**QN**KR**GGN**E**GSIMWLASLAVVIACAGA/M**K**LSNFQG**K** | (SEQ ID NO: 35) | 0.791 | 0.199 | 0.623 | im × 1/ 100% |
| pcDNA3prM-E | MS**KKR**GGS**E**TSVLMVIFMLIGFAAA/L**K**LSNFQG**K** | (SEQ ID NO: 36) | 0.721 | 0.277 | 0.622 | im × 4/ Partial |
| | | | | | | gg × 2-4/ 100% |
| pCBWN | MG**KR**SAGSIMWLASLAVVIACAGA/VTLSNFQG**K** | (SEQ ID NO: 37) | 0.976 | 0.024 | 0.526 | im × 1/ 100% |
| p1012D2ME | MNVL**R**GF**RKE**IG**R**MLNILN**RRRR**TAGMIIMLIPTVMA/F**H**LTT**R**NG**E** | (SEQ ID NO: 38) | 0.165 | 0.778 | 0.164 | id × 2/ None |
| SV-PE | MVGLQ**KR**G**KRR**SATDWMSWLLVITLLGMTLA/ATV**RKER**GD | (SEQ ID NO: 39) | 0.943 | 0.056 | 0.899 | im or gg × 2/100% |
| pWRG7077-RSSE | MGWLLVVVLLGVTLA/ATV**RKER**GD | (SEQ ID NO: 40) | 1.000 | 0.000 | 0.912 | gg × 2/ 100% |
| pWRG7077-CEE | MSWLLVITLLGMTIA/ATV**RKER**GD | (SEQ ID NO: 41) | 0.999 | 0.000 | 0.821 | gg × 2/ 100% |

[a]The SignalP HMM program was applied to calculate signal peptide (SP), anchor peptide (AP) and signalase cleavage site (C site) probabilities. Single amino acid codes were used, and charged amino acids were highlighted by underline-bold letters. The signalase cleavage site separating SP and prM is indicated by "/". DNA vaccines were inoculated by intramuscluar (im), intradermal (id), or gene gun (gg) method.

TABLE 8

Neutralizing antibody (Nt) responses in mice immunized with different doses of the combined WN and JE virus DNA vaccines.

| | pCBWN + pCBJE1-14 | | | | pCB Control |
|---|---|---|---|---|---|
| Dose per plasmid (μg) | 100 + 100 | 40 + 40 | 20 + 20 | 10 + 10 | 100 |
| Percentage of mice with Nt: | | | | | |
| WN virus/JE virus: | 100/100 | 100/70 | 70/0 | 60/0 | 0/0 |
| Range of $PRNT_{90}$ titer: | | | | | |
| WN virus: | 1:320-1:80 | 1:80-1:20 | 1:80-<1:10 | 1:20-<1:10 | <1:10 |
| JE virus: | 1:40-1:10 | 1:10-<1:10 | <1:10 | <1:10 | <1:10 |

Groups of ten, three-week-old female ICR out-bred mice were i.m. injected with a single dose of Combined plasmid DNAs as indicated. The serum specimens collected 12-week after immunization were assayed by the plaque-reduction neutralization test (PRNT). The end-point titers against JE and WN virus were calculated based on the 90% percent plaque reduction using JE virus (strain SA-14) and West Nile virus (strain NY-6480), respectively.

TABLE 9

Oligonucleotides used to construct DEN-2 virus prM-E expression plasmids, and the junction region of chimeric DEN-2 and JE E indicated.

| | | |
|---|---|---|
| 100% DEN-2 prM-E: | | |
| D2KasI-438[a] | 5' TGTGCA***GGCGCC***TTCCATTTAACCACACGTAACG | (SEQ ID NO: 48) |
| CD2NotI-2402 | 5' TCGA***GCGGCCGC***TCAACTAATTAGGCCTGCACCATGACTC | (SEQ ID NO: 49) |
| 90% DEN-2 E & 10% JE E: | | |
| T7 | 5' CTTATCGAAATTAATACGACTCACTATAGG | (SEQ ID NO: 50) |
| CD2BstXI-2244 | 5' ATAGATTGCT***CCA***AACACT***TGG***TGG | (SEQ ID NO: 51) |
| JE-2281 | 5' ACTCCATAGGAAAAGCCGTTCACC | (SEQ ID NO: 52) |
| CSP6 | 5' GCGAGCTCTAGCATTTAGGTGACACTATAG | (SEQ ID NO: 53) |
| | **DEN-2← →JE** | |
| 90-10 Junction: | **Leu His Gln Val Phe Gly Gly Ala Phe Arg Thr** | (SEQ ID NO: 55) |
| | **CTC CAC CAA GTG TTT GGT GGT GCC TTC AGA ACA** | (SEQ ID NO: 54) |
| 80% DEN-2 E & 20% JE E: | | |
| T7 | 5' CTTATCGAAATTAATACGACTCACTATAGG | (SEQ ID NO: 56) |
| CD2BsmBI-2097 | 5' GAATT***CGTCTC***ACTTCCTTTCTTAAACCAGTTGAGCTTC | (SEQ ID NO: 57) |
| JEBsmBI-2175 | 5' GGAATT***CGTCTC***GGAAGCACGCTGGGCAAGG | (SEQ ID NO: 58) |
| CSP6 | 5' GCGAGCTCTAGCATTTAGGTGACACTATAG 3' | (SEQ ID NO: 59) |
| | **DEN-2← →JE** | |
| 80-20 Junction: | **Asn Trp Lys Lys Gly Ser Thr Leu Gly Lys Ala** | (SEQ ID NO: 61) |
| | **AAC TGG TTT AAG AAA GGA AGC ACG CTG GGC GCC** | (SEQ ID NO: 60) |

[a]Restriction enzyme sites encoded in oligonucleotides were highlighted by the bold, italic and underline.

TABLE 10

Characterization of DEN-2 E glycoprotein epitopes expressed by the recombinant DEN-2 plasmids as determined by the indirect fluorescent antibody assay (IFA).

| Antibody | | | Controls[a] | | Plasmid construct[a] | | |
|---|---|---|---|---|---|---|---|
| | | | DEN-2 | Normal | | | |
| MAb (Epitope)[b] | Antigenic Domain[c] | PRNT[d] | infected cells | cells | pCBD2-14-6 | pCB9D2-1J-4-3 | pCB8D2-2J-2-9-1 |
| 4G2 (A1) | 2 | +/− | 4+ | — | 4+ | 4+ | 4+ |
| 4E5 (A2) | 2 | Yes | 3+ | — | 3-4+ | 3-4+ | 2-3+ |
| 1B7 (A5) | 2 | Yes | 3-4+ | — | 4+ | 4+ | 2-3+ |
| 1B4C-2 (C1) | 1 | No | 3-4+ (8000) | — | 2-3+ (4000) | 2-3+ (4000) | 2-3+ (8000) |
| 2B3A-1 (C3) | 1 | No | 3-4+ (≧3200) | — | 3+ (100) | 2+ (100) | 2-3+ (≧3200) |
| 9A4D-1 (C4) | 1 | No | 3-4+ | — | 2-3+ (400) | 1-3+ (400) | 3+ (≧12800) |
| 3H5 (B2) | 3 | Yes | 4+ | — | 4+ | 4+ | 4+ |
| 10A4D-2 (B3) | 3 | Yes | 2-3+ | — | 3-4+ | 3-4+ | 2-3+ |
| 1A1D-2 (B4) | 3 | Yes | 4+ | — | 3-4+ | 4+ | 3-4+ |
| 9D12-6 | | Yes | 2-4+ | | 2-3+ | 2-3+ | 3-4+ |
| 2H2 | prM | No | 4+ | — | 4+ | 3-4+ | 3-4+ |
| 1A2A-1 | Capsid | No | 2-3+ | — | 1+ | 2+ | 1-2+ |

[a]IFA substrates were acetone-fixed COS-1 cells, either infected with DEN-2 16681, uninfected controls, or transformed with a DEN-2 recombinant plasmid.

[b]Monoclonal antibodies were used at a predetermined optimum dilution based on reactivity with DEN-2 16681 virus. For some MAbs, endpoint titers, shown in parentheses, are reported and for others, only qualitative values are reported based on a scale from 1+ to 4+, with 3-4+ considered positive, 2+ equivocal, and 1+ negative.

[c]Antigenic domains based on the E-glycoprotein of TBE virus (Mandl et al., "Antigenic structure of the flavivirus envelope protein E at the molecular level, using tick-borne encephalitis virus as a model," J. Virol. 63: 564-571 (1989); Rey et al., "The envelope glycoprotein from tick-borne encephalitis virus at 2 A resolution," Nature 375: 291-298 (1995)).

[d]Plaque-reduction neutralization activity at a 1:100 dilution of ascitic fluid, using a 90% plaque-reduction endpoint, except for 4G2 and 9D12-6, for which a 50% neutralization endpoint is reported (Henchal et al., "Epitopic analysis of antigenic determinants on the surface of dengue-2 virions using monoclonal antibodies," Am. J. Trop. Med. Hyg. 34: 162-169 (1985); Roehrig et al., "Monoclonal antibody mapping of the envelope glycoprotein of the dengue 2 virus, Jamaica," Virology 246: 317-328 (1998)).

TABLE 11

Detection of secreted and membrane-bound DEN-2 recombinant protein by antigen-capture ELISA.

| Plasmid | Sample type | Endpoint ELISA titer |
|---|---|---|
| pCBD2-14-6 | PEG-precipitated culture fluid[a] | <1:10 |
| pCBD2-14-6 | PEG-precipitated, ethanol-extracted culture fluid[b] | <1:20 |
| pCBD2-14-6 | Hydrophobic membrane protein preparation[c] | 1:160 |
| pCB9D2-1J-4-3 | PEG-precipitated culture fluid[a] | <1:10 |
| pCB9D2-1J-4-3 | PEG-precipitated, ethanol-extracted culture fluid[b] | <1:20 |
| pCB9D2-1J-4-3 | Hydrophobic membrane protein preparation[c] | 1:80 |
| pCB8D2-2J-2-9-1 | PEG-precipitated culture fluid[a] | 1:640 |
| pCB8D2-2J-2-9-1 | PEG-precipitated, ethanol-extracted culture fluid[b] | 1:80 |

TABLE 11-continued

Detection of secreted and membrane-bound DEN-2 recombinant protein by antigen-capture ELISA.

| Plasmid | Sample type | Endpoint ELISA titer |
|---|---|---|
| pCB8D2-2J-2-9-1 | Hydrophobic membrane protein preparation[c] | 1:80 |
| pEGEP | PEG-precipitated culture fluid[a] | <1:10 |
| pEGFP | PEG-precipitated, ethanol-extracted culture fluid[b] | <1:10 |
| pEGFP | Hydrophobic membrane protein preparation[c] | <1:10 |

[a]Culture supernatant from plasmid-transformed cells was precipitated with 10% polyethylene glycol (PEG) and resuspended in 1/100th of orginal volume.

[b]PEG-precipitated culture supernatant was extracted with 4% ethanol to remove PEG and the pellet was resuspended in 1/5 of the volume extracted.

[c]Hydrophobic membrane fractions were prepared as described in Materials and Methods.

TABLE 12

Immunogenicity of three DEN-2 recombinant plasmids in ICR mice.

| | | ELISA on DEN-2 virus | | | | | | |
|---|---|---|---|---|---|---|---|---|
| | | Screen 3 wks, p.v.[c] | | Screen 6 wks, p.v.[c] | | Endpoint titer | PRNT on DEN-2 virus[a] Endpoint titer | PRNT on JE virus[a] Endpoint titer |
| Plasmid DNA[b] | Mouse # | 1:100 | 1:400 | 1:100 | 1:400 | 9 wks, p.v. | 9 wks, p.v. | 9 wks, p.v. |
| pCB8D2-2J-2-9-1 | Pool, 1, 2, 4-10 | ND[d] | ND | + | + | 64,000 | ND | ND |
| | 1 | + | + | + | + | 64,000 | >1000 | <2 |
| | 2 | + | + | + | + | 32,000 | >1000 | <2 |

TABLE 12-continued

Immunogenicity of three DEN-2 recombinant plasmids in ICR mice.

| Plasmid DNA[b] | Mouse # | ELISA on DEN-2 virus: Screen 3 wks, p.v.[c] 1:100 | 1:400 | Screen 6 wks, p.v.[c] 1:100 | 1:400 | Endpoint titer 9 wks, p.v. | PRNT on DEN-2 virus[a] Endpoint titer 9 wks, p.v. | PRNT on JE virus[a] Endpoint titer 9 wks, p.v. |
|---|---|---|---|---|---|---|---|---|
| | 4 | + | + | + | + | 16,000 | 200 | <2 |
| | 5 | + | + | + | + | 4,000 | <10 | <2 |
| | 6 | + | + | + | + | 16,000 | 200 | <2 |
| | 7 | + | − | + | + | 64,000 | 100 | <2 |
| | 8 | + | − | + | + | 8,000 | 40 | <2 |
| | 9 | + | + | + | + | 6,400 | <2 | <4 |
| | 10 | + | + | + | + | 64,000 | >1000 | <2 |
| pCB9D2-1J- | Pool, 1-10 | ND | ND | + | + | 1,000 | ND | <2[e] |
| 4-3 | 1 | − | − | + | − | 400 | <10 | ND |
| | 2 | + | − | + | + | 200 | <10 | ND |
| | 3 | + | + | + | + | 4,000 | <2 | ≦4 |
| | 4 | + | − | + | − | 200 | <10 | ND |
| | 5 | − | − | + | + | 400 | <10 | ND |
| | 6 | + | + | + | + | 4,000 | <2 | 2 |
| | 7 | − | +/− | − | − | 100 | <10 | ND |
| | 8 | − | − | − | − | 200 | <10 | ND |
| | 9 | + | − | + | − | 4,000 | <2 | <2 |
| | 10 | − | − | + | + | 4,000 | <2 | <2 |
| pCBD2- | Pool, 1-10 | ND | ND | + | − | 200 | <2[f] | <2[g] |
| 14-6 | 1 | − | − | − | − | 400 | <10 | ND |
| | 2, 3, 6-9 | − | − | − | − | <100 | ND | ND |
| | 4 | + | + | + | + | 1,000 | <2 | <2 |
| | 5 | − | − | + | − | 2,000 | 8 | <2 |
| | 10 | + | − | − | − | <100 | ND | ND |
| pEGFP | Pool, 1-10 | − | ND | − | ND | <100 | <2 | <2 |

[a]PRNT, plaque-reduction neutralization test, 90% neutralization endpoint.
[b]Mice were immunized intramuscularly with 100 μg plasmid DNA on weeks 0 and 3.
[c]ELISA screens used sera diluted 1:100 and 1:400.
[d]ND, not done.
[e]Pool, 1, 2, 4, 5, 7, 8.
[f]Pool, 2, 3, 6-10.
[g]Pool, 1-3, 6-10.

TABLE 13

Summary of the characteristics of three DEN-2 recombinant plasmids.

| Plasmid | IFA[a] +/− | Globular/Diffuse | Ag-capture ELISA titer: Secreted antigen | Hydrophobic membrane protein prep | ELISA titer on DEN-2[b]: No. sera ≧ 1:100 | Pooled sera titer | DEN-2 PRNT[c] No. sera ≧ 1:10 |
|---|---|---|---|---|---|---|---|
| pCB8D2-2J-2-9-1 | + | Diffuse | 1:640 | 1:80 | 9/9 | 1:64000 | 7/9[d] |
| pCB9D2-1J-4-3 | + | Globular | <1:10 | 1:80 | 10/10 | 1:1000 | 0/10 |
| pCBD2-14-6 | + | Globular | <1:10 | 1:160 | 3/10 | 1:200 | 0/10 |

[a]Indirect fluorescent antibody assay (IFA) staining characteristics, + or −, and diffuse or globular pattern.
[b]Anti-DEN-2 ELISA titer of sera from mice immunized with the recombinant plasmids. Sera were collected 9 weeks post-vaccination (weeks 0 and 3). Number of mice with titer of ≧1:100/total number of mice is shown, including the endpoint ELISA titer of the pooled serum sample.
[c]Number of mice with plaque-reduction neutralization titers (PRNT, 90% reduction) ≧ 1:10/total number of mice. Sera were collected 9 weeks post-vaccination.
[d]Of the 7 mice with neutralizing antibody, 3 mice had PRNT titers of > 1:1000, 3 had titers of ≧ 1:100 < 1:1000, and one had a titer of 1:40.

What is claimed is:

1. An isolated nucleic acid comprising a transcriptional unit encoding a signal sequence of a structural protein of a first *flavivirus* and an immunogenic *flavivirus* antigen, wherein the antigen is of a second *flavivirus* or the antigen is a chimeric antigen comprising amino acid sequence from more than one *flavivirus*, wherein the signal sequence is a Japanese encephalitis virus prM signal sequence, and wherein the transcriptional unit directs the synthesis of the antigen.

2. The nucleic acid of claim 1, wherein the immunogenic *flavivirus* antigen is of a *flavivirus* selected from the group consisting of yellow fever virus, dengue serotype 1 virus, dengue serotype 2 virus, dengue serotype 3 virus, dengue serotype 4 virus, St. Louis encephalitis virus, Powassan virus and West Nile virus.

3. The nucleic acid of claim 1, wherein the transcriptional unit encodes a prM signal sequence of Japanese encephalitis virus and an M protein and an E protein of West Nile virus.

4. The nucleic acid of claim 1, wherein the transcriptional unit encodes a prM signal sequence of Japanese encephalitis virus and an M protein and an E protein of yellow fever virus.

5. The nucleic acid of claim 1, wherein the transcriptional unit encodes a prM signal sequence of Japanese encephalitis virus and an M protein and an E protein of St. Louis encephalitis virus.

6. The nucleic acid of claim 1, wherein the transcriptional unit encodes a prM signal sequence of Japanese encephalitis virus and an M protein and an E protein of Powassan virus.

7. The nucleic acid of claim 1, wherein the *flavivirus* antigen is selected from the group consisting of an M protein, an E protein, both an M protein and an E protein, a portion of an M protein, a portion of an E protein, and both a portion of an M protein and a portion of an E protein, or any combination thereof.

8. The nucleic acid of claim 7, wherein the antigen is both the M protein and the E protein.

9. The nucleic acid of claim 1, wherein the nucleic acid is DNA.

10. The nucleic acid of claim 9, comprising a nucleotide sequence selected from the group consisting of SEQ ID NO:15, SEQ ID NO:19, SEQ ID NO:21 and SEQ ID NO:23.

11. The nucleic acid of claim 1, wherein the transcriptional unit comprises a control sequence disposed appropriately such that it operably controls the synthesis of the antigen.

12. The nucleic acid of claim 11, wherein the control sequence is the cytomegalovirus immediate early promoter.

13. The nucleic acid of claim 1, comprising a Kozak consensus sequence located at a translational start site for a polypeptide comprising the antigen encoded by the transcriptional unit.

14. The nucleic acid of claim 1 wherein the transcriptional unit comprises a poly-A terminator.

15. An isolated cell comprising the nucleic acid of claim 1.

16. A composition comprising the nucleic acid of claim 1 and a pharmaceutically acceptable carrier.

17. A method of eliciting an immune response in a subject against infection by a *flavivirus*, comprising administering to the subject an effective amount of the composition of claim 16.

18. The method of claim 17, wherein the *flavivirus* antigen is of a second *flavivirus* selected from the group consisting of yellow fever virus, dengue serotype 1 virus, dengue serotype 2 virus, dengue serotype 3 virus, dengue serotype 4 virus, St. Louis encephalitis virus, Powassan virus and West Nile virus, or the *flavivirus* antigen is a chimeric antigen comprising amino acid sequence from more than one *flavivirus*, wherein the flaviviruses are selected from yellow fever virus, dengue serotype 1 virus, dengue serotype 2 virus, dengue serotype 3 virus, dengue serotype 4 virus, Japanese encephalitis virus, St. Louis encephalitis virus, Powassan virus and West Nile virus.

19. The method of claim 17, wherein the *flavivirus* antigen is selected from the group consisting of an M protein, an E protein, both an M protein and an E protein, a portion of an M protein, a portion of an E protein, and both a portion of an M protein and a portion of an E protein, or any combination thereof.

20. The method of claim 19, wherein the *flavivirus* antigen is both the M protein and the E protein, and wherein a cell within the body of the subject, after incorporating the nucleic acid within it, secretes subviral particles comprising the M protein and the E protein.

21. The method of claim 17, wherein the transcriptional unit encodes a signal sequence of Japanese encephalitis virus, and an M protein and an E protein of West Nile virus.

22. The method of claim 17, wherein the transcriptional unit encodes a signal sequence of Japanese encephalitis virus, and an M protein and an E protein of yellow fever virus.

23. The method of claim 17, wherein the transcriptional unit encodes a signal sequence of Japanese encephalitis virus, and an M protein and an E protein of St. Louis encephalitis virus.

24. The method of claim 17, wherein the transcriptional unit encodes a signal sequence of Japanese encephalitis virus, and an M protein and an E protein of Powassan virus.

25. The method of claim 17, comprising administering the composition to the subject in a single dose.

26. The method of claim 17, wherein the composition is administered via a parenteral route.

27. The nucleic acid of claim 1, wherein the antigen comprises a St. Louis encephalitis virus antigen.

28. The method of claim 17, wherein the antigen comprises a St. Louis encephalitis virus antigen.

29. The nucleic acid of claim 1, wherein the chimeric antigen comprises a Japanese encephalitis virus antigen.

30. The method of claim 17, wherein the chimeric antigen comprises a Japanese encephalitis virus antigen.

31. The nucleic acid of claim 1, wherein the antigen comprises a yellow fever virus antigen.

32. The method of claim 17, wherein the antigen comprises a yellow fever virus antigen.

33. The nucleic acid of claim 1, wherein the antigen comprises a dengue virus antigen.

34. The method of claim 17, wherein the antigen comprises a dengue virus antigen.

35. The nucleic acid of claim 1, wherein the antigen comprises a West Nile virus antigen.

36. The method of claim 17, wherein the antigen comprises a West Nile virus antigen.

37. The nucleic acid of claim 1, wherein the signal sequence is a modified Japanese encephalitis virus signal sequence comprising the nucleotide sequence of SEQ ID NO: 14 or SEQ ID NO: 27.

38. The nucleic acid of claim 1, wherein the immunogenic *flavivirus* antigen is a chimeric antigen comprising amino acid sequence from more than one *flavivirus*, wherein the flaviviruses are selected from yellow fever virus, dengue serotype 1 virus, dengue serotype 2 virus, dengue serotype 3 virus, dengue serotype 4 virus, Japanese encephalitis virus, St. Louis encephalitis virus, Powassan virus and West Nile virus.

39. The nucleic acid of claim 1, wherein the immunogenic *flavivirus* antigen is a chimeric antigen comprising amino acid sequence from the first *flavivirus* and a second *flavivirus*, wherein the flaviviruses are selected from yellow fever virus, dengue serotype 1 virus, dengue serotype 2 virus, dengue serotype 3 virus, dengue serotype 4 virus, Japanese encephalitis virus, St. Louis encephalitis virus, Powassan virus and West Nile virus.

40. The nucleic acid of claim 39, wherein the first *flavivirus* is Japanese encephalitis virus.

41. The nucleic acid of claim 39, wherein the immunogenic *flavivirus* antigen comprises a chimeric E protein.

42. The nucleic acid of claim 39, wherein the immunogenic *flavivirus* antigen comprises an M protein from the second *flavivirus* and a chimeric E protein comprising amino acid sequence from Japanese encephalitis virus and the second *flavivirus*.

43. The nucleic acid of claim 42, wherein the chimeric E protein comprises a carboxy terminal portion from Japanese encephalitis virus, wherein the carboxy terminal portion is 5%, 10%, 15%, 20%, 25%, 30%, 40%, 50% or 75% of the chimeric E protein.

44. The nucleic acid of claim 43, wherein the carboxy terminal portion is at least 10% of the chimeric E protein.

45. The nucleic acid of claim 44, wherein the carboxy terminal portion is at least 20% of the chimeric E protein.

46. The nucleic acid of claim 42, wherein the second *flavivirus* is a dengue virus.

47. The nucleic acid of claim 42, wherein the second *flavivirus* is a St. Louis encephalitis virus.

* * * * *

UNITED STATES PATENT AND TRADEMARK OFFICE

CERTIFICATE OF CORRECTION

PATENT NO. : 7,662,394 B2
APPLICATION NO. : 10/500796
DATED : February 16, 2010
INVENTOR(S) : Chang It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 868 days.

Signed and Sealed this
Fifteenth Day of February, 2011

David J. Kappos
*Director of the United States Patent and Trademark Office*